US005597373A

United States Patent [19]
Bond et al.

[11] Patent Number: 5,597,373
[45] Date of Patent: Jan. 28, 1997

[54] PHYSIOLOGICAL EVALUATION AND EXERCISE SYSTEM

[75] Inventors: Malcolm Bond, Winters; Gary Engle, Fair Oaks; Joseph J. Forma, Grass Valley; Theodore F. Naumann, Shingle Springs, all of Calif.

[73] Assignee: Cedaron Medical, Inc., Davis, Calif.

[21] Appl. No.: 789,834

[22] Filed: Nov. 8, 1991

(Under 37 CFR 1.47)

[51] Int. Cl.⁶ ..................................................... A63B 21/00
[52] U.S. Cl. ........................... 482/4; 482/1; 482/5; 482/7; 482/8; 482/9; 482/901; 482/902; 601/23
[58] Field of Search ............................... 482/1–9, 92, 900, 482/901; 128/774; 601/23

[56] References Cited

U.S. PATENT DOCUMENTS

| 3,465,592 | 9/1969 | Perrine . |
| 3,848,467 | 11/1974 | Flavell . |
| 4,235,437 | 11/1980 | Ruis et al. . |
| 4,337,050 | 6/1982 | Engalitcheff, Jr. . |
| 4,601,468 | 7/1986 | Bond et al. ................. 482/7 |
| 4,628,910 | 12/1986 | Krukowski . |
| 4,679,786 | 7/1987 | Rodgers . |
| 4,691,694 | 9/1987 | Boyd et al. .......... 482/900 X |
| 4,711,450 | 12/1987 | McArthur . |
| 4,768,783 | 9/1988 | Engalitcheff, Jr. . |
| 4,869,497 | 9/1989 | Stewart et al. ....... 482/901 X |
| 4,885,687 | 12/1989 | Carey . |
| 4,889,108 | 12/1989 | Bond et al. .......... 482/901 X |
| 4,907,797 | 3/1990 | Gezari et al. ............ 482/92 X |
| 4,934,694 | 6/1990 | McIntosh ............. 482/901 X |
| 5,020,795 | 6/1991 | Airy et al. ........... 482/901 X |
| 5,050,618 | 9/1991 | Larsen ........................ 128/774 |
| 5,186,695 | 2/1993 | Mangseth et al. ............ 482/6 |
| 5,201,772 | 4/1993 | Maxwell ............. 482/901 X |

Primary Examiner—Richard J. Apley
Assistant Examiner—Glenn E. Richman
Attorney, Agent, or Firm—Fliesler, Dubb, Meyer & Lovejoy

[57] ABSTRACT

A system for isolating, evaluating and exercising the muscle groups of the human hand, wrist, arm and shoulder including an adaptable detector for interpreting the cardinal movements of at least one muscle group of the hand during flexion, extension, or deviation of the wrist, or abduction, opposition, flexion or hyperextension of individual digits of the hand. The detector translates the movements of the muscle group into rotational data for the system and effectively isolates the movements of the muscle group so that the movements of other muscle groups of the body are not detected by the system. The system also includes a controlled resistance coupled to the detector which provides a variable resistance against the muscle group and ascertains the force applied to the detector by the movements of the one muscle group. The resistance can be varied to provide isotonic, isokinetic, or isometric modes of testing against said at least one muscle group.

17 Claims, 40 Drawing Sheets

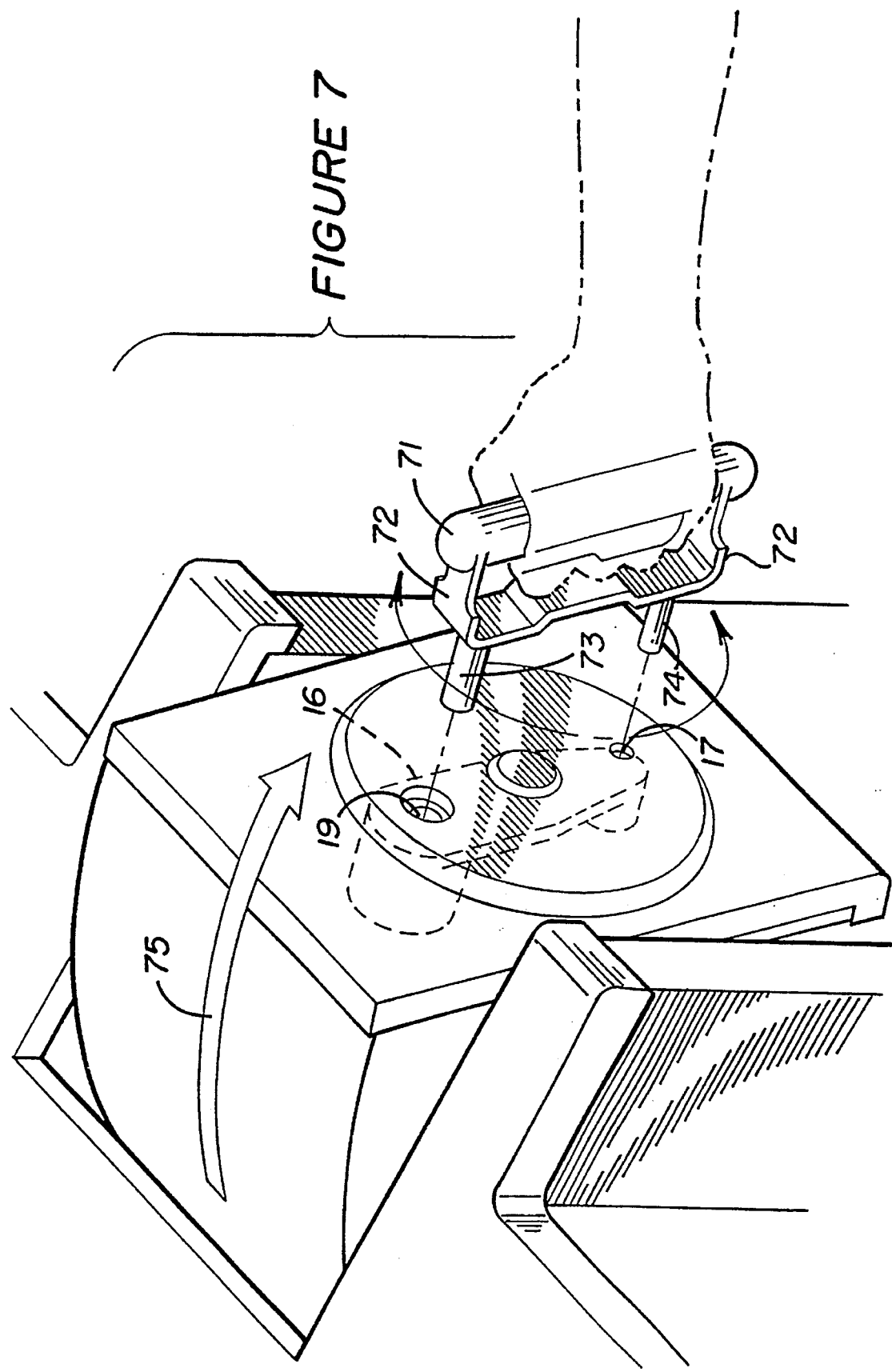

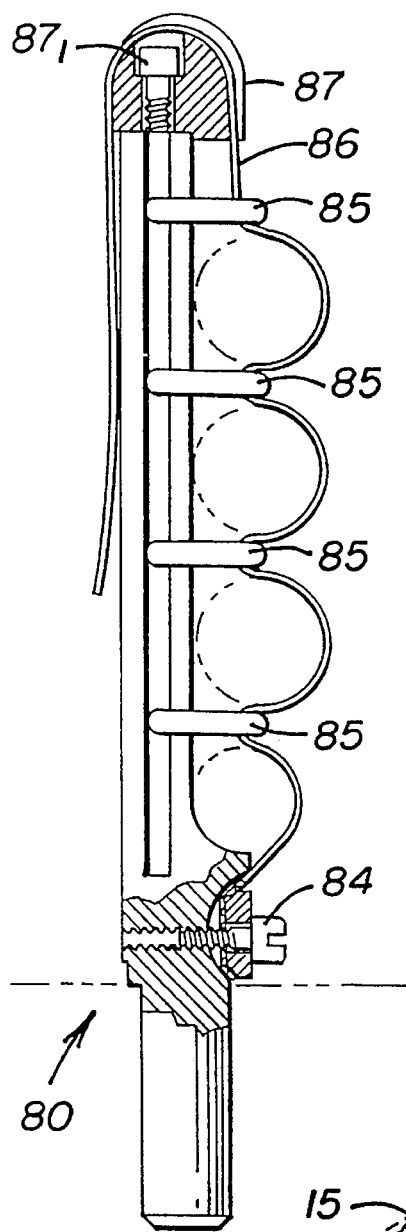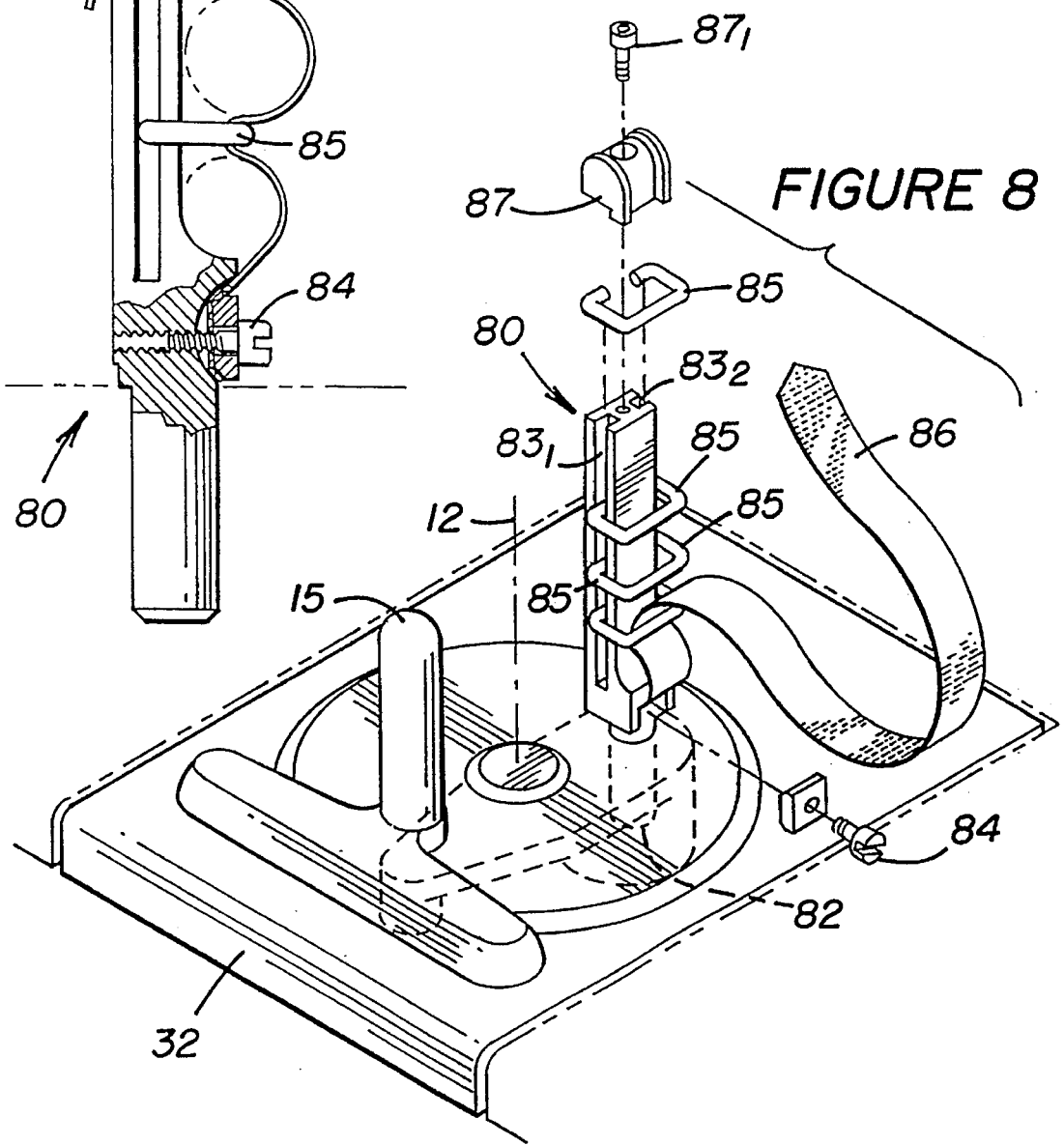
FIGURE 8A
FIGURE 8

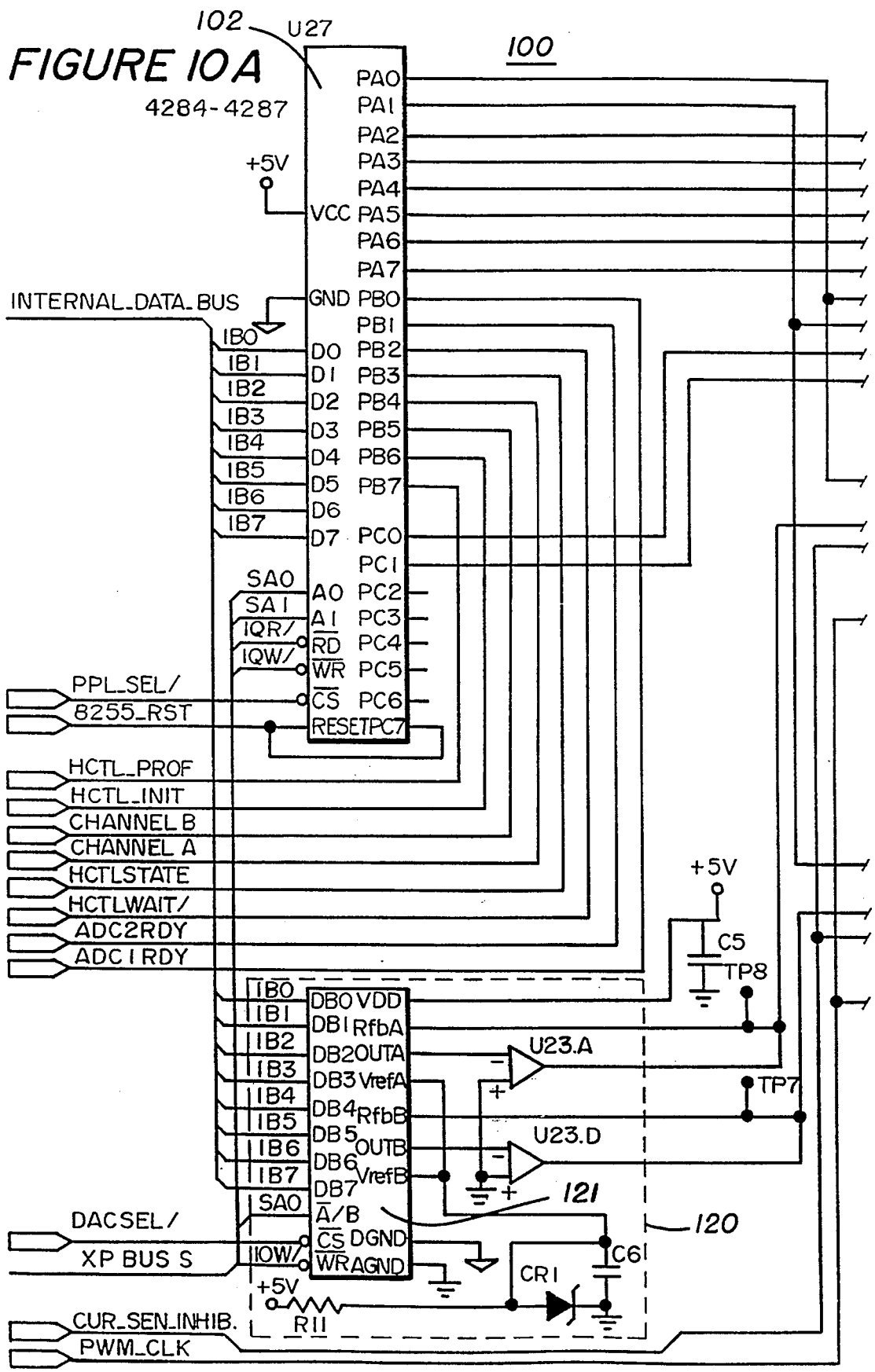

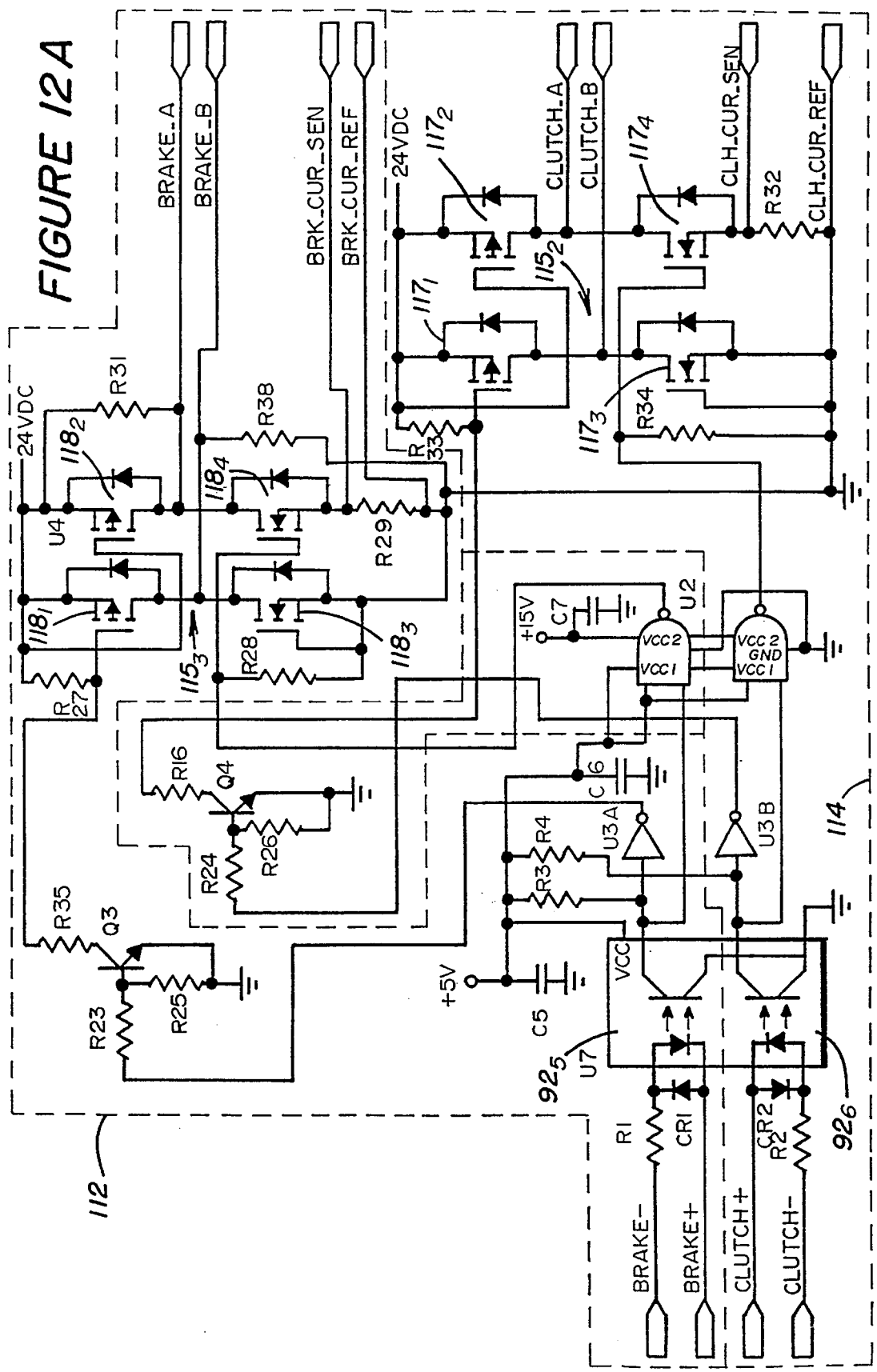

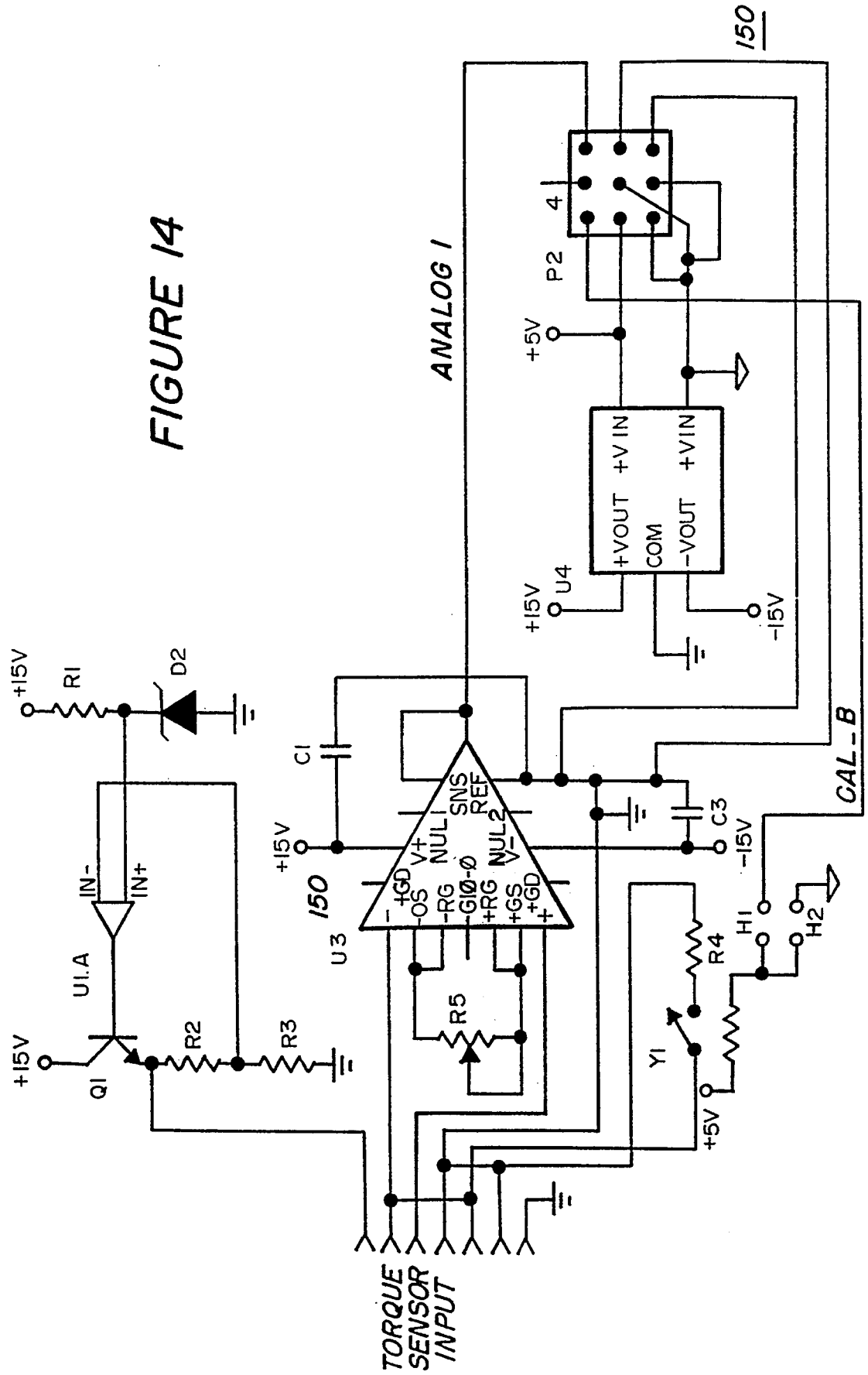

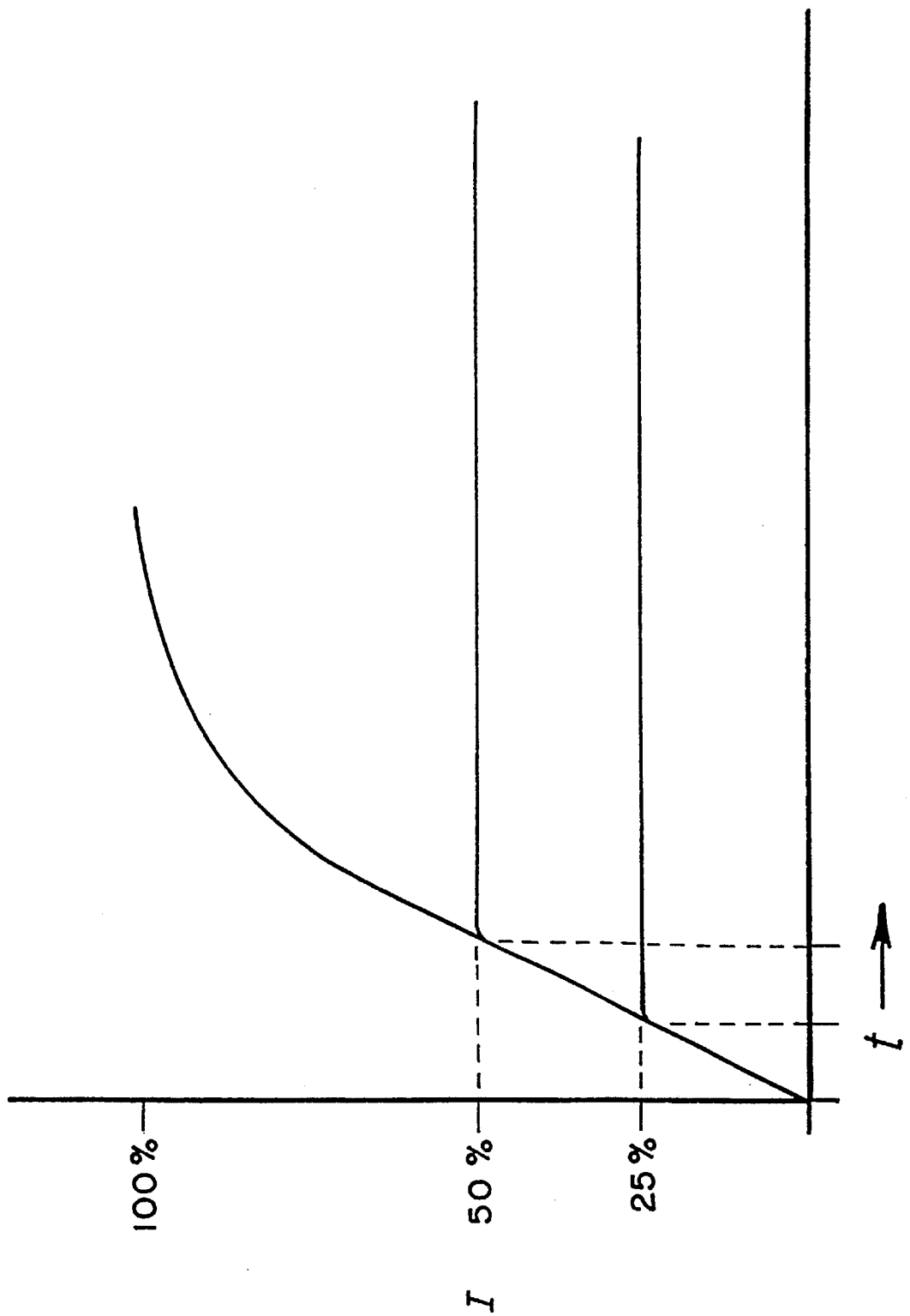

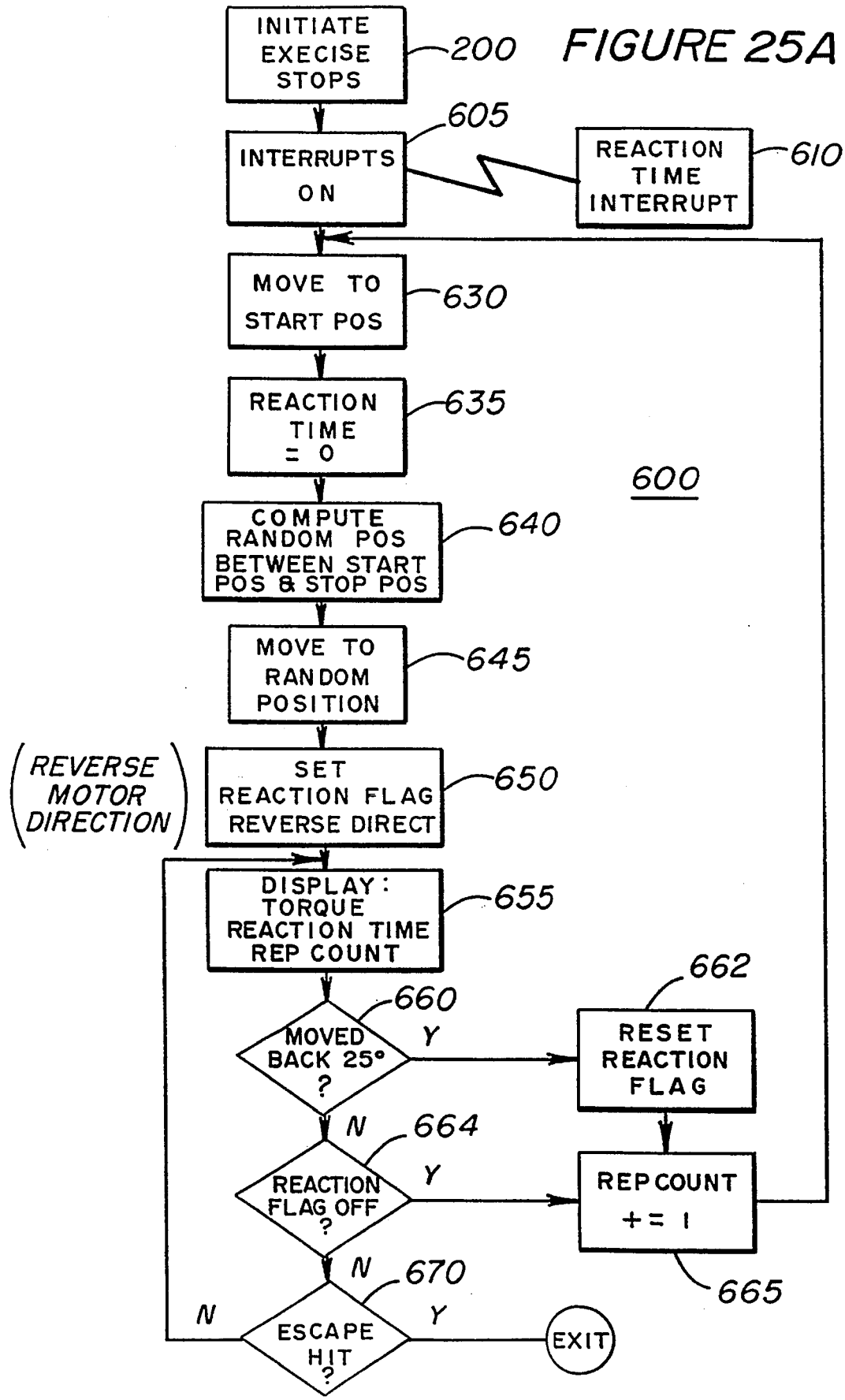

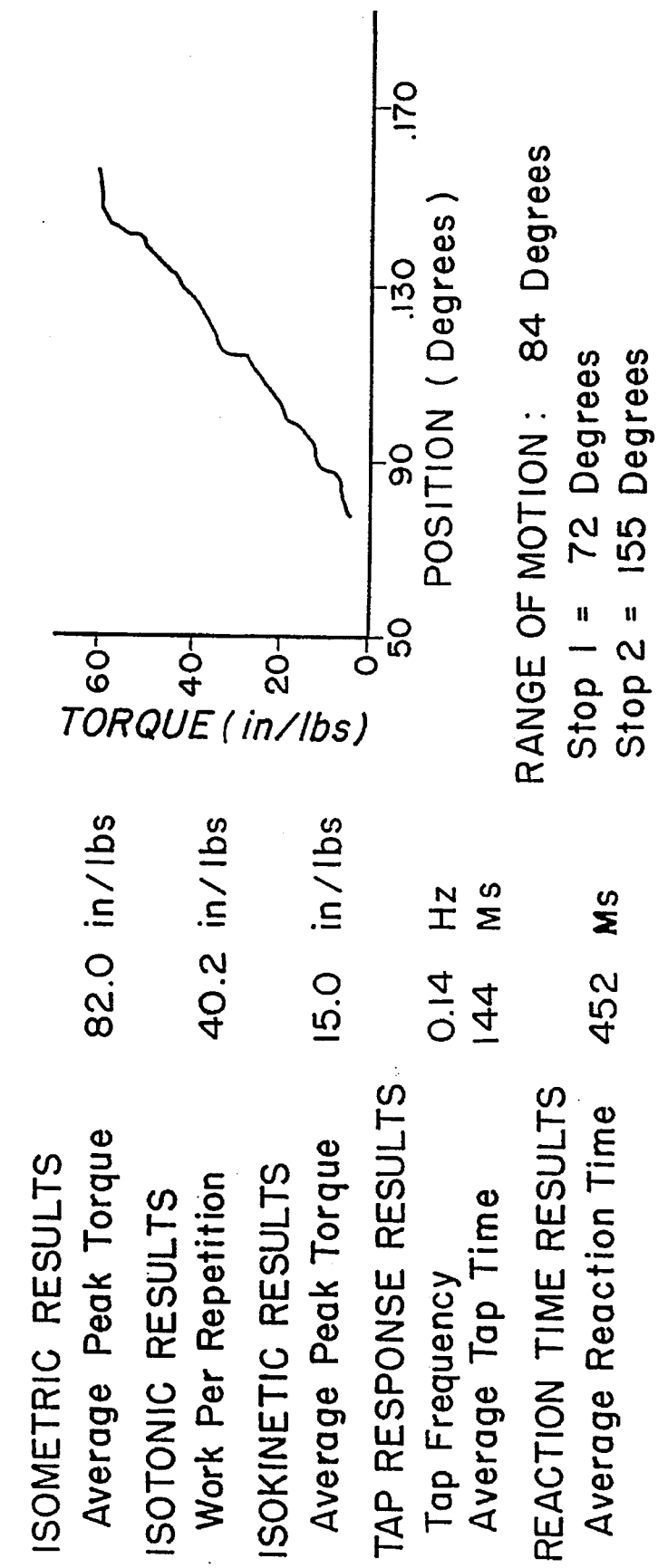

PHYSIOLOGICAL EVALUATION AND EXERCISE SYSTEM

NOTICE OF GOVERNMENT INTEREST

The United States government has a paid-up license in this invention and the right in limited circumstances to require the patent owner to license others on reasonable terms as provided for by the terms of Contract Number NAS 9-18470 awarded by the National Aeronautics and Space Administration.

LIMITED COPYRIGHT WAIVER

A portion of the disclosure of this patent document contains material to which the claim of copyright protection is made. The copyright owner has no objection to the facsimile reproduction by any person of the patent document or the patent disclosure, as it appears in the U.S. Patent and Trademark Office file or records, but reserves all other rights whatsoever.

BACKGROUND OF THE INVENTION

1. Field of the Invention

The invention relates to the training, evaluation, and retraining of factors that limit human performance. Specifically, the invention relates to a method and apparatus for training, evaluating and reconditioning the performance of the hand, wrist, forearm, elbow and shoulder.

2. Description of the Related Art

Rehabilitation specialists are often asked to conduct an assessment of patients that have acquired a limitation to their optimal independent activity. Reconditioning or retraining of functional human performance is also an important goal of rehabilitation.

Although the parameters of human performance vary widely, one may identify several principles which are common to all forms of independent activity. Such common principles are muscular strength, endurance, joint range of motion, and motor coordination. It is these parameters of performance that the rehabilitation specialist will focus upon. The specialist directs attention upon the identified parameter's which are limiting performance and evaluates the degree of the limitation.

In the process of reconditioning, each of these principles will also be the focus of attention. Each of them will be enhanced by retraining therapy. The underlying physiological adaptations responsible for performance enhancement include, but not limited to, vascularity, cell biochemistry and motor coordination skills.

The methods used in both the assessment and retraining process of the muscle groups are closely related. Both procedures physically tax or overload the affected muscle group to quantify its performance and also to cause biological adaptations to improve the performance of that muscle group. Historically, the rehabilitation specialist will have a hands on approach using his own healthy limb to resist the movement of the patient's limb. In this way, the clinician evaluates the patient's performance through feel and, at the same time, offers exercise to the limited muscle group. By repetitive, hands on, accommodating exercise, the limited muscle group is overloaded and adapts biologically with improved performance.

For example, muscle strength is a performance parameter which is quite plastic in quickly adapting to immobilization or disuse as well as to increased activity or overuse. That is, muscle strength quite quickly increases or decreases with respect to use or disuse. Disuse, such as immobilization following injury or casting after surgery, results in a significant decrement in muscle size and hence muscle strength. In contrast, if free weight lifting is used as the method of choice for the rehabilitation therapy, the end result is a quick response of increased muscle cell size and hence gains in muscle strength.

Weight lifting equipment will overload a muscle group by using gravity against which a muscle must move the weight. With free weights, no controls are present to direct the speed of movement of the limb nor the resistance throughout the range of motion that the muscle must work against. The maximum free weight resistive load that can be applied to a limb is determined by the capacity of the associated muscle group as measured throughout the range of motion of the limb. The maximum load that the limb can support varies throughout its range of motion where at some point it is at a minimum and at another it is at a maximum. Hence, the maximum resistive free weight load that can be applied is equal to the maximum supportable load in the weakest area of the range of motion.

Conventional methods of subjective assessment and reconditioning, such as subjective "through the clinician's hands" evaluations and free weight exercise, are now reinforced with technology.

Technology has been developed which provides for assessment and reconditioning of muscular deficiencies by electronic control of the rate of movement of the limb. This rate of movement control is achieved by constantly varying the amount of resistance offered the moving limb throughout the range of motion. This category of devices are to allow the muscle group, usually a whole limb or limb segment, to accelerate to a pre-selected speed. These constant speed devices use the methods of isokinetic or accommodating resistance.

In the isokinetic system, once the moving limb achieves the selected speed, the device then offers the muscle group an accommodating resistance which is proportional to the contractile force such that the limb continues to move at the selected speed. These mechanisms usually have some form of position/time feed back, servo loop which directs the resistance, for example, through feeding a variable current to a DC servo motor, to be such that, no matter what constantly varying force is executed by the contracting muscle group, the limb does not exceed or fall below the speed selected.

The goal with isokinetic systems is that throughout the entire range of motion of the limb, the associated muscle groups are working at their utmost level while receiving an optimal overloading resistance.

The contractile effort of a muscle group against this type of microprocessor based resistance is registered by the system and produces a profile of contractile performance which is widely recognized as accurate and repeatable. The data from such a system can be used in a court of law as evidence in disability claims.

Examples of such isokinetic systems are the Cybex, manufactured by Lumex, U.S. Pat. No. 3,465,592, inventor J. Perrine; the LIDO manufactured by Loredan, U.S. Pat. No. 4,601,468; inventor M. Bond, KIN COM manufactured by Chattanooga, U.S. Pat. No. 4,711,450, inventor J. McArther; the Biodex, U.S. Pat. No. 4,628,910, inventor R. Krukowski and U.S. Pat. No. 4,691,694, inventor R. Boyd, et al.; and the devices disclosed in U.S. Pat. Nos. 3,848,467 and 4,235,437. Each of these systems use the method of isokinetic resistive exercise/assessment applied to the large muscle groups of the legs particularly the knee.

Attachments are also available to modify these devices to address the arms and, secondarily, the ankle, wrist and hand. With respect to the hand, gross movements are allowed by these systems which include a.) an attachment which simulates the grip motion one would use with pliers and b.) an attachment which has a moving rod element with the forearm rigidly fixed for simulation of certain wrist activities. In each case a specific work task is simulated with these accessories.

The shortcoming of these devices is that the movements described by the hand are those which are seen specifically at job sites or only rarely in life. Reliability of the assessment data is questionable with these systems due to the inability to accurately reproduce the same posture and set up for each trial. These devices are best suited to exercise muscle groups and areas of muscle groups. The assessment aspect of these devices is severely limited by the design.

Other devices have been developed with similar intentional designs limiting the use of the system to simulations of specific work tasks. For example, U.S. Pat. Nos. 4,337,050 and 4,768,783 issued to Engalitcheff, Jr. disclose a method and apparatus for rehabilitating injured muscles. Engalitcheff, Jr. teaches an apparatus which includes a number of specific accessory elements simulating various tools coupled to a controlled resistance device. These accessories allow the therapy to address the particular work tasks an individual may be expected to perform. Each accessory element is specifically adapted to the resistance device, which includes a rotatable shaft, controlled, in one embodiment, by an electric brake coupled to an adjustable voltage source. Ostensibly, selective resistance is provided to each of the variety of various accessories to permit exercise of specific muscles or joints in simulated industrial applications. Feedback regarding the amount of force applied to each particular exercise is provided by a voltmeter; no other type of data feedback is provided.

A more sophisticated rehabilitation system which also includes means for evaluating muscle degradation is the LIDO® WorkSET, manufactured by Loredan Biomedical, Inc., Davis, Calif. The Loredan device includes an adjustable resistance head, to which a number of accessories may be coupled, and various other tool-type accessories for simulating work-related activities. The resistance head generally includes a gear reducing element and a D.C. servo motor, appropriately sized to provide resistance for the various tool accessories. A personal computer controls the resistance applied to all accessories of the system, providing variable resistance to each of the accessories attached thereto for a series of exercise and evaluation modes. The Loredan system is capable of automatically implementing three general types of exercise for a test subject: isokinetic, isotonic and isometric exercise. The isokinetic exercise mode generally provides a variable force against the particular motion undertaken by subject with the exercise accessory to maintain a constant velocity on the test subject's action. The isotonic exercise mode provides a constant force against the test subject's actions to allow the subject to move the accessory device at varying speeds. The isometric exercise mode deals generally with the static measurement of the flexing and extension of particular muscles, including both concentric and eccentric contractions.

The Loredan system requires a physical floor space area of approximately 8' by 8', generally making it suitable only for large scale rehabilitative efforts. The numerous attachments are adaptable to allow rehabilitation of many muscle groups in a manner similar to the of the Engalitcheff, Jr. devices.

Disuse atrophy, caused by such things as cast immobilization, results in a loss in human performance by negatively effecting muscular strength, endurance, joint range of motion, and motor coordination skills. Disuse can be a consequence of a variety of factors, including being forced into a bedridden condition following traumatic injury. Another circumstance that can bring about disuse atrophy is living in a weightless environment. Clearly, the degradation of muscular systems of astronauts can have a deleterious effect not only on the success of any particular flight mission, but the basic safety of all members of the flight vehicle crew. As noted above, exercising particular muscle groups can prevent muscle deterioration. Studies have shown that individuals exposed to simulated weightlessness who exercised daily were able to maintain muscle strength in the particular muscles exercised. In particular, isokinetic exercise of particular muscle groups has been found clearly effective in maintaining muscle strength under conditions of simulated weightlessness. Naturally, it would be desirable to provide astronauts on flight missions with the means to effectively exercise muscles to maintain muscle strength, particularly in key muscle groups.

Physical space and astronaut time are at a premium on all space flight missions. The machines discussed above are generally not suitable for use on flight missions because of the physical space required for their effective operation. For example, the Loredan device, while providing a comprehensive means to evaluate and recondition loss of performance, is prohibitively large to allow its use on, for example, the Space Shuttle. Further, it is not an effective device to use for hand movements having the basis of its design a focus on large arm movements such as using a steering wheel of an automobile.

Further, exercise suitable for maintaining muscular strength must impose sufficient force and inertia on the muscles under treatment to maintain the muscular endurance of flight crews. One particular study has advocated the use of a treadmill; however, certification of such a device for the stresses to which it will be exposed in space flight use is a major endeavor.

It is also critical to determine the extent of any damage or loss of control to muscular groups on spaceflight missions. One apparatus for testing the strength and control of muscular systems of the hand is disclosed in U.S. Pat. No. 4,885,687 issued to Carey. Carey discloses a device which requires a test subject to trace a number of force patterns by altering the force of the subject's grip on a handgrip dynamometer and load cell. Carey provides a significant amount of quantitative data for evaluation of the subject's performance on each of a number of increasingly difficult tests. However, Carey provides no significant therapeutical means for improving the subject's performance. Further, Carey contemplates use of the subject's entire hand and is limited to testing contractile force of the basic hand grip. Thus, the data provided by Carey as to the condition of the muscles of the hand is rather limited.

Thus, an object of the invention is to provide a system for the comprehensive evaluation and correction of muscular systems of the human body.

A further object of the invention is to provide a comprehensive system for the evaluation and training of the human hand, wrist, elbow, and shoulder.

Yet another object of the invention is the provision of the above objects within compact physical dimensions making the system suitable for use on orbital vehicles.

Another object of the invention is to provide a evaluation and exercise system which is capable of testing and evaluating all cardinal movements of the human hand, including the individual fingers thereof.

Yet another object of the present invention is the provision of a novel means for controlling a testing and evaluation system.

Another object of the present invention is the provision of the above objects in a system which provides comprehensive, high resolution feedback to the control mechanism of the evaluation system, and also provides comprehensive feedback on the condition of the muscle groups under test by the evaluation system.

A further object of the present invention is the provision of the above objects in conjunction with an automatic software control system which automatically provides a series of testing and correction schemes.

A further object of the present invention is the provision of a control system including control software which simulates a variety of Activities of Daily Living (ADL) to measure the performance of the test subject and train the muscular groups associated with each activity.

A still further object of the present invention is to provide a system for evaluating and training the muscular systems of the human body which utilizes a unique ergonomic testing mechanism.

Yet another object of the invention is the provision of novel means for the application of isokinetic loading against the motions of the hand including the thumb and digits and upper extremity.

Yet another object of the invention is the application of isokinetic loading methods in motor coordination skill assessment specifically reaction time to mechanical movement and frequency of tapping/squeeze movements.

The present invention looks to applying the accepted methods of isokinetic assessment and reconditioning to the function of the hand by isolating cardinal movements of the hand.

SUMMARY OF THE INVENTION

These and other objects are provided in a system for isolating, evaluating and exercising the muscle groups of the human hand. Generally, the system comprises means for detecting the cardinal movements of the hand and translating the movements into rotational data for the system, the means for detecting effectively isolating the movements of the hand so that the movements of other muscle groups of the body are not detected by the system. The system also generally includes means for providing a selective variable resistance to the means for detecting and for ascertaining the force applied to the means for detecting by the movements of the hand.

The means for detecting may comprise a stationary element and a rotational element mounted for rotation about an axis positioned adjacent the stationary element. The means for providing a selective resistance may comprise a magnetic particle resistance element coupled to a means for controlling the resistance to rotation of the rotational element when a force is applied to the rotational element by an individual test subject, the means applying a variable or constant resistance to the rotational element.

The system may also include a sensor for sensing torque applied to the rotational element by the test subject, and a detector for detecting the rotational velocity and position of the rotatable element. A motor for positioning the rotatable element, and a clutch for selectively coupling the motor to the rotatable element may also be provided.

Preferably, the means for controlling comprises: a central processing unit providing control signals; a motor control system responsive to the sensor and detector and the central processing unit; a motor drive system coupled to the motor control system, the motor drive system providing drive current to the motor; a torque sensing system coupled to the torque sensor providing an analog output of the force applied by the test subject to the test element; an analog-to-digital converter, coupled to the torque sensing system and the central processing unit, providing digital signals to the central processing unit indicative of the torque applied by the test subject to the test element; first and second digital-to-analog converters providing a first and second analog outputs responsive to the central processing unit, respectively; a brake drive system coupled to the first digital-to analog converter and the electromagnetic brake to provide drive current to the electromagnetic brake; a clutch drive system coupled to the second digital to analog converter and the clutch to provide drive current to the clutch; and software means for directing the central processing unit to control the motor control system, brake drive system and clutch drive system to provide a series of test exercises to the test subject.

The present invention also includes novel attachments which isolate defined simple movements of the hand, wrist, forearm and shoulder. The attachments that are included offer unique isolation of movement patterns and hence give the data collected a quantitative nature which is not found in older systems.

The present invention addresses the posture of the subject during the assessment and reconditioning program and hence provides for reproducible quantitative data wherein the subject is seated with the shoulder adducted against his side which is generally the position of choice when injury is present and a pain induced protective posture is taken.

BRIEF DESCRIPTION OF THE DRAWINGS

FIGS. 7 and 7A are perspective views showing the forearm rotation attachment for use in conjunction with a evaluation and training device which has been rotated approximately 85° in accordance with one aspect of the present invention.

FIGS. 8, 8A and 8B are side perspective and top views showing the bidirectional motion attachment for use in conjunction with the evaluation and training system of the present invention.

FIG. 14 is a schematic diagram of the bridge amplifier utilized in accordance with the torque transducer of the evaluation and training system of the present invention.

FIG. 18 is a graph of the current vs. time for the magnetic particle resistance element and clutch of the present invention in accordance with the novel control scheme of the present invention.

FIGS. 25a and 25b are flowcharts of the subroutines for implementing the reaction time test mode of the evaluation and training system of the present invention.

FIGS. 25a and 25b are flowcharts of the subroutines for implementing the reaction time test mode of the evaluation and training system of the present invention.

FIG. 28 is a sample of the data printout of the physiological evaluation and exercise system of the present invention showing the isometric, isotonic, isokinetic and proprioceptive test data acquired by the system for a particular test subject.

DESCRIPTION OF THE PREFERRED EMBODIMENT

The present invention comprises a system for evaluating and training the performance of the hand, wrist, forearm, elbow and shoulder. The invention provides a system which isolates the particular muscle groups under test with greater specificity than previously accomplished by prior art exercise systems.

Several specific unique features of the system serve to provide inventive aspects thereof. A unique ergonomic environment for testing and evaluating the performance parameters of the specific muscle groups of the hand, wrist, forearm, elbow and shoulder is provided. In one embodiment, the ergonomic environment comprises a basic configuration, including a rotating element and a stationary element. The rotating element positioned for rotation about an axis located adjacent a stationary element. In other embodiments, a number of attachments make the ergonomic environment adaptable to test various performance parameters of each of the aforementioned muscle groups. In the base ergonomic configuration, the device is suitable for testing the cardinal movements of the hand and fingers, including both flexion and extension thereof. The attachments, discussed further below, provide more suitable means for testing portions of the wrist, forearm, elbow and shoulder, in addition to specific muscle groups of the hand and individual fingers.

Figure 1:
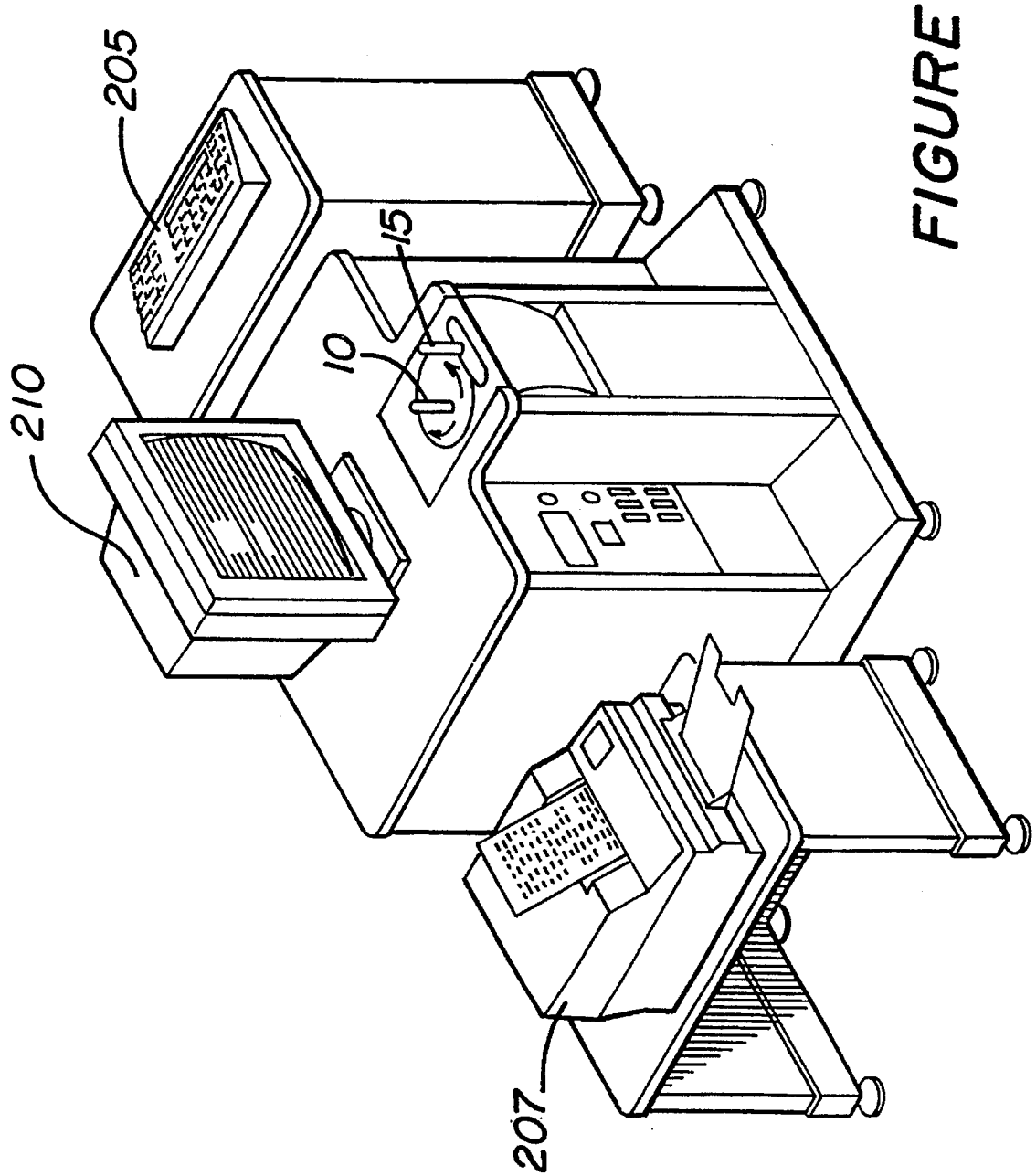
FIG. 1 is a perspective view of one embodiment of the evaluation and training system of the present invention.

In general, the system operates by utilizing a passive resistance element coupled to the rotatable element and, in another feature unique to the system, the passive resistance element comprises a magnetic particle resistance element which allows for a variable, microprocessor controlled resistance to be applied to the rotating element in a variety of evaluation modes. Use of the magnetic particle resistance element as the passive resistance element allows for a downsizing of the evaluation and training system with respect to those physical therapy systems discussed in the Background section. As such, the evaluation and training system of the present invention may be provided in a number of various physical packaging schemes, including: an embodiment suitable for use on the United States Space Shuttle, for the training and evaluation of the condition of astronauts; a small form factor, portable unit suitable for use in field testing of workers' compensation claims; and an integrated, carriage built system, such as is shown in FIG. 1, for hospitals or physical therapy facilities. As illustrated in FIG. 1, the carriage system includes facilities for the close range positioning of keyboard 205, monitor 210, and printer 207.

The system also utilizes a novel, computer controlled, test mode control system, providing output data on the condition of an individual test subject's physical condition. A unique electronic control system is provided in the system to allow the computer to accurately control the electromechanical elements of the present invention. In addition, a unique method of programing the master and slave microprocessors utilized in the control electronics is incorporated in the evaluation and training system of the present invention. All of the above features are provided in a configuration which, when included with the specific technical performance parameters of the system, yields a highly efficient, improved physical exercise and evaluation system.

As noted above, FIG. 1 is a perspective view of one embodiment of the physiological evaluation and training system of the present invention. Shown therein is a basic ergonomic configuration suitable for implementing a number of test modes, comprising rotatable element 10 and stationary element 15. As shown generally in FIG. 1, element 10 rotates about an axis 12 adjacent stationary element 15.

The electromechanical elements of the system allow for the basic ergonomic configuration to translate the spiral motion of the hand into rotational data for the control system of the device thereby facilitating measurement by the microprocessor-based control system, discussed in detail below. By adjusting the angle of the device (or axis 12) relative to the test subject, and/or utilizing the attachments discussed below, the device is capable of measuring the performance of: flexion and extension of the fingers; flexion and extension of the wrist; circumduction, abduction, and adduction of the wrist with fingers extended or flexed; partial complex movement; of the thumb; certain types of basic grasp; supination and pronation of the forearm; and internal and external rotation of the shoulder.

Figure 2A:
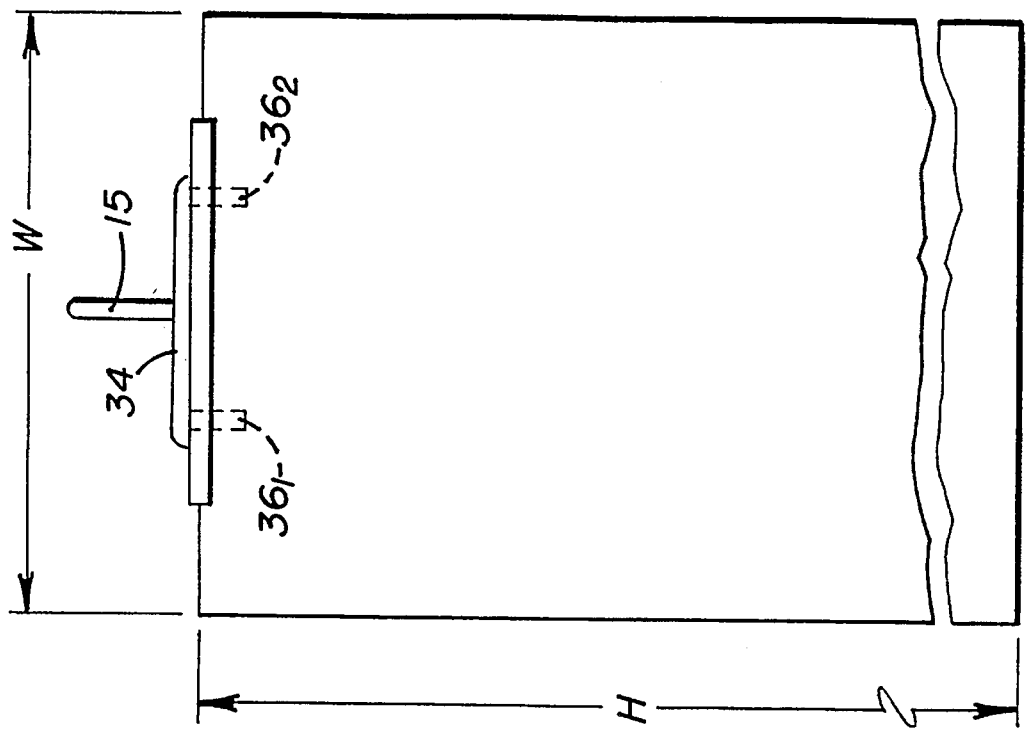
FIGS. 2 and 2A are front side views of the electromechanical components of the evaluation and training system of the present invention.
Figure 2:
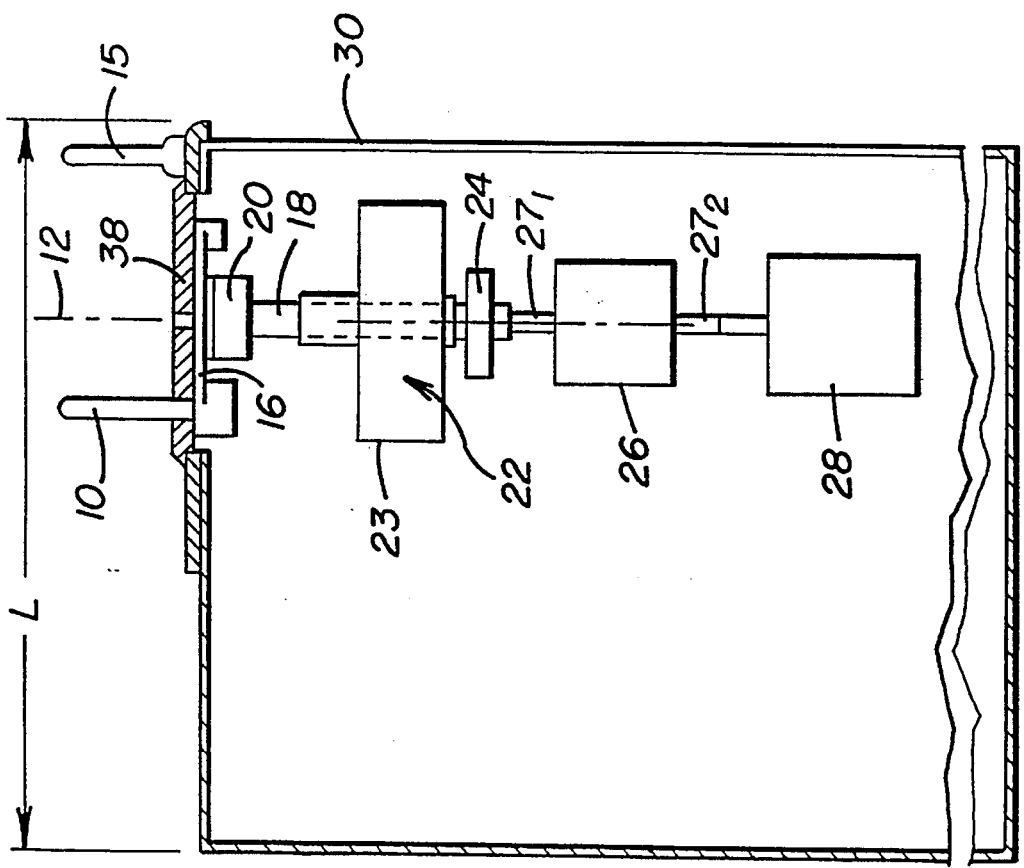

As shown in FIGS. 1 and 2, rotating element 10 is coupled to main shaft 18 by arm 16. Main shaft 18 is rotatable about axis 12 in like manner as rotating post 10. Axis 12 is positioned adjacent stationary element 15 and it may be appreciated that the evaluation and training system may be utilized with the vast number of various human hand sizes by varying the rotational position of rotational element 10 relative to shaft 15. That is, as shown in FIG. 3, by adjusting the linear distance D between rotating post 10 and stationary post 15, any number of various sized hands can be evaluated and trained with the system using the basic ergonomic configuration.

Figure 3:
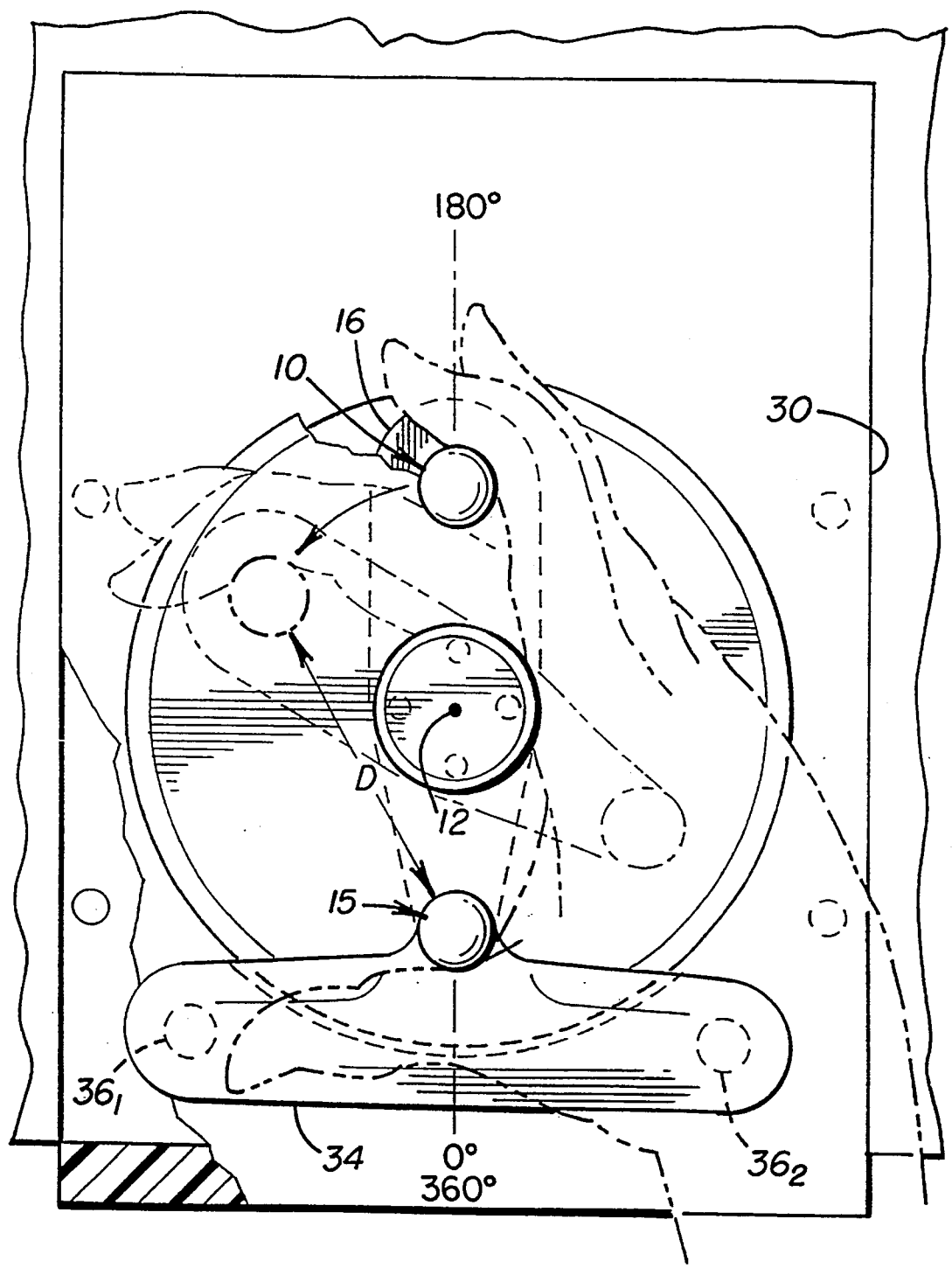
FIG. 3 is a top view of the stationary element and rotating element comprising the basic ergonomic configuration of the evaluation and training system of the present invention.

In operation, a particular subject will be directed to place his hand about rotational element 10 and stationary element 15 in a manner as shown in FIG. 3, with the fingertips positioned about rotating element 10 and the thumb about stationary post 15. The particular positioning of rotational element is generally limited to between 0°–180° for a right hand test and 180°–360° for a left hand test. As will be discussed further below, movement of element 10 is limited to preset stop positions based on the particular linear distance D suitable for the hand size of the particular test subject. Using the basic ergonomic configuration in this manner, isokinetic, isotonic, isometric and proprioceptive tests may be performed.

In the isokinetic test, the test subject will be directed to contract his hand so as to reduce the distance between rotating element 10 and stationary element 15. During this action, the evaluation and training system will continuously measure the torque translated to the shaft 18 by the force exerted by the test subject on element 10 and provide a variable resistance against the rotation of element 10 such that the speed at which element 10 rotates about axis 12 remains essentially constant. Generally, the test is repeated a number of times to provide a statistically valid measurement of the force applied to element 10 by the test subject. Over a series of measurements, the variation in the force applied by the test subject to element 10 can be useful in determining whether the subject is intentionally attempting to deceive the device by, for example, not applying a full rotational force on element 10 during each repetition of the test, which may be indicative of false claims of debilitation.

In the isotonic test mode, the test subject will again be directed to place his hand in a manner as shown in FIG. 3 about rotational element 10 and stationary element 15. The device will thereafter measure the torque on the main shaft 18 and vary the resistance to rotation of the shaft so that the force applied by the test subject is not greater than the isotonic force selected.

In the isometric mode, the system will apply a maximum resistance against rotating element 10, to an extent such a test subject will generally be unable to move element 10 towards element 15. Again, when prompted, the test subject will be directed to contract his or her hand in an attempt to move element 10 toward element 15 by contracting his/her hand. The torque translated to the shaft 18 by the force exerted on element 10 by the test subject will be measured by the system.

In a proprioceptive test, the test subject's reaction to stimuli from the rotational element is measured. In a "reaction time" test, element 10 will be moved to a preselected position at a suitable distance D selected relative to the size of the individual's hand being tested. When the test begins, rotational element 10 will move in a counterclockwise direction (for the right hand) and the individual test subject will be directed to follow element 10, maintaining light pressure thereon. At a random position, the system will rapidly reverse the direction of element 10 so as to move it in the clockwise direction, and the test subject will be directed to contract his/her hand, moving element 10 toward the 0° position, once the direction reversal of element 10 is felt. Ideally, the test subject should not be able to visually detect the reverse direction of element 10. An alternative proprioceptive test, is the "tap" response test, requiring quick, successive contractions of the hand of the test subject, with the test objective being to detect the time between contractions.

In both the basic ergonomic configuration, and when using the particular attachments discussed below, the physiological evaluation and training device of the present invention provides the only known means available for isolating cardinal movements of the hand. Specifically, the device of the present invention requires that the shoulder be adducted to the body to prevent the test subject from incorporating other muscular groups into the test, thereby potentially yielding test results which are not indicative of the true state of the muscular group under test. For example, using the Loredan LIDO® WorkSET device, discussed above in the Background section, a test subject using the hand attachment may be able to use other parts of the body including different muscle groups than those the device is designed to test, to assist in providing the linear motion incorporated by the WorkSET hand attachment. In the basic ergonomic system of the present invention, prehension patterns of the hand are isolated by the rotational and stationary test elements, and the specific attachments of the system, specifically requiring the muscles of the hand to be utilized, thereby isolating the muscles of the hand which are under test and providing more precise test results.

FIG. 2 is a block diagram showing the main electromechanical components of the evaluation and training system of the present invention. The basic ergonomic configuration of rotating element 10 and stationary element 15 is shown for explanation purposes. It should be understood that the operation of the electromechanical elements of the evaluation and training system is the same whether the basic ergonomic system is implemented or whether the various attachments for the specific testing of particular muscle group functions are utilized. The electromechanical elements of the evaluation and training system of the present invention include torque sensor 20, magnetic particle variable resistance element 22, rotary optical encoder 24, magnetic particle clutch 26, and motor 28. Each of the aforementioned elements, with the exception of motor 28, is mounted to a main shaft 18 provided in a casing such as, for example, that shown in FIGS. 1 or 2.

The electromechanical elements used in the system will be hereinafter be described in relation to their operation in effecting the specific test modes discussed above. The evaluation and testing system of the present invention is essentially a passive resistance system wherein, during most evaluation sequences, no active resistance is utilized. The main passive resistance element is magnetic particle resistance element 22. A magnetic particle element such as Model B150, available from Placid Industries, Inc., Lake Placed, N.Y., having a torque rating of 150-inch-lbs., with a maximum torque of 250-inch-lbs., is suitable for use in the system. Magnetic particle resistance 22 is selected for use in the present invention because of its ability to provide a significantly high amount of torque (i.e., 250-inch-lbs.) with no active moving mechanical parts, thereby providing smooth resistive operation, free of backlash, for rotational element 10. The resistive torque response of magnetic particle resistance element 22 is also precisely controllable. In the present embodiment, electronic control circuitry in conjunction with a computer controlled, pulse width modulated current mode drive is utilized to provide a variable torque in opposition to the rotation of rotational element 10. A unique feature of magnetic particle resistance element 22 is the fact that the output, coupled to main shaft 18, does not engage housing 23 of magnetic particle resistance element 22. Housing 23 is filled with a fine, dry stainless steel powder which is free flowing until a magnetic field is applied from a stationary coil within the housing 23. The torque resistance is proportional to the magnetic field and thus the applied DC input current.

The resistance element 22 is coupled by main shaft 18 to a torque sensor 20. Torque sensor 20 is a conventional torque sensor and may comprise, for example, a Model TRT-200 available from Transducer Techniques, Inc., Temecula, Calif., capable of measuring up to 200-inch-lbs. of torque with a resolution which allows it to resolve forces applied to element 10 to a resolution of 225 grams (0.5 lbs.).

Optical encoder 24, coupled to shaft 18, is utilized by the system for determining the position, between 0°–360°, of rotational element 10. Optical encoder 24 is a standard optical encoder, such as Model LD23-DM-2500-5LD-1B, available from Lucas Ledex Corporation, capable of a resolution of at least 25 counts per degree of motion (2500 line counts per 360° measurement). As will be explained in further detail below, the control system of the present invention multiplies the output of the optical encoder in quadrature, thus providing a total of 5000 data samples per 180° motion by a particular individual test subject. In an alternate embodiment, appropriate gearing or belt coupling can be utilized between shaft 18 and encoder 24 to increase the number of counts per revolution.

Magnetic particle clutch 26 is provided to selectively couple motor 28 to shaft 18. Clutch 26 includes input shaft 27$_1$ and output shaft 27$_2$. Input shaft 27$_1$ is coupled to motor 28, while output shaft 27$_2$ is coupled to shaft 18. Clutch 26 may be a Model C25 magnetic particle clutch, also available from Placed Industries, Inc., supra. Clutch 26 has a maximum torque of 25-inch-lbs. and couples input shaft 27$_1$ to output shaft 27$_2$ when electric current is applied thereto. Clutch 26 operates on the same principles as magnetic resistance element 22, but is generally utilized in a "full on" or "full off" mode. In addition, whereas main shaft 18 is not coupled to housing 23 of magnetic particle resistance element 22, housing 29 of clutch 26 is not coupled to input shaft 27$_1$ or output shaft 27$_2$.

Output shaft 27$_2$ of clutch 26 is coupled to a D.C. gearhead motor 28, capable of approximately 30 rpm, an applied force of 25-inch-lbs., and having an output power of approximately ⅕₀ horsepower. Motor 28 may comprise Model GPP1009 available from Baldor/Boehm, Fort Smith, Ark.

As noted above, the aforementioned test modes utilized for a particular individual test subject are performed using magnetic particle resistance element 22 as the main resistance element of the system to provide controlled resistance on shaft 18, and thus rotational element 10. Motor 28 serves primarily to position element 10 at any point along its 360° rotational travel path as shown in FIG. 3, and provides no appreciable resistance to element 10 during isometric, isotonic or isokinetic tests. Magnetic particle clutch 26 serves to sever main shaft 18 from DC gear head motor 28.

However, during the constant passive motion (CPM) mode, motor 28 is utilized to direct the motion of element 10 responsive to the particular control program implemented by the control system. During this mode, motor 28 supplies the force of movement of element 10, and motor 28 effectively guides movement of the patient's hand, or other appendage. In addition, in one proprioceptive test mode, motor 28 is utilized to position element 10 at a preselected location, is thereafter directed to rotate the element for a random amount of time in a clockwise or counterclockwise direction, (depending on the particular hand under test), and to selectively reverse the direction of element 10 at a particular point in time to test the reaction time of the test subject. It should be noted that once the reverse direction operation is completed by the motor (the element is reversed in direction for a maximum of 25°), clutch 26 disengages the motor. Thus, in CPM mode, motor 28 does effectively provide some resistance to the test subject by guiding movement of the subject's hand. However, during the isometric, isokinetic, isotonic, and tapping test modes, motor 28 merely acts to position element 10 at a preselected test point in its 360° rotation and resistance is thereafter supplied by magnetic particle resistance element 22.

Operation of the aforementioned electromechanical elements is discussed below with respect to the detailed discussion of the electronic control system. One key feature of the aforementioned electromechanical elements, and particularly the magnetic particle resistance element, is that these components occupy a relatively small form factor compared with prior art systems. For example, the configuration shown in FIG. 2 may be provided within a physical casing 30 having a height H of 12", a length L of 6" and a width W of 6". By removing motor 28, and positioning rotational element 10 solely by hand, the form factor of the system may be reduced even further.

As noted above, the evaluation and training system of the present invention includes a number of adaptive attachments which augment the basic ergonomic environment of elements 10 and 12 with devices which are specifically adapted to allow for ease in testing particular motions of the hand, wrist, forearm, elbow and shoulder. As noted above, the basic configuration of element 10 and element 12 is suitable for any number of applications in isolating the particular movements of the hand and fingers.

Figure 4:
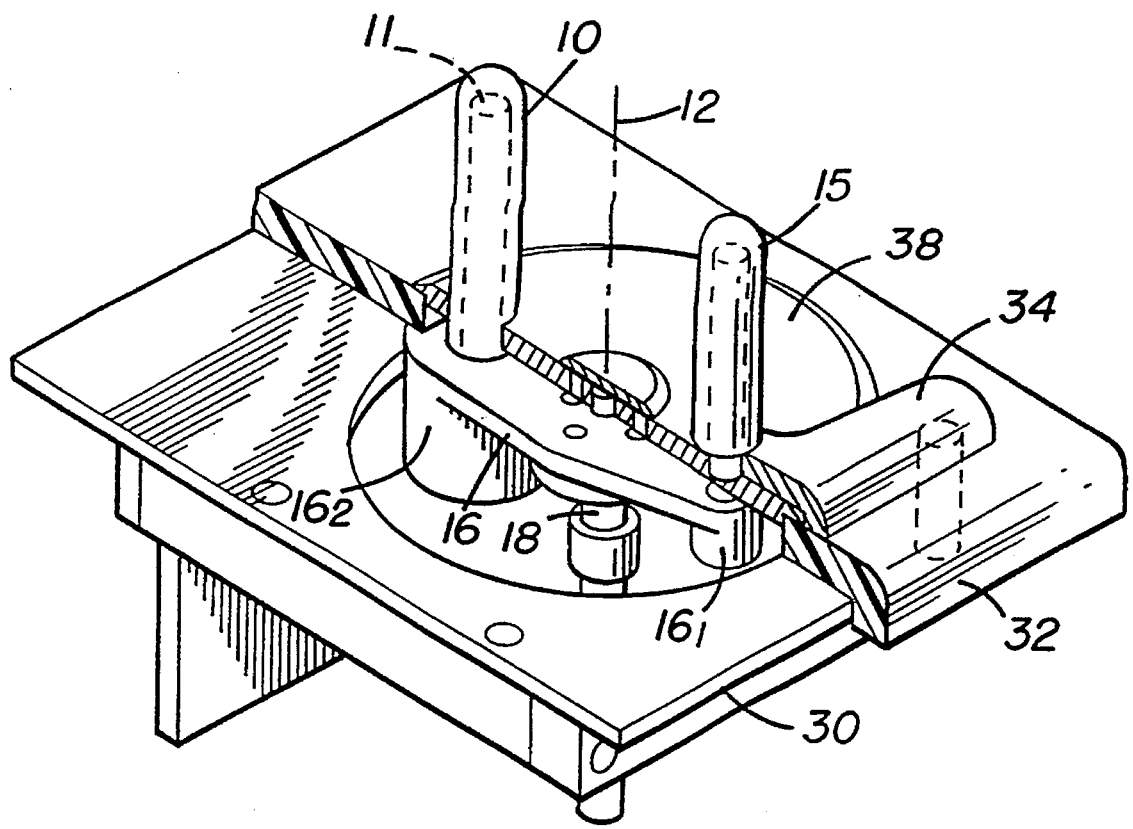
FIG. 4 is a perspective view of one embodiment of the evaluation and training system utilizing removable stationary and rotating post elements in the basic ergonomic configuration.

FIG. 4 shows one embodiment of arm 16 used to couple rotating element 10 to main shaft 18. Arm 16 includes a first and second ends 16$_1$ and 16$_2$ on opposite sides of axis 12.

First bore 17 (FIG. 5A) is provided on first end $16_1$ of arm 16. Second end $16_2$ includes a cup (not shown) in which a bearing (not shown) is inserted. The bearing includes an inner bore 19 (FIG. 6) for receiving various rotational attachments therein. Bores 17 and 19 are included on arm 16 to allow the various different attachments to be quickly interchanged in the testing sequence of the system of the present invention.

Also shown in FIG. 4 is rotating element 10 suitable for use in conjunction with arm 16. Post 10 has a diameter which is suitable to allow post 10 to be received in bearing bore 19 of arm 16. Element 10 may include, for example, a foam rubber sleeve 11, positioned thereabout, to provide comfort to the test subject when engaged in various tests. As shown in FIG. 5A in one embodiment of the invention, the upper cover surface 32 of casing 30 has two bores $32_1$ and $32_2$ (FIG. 6) positioned therein, which are utilized to receive fixed element attachments for use in conjunction with the system of the present invention.

As shown in FIGS. 2A and 4, one embodiment of stationary element 15 of the present invention is adapted to be received and mountable in bores $32_1$ and $32_2$ and casing 30. Stationary post 15 may also include a foam rubber sleeve 11 similar to that used with rotating element 10. Stationary post 15 is preferably cast molded to include a base member 34, having two mounting members $36_1$ and $36_2$ which are adapted to be received into bores $32_1$ and $32_2$, respectively. Mounting members $36_1$, $36_2$ are offset from post 15 by a specified distance. It should be understood that this offset is not required, but is utilized in the present invention to allow post 15 to be as close as possible to the rotational path of rotating element 10 while providing ease in adapting other stationary attachments for use with the evaluation and training system of the present invention. Generally, arm 16 and the electromechanical components of the system are covered by plate 38.

Figure 5:
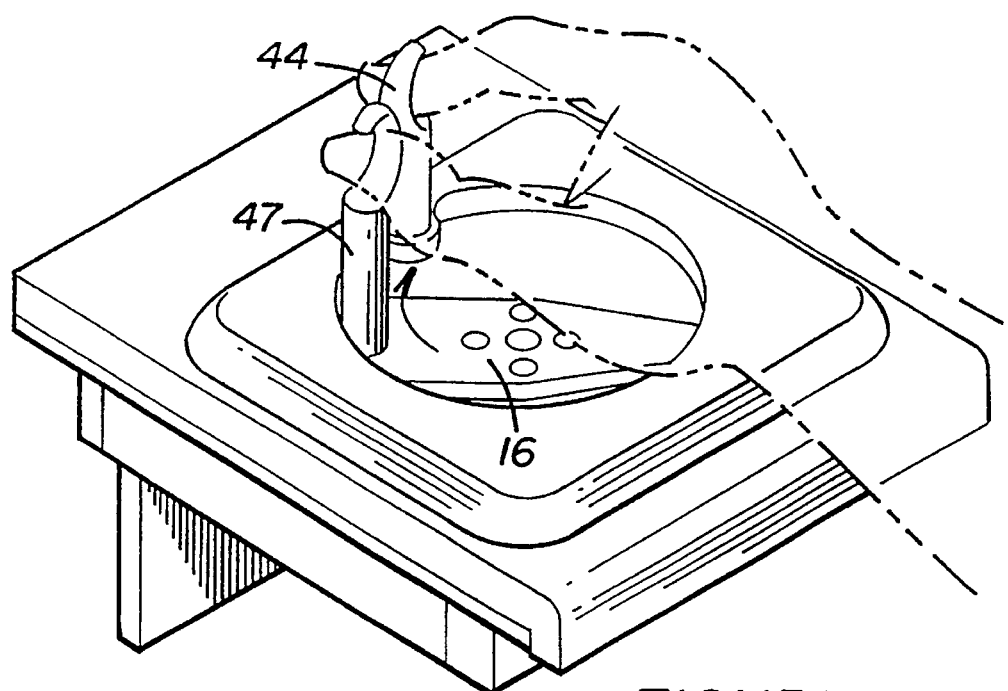
FIGS. 5 and 5A are perspective views showing the pinch measurement attachments for use in conjunction with the evaluation and training system of the present invention.
Figure 5A:
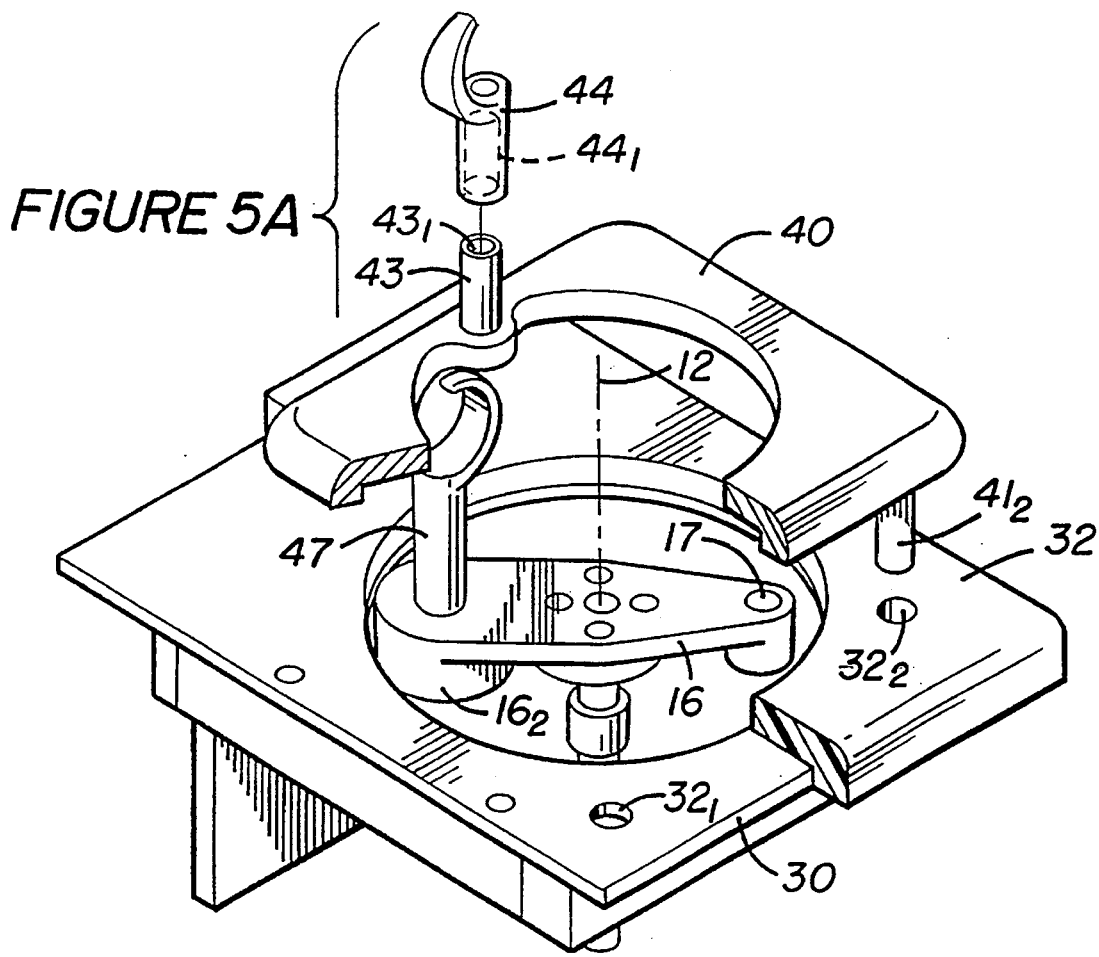

FIGS. 5 and 5A are perspective, and exploded perspective views, respectively, showing pinch test attachment accessories suitable for use in testing each of the individual fingers of the hand with respect to pinching movement in opposition to the thumb. The accessories shown in FIGS. 5 and 5A are designed to allow for the pinching motion of each of the test subject's fingers in opposition to the thumb to be tested. In applying these particular attachments, stationary post 15 and rotating post 10 are removed from respective bores 19, $32_1$, $32_2$. The pinch attachment accessories include an adaption plate 40 to provide a stationary element in the pinch testing configuration at a position which is 180° opposite the location of stationary element 15 in the basic ergonomic configuration. Adaption plate 40 includes first and second mounting members $41_1$ and $41_2$ which are adapted to be inserted in bores $32_1$ and $32_2$ of the casing cover 32. Adaption plate 40 includes a stationary mount post 43, utilized for mounting a curved stationary element 44. Element 44 includes cavity 44, which is sized to allow element 44 to slide over post 43. A threaded bore $43_1$ is provided in post 43 so that a set screw may be utilized to secure element 44 onto post 43. Rotating element 47 includes a curved region similar to that of stationary element 44 and is designed to be insertable in bore 19 of arm 16. As shown in FIG. 5, elements 44 and 47 allow for the comfortable placement of the finger and thumb, respectively, for testing the pinch motion with respect to individual digits of the test subject's hand. It should be understood that each of the aforementioned modes of operation—isotonic, isokinetic, isometric and proprioceptive—can be utilized to test the pinch strength of the test subject between two points in the manner as described above simply by adjusting the preset exercise points of rotating element 47. While it will be readily included that pinch measurements could be performed using the basic ergonomic configuration, the pinch attachments (adaption plate 40, element 47 and element 44) are more effective at isolating the motion to the muscle groups being tested.

Figure 6:
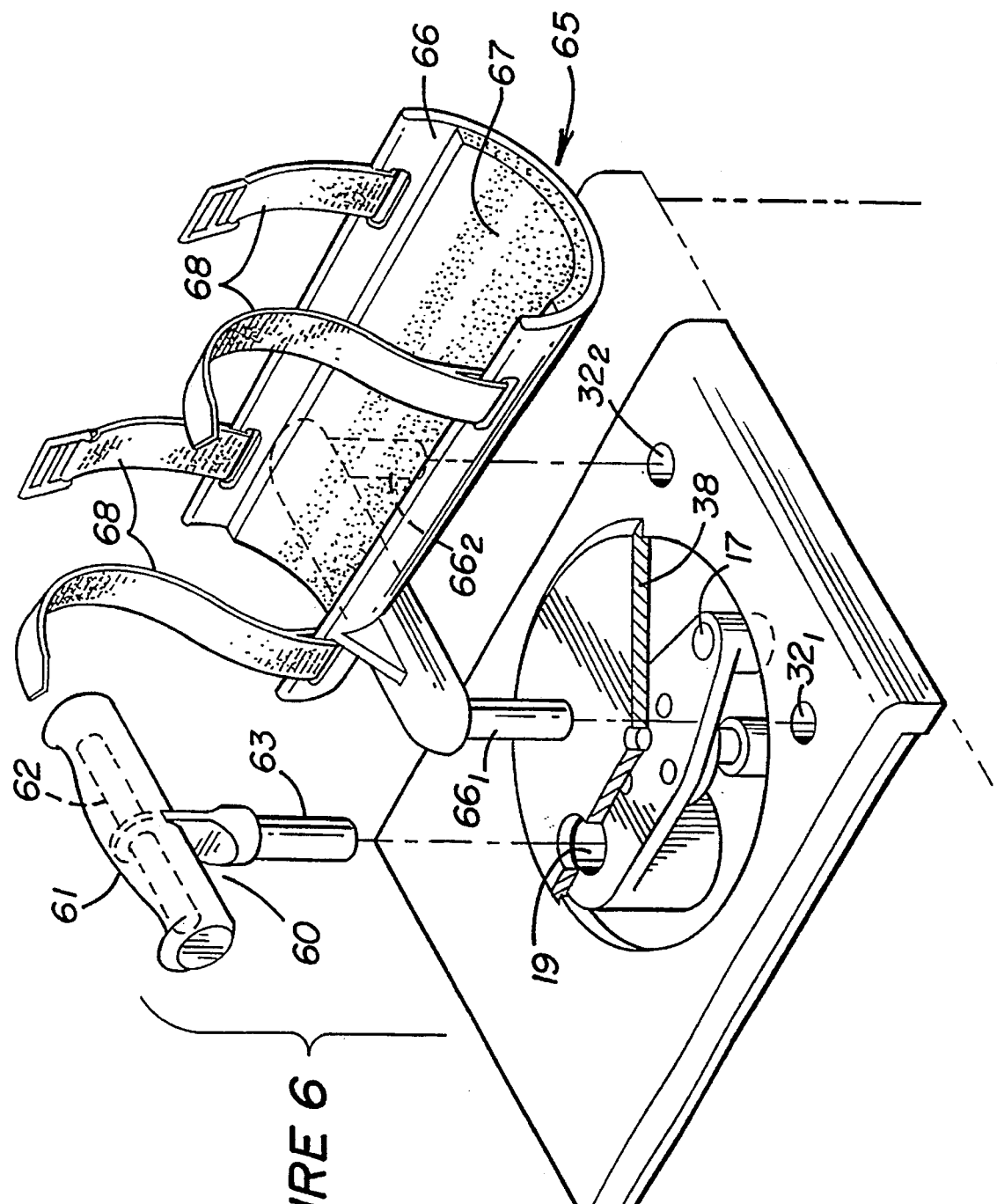
FIGS. 6 and 6A are perspective and top views showing the wrist rotation attachment and forearm support attachment for use in conjunction with the evaluation and training system of the present invention.
Figure 6A:
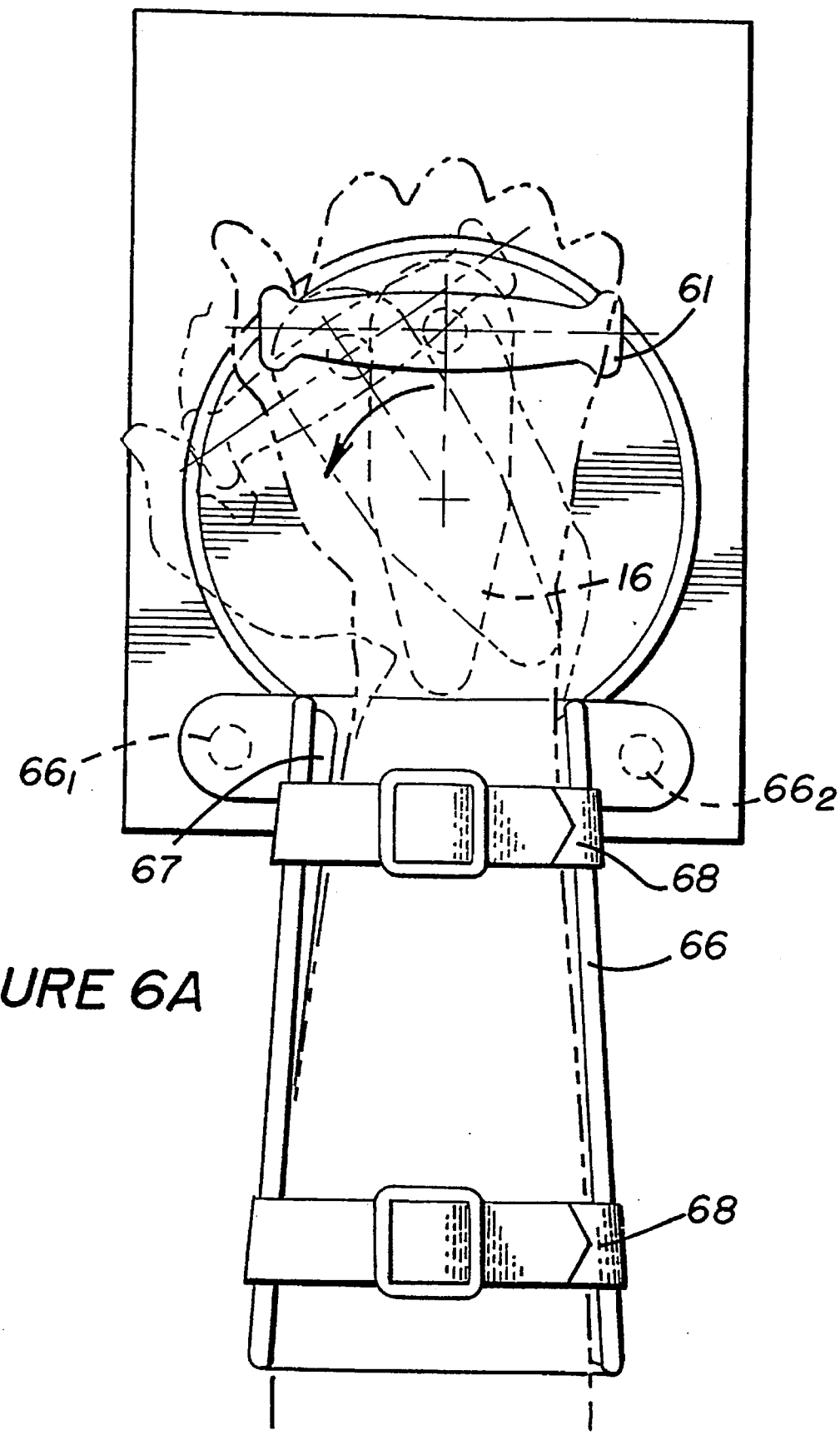

FIGS. 6 and 6A show accessory attachments which are adapted for use in conjunction with the testing of the rotative motion of the wrist. Accessory 60 comprises a handle portion 61 mounted via frame member 62 to a mounting post 63. Mounting post 76 is adapted for insertion into first bore 19 of arm 16. Accessory 60 is used in conjunction with forearm support accessory 65 which comprises a metal trough 66, having an interior insert of foam padding 67, in which a forearm of the test subject may rest when using the wrist accessory 60. Straps 68 are provided to secure the forearm of the test subject in the forearm support 65. Mounting posts $66_1$ and $66_2$ are secured to trough 66 and are adapted for insertion in bores $32_1$ and $32_2$ of casing 32 to secure accessory 65 to casing 32. As shown in FIG. 6A, the forearm support 65 and wrist accessory 60 allow for testing of the radial/ulnar deviation of the test subject. A test subject's forearm is supported in support member 65 while the subject is instructed to grip handle 61. In this manner, isometric, isotonic, isokinetic and proprioceptive testing of the wrist may be effected.

Forearm support 65 may also be used in conjunction with rotational element 10 for testing flexion and extension of the wrist. In the wrist flexion and extension testing, the subject's right arm (shown in FIG. 6A) would be rotated 90° counterclockwise in forearm support 65. Rotating element 10 would replace accessory handle 60, with the subject's fist fully closing about element 10.

Figure 7A:
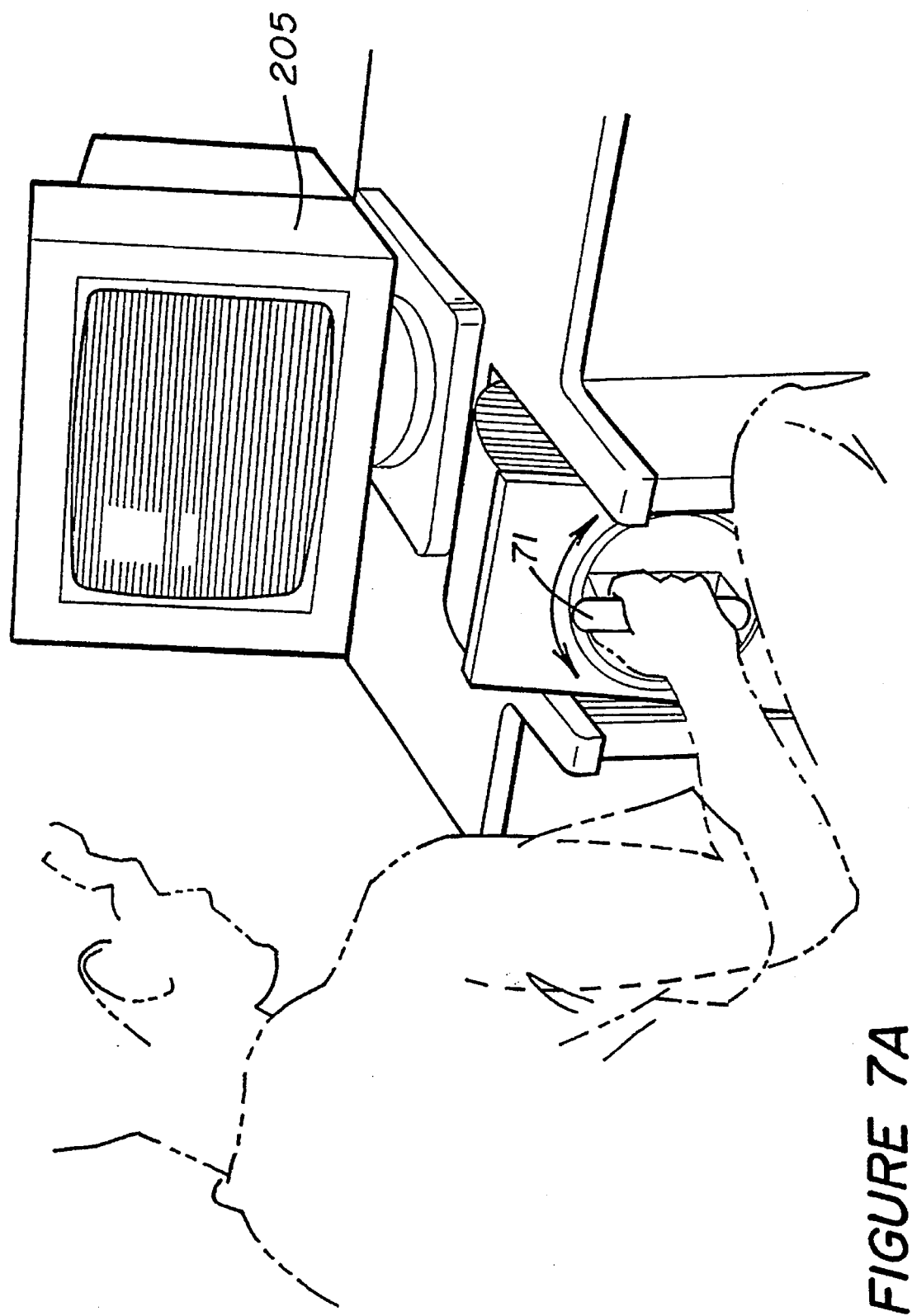

In FIG. 7, forearm test accessory 70 is shown for adapting the testing and evaluation system to test supination and pronation of the forearm. Forearm attachment 70 comprises handle 71 mounted to frame 72 having mounting members 73 and 74 projecting therefrom. Members 73 and 74 are adapted to be received in bore 19 and bore 17, respectively, of arm 16. Forearm attachment 70 requires that arm 16, and the electromechanical components of the system attached thereto, be rotated slightly less than 90° (approximately 85°) (see arrow 75) so that rotational axis 12 is roughly parallel to the ground. As shown in FIG. 7A, this allows a test subject to be seated adjacent the test system, with the shoulder adducted to the body, with rotational axis 12 extending through the forearm of the test subject. The subject's forearm is then rotated clockwise and counterclockwise to evaluate forearm strength using any of the test modes discussed herein.

FIG. 8 shows an alternative embodiment of rotational element 10 for use in conjunction with the continuous passive motion (CPM) mode, as well as the aforementioned mode, of the evaluation and training system of the present invention. As shown in FIG. 8A, individual fingers 89 of the test subject's hand are secured to grip rotation element 80 to allow the range of motion directed by the CPM mode of the evaluation and training system to be translated into the test subject's hand. As shown in FIGS. 8 and 8A, element 80 comprises a metal, vertical rotation element 80, including a mounting post 82 adapted to be receivable in bore 19 on arm 16. Element 81 is comprised of a rectangular shaped finger having notches $83_1$ and $83_2$ formed therein on respective opposite sides of finger 81. D-shaped elements 85 are manufactured to be receivable in grooves $83_1$ and $83_2$ to secure a nylon ribbon 86 about the fingers of the test subject.

Figure 8B:
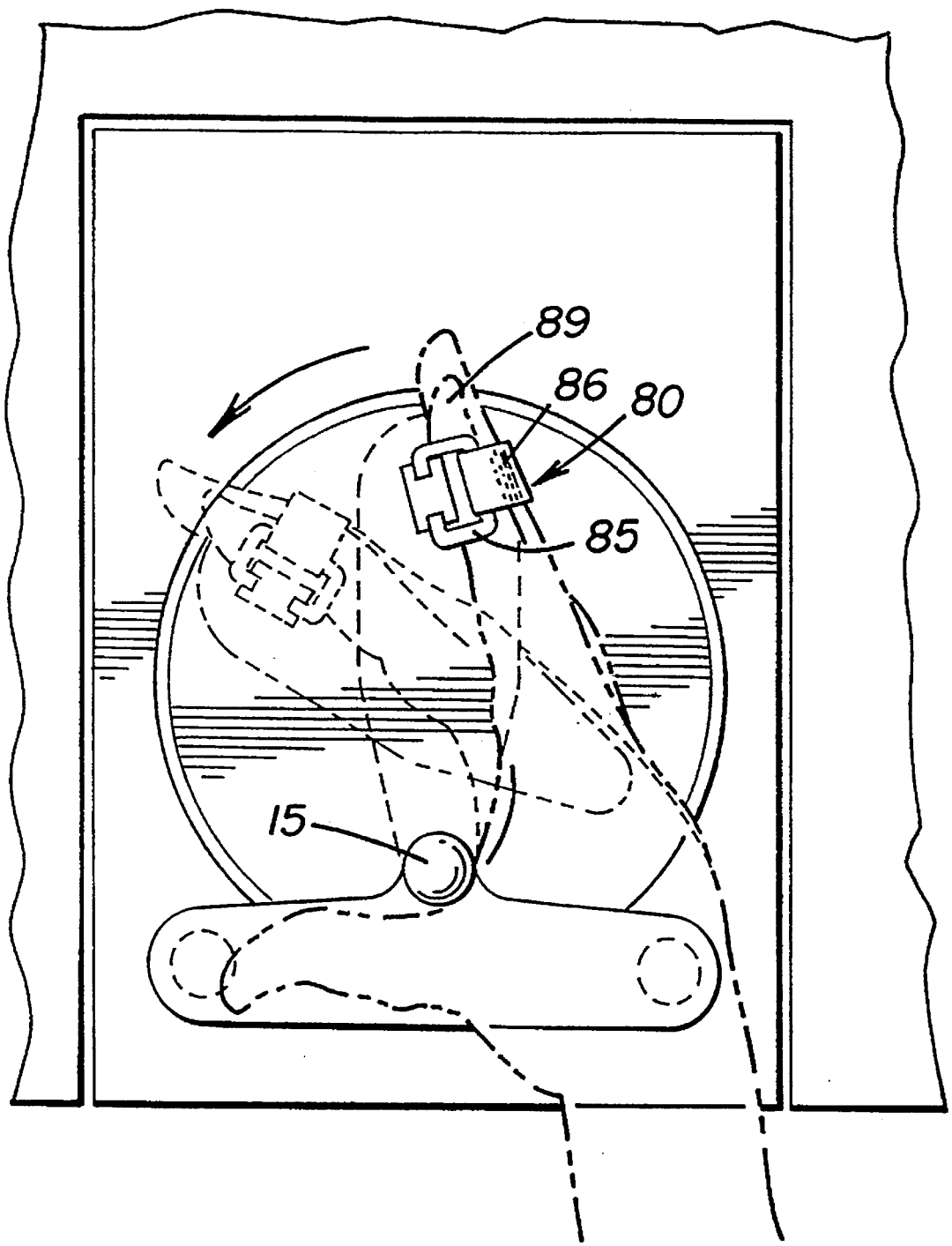

Approximately four (4) D-shaped elements 85 are provided. One end of ribbon 86 may be secured, for example, by a set screw 84 provided at the base of element 80, as shown in FIG. 8A. Cap 87 may be secured to post 80 by a set screw 87₁ provided in threaded bore 88 in element 81. The top end of ribbon 86 may be wrapped over the top of cap 87 and attached by a loop and hook fastener to the back side of element 80. In CPM operation, as shown in FIGS. 8A and 8B, a test subject will place each individual finger between the D-shaped elements 85 and mounted on element 81 and the fingers will thereafter be secured by nylon ribbon 86. The control system of the present invention will thereafter move rotational element 80 through a pre-programmed rotational sequence. In accordance with the objectives of the CPM mode, the system will thereafter supervise the movement of the test subject's hand between preset selected positions within the 360° range of motion of moveable element 10. The CPM sequence may be repeated any number of times in accordance with the therapy objectives for the patient. The accessory post shown in FIGS. 8 and 8A can also be used to isolate a single finger for exercise or evaluation.

Figure 9:
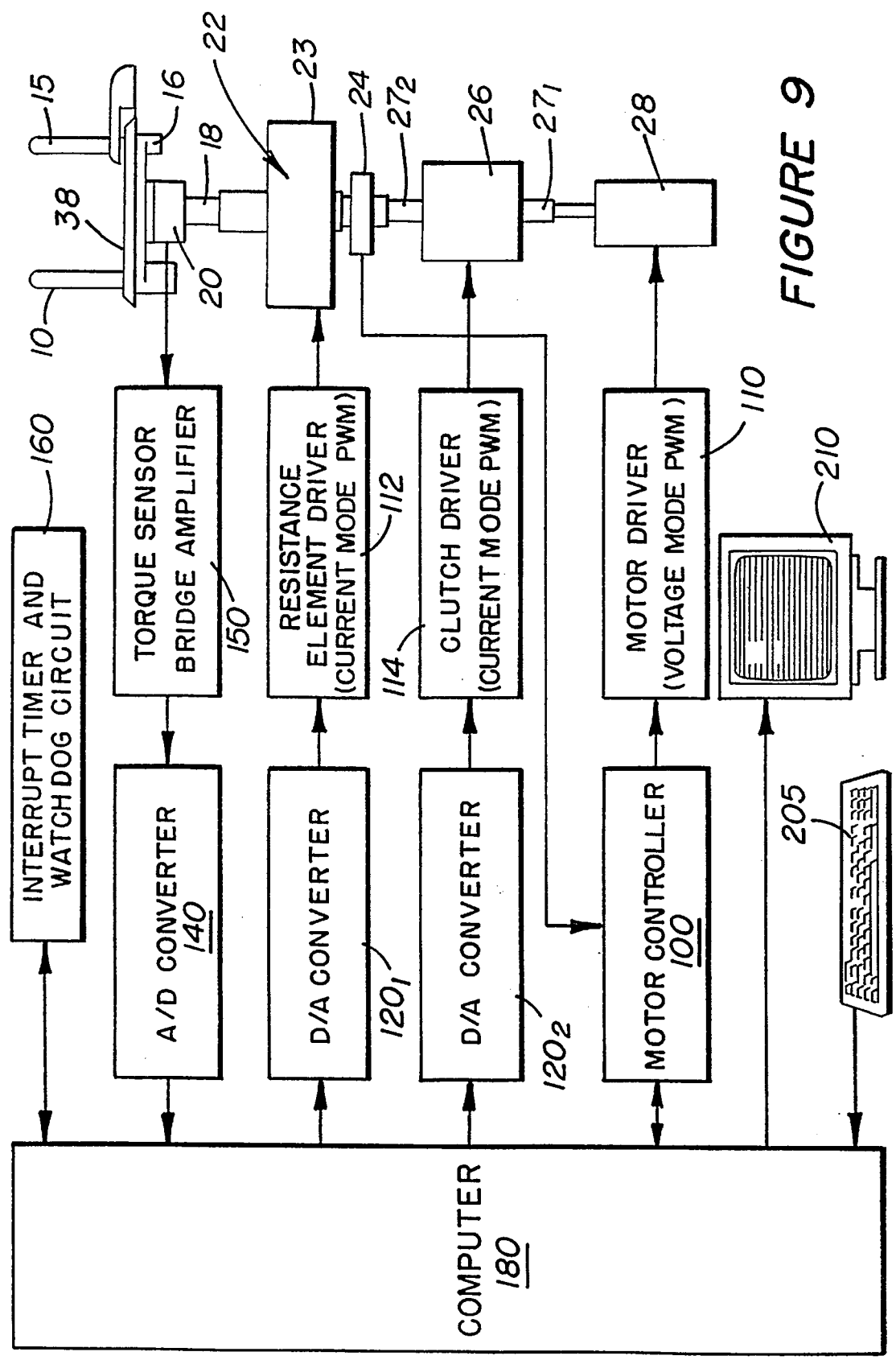
FIG. 9 is a block diagram of the electronic control system of the present invention.

FIG. 9 is a block diagram of the electronic control system for interfacing to the mechanical components of the evaluation and testing system of the present invention. As shown in FIG. 9, the control system of the present invention includes computer 180, motor controller 100, motor driver circuitry 110, clutch driver circuitry 114, resistance element driver circuitry 112, two digital-to-analog converters 120₁, 120₂, a bridge amplifier 150, analog-to-digital converter 140, and interrupt timer and watchdog circuit 160. Motor controller 100 provides a voltage mode, pulse-width modulated signal output to motor driver circuitry 110, and can detect the rotational position of element 10 from rotary optical encoder 24. Personal computer 180, such as an Intel 83086 microprocessor-based personal computer or equivalent, is utilized to program input to motor controller 100, DAC's 120, and interrupt timer 160. A display monitor 210 and keyboard 205 may be attached to computer 180 to provide a user interface therefore. Preferably, motor controller 100, drivers 110, 112, and 114, converters 120, converter 140, and torque sensor bridge amplifier 150, are all provided on a full slot plug-in expansion board in computer 180. As should be understood by one skilled in the art, keyboard 205 and display monitor 210 may be implemented using a touch screen interface system to simplify the interaction process between the test subject/patient and the system.

Computer 180 also reads position input from encoder 24 through controller 100 to dynamically control the resistance in the various modes of system operation. Two digital analog converters 120₁ and 120₂ are coupled to resistance element drive circuitry 112 and clutch drive circuitry 114, respectively. DAC's 120₁, 120₂ provide a current mode, pulse-width modulated output to clutch drive circuitry 114 and resistance element drive circuitry 112 to control the resistance element 22 and clutch 26. The output of torque sensor 20 is provided to bridge amplifier 150, having its output coupled to analog-to-digital converter 140, to provide data on torque translated to shaft 18 by the force applied to element 10 directly to computer 180. Interrupt timer and watchdog circuit 160 acts as a status monitor for the control system software, disabling the control circuitry when board access by the software does not occur at regular intervals, and provides the timing signals for the pulse-width modulated controllers and processor interrupts of the system. The specific implementation of the control system of the present invention are hereafter discussed with respect to FIGS. 10–15. The processes embodied in the control software utilized to control the electronics of the system will be discussed with respect to FIGS. 19–27.

Figure 10B:
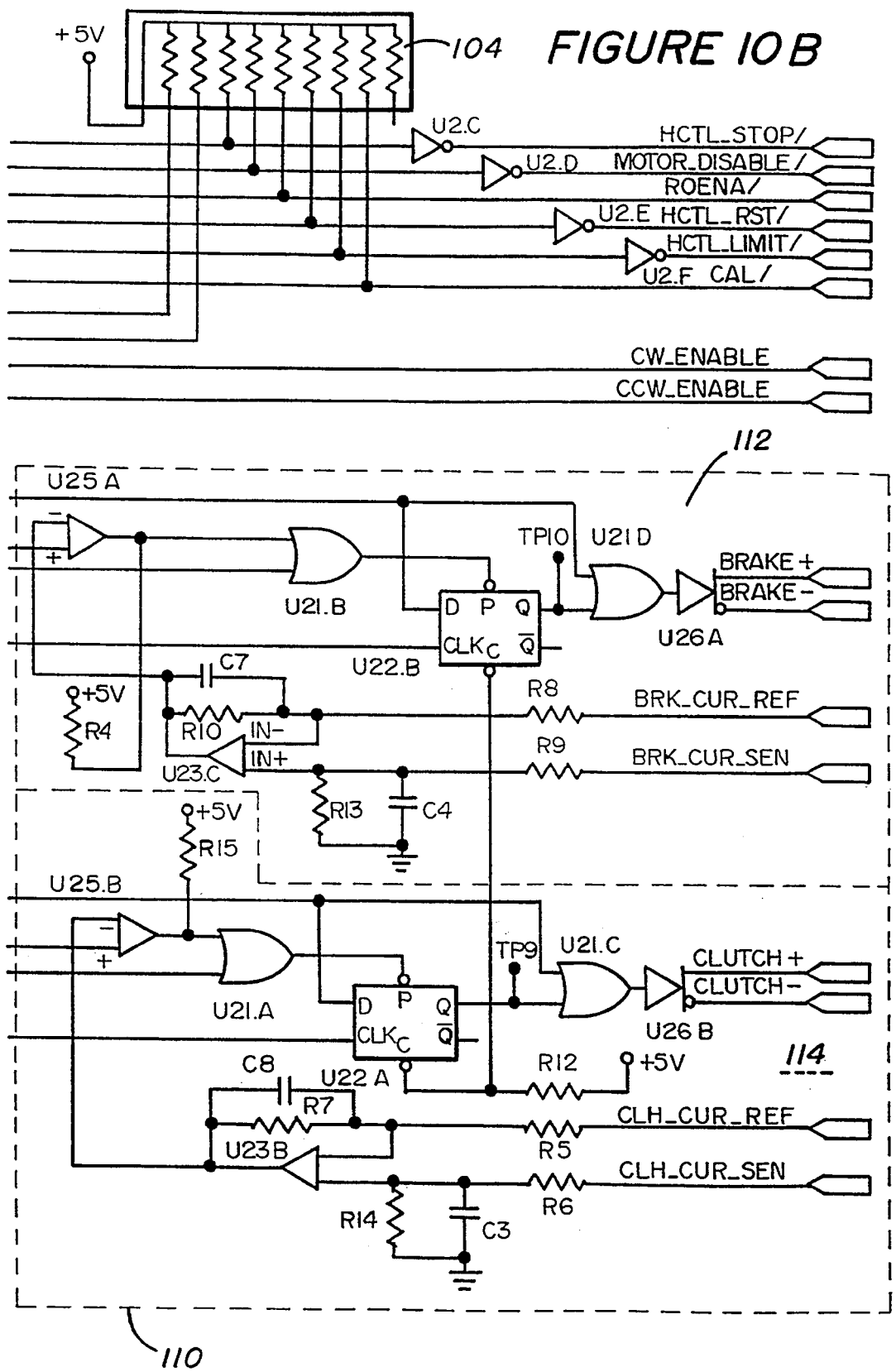
FIG. 10 is a schematic diagram of the digital-to-analog converter, peripheral port controller, and a portion of the resistance element and clutch drive circuitry of the evaluation and training system of the present invention.
Figure 11A:
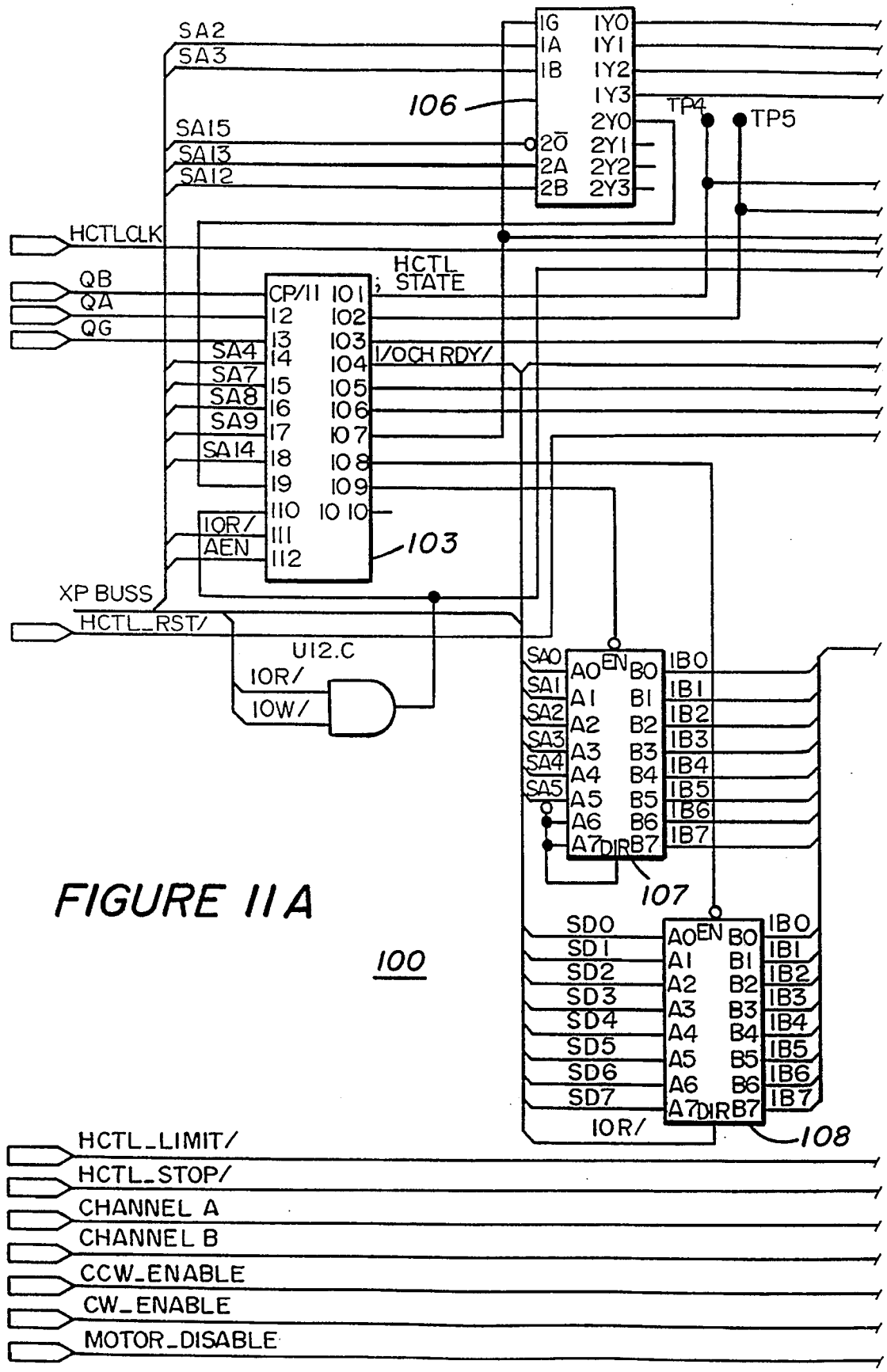
FIG. 11 is a schematic diagram of the motor controller utilized to drive the d.c. motor of the evaluation and training system of the present invention.
Figure 11B:
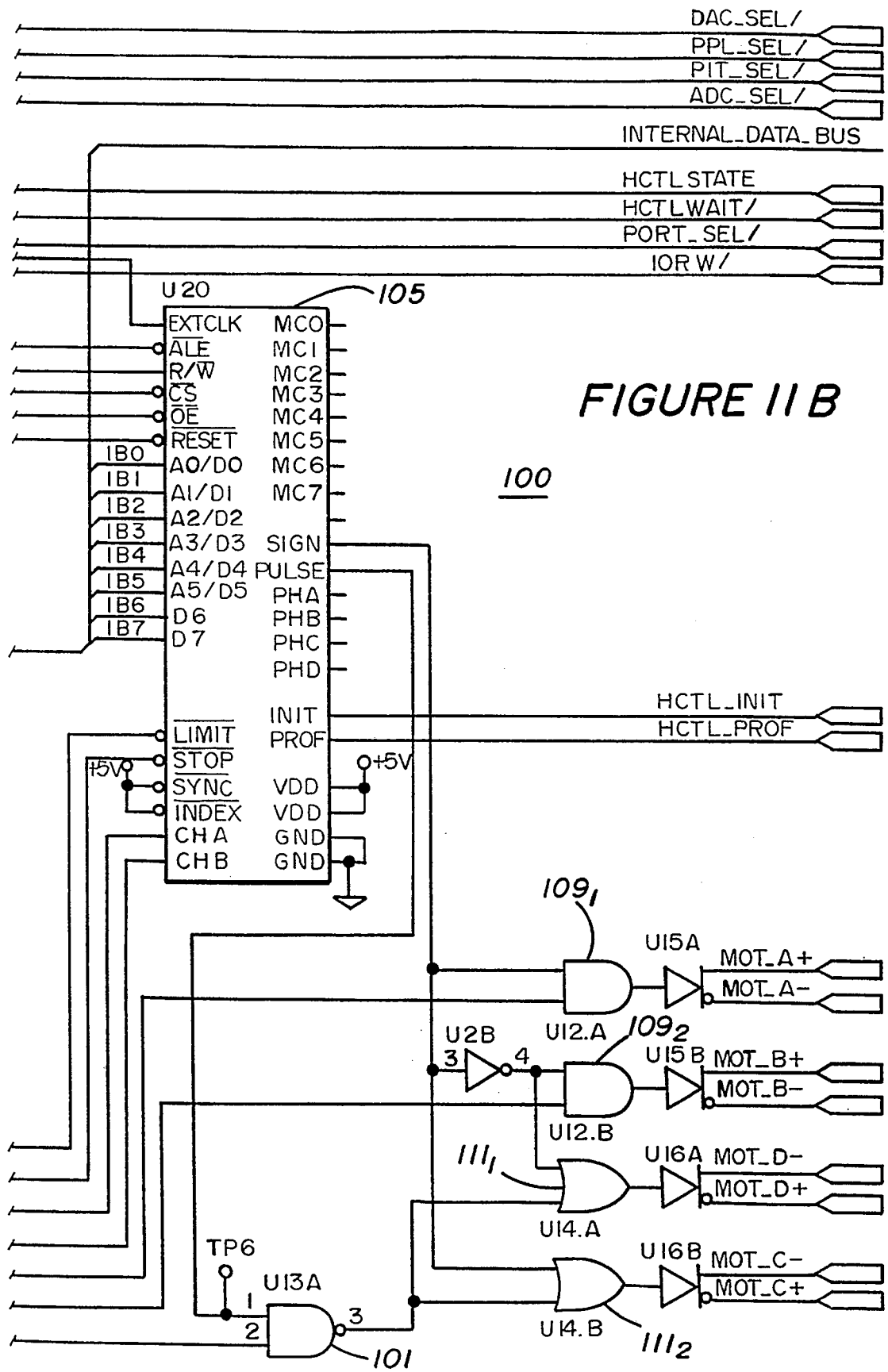

FIGS. 10 and 11 are schematic diagrams detailing the configuration of motor controller 100. As noted above, motor controller 100 provides a voltage mode, pulse-width modulated output to motor driver circuitry 110 to control the velocity, direction, and position of motor 28. Motor controller 100 includes peripheral port controller 102 (FIG. 10) (type 82C55A) coupled to both the internal data bus and address bus (XP) of computer 180 to allow selective read/write of any of three different 8-bit ports (PA0–PA7, PB0–PB7, PC0–PC7). Programmable-array-logic device 103 (type 22V10) is included in motor controller 100 to provide selected control signals for other components of controller 100, and status indicators to computer 180. Controller 100 also includes: a dedicated motor control slave processor 105, such as a HCTL1100, available from Hewlett-Packard Corporation, for driving the PWM control output of motor controller 100; a 2–4 decoder 106, such as a type 74ALS139, for generating chip select signals; and two tri-state buffers 107 and 108, such as 74ALS245 for allowing interruption and read/write between processor 105 and computer 180.

At system power-up or watchdog reset, port A will initially be an input prot with all inputs pulled to a logic high level with resistor array 104. The high levels on these lines will disable all control circuitry, thus putting the system in a "safe" state.

At system initialization, port A of peripheral port controller 102 is selected as an output port to drive all outputs thereof low, thereby enabling the resistance element and clutch drivers (PA0, PA1), HCTL_STOP (enabling processor 105), MOTOR_DISABLE (enabling motor driver circuitry 100), HCTL_RST (disabling the reset of processor 105), HCTL_LIMIT (disabling the LIMIT pin on processor 105), all having logic level high output via inverters U2C–U2F, and signals IR2QENA (enabling interrupt driver) and CAL (enabling the calibration resistor of bridge amplifier 150), having logic level high output.

Port B is generally selected by computer 180 to read various state signals of the devices used in the electronic control system. Port C allows computer 200 to read the timing chips reset signal (8255_RST) and to output enable the clockwise and counterclockwise driver (CW_ENABLE and CCW_ENABLE) signals to motor driver circuitry 110.

Figure 12B:
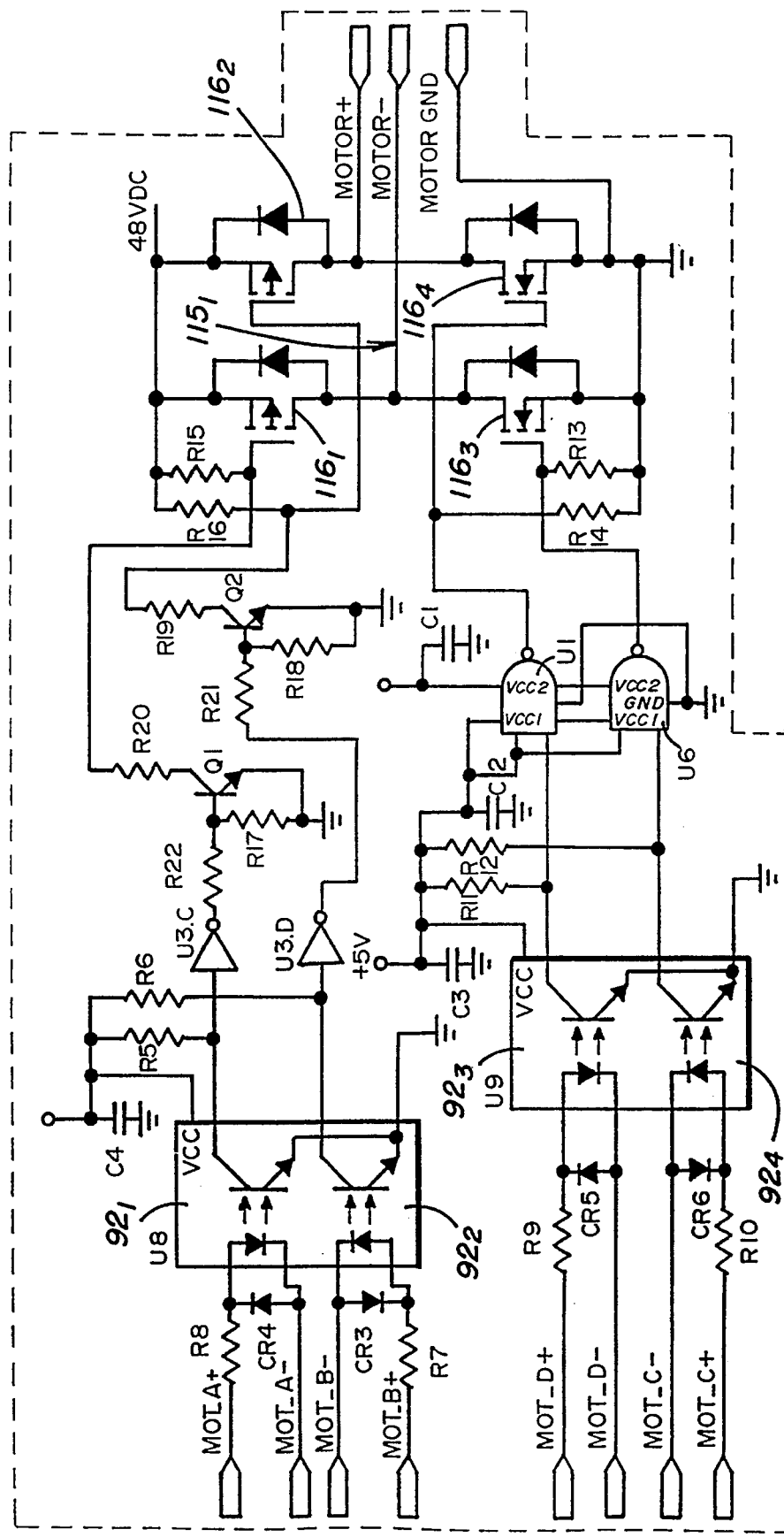
FIG. 12 is a schematic diagram of a the motor drive circuitry and a second portion of the clutch and resistance element drive circuitry of the evaluation and training system of the present invention.
Figure 13A:
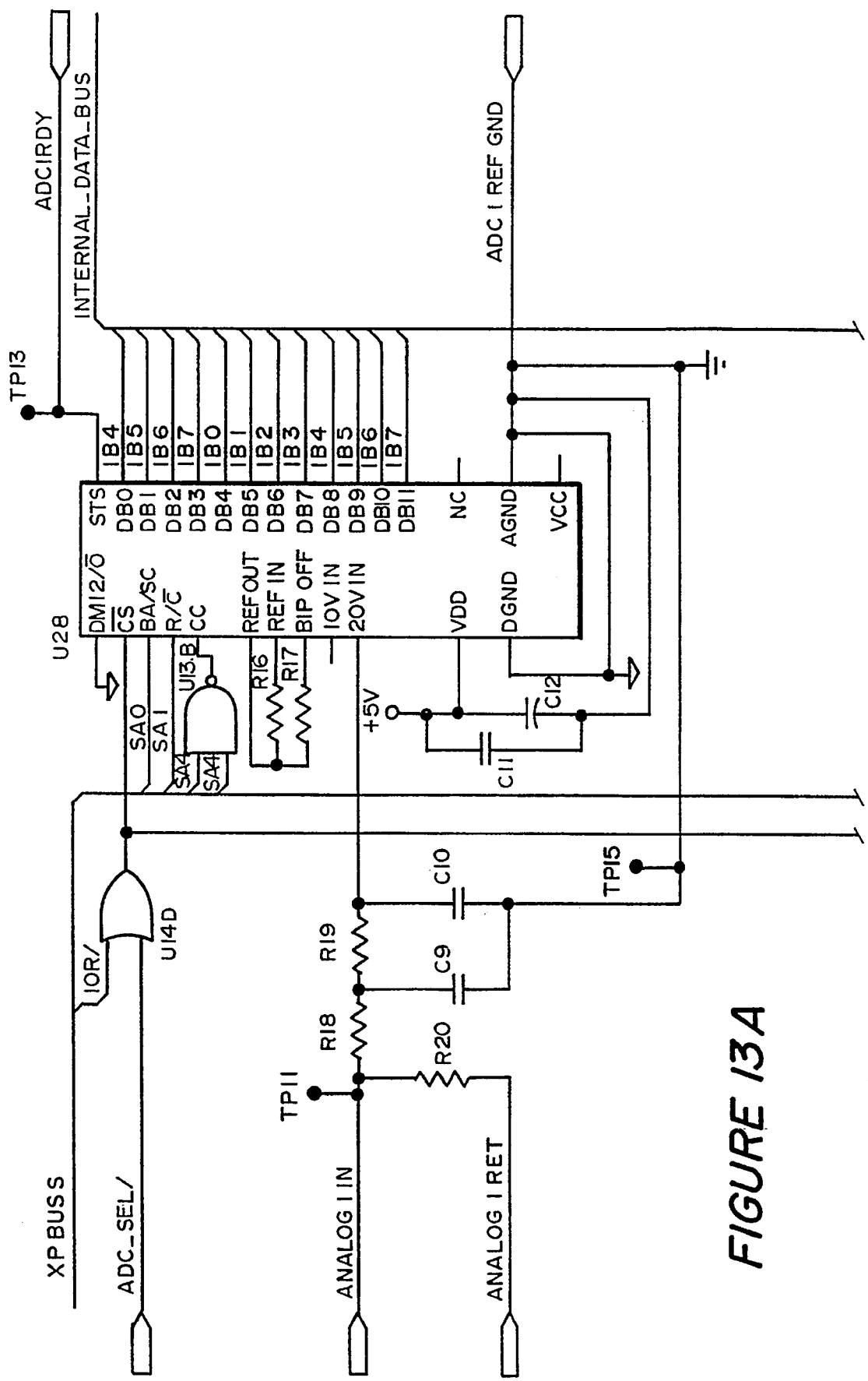
FIG. 13 is a schematic diagram showing the analog-to-digital converters of the evaluation and training system of the present invention.
Figure 13B:
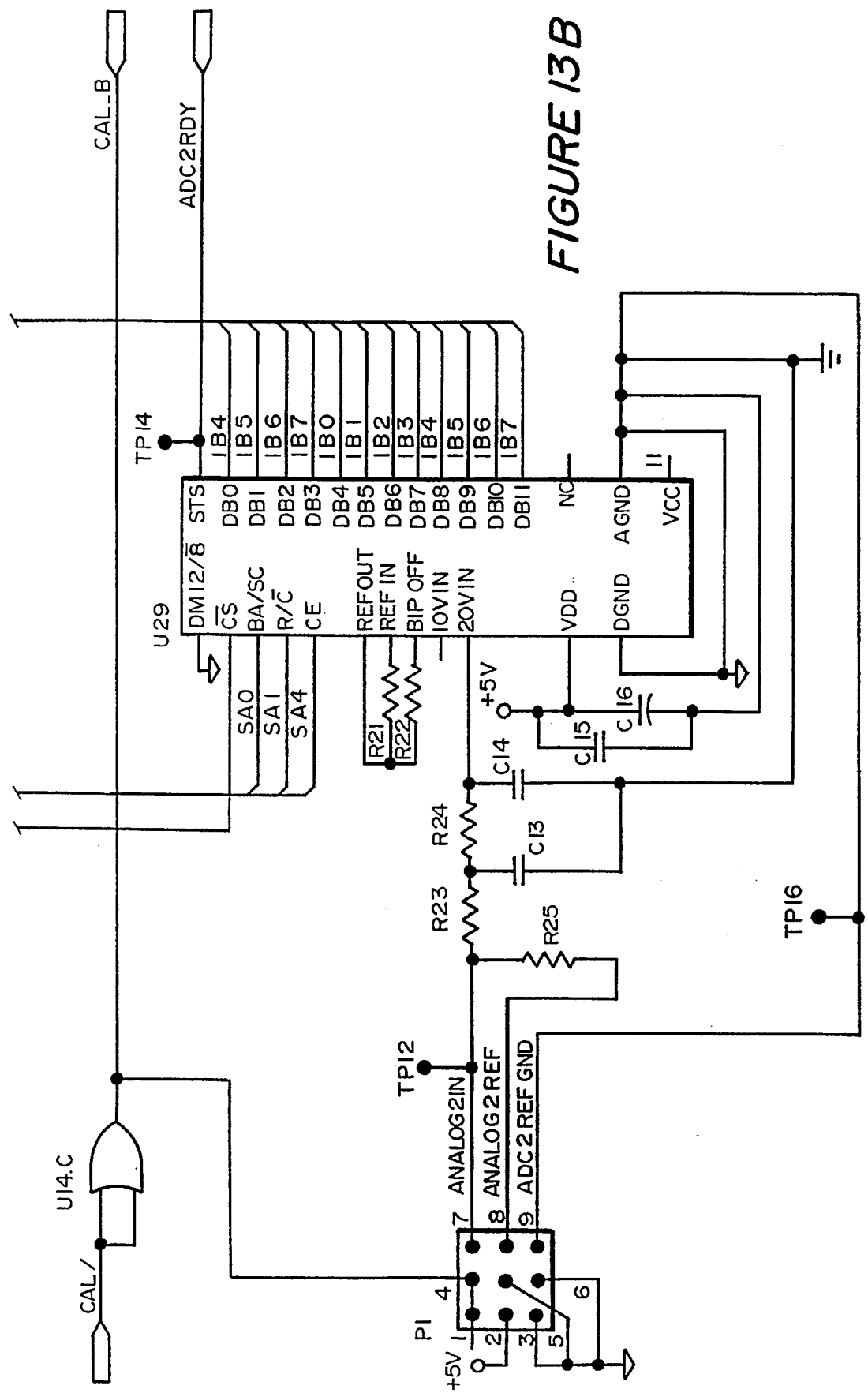

Processor 105 occupies 64 locations in the input/output address space and includes its own onboard slave microprocessor for controlling motor control output signals (SIGN and PULSE) driving the motor driver circuitry 110. Motor control processor 105 is coupled to the address and data buses of computer 200 to allow processor 105 to be selectively programmed by computer 180 in response to the particular software operation modes implemented for each test sequences. Processor 105 directs the SIGN and PULSE outputs to provide a current steering through H-bridge 115₁ (FIG. 12) through AND gates 109₁ and 109₂, and OR gates 111₁ and 111₂. As shown in FIG. 12, the four motor driver signals MOT_A+–MOT_D+ drive H-bridge 115₁ comprised of four power MOSFETs 116₁–116₄ to provide the pulse width modulated (PWM) voltage output for motor 28. As shown in FIG. 11, the SIGN output is coupled to AND gate 109₁ and OR gate 111₂, and the inverted SIGN output, via inverter U2B, is coupled to AND gate 109₂ and OR gate 111₁. The PULSE output is gated, via NAND gate 101, with the MOTOR_DISABLE control signal from peripheral port controller 102, and the output of NAND gate 101 is coupled to OR gates 111$_1$ and 111$_2$. By selectively addressing processor 105 and programming its onboard microprocessor, motor 28 may be controlled to position rotating element 10 in either the clockwise or counterclockwise direction at any point within the 360° rotational positions shown in FIG. 3. The registers of processor 105 can store command position, read and preset actual position, velocity set points, command velocity, acceleration, final position, and actual velocity for motor 28. Position data is acquired through the CHA, CHB inputs, whose inputs comprise the CHANNEL A, CHANNEL B data from optical encoder 24. The CHA, CHB inputs are quadrature detected, thereby providing a position resolution of 10,000 samples per 360°. The PWM output of processor 105 is timed via an external clock (HCTLCLK) driven by interrupt timer and watchdog circuit 160.

Because processor 105 is executing its own program, reading of the registers therein requires interruption of the program running in processor 105 and transfer of the data in its internal registers to an output buffer. As shown in FIG. 11, tri-state buffer 107 is utilized in a unidirectional fashion (DIR wired to +5 v) to address processor 105. Buffer 108 is used to read and write data out of processor 105. During a read of processor 105, the internal program is interrupted, the internal data register read, and the data therein placed in output buffer 108. The time required for this depends on the clock rate programed via timing chip 162 (FIG. 15) of timer circuit 160. Typically, HCTLCLK is between 2 megahertz and 100 kilohertz. Normally, HCTLCLK is at 1 megahertz. To prevent the system ready signal (I/O CH RDY/) from being inactive for an excessive period of time while processor 105 is being read, a two-step read process is used. Generally, the register address is strobed to processor 105 via buffer 107. PLD 103 generates status lines HCTLSTATE and HCTLWAIT which can be read by the CPU of computer 180 before proceeding with the second step of the read. The equations for PLD 103 are set out in Appendix B. When the status indicates that the data is ready, the data can be read by executing an I/O read operation from any register in the HCTL1100. A write to processor 105 is performed in a single operation by writing to the desired I/O address. However, there is a minimum time required between consecutive write operations due to the clocking cycle of HCTLCLK. Normally this cycling will not be a problem; however, if the clock rate is slow, status lines HCTLSTATE and HCTLWAIT may be checked before proceeding.

A typical command control sequence will first involve setting the sample timer to determine the sampling rate for the internal position control loop of processor 105. Next, the SIGN output reversal inhibit is set to ensure that no extra electronic noise is generated while the motor is under the control of processor 105. Since processor 105 implements a digital filter on the error signal, the digital filter parameters must be set according to the transfer function provided for the filter. Next, the actual position of rotational element 10 must be set. As will be noted below, this is done, in one embodiment, by initializing the index or "extreme" stops for element 10. The next input is to set the command position, which initially should be set to the same value as the actual position. Finally, the execute program mode is set. After entering the control mode, values can be written to the command position register. If the clutch is engaged and the resistance element disengaged, the handle will move to the commanded position unless resisted by the user.

Specific aspects of motor drive circuitry 110 will be discussed with reference to FIGS. 11 and 12. As will be understood by those skilled in the art, if the MOTOR_ DISABLE signal input to NAND gate 101 is logic level high, the PULSE output of processor 105 will be directed to steer H-bridge 115$_1$ by the SIGN output of processor 105. The clockwise enable (CW_ENABLE) and counterclockwise enable (CCW_ENABLE) outputs of peripheral port controller 102 are provided to AND gates 109$_1$ and 109$_2$. As will be understood from an examination of the coupling of the SIGN output, and CCW_ENABLE and CW_ENABLE signals, the output of AND gates 109$_1$ and 109$_2$, and OR gates 111$_1$ and 111$_2$, is such that a logic level high on either CW_ENABLE or CCW_ENABLE will enable the output of AND gate 109$_1$ or 109$_2$, thereby driving photoactive transistors 92$_1$ or 92$_2$. Transistors 92$_1$ and 92$_2$, in turn, steer power MOSFETs 116$_1$ or 116$_2$ by enabling a current path for the 48 volt DC input coupled to the respective source electrodes of transistors 116$_1$ and 116$_2$. Similarly, the PULSE signal is directed to OR gates 111$_1$ and 111$_2$ by the SIGN signal output and the inverted SIGN signal output (via inverter U2.B) coupled, respectively, to OR gates 111$_2$ and 111$_1$. The outputs of OR gates 111$_1$ and 111$_2$ in turn drive photoactive transistors 92$_3$ and 92$_4$ to steer current through power MOSFETs 116$_3$ and 116$_4$, each having a source coupled to ground and a drain coupled to the drains of transistors 116$_1$ and 116$_2$, respectively. The PWM duty cycle of the PULSE signal will determine the velocity of rotational element 10. MOSFET 116$_4$ is activated by a 2-state NAND gate U1, having a 15 volt output coupled to the gate of MOSFET 116$_4$, MOSFET 116$_3$ has its gate coupled to the 15 volt output of NAND gate U6.

Certain aspects of resistance element drive circuitry 112 and clutch drive circuitry 114 will be discussed hereafter with respect to FIGS. 10 and 12. Resistance element drive circuitry 112 and clutch drive circuitry 114 are somewhat similar to the motor drive circuitry 110, but are controlled by a dual output digital analog converter 121 having, effectively, two digital-to-analog converters 120$_1$, 120$_2$, shown in FIG. 10. The DAC converter chip 121 may comprise, for example, an AD7528-type analog-to-digital converter, having an 8-bit data input coupled to the internal data bus of computer 180 and being selectively addressable via the address bus XP of computer 180. Digital analog converters 120$_1$, 120$_2$ are used to set the current, and thus the resistance, of both resistance element 22 and clutch 26. The output of each DAC drives a current mode, pulse-width-modulated amplifier with linear, unipolar signals corresponding to 1.66 amps full scale or 6.5 milliamps per least significant bit.

As noted above, port A outputs PA0 and PA1 of peripheral controller 102 are gated with the PWM current outputs through OR gates U21D and U21.C to enable the BRAKE± and CLUTCH± drive outputs. Flip flops U22a and U22b are clocked by the PWM_CLK signal provided by interrupt timer and watchdog circuit 160. Thus, BRAKE± and CLUTCH± provide the drive for resistance element drive circuitry 112 and clutch drive circuitry 114 in a PWM mode to regulate the current output to magnetic particle resistance element 22 and clutch 26, thereby regulating the resistance thereof. As will be generally understood, the output of DAC 120$_1$, 120$_2$ provide a generally linear relationship between its output and the applied resistance of resistance element and clutch.

The BRAKE+ and BRAKE− outputs drive photoactive transistor 92$_5$ to control H-bridge 115$_3$ comprised of MOSFETS 118$_1$–118$_4$, to supply current at the BRAKE_A and BRAKE_B outputs to drive resistance element 22. A 24 volt DC voltage is coupled to the respective drain electrodes of transistors 118$_1$ and 118$_2$, the sources of transistors 118$_3$ and 118$_4$ are coupled to ground and the drains of 118$_1$ and 118$_3$, and $118_2$ and $118_4$ are coupled together. The gates of transistor and $118_2$ is coupled to the 24 volt DC rail and transistor $118_3$ has a gate coupled to ground to allow transistors $118_1$ and $118_4$ to steer current through the H-bridge to control resistance element 22. The 15 volt DC output of two state NAND gate U2 is coupled to the gates of transistor $118_4$ while the gate of transistor $118_1$ is coupled to bipolar transistor $Q_3$, whose base is controlled by photoactive transistor $92_5$. Likewise, clutch signals CLUTCH+ and CLUTCH− control photoactive transistor $92_6$ where output controls transistor $117_1$ of H-bridge $115_2$. Transistors $117_1$–$117_4$ of H-bridge $115_2$ are coupled in the same manner as transistors $118_1$–$118_4$. In most modes, clutch 26 will be used in a full-on/full-off mode where its main purpose is to decouple motor 22 from main shaft 18. The clutch torque is not calibrated, but the output of DAC $120_2$ drives clutch drive circuitry 114 at 1.67 amps which provides a "full on" torque of 40 inch-lbs.

Figure 17:
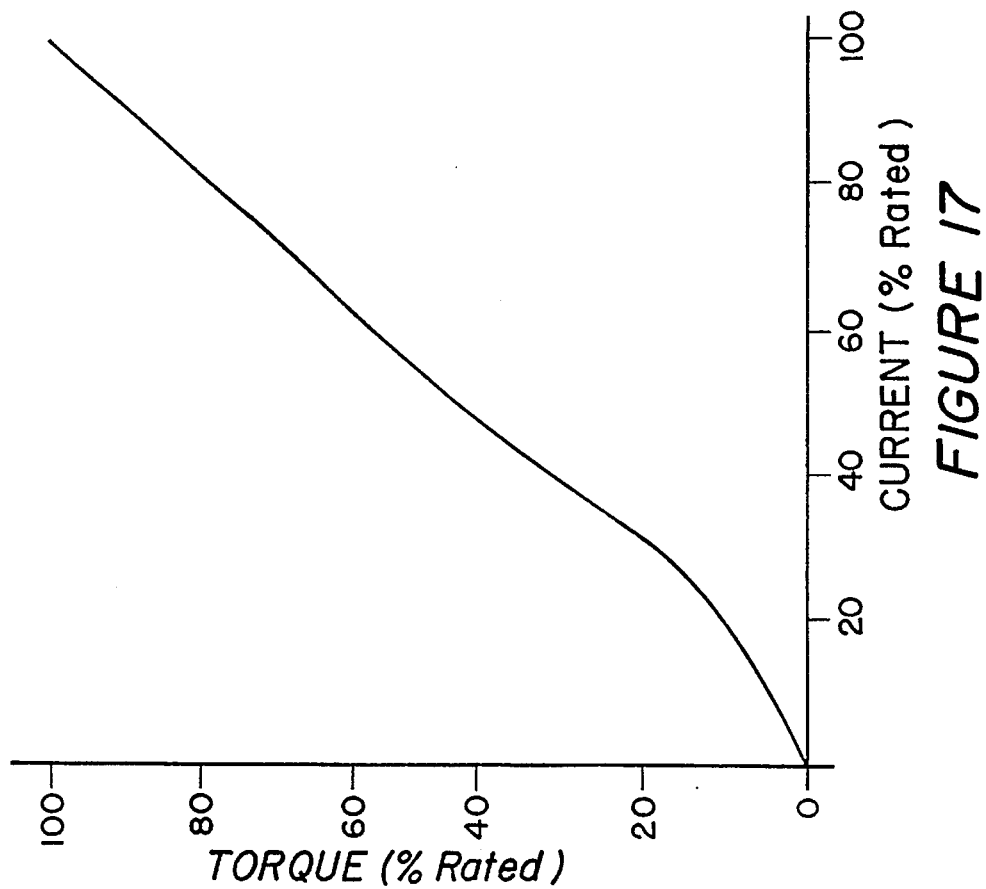
FIG. 17 is a graph depicting the torque vs. the current applied to and by the resistance element of the evaluation and training device of the present invention.

Signals BRK_CUR_REF, BRK_CUR_SEN; CLH_CUR_REF, CLH_CUR_SEN) are provided to sense the drive current provided by H-bridges $115_3$ and $115_2$, respectively. Current output feedback signals of the resistance element BRK_CUR_SEN and clutch CLH_CUR_SEN are compared with the outputs of DAC $120_1$, $120_2$ by comparators U25a and U25b, respectively, which preset flip flops U22b and U22a, through OR gates U21b and U21a, respectively. The resistance element and clutch current output feedback ensure that the output drive of the resistance element drive circuitry 112 and clutch drive circuitry 114 is regulated to the reference output provided by the digital analog converters $120_1$, $120_2$. The frequency of the PWM clock input to flip flops U22b and U22a is approximately 2 kilohertz and is provided by counter 162. The resistance of resistance element 22 is nearly linear with the current provided by the output drive of circuitry 112 (FIG. 17). Current is controlled by writing to the DAC A output of DAC chip 121. Maximum output of the DAC corresponds to 1.67 amps which will provide a resistance torque of approximately 250 inch-lbs.

Figure 16:
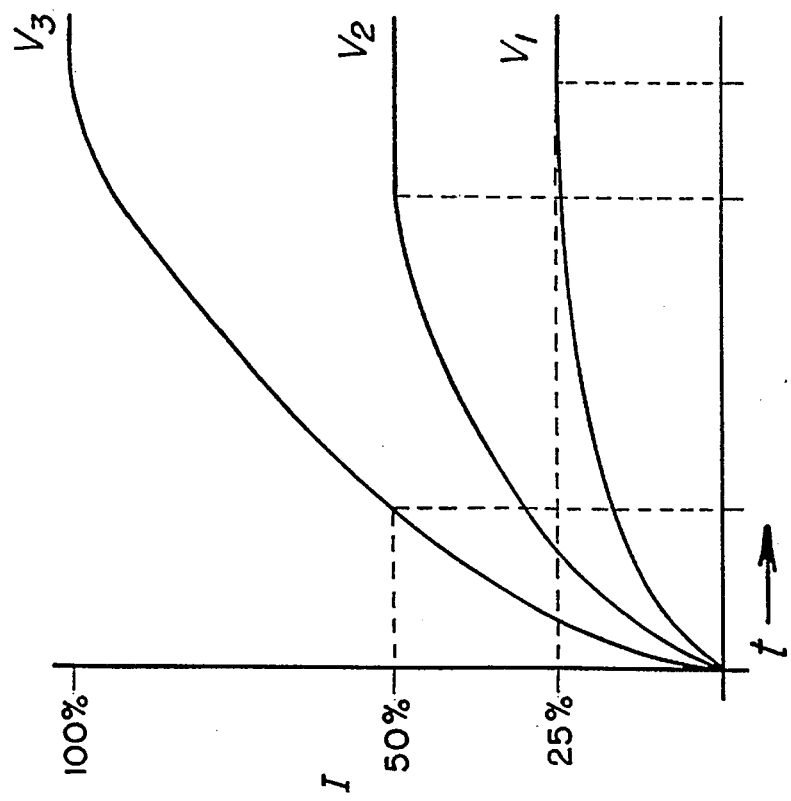
FIG. 16 is a graph depicting the current vs. time when a voltage is applied to either the magnetic particle clutch or magnetic particle resistance element of the evaluation and training device of the present invention.

A unique feature incorporated into the system for controlling resistance element 22 is provision for full power voltage ramping of resistance element 22 when increasing the resistance thereof. Magnetic particle resistance element 22 and clutch 26 are high inductance devices which require a certain time t to reach the requisite torque desired. As shown in FIG. 16, the ramp-up time of the current is proportional to the amount of voltage which is provided, and the slope of the current increase with respect to time t is proportional to the amount of voltage provided into the internal coils of resistance element 22 and clutch 26. Although the proportionality of resistance torque to the current i is almost linear, as shown in FIG. 17, it is desireable in the evaluation and training system of the present invention and particularly the isokinetic test mode, to reduce the time t required for resistance element 22 to provide resistance in response to the changes in torque on shaft 18 to provide dynamic resistance for the test subject. Thus, as shown in FIG. 18, the electronic control system and software of the present invention provide that the current output on BRAKE_A, BRAKE_B is driven to 100% when ramping resistance element 22 to a particular resistance level, such as 25% of full power or 62.5 inch-lbs. In order to control the ramp-up of resistance element 22 in this manner, the resistance element output sense signals BRK_CUR_SEN and clutch output sense signals CLH_CUR_SEN are fed back to comparators U25a and U25b, respectively, which compare the actual current output to the reference output provided by digital analog converter $120_1$, $120_2$, respectively. If the current is below the desired level, flip flops U22b and U22a are clocked low on the next incoming clock cycle from PWM_CLK. Thus, once the resistance element or clutch current reaches its threshold level to provide the desired amount of torque, the drivers are turned off.

In addition, a 200Ω resistor R31 is provided between the BRAKE_A output and the 24 volt DC input to provide a reverse current to the resistance element when the resistance element is turned off to reduce the residual drag thereof. There is a current offset of approximately −60 milliamps to supply a reverse current to reduce the residual drag when the resistance element is shut off. As the clutch is lower in torque, this reverse current is not necessary.

Torque sensor 20 provides an analog voltage output to bridge amplifier 150, whose output (ANALOG1) is coupled to analog-to-digital converter U28 (FIG. 13) which digitizes the signal for computer 180. While two analog converters U28 and U29 are provided on the board, presently only A/D converter U28 is used. A/D converter U29 is provided for future use and may, in one embodiment, be used in conjunction with a force transducer for sensitivity testing with respect to stationary post 15. A/D converter U29 has an input coupled to a plug P1 which may also be used to couple A/D converter U29 to the torque sensor if necessary.

Figure 15:
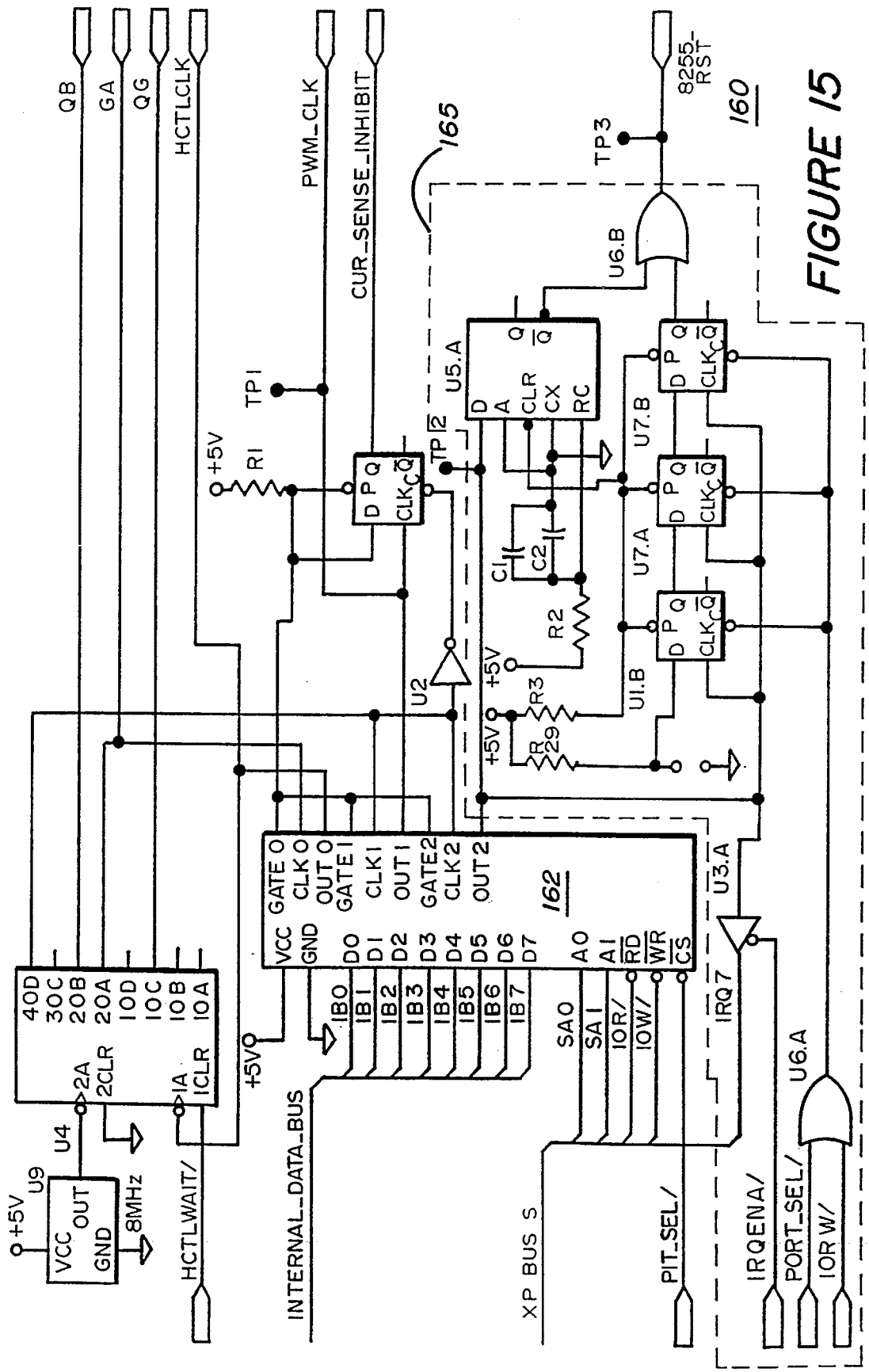
FIG. 15 is a schematic diagram of the watchdog circuit and interrupt timer of the evaluation and training system of the present invention.

FIG. 15 shows timing and watchdog circuit 160 of the present invention. Many of the signals generated by timing chip 162 have been discussed previously in the context of their operations with respect to the particular circuits utilized in the electronic control system of the present invention. The specific means chosen to implement the requisite timing signals required for the electronic controller of the system may be 82C54-2 programmable clock generator 162. The counter 0 output of chip 162 is utilized to generate the HCTL clock in a range of 2 Mhz–100 kHz nominally 1 Mhz. The counter 1 output generates PWM_CLK in a range of 10 Khz–500 Hz, normally provided at 2 kHz. The counter 2 output provides the interrupt time-through buffer U3A which, as discussed above, must be enabled by IRQENA (low) from port A of peripheral port controller 102.

Watchdog circuit 165 ensures that the electronic controller and drive hardware is shut down in the event of a software problem. For the watchdog circuit to remain inactive, there must be a port access at least every other interrupt clock (OUT2). A watchdog activation will also occur if the interrupt clock is too slow, e.g., less than 0.5 hertz. The CLOCK2 output is provided to monostable multi-vibrator U5A, whose output is coupled to watchdog circuit U5A. Watchdog circuit 165 essentially comprises monostable multivibrator U5A, and flip flops U1B, U7A, and U7B. Flip-flops U1B, U7A, and U7B have clock output OUT2 coupled to their clock (CLK) inputs, and have their preset P inputs held high.

The clear C inputs of flip-flops U1B, U7A, and U7B are gated from the PORT_SEL and IORW signals via OR gate U6A. Thus, as long as the system software accesses peripheral port controller 102, the flip-flops will not increment, remaining cleared by the output of OR gate U6A. If, however, the software is not accessing the board, flip flops U1B, U7A and U7B will act as a sequential shift register to output signal 8255_RST via OR gate U6B which, when cycled with the output of multivibrator U5A, will generate the 8255_RST signal to reset the peripheral port controller 102. In turn, the motor controller 105 will be reset.

The status of watchdog circuit 165 can be read on port C of peripheral port controller 102. As watchdog circuit 165 is not latched, if it becomes active for a short time and then becomes inactive, the reset output (8255__RST) is removed. This reset condition can be detected by reading the control word of peripheral port controller 102.

Dual ripple counter U4 provides signals QA, QB and QG for use by PLD103 to provide control outputs. An 8-megahertz oscillator U9 is coupled to the 2A input of dual ripple counter U4. The 1A input is coupled to the clock 0 output (OUT0) of timing chip 162.

FIGS. 19–27 are flowcharts depicting the logical steps executed by the software resident in computer 180 to perform various test modes discussed above. A printout of this software is included as Appendix A of this application. It should be understood by those skilled in the art that the flowcharts represent one embodiment of a method for implementing the test modes of the evaluation and training system of the present invention; numerous other methods are suitable within the context of the system of the present invention and are intended to be within the scope of the claimed invention.

Figure 19:
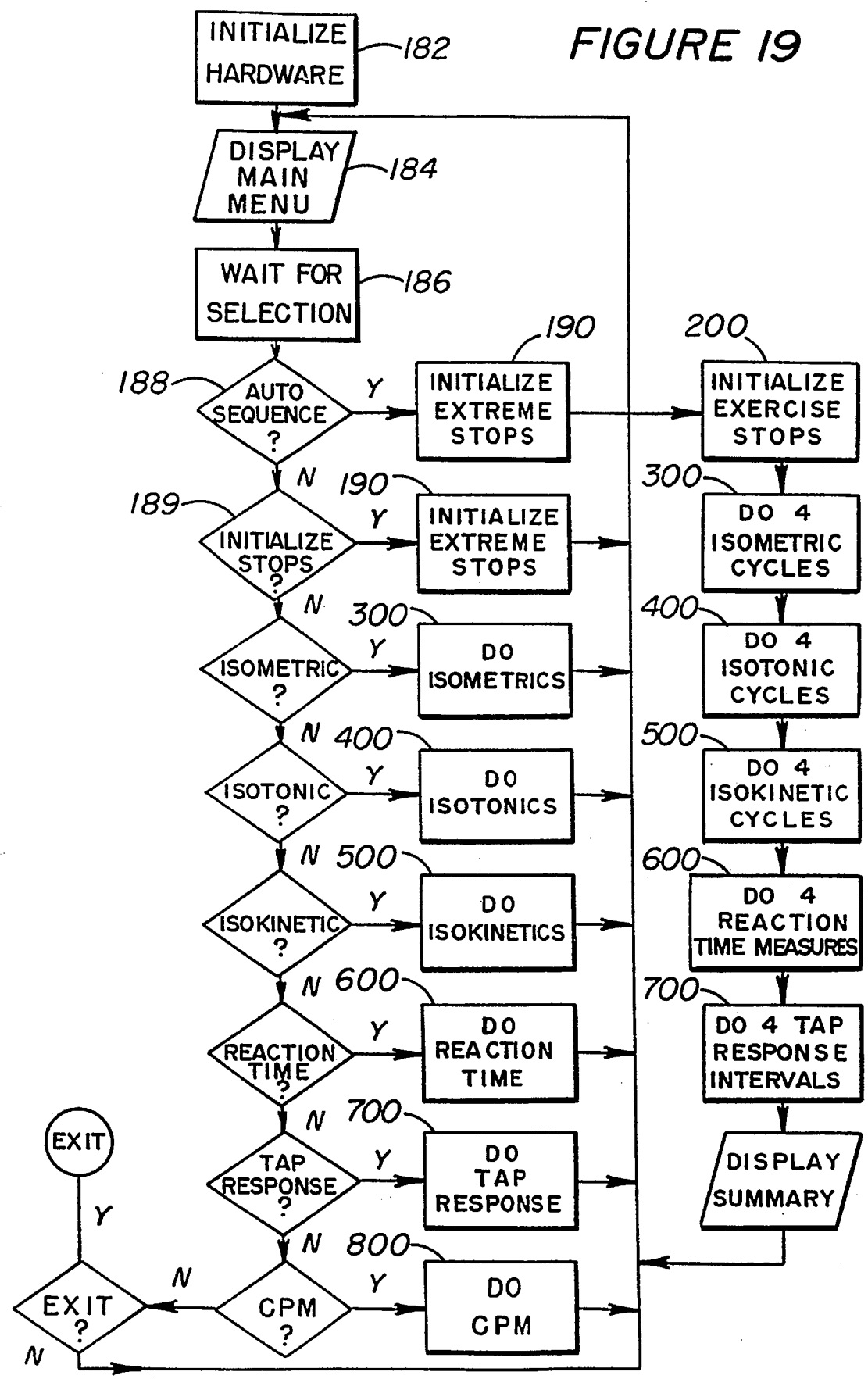
FIG. 19 is a flowchart of the main control software of the present invention.

FIG. 19 is a flowchart of the main control program of the evaluation and training system of the present invention. As shown in FIG. 19, the software control system first initializes the port hardware (step 182) discussed above with respect to FIGS. 9–15. A menu is then displayed on monitor 210 (step 184) and the therapist prompted for a selection of operation modes by an input from keyboard 205 (step 186). The therapist has an option to request an automated test sequence wherein the software will implement, sequentially, isometric testing, isotonic testing, isokinetic testing, reaction time testing, and tap response testing. Alternatively, the therapist may select to individually perform the isometric, isotonic, isokinetic, reaction time, and tap response testing. The continuous passive motion mode is individually selectable and is, in the embodiment shown in FIG. 19, not part of the automated test sequence. It should be understood by those skilled in the art that is within contemplation of the invention to incorporate the continuous passive motion mode sequence into an automated test and training routine for the evaluation and training system. It should also be understood by those skilled in the art that it is within contemplation of the invention to allow the therapist to preprogram any number of automated test sequences utilizing the individual isokinetic, isometric, isotonic, reaction time, tap response, and continuous passive motion mode subroutines. For example, in a customized sequence, different individual subroutines may be linked to provide selective automated sequences for particular test subjects.

Further, it should be understood that while for the sake of simplicity the ensuing discussion refers to the selection of modes and initialization of the system in terms of a therapist, as test monitor, and a test subject, as an individual whose muscles are under test, a suitable interface system may be utilized to allow the test subject to set system parameters and perform self testing and training exercises. Finally, the ensuing discussion also describes each of the operational and test modes in terms of the basic ergonomic system incorporated in the testing and evaluation system of the present invention. It should be understood that each of the attachments described above can be substituted for rotational element 10 and stationary element 15 in the context of the following discussions.

In general, if the automatic testing sequence is selected (step 188), before proceeding with any of the specific testing subroutines, the extreme stops for rotating element 10 must be established by the software control system. The extreme stops generally comprise rotational positions 0° and 360° of rotational element 10 with respect to stationary element 15. The initialize extreme stops function is also individually selectable from the main menu (189) and must be preformed at least once before implementing any of the individual test mode sequences.

Figure 20:
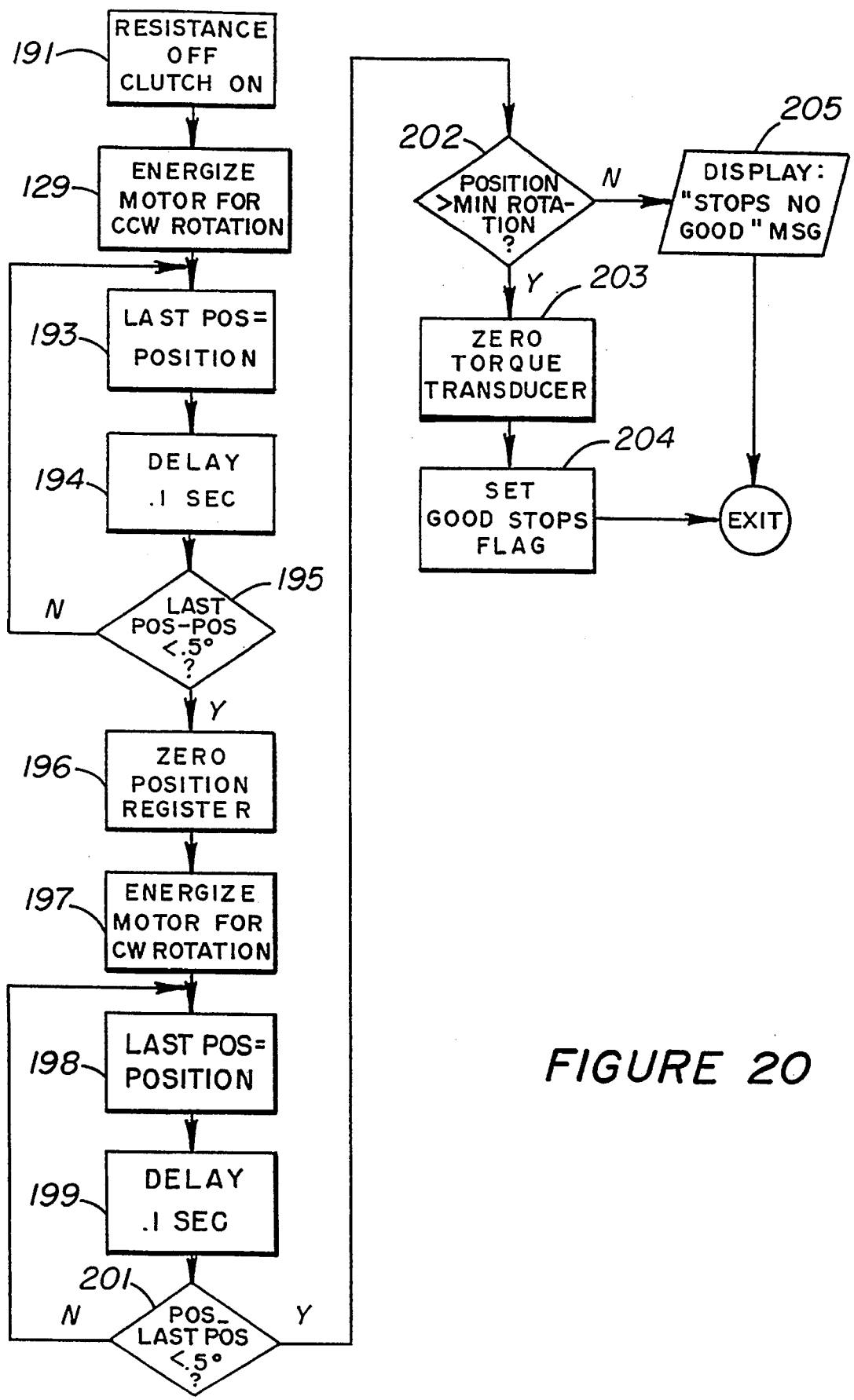
FIG. 20 is a flowchart of the subroutine for initializing the extreme rotational element stops of the evaluation and training system of the present invention.

FIG. 20 shows the initialize extreme subroutine 190. Initially (step 191), the software turns the resistance element current off and engages clutch 26 at a "full on" mode. Motor 22 is energized for counterclockwise rotation at step 192 and rotary optical encoder 24 is read by motor controller 100 to determine the specific position of element 10 with respect to element 15. The control software monitors movement of element 10 via rotatory optical encoder 24 following the motion of element 10 to ensure that motor 22 has moved element 10 in at least 0.5° increments every 0.1 sec. as shown by steps 193, 194, and 195. When motor 22 stops, the equation (LAST__POS - POSITION)<0.5° will be true, and processor 180 will set the position register in motor controller 105 to zero. Subroutine 190 thereafter initializes motor 22 for clockwise rotation (step 197). In the control loop represented by steps 198, 199 and 201, the software again ensures that motor 22 has moved element 110 in at least 0.5° increments every 0.1 sec., this time in the clockwise direction. When motor 22 stops, the software checks the position of rotational element 10 and compares POSITION with the MIN__ROTATION value stored in processor 180. If POSITION is greater than the MIN__ROTATION of element 10, torque transducer 20 is set to 0 (step 203), the system is initialized and the GOOD STOPS flag set (step 204), and the routine exits. If not, the therapist is prompted with a "STOPS NO GOOD" message (step 205).

Figure 21:
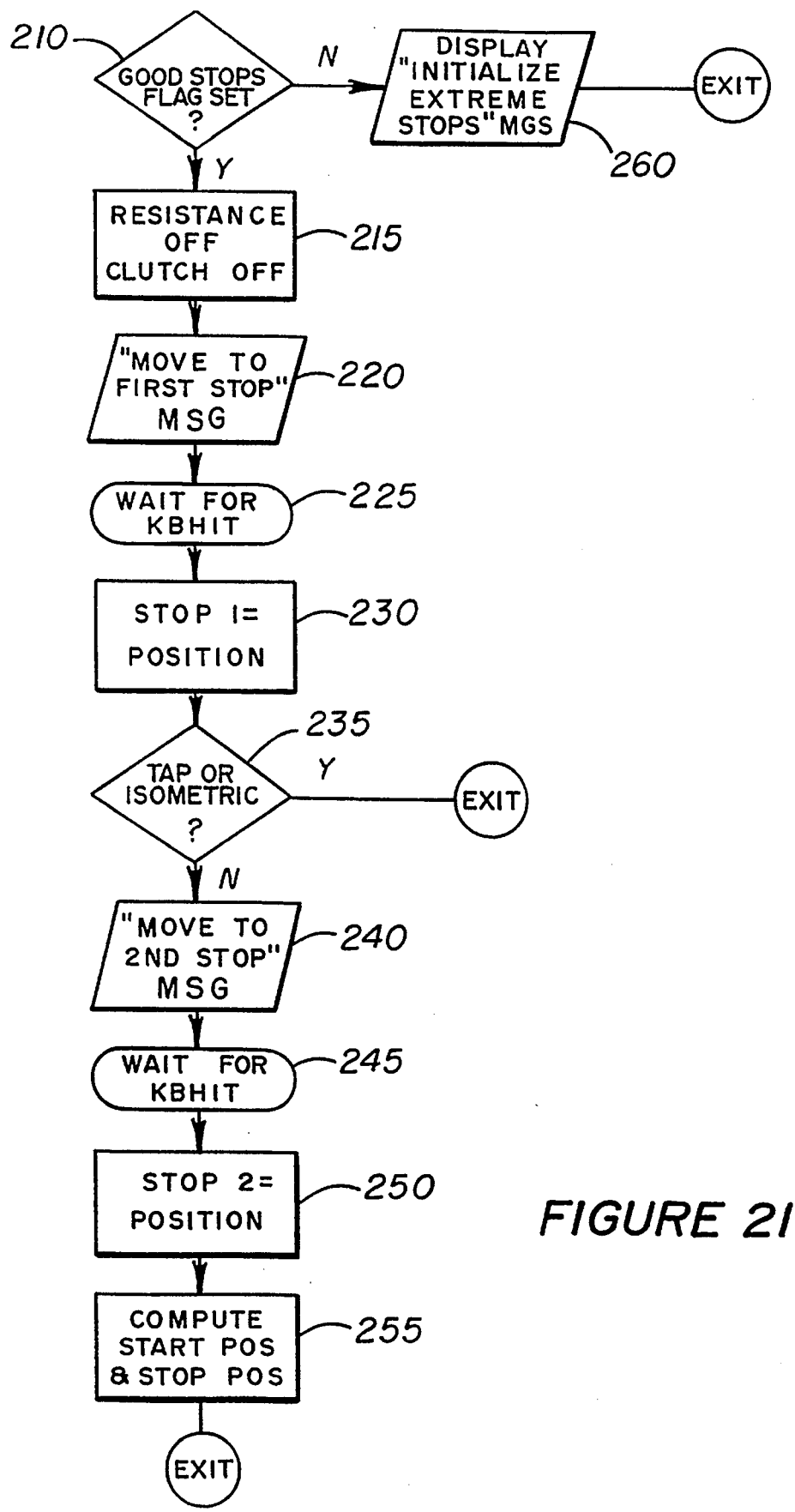
FIG. 21 is a flowchart of the subroutine for initializing the exercise stop positions of the rotational element for individual test subjects in accordance with the evaluation and training system of the present invention.

FIG. 21 shows the initialize exercise stop subroutine 200. The function of this subroutine is to allow the therapist to set the maximum rotational exercise positions for element 10 which are suitable for evaluating and testing the left and right hands of the particular test subject during each testing sequence. Subroutine 200 initially checks to see if the GOOD STOPS flag has been set by the initialize extreme stop subroutine 190. If not, the subroutine displays a "INITIALIZE EXTREME STOPS" message (step 260) to display monitor 210, and exits subroutine 200. The system thus requires that the extreme stops be initialized before proceeding into any of the test modes. If the "GOOD STOPS FLAG" is set, the system sets resistance element 22 and clutch 26 "off" (step 215) and issues a "MOVE TO FIRST STOP" message (step 220) to monitor 210. The "MOVE TO FIRST STOP" message is a signal to the therapist to move rotatable element 10 to the first position the size of the patient's hand with respect to the stationary post 15. Such position would be equivalent to the maximum linear length D (FIG. 3) which is suitable for the hand size of the particular test subject. This position may be anywhere between 0° and 180° for example, for a test of the right hand of the test subject, and likewise between 180° and 360° for a left hand test. Subroutine 200 thereafter waits (step 225) for the therapist to enter a particular key hit, such as the "ENTER" key on keyboard 205, to indicate that element 10 has been moved to the first exercise stop position. When the particular key is depressed by the therapist (step 230), the software stores the first stop position (STOP 1) and proceeds to step 235 where, if the manual tap or isometric mode test has been implemented, the subroutine exits to proceed with subroutine 300, for isometric testing, or subroutine 700 for tap testing. If the therapist has selected the isokinetic, isotonic, reaction time modes, or automatic test sequence modes, the message "MOVE TO SECOND STOP" is issued (240) to display monitor 210. The system then waits (245) for the therapist to set the second stop at a position (between 0°–180° or 180°–360°) equivalent to the maximum length D which is suitable for the testing of the test subject's hand. It should be understood that if the first stop position is set for the right hand, the second stop position is set for the left hand, and vice-versa. When element 10 has been positioned in accordance with the distance D suitable for a test subject, the therapist will hit the ENTER key the STOP2 position will be stored (step 250). Subroutine 200 thereafter computes the start position (STARTPOS) and the stop position (STOPPOS) which may thereafter be used to direct motor processor 105 to position element 10 during the series of testing sequences.

Figure 22A:
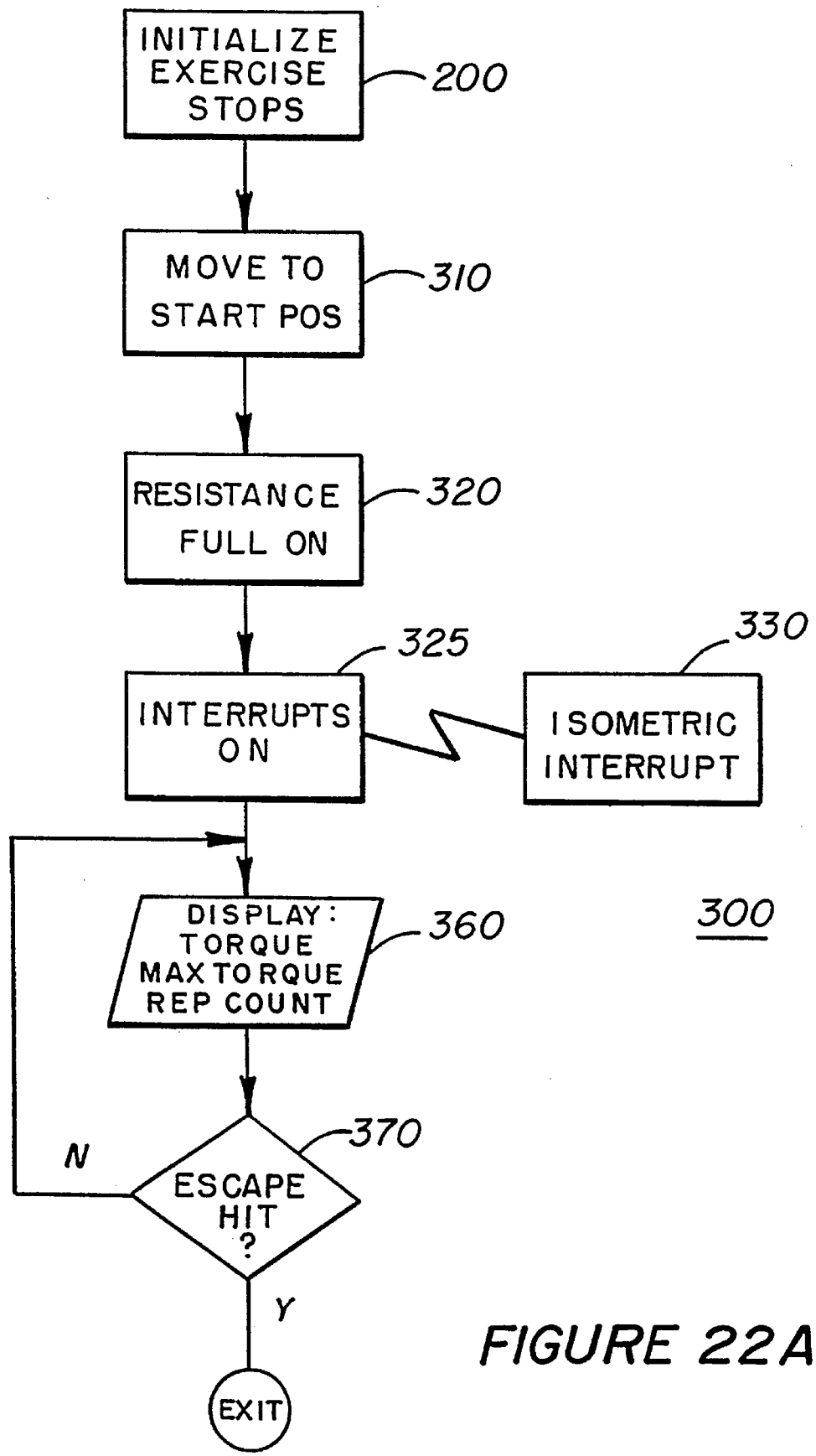
FIGS. 22a and 22b are a flowcharts of the subroutines for implementing the isometric test mode of the evaluation and training system of the present invention.
Figure 22B:
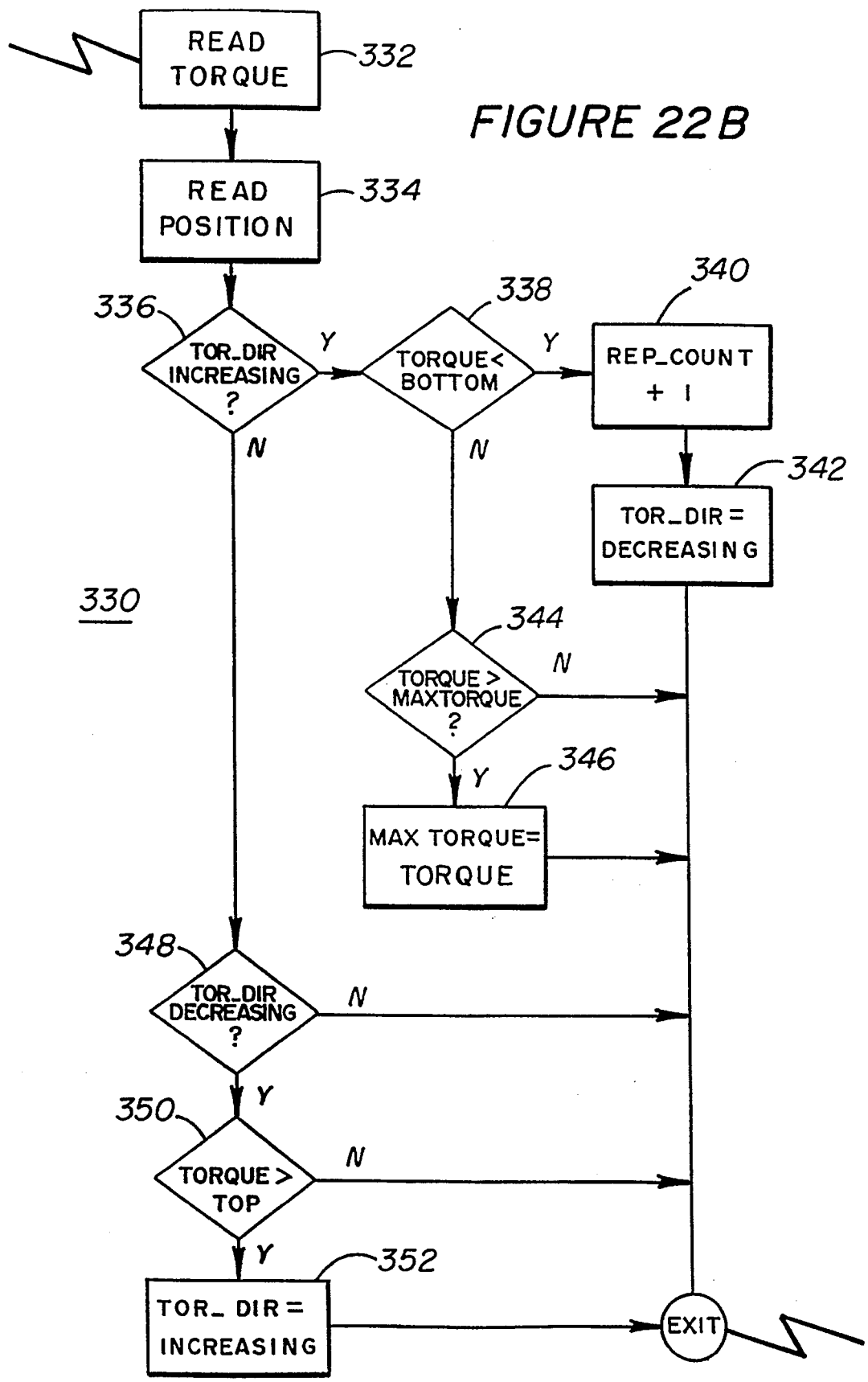

Subroutine 300 for executing the isometric testing in accordance with the system of the present invention is shown in FIGS. 22A and 22B. Subroutine 300 begins with execution of exercise stop subroutine 200 discussed above. It should be understood from a study of the main control program in FIG. 19, that if the software is executing the automatic test sequence, subroutine 200 is only executed once for all exercise modes.

The purpose of isometric subroutine 300 is to allow the system of the present invention to provide a maximum resistive force to resistance element 22 and thereafter measure the torque which was applied by the test subject to rotating element 10 relative to the axis 12 while not allowing the test subject to actually move element 10. In one embodiment, the output of subroutine 300 is a numerical measurement of the torque and the maximum torque achieved in a sequence of testing repetitions. At step 310, subroutine 300 directs motor 28 to move element 10 to the first start position established in the first half of subroutine 200. Subroutine 300 thereafter sets the resistance to a "full on" mode (step 320). Subroutine 300 then enables (step 325) the isometric interrupts 330. As will be understood by those skilled in the art, the interrupt sequence will be enabled by the interrupt clock signal output from clock 2 (OUT2) of timing chip 162.

As pressure is applied to element 10, interrupt sequence 330 reads the torque translated to shaft 18 (step 332), and the position movement of (step 334), rotational element 10. At step 336, subroutine 330 checks the variable TOR_DIR to determine whether the subject is applying increasing or decreasing torque on element 10. TOR_DIR is set by the previous output data of interrupt sequence 330. In essence, interrupt 330 continues testing for the maximum torque applied to rotational element 10 by the test subject until the test subject eases his or her grip and the applied torque is decreased.

On the initial interrupt cycle, TOR_DIR is set to DECREASING. At step 350, interrupt 330 queries whether the torque is greater than the TOP torque, a constant of approximately 5 in-lbs. If so, TOR_DIR is set to INCREASING and the interrupt exits. If not, the interrupt routine exits.

On the next interrupt cycle, if the magnitude of the torque is increasing (TOR_DIR INCREASING), subroutine 330 checks to determine whether the magnitude of the torque is less than the "bottom" torque, the "bottom" torque being a constant of approximately 2 in-lbs. If so, the subroutine 330 increments the repetition count (step 340) and the TOR DIR is set to DECREASING. If the applied torque is greater than BOTTOM subroutine 330 checks whether the applied torque is a new maximum measured torque (MAX_TORQUE) (step 344). If measured TORQUE is a new MAX_TORQUE, the MAX_TORQUE variable is set to the new measured maximum value and the interrupt exits. If not, the interrupt exits without resetting MAX-TORQUE. When the requisite number of repetitions have been incremented, subroutine 300 displays the maximum torque, torque average and the number of repetitions programmed by the therapist (360) and waits for an escape key hit by the therapist on keyboard 210. When the escape key is hit, subroutine 300 exits to the next sequential step of the automatic process, or the main menu depending on the preselected independent or automatic routine (see FIG. 19).

Figure 23A:
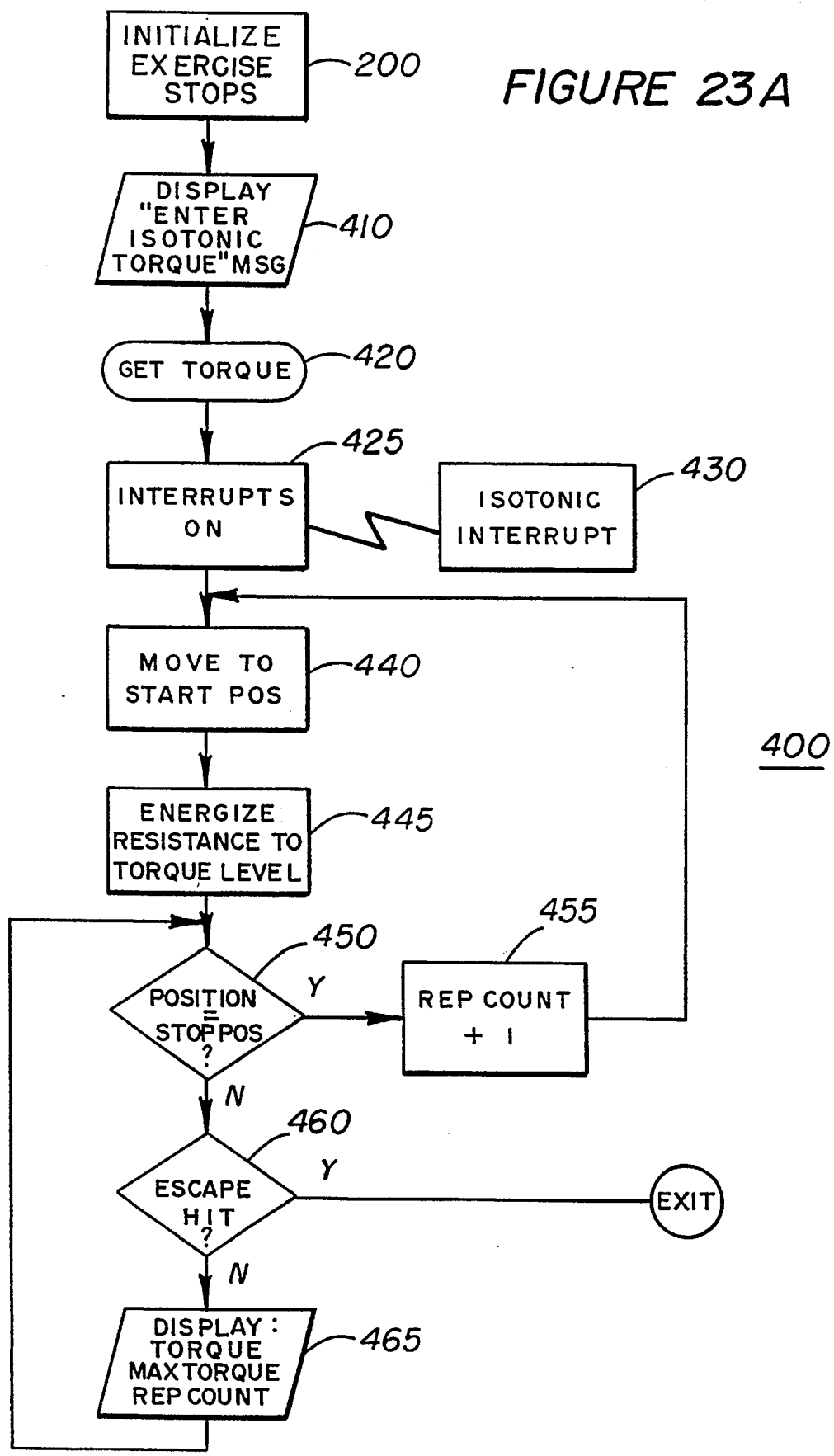
FIGS. 23a and 23b are flowcharts of the subroutines for implementing the isotonic test mode of the evaluation and training system of the present invention.
Figure 23B:
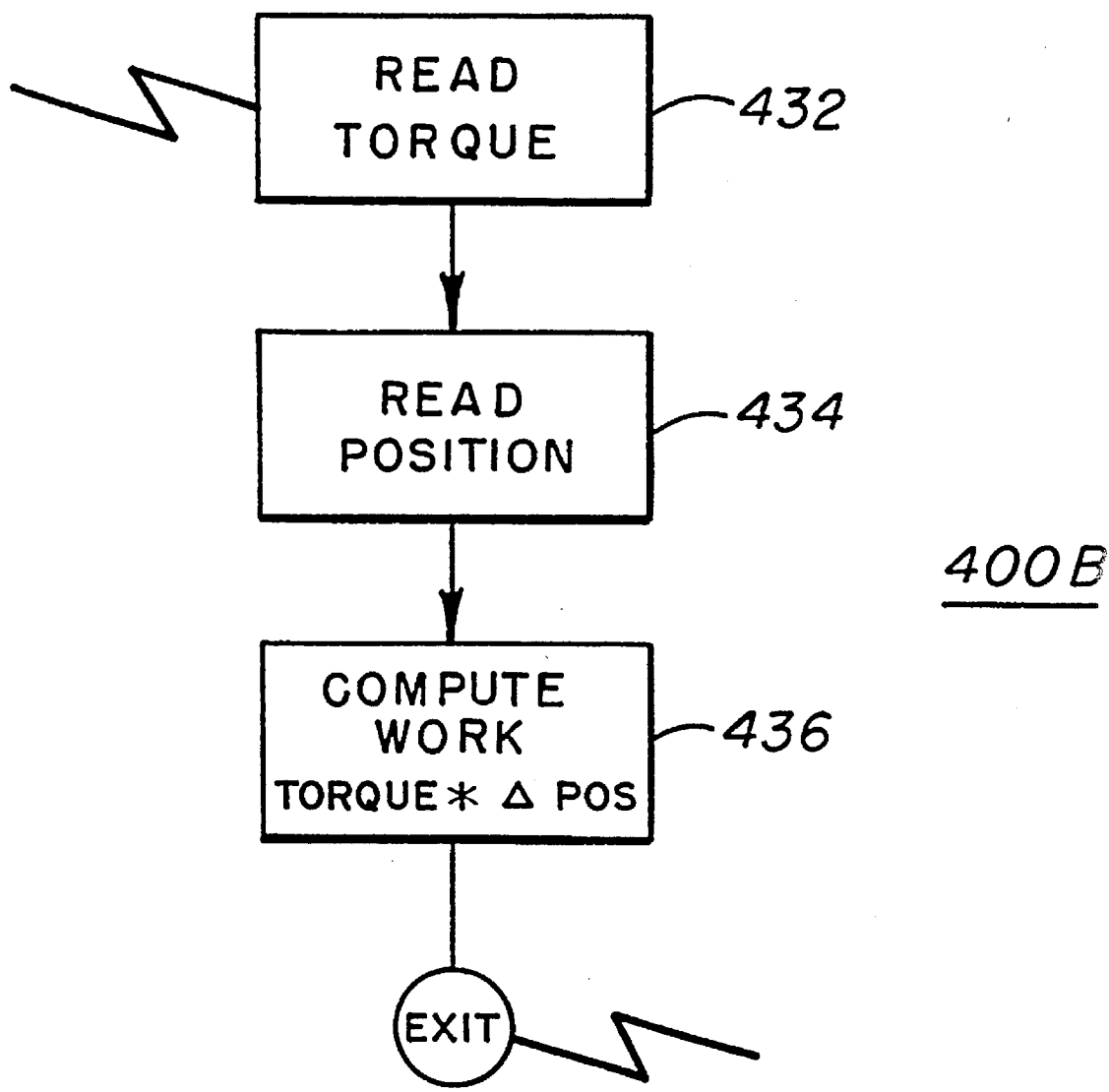

Subroutine 400 for implementing the isotonic test mode of the present invention is shown in FIGS. 23A and 23B. In an isotonic mode sequence, the system will apply a constant current drive to resistance element 22, therefore providing a constant torque resistance against any movement by the test subject of element 10. The rotational velocity applied by the test subject to element 10 is allowed to vary. Subroutine 400 begins with initialize exercise stop subroutine 200 to ensure that the exercise stops have been preprogrammed in accordance with the sequences discussed above. Again, in the automated test sequence, this subroutine will have been performed prior to the isometric test sequence.

At step 410, the isotonic subroutine 400 displays a "ENTER ISOTONIC TORQUE" message on display monitor 210 and awaits input from the therapist at step 420. When the requisite torque determined by the therapist to be suitable for the particular test subject has been entered, the system moves to initialize interrupts 430.

Again, the interrupt sequence is controlled by the interrupt clock. Essentially, interrupt sequence 430 reads the torque translated to the shaft 18 by force applied by the test subject onto element 10 (step 432) reads the rotational position of element 10 (step 434), and computes the work provided by the test subject on shaft 18 by multiplying the torque by the change in position of element 10.

After the interrupts are enabled (step 425), the test begins when rotational element 10 is moved to the first start position (the first exercise stop) (step 440) and resistance element 22 is energized by programming the requisite torque level into digital analog converter 120. After energizing resistance element 22 to the specified torque level, at step 450, the system will wait for the test subject to position rotating element 10 at the end-stop position. When movement of rotating element 10 has been completed, at step 455, the repetition count will be incremented, and the system will return rotational element 10 to the start position (step 440). If, at step 450, the repetition count has reached the desired level or the element 10 is not at the stop position, the subroutine will proceed to step 460 where, if an escape sequence is initiated, the subroutine will exit. If the escape sequence is not initiated, the system will continually display the torque, maximum torque and repetition count of the isotonic test sequence (step 465). The display will remain on and the subroutine will await positioning of the element 10 at the stop position.

Figure 24A:
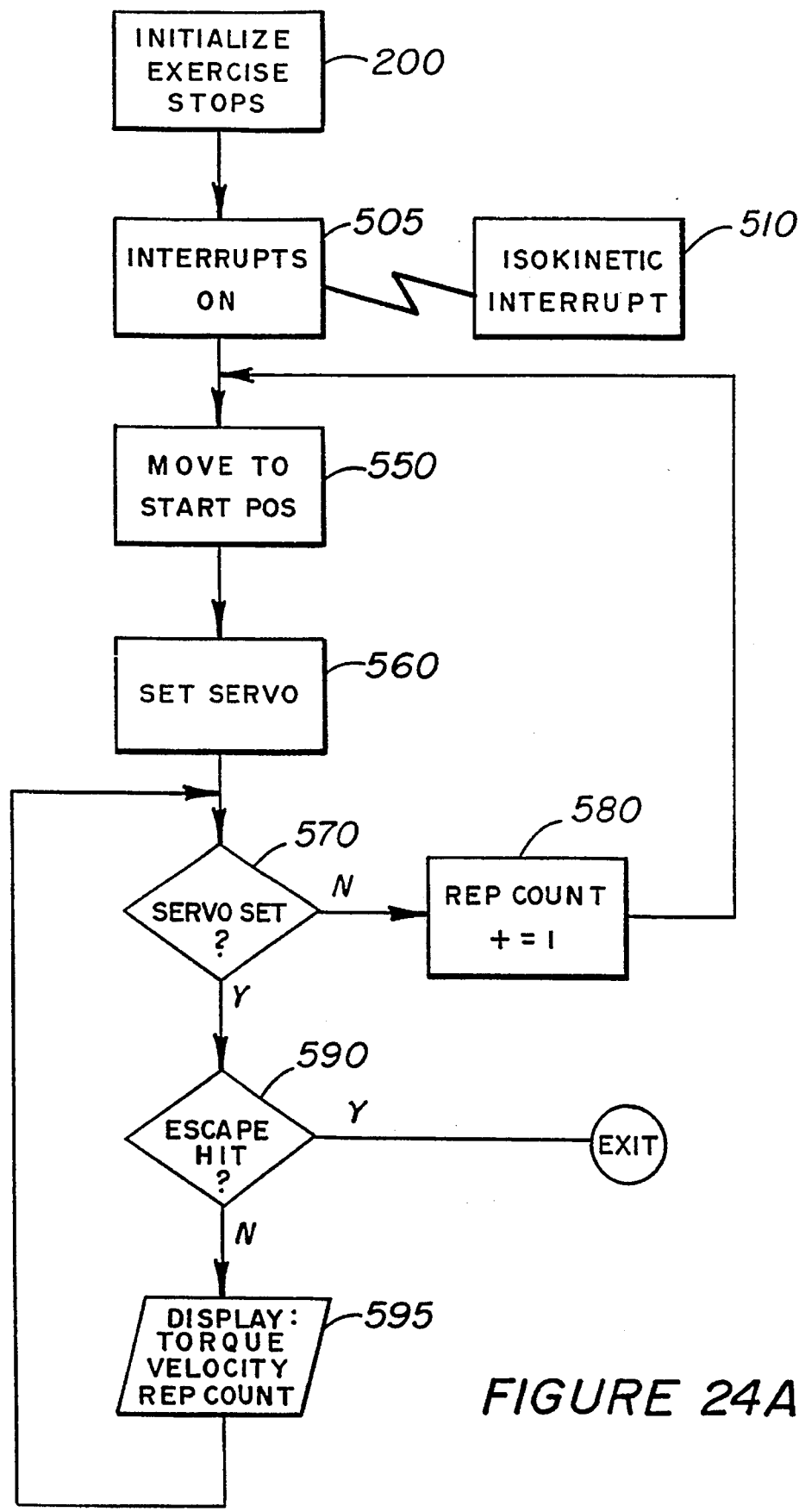
FIGS. 24a and 24b are flowcharts of the subroutines for implementing the isokinetic test mode of the evaluation and training system of the present invention.
Figure 24B:
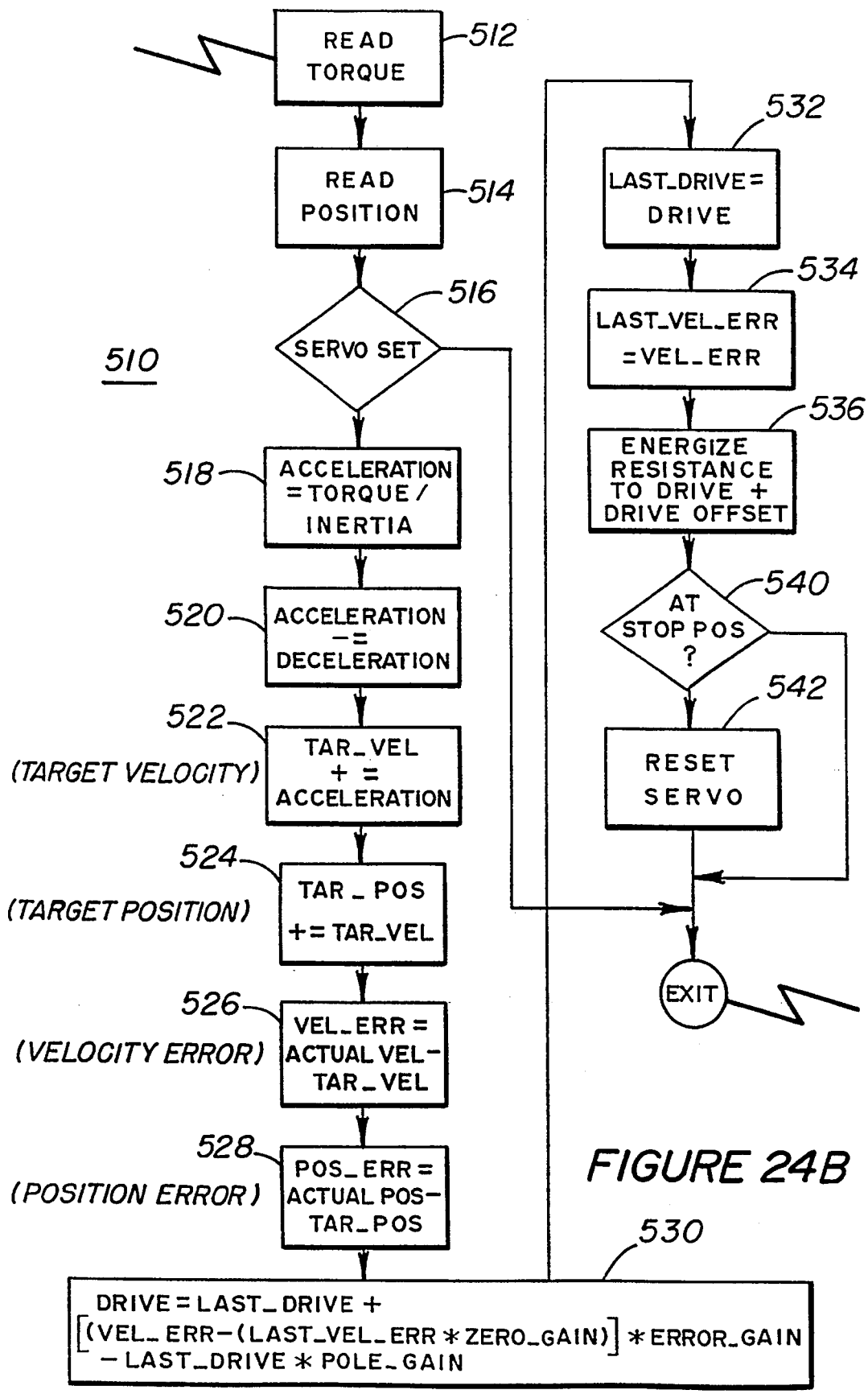

Isokinetic subroutine 500 for implementing the isokinetic test mode in accordance with the present invention is shown in FIGS. 24A and 24B. Again, subroutine 500, like subroutines 400 and 300, requires the exercise stops for the particular test subject to be programmed in accordance with the instructions set forth under subroutine 200 discussed above, either at the beginning of the individual isokinetic test sequence or at the beginning of an automated test sequence. In the isokinetic test mode, the system will dynamically adjust the torque resistance applied to the shaft 18 under a force supplied by test subject to maintain a constant velocity of movement of element 10 with respect to element 15.

Subroutine 500 immediately initializes interrupts 510 shown in FIG. 24B.

The isokinetic interrupt sequence 510 represents a dynamic control loop for providing the variable position/torque data to computer 180 to determine and implement the requisite resistive force required to maintain constant rotational velocity under the force applied by the test subject, which is necessary in isokinetic testing.

Isokinetic subroutine 500 first positions rotational element 10 at the first exercise stop position (step 550). Subsequently, at step 560, the servo loop which is utilized to dynamically adjust the torque resistance applied to shaft 18 is set. The system then checks, at step 570, to determine whether the servo loop flag is set. As will be understood after an analysis of the isokinetic interrupt sequence 510, if the servo loop flag is not set, the repetition counter increments at step 580 and the subroutine 500 loops to step 550. If the servo is set at step 570, the system awaits an escape sequence at step 590. If the escape sequence is not supplied at step 595, the system will display the torque, velocity, and repetition count.

Isokinetic interrupt sequence 510 will be hereafter described with reference to FIG. 24B. Interrupt sequence 510 begins with step 512 and 514 wherein the torque and position of shaft 18 are read via torque sensor 20 and rotary optical encoder 24, respectively. At step 516, interrupt sequence 510 checks to determine if the servo flag is set via step 560 as discussed above. If the servo flag is not set, the interrupt exits. If the servo is set at step 518, the system sets the ACCELERATION variable equal to the measured TORQUE divided by INERTIA. At step 520, the ACCELERATION variable is set to the current ACCELERATION variable value minus the DECELERATION. At step 522, the target velocity variable (TAR-VEL) is set to the current value of TAR_VEL plus ACCELERATION. Next, at step 524, the target position (TAR_POS) is set equal to the current TAR_POS plus TAR_VEL. At step 526, the velocity error (VEL_ERR) is set to be equal to the actual velocity (ACTUAL_VEL) minus the target velocity (TAR_VEL). The position error variable is then set to be equal the actual position (ACTUAL_POS) minus the target position (TAR_POS). The output drive current necessary is then computed by the equation: DRIVE=(LAST DRIVE+((VEL_ERR) - (LAST_VEL_ERR * ZERO_GAIN)) * ERROR_GAIN - LAST_DRIVE * POLE_GAIN) where the velocity error (VEL_ERR) is computed as set forth above, the last velocity error (LAST_VEL_ERR) and last drive (LAST_DRIVE) are variables recording the velocity error and drive value set forth in the previous interrupt cycle; ZERO_GAIN is approximately 20; ERROR_GAIN is approximately 100; and POLE_GAIN is approximately 5. The dynamics of the servo response can be changed by varying the values of ZERO_GAIN, ERROR_GAIN, and POLE_GAIN, as will be understood by those skilled in the art. The sequence then proceeds to step 532 where the LAST_DRIVE variable is set to the current DRIVE value. The LAST_VEL_ERR variable is sent to the current VEL_ERR value, and, at step 536, resistance element 22 is energized to provide the drive current plus drive offset values computed at step 530. If, at step 540, the rotatable element 10 is not at the stop position, the interrupt loops to exit. If rotational element 10 is at the stop position, interrupt sequence 510 proceeds to step 542 where the servo loop flag is reset and the interrupt exits. As will be well understood by those skilled in the art, the resolution of the isokinetic test sequence is thus dependent on the interrupt clock cycle.

Reaction time subroutine 600 will be described with reference to FIGS. 25A and 25B. The reaction time proprioceptive test operates by moving rotatable element 10 in a first direction and, at a random point in time, reverses the direction of element 10, requiring the test subject to respond by applying force against the direction reversal as soon as the direction reversal is detected. In this manner, the reaction time of the test subject to the direction reversal is measured.

Figure 25B:
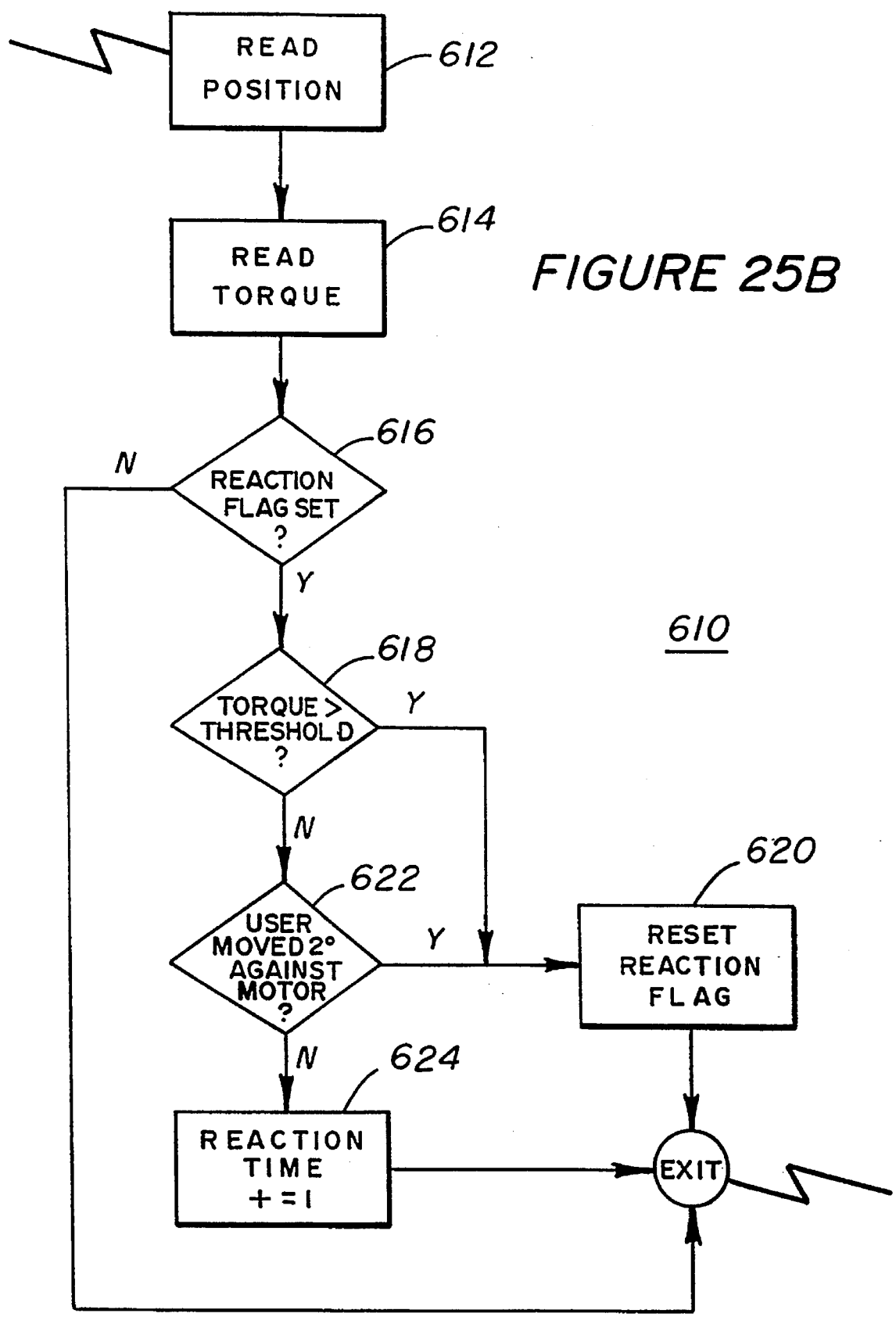

As shown in FIG. 25A, subroutine 600 begins by requiring that the exercise stops be initialized using subroutine 200. At step 605, reaction time interrupts 610 are enabled; the interrupt sequence is described below with respect to FIG. 25B. Sequence 600 thereafter moves rotatable element 10 to the start position for the test at step 630. At step 635, the reaction time variable is set to 0. At step 640, a random position between start position and stop position is generated and rotating element is allowed to move to the set random position. At step 650, when the rotatable element 10 has reached the random position, reaction flag is set and motor 28 is caused to reverse direction. After interrupt sequence 610, described below, computes the reaction time, the display sets forth the torque, reaction time, and repetition count at step 655. The system then queries whether the rotating element has been moved 25° against the test subject. If so, at step 662, the reaction flag is reset and, at step 665, the repetition counter is incremented. If, at step 660, the rotatable element 10 is not moved 25°, the subroutine 600 queries whether the reaction flag has been turned off. If the reaction flag has been turned off, the repetition counter increments. If not, the subroutine checks to see if the escape key was hit at 670 before looping back to step 655. Once the repetition counter has been incremented, the subroutine loops to step 630 and begins the next increment sequence of the test.

Reaction time interrupt sequence 510 will be described as with respect to FIG. 25B. At the beginning of interrupt sequence 610, the position of rotational element 10 is read (step 612) and the torque translated to the shaft 18 by force applied to element 10 by test subject is also read (step 614). At step 616, the interrupt checks to see if the reaction flag has been set at step 650 of subroutine 600. If not, the interrupt exits. If the reaction flag has been set, at step 618, interrupt 610 determines whether the torque is greater than the threshold torque. If so, the reaction flag is reset at step 620. If not, the system checks to determine whether the test subject has moved rotatable element 10 2° against the rotational direction of motor 28. If so, the reaction flag is reset. If not, the REACTION TIME counter is incremented by one at step 624. Thus, the resolution of the reaction time counter is dependent on interrupt clock sequence. Once the REACTION TIME counter variable is incremented, the interrupt exits.

Figure 26A:
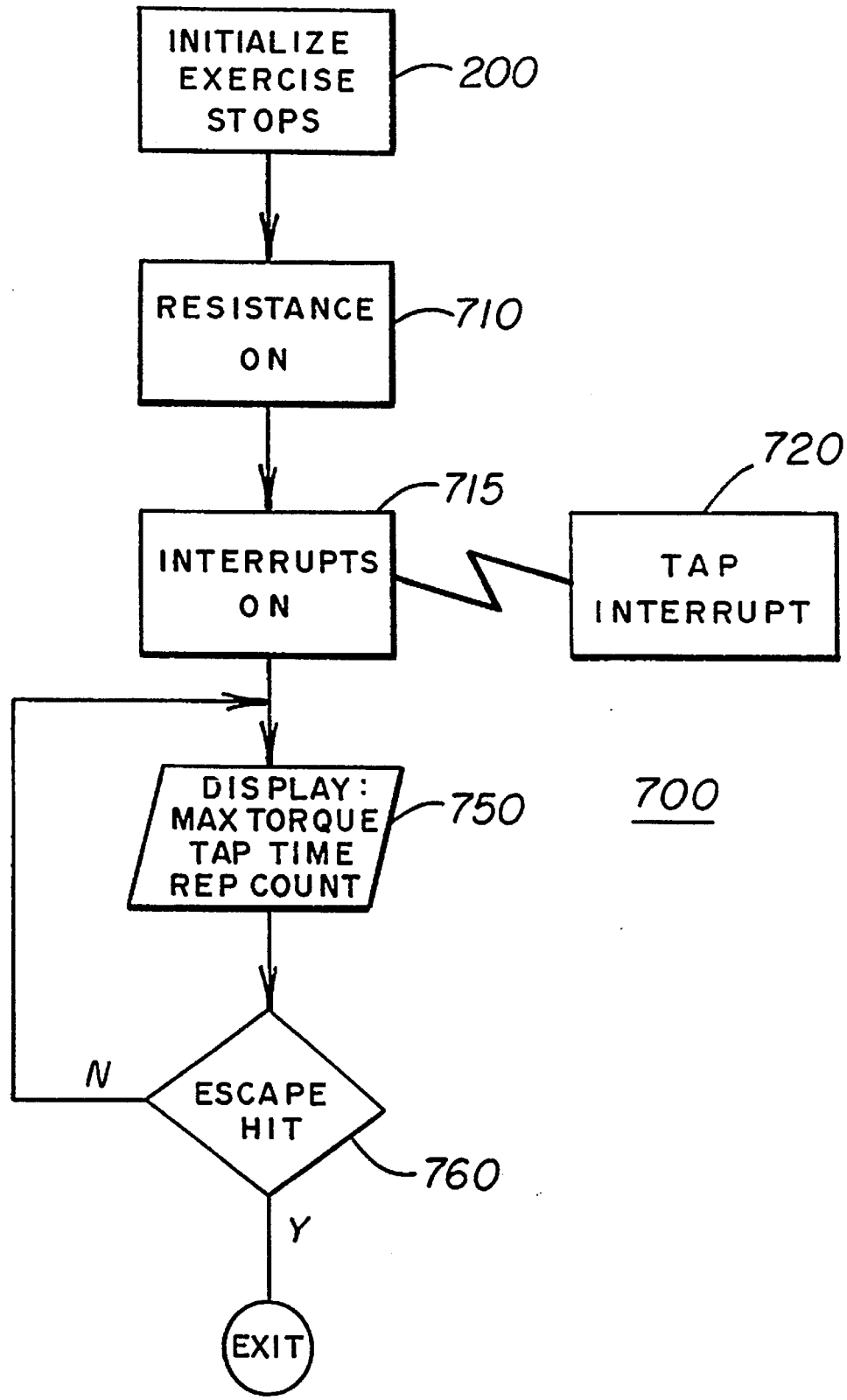
FIGS. 26a and 26b are flowcharts of the subroutines for implementing the tap response test mode of the evaluation and training system of the present invention.
Figure 26B:
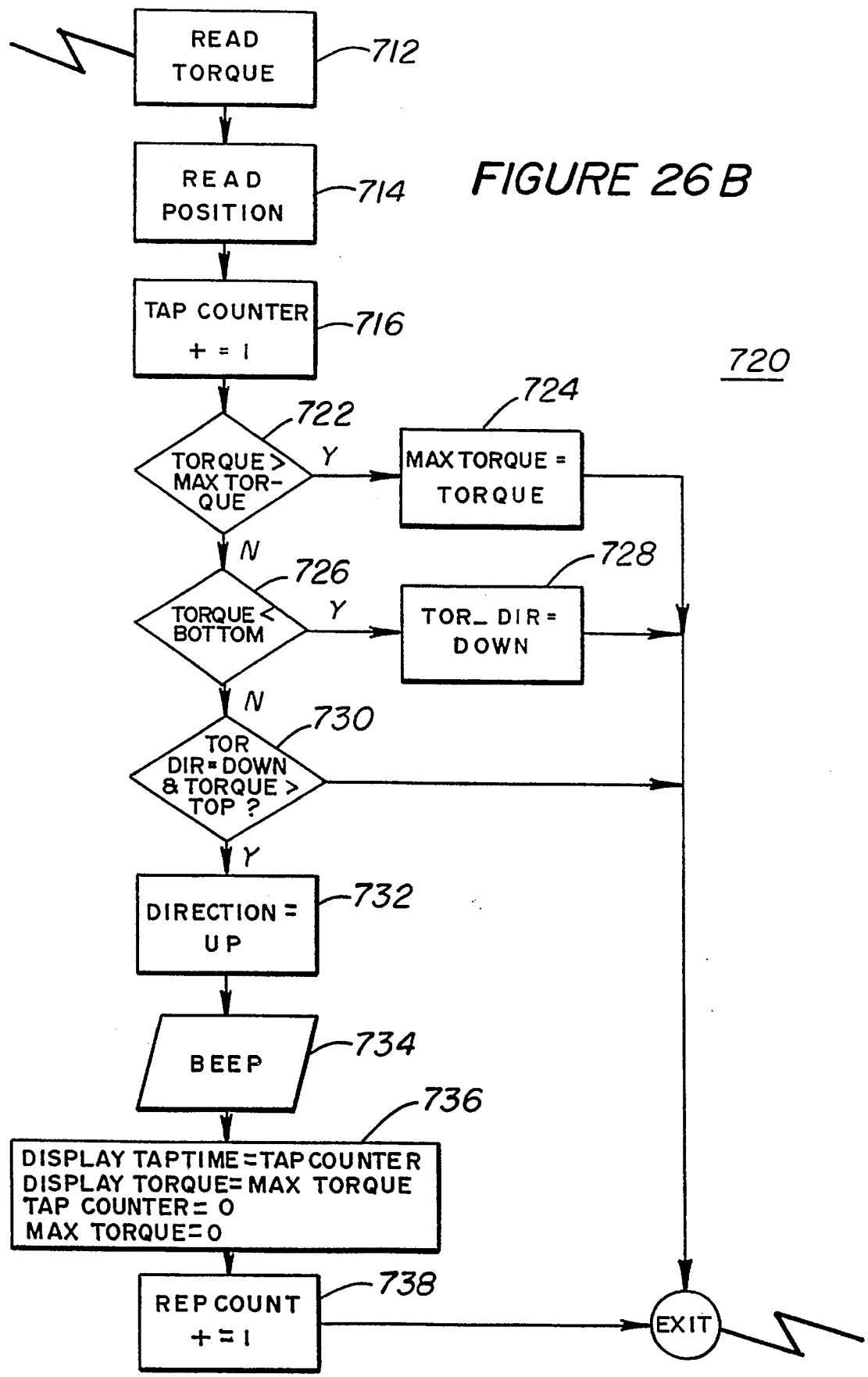

FIG. 26A shows the functional sequence for implementing the tap response mode of the testing and evaluation system of the present invention. In the tap response testing mode, rotational element 10 will be moved to the first exercise stop set in subroutine 200, the resistance element will provide a high rotational resistance, and the subject will be prompted to repeatedly contract his or her grasp on rotational element 10 and stationary element 15. The tap response mode thus measures the reactive contraction time of the particular test subject.

As shown in FIG. 26A, tap response subroutine 700 begins by requiring that at least one of the exercise stops be initialized by initialize exercise stops subroutine 200, as discussed above. Subsequently, brake 22 is turned to a "full on"0 mode (step 710) and tap interrupts 720 for the system are enabled. Subsequently, subroutine 700 displays maximum torque provided by the test subject during the test sequence (MAX_TORQUE), the tap time, and number of repetitions completed for each tap test sequence. Step 760 requires an escape key be hit to exit the tap mode. Until the escape is issued, the subroutine loops maintains the test result display.

Tap interrupt sequence 720 controls the tap measurement sequence and begins by reading the shaft torque (step 712), reading the position of rotational element 10 (step 714), and incrementing the tap counter (step 716). If the incoming tap cycle detects that the grip of the test subject is applying a maximum torque, at step 722, the MAX_TORQUE is set equal to the measured torque and the interrupt exits. If not, at step 726, the interrupt checks to determine whether the measured torque is less than the lower torque setpoint (BOTTOM). If so, the torque direction variable (TOR_DIR) is set DOWN (step 728) and the interrupt exits. As will be readily understood, the TOR_DIR, DOWN condition will only be met when the grip of the test subject is effectively released.

On the next succeeding grip by the test subject, if TORQUE is not greater than MAX_TORQUE, and not less than the BOTTOM torque, at TOR_DIR set to DOWN and TORQUE greater than the upper torque setpoint (TOP), at step 730, TOR_DIR is set to UP (step 732), and an audible tone is issued (step 734). Subsequently, at step 736, the display issues the TAP TIME (equal to the value of TAP_COUNT,) and the maximum torque, and resets the TAP COUNT and MAX_TORQUE equal to 0. Finally, the repetition counter is incremented (step 738).

Figure 27A:
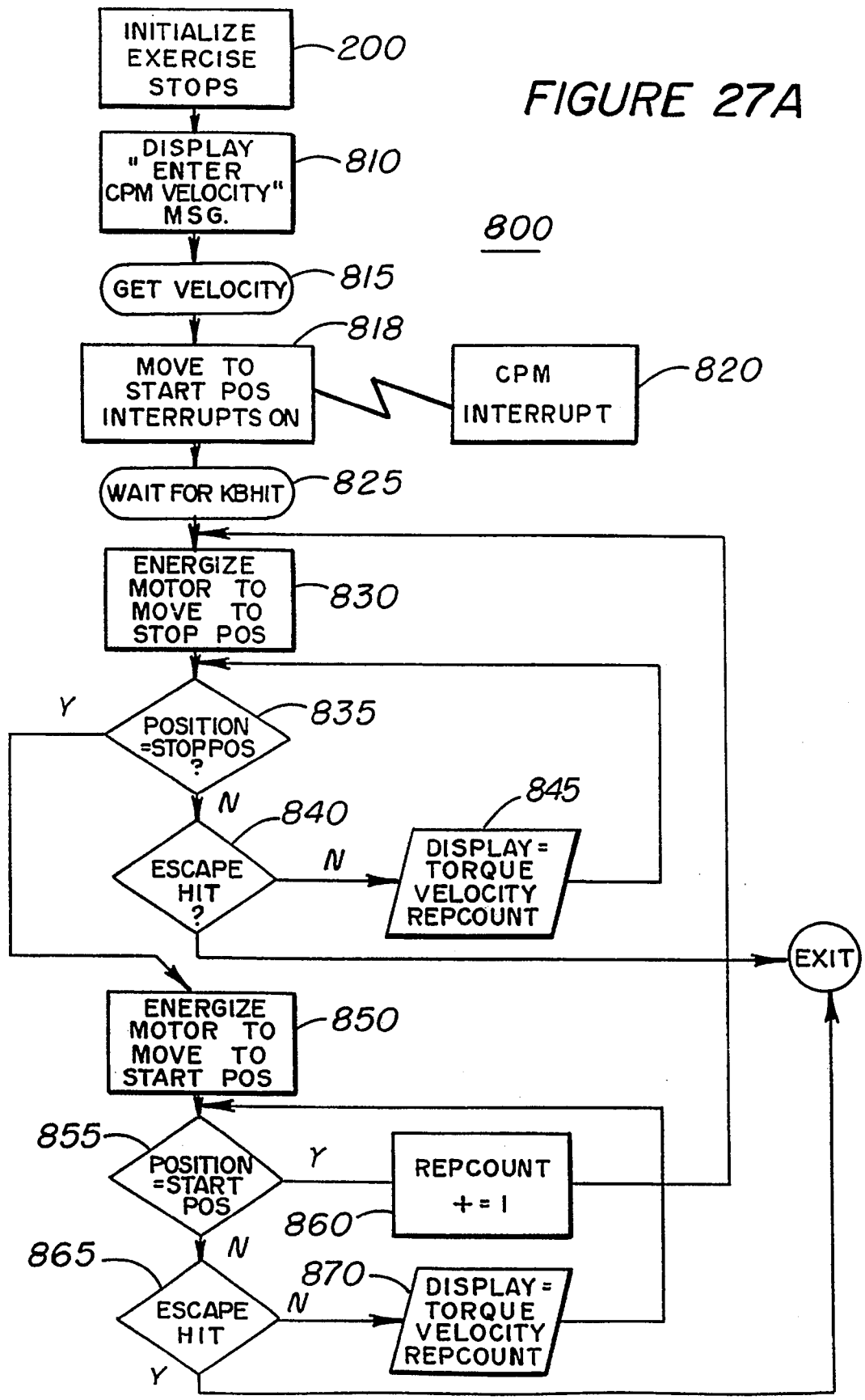
FIGS. 27a and 27b are flowcharts of the subroutines for implementing the continuous passive motion mode of the evaluation and training system of the present invention.
Figure 27B:
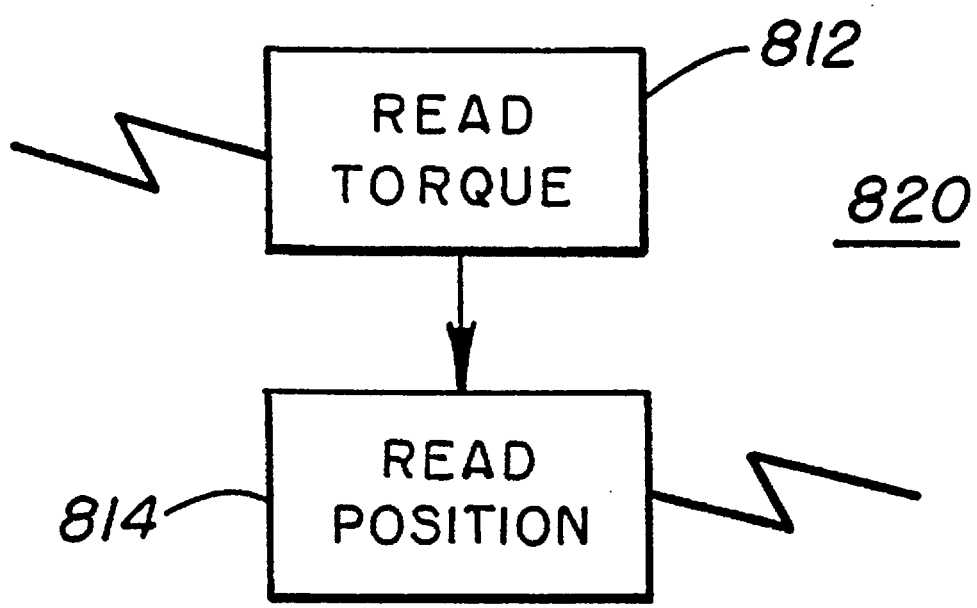

Continuous passive motion subroutine 800 for implementing the continuous passive motion mode of the testing and evaluation system of the present invention is shown in FIGS. 27A and 27B. As noted above, the continuous passive motion mode directs rotational element 10 about a predetermined rotational exercise movement scheme which directs the extension and contraction of the test subject's muscles.

Subroutine 800 begins by requiring execution of initialize exercise stops subroutine 200, described above. At step 810, an "ENTER CPM VELOCITY" message is output to display monitor 210. The therapist is thus prompted to enter a suitable velocity for the individual test subject via keyboard 205. At step 815, the subroutine 800 will retrieve the input velocity and at step 818, move element 10 to the start position (the first exercise stop) and enable the CPM interrupts 820. As shown in FIG. 27B, CPM interrupts 820 comprise reading the torque 812 and then reading the position 814 to allow the system to monitor both these elements during the CPM mode. At step 825, subroutine 800 waits for the keyed signal from the therapist governing the test. Once the key signal is entered (step 830), motor 28 is energized to move rotational element to the first position. Subroutine 800 continuously checks (step 835) to determine whether motor 28 has moved element 10 to the stop position (STOP_POS). Until rotational element 10 reaches the stop position, the therapist has an option to hit the ESCAPE key (step 840) and end the continuous passive motion mode. Otherwise, at step 845, during the rotational movement of rotational element 10, the display will output the torque, velocity, and repetition count while moving rotational element 10 from the start position to the stop position. If rotational element 10 reaches the STOP position, motor 28 is energized (step 850) to move in a reverse direction, back to the START position. Again, subroutine 800 continuously checks to determine if rotational element 10 has reached the START position. When the START position is reached, the repetition counter is incremented (step 860) and subroutine loops back to step 830. If the rotational element has not reach the STOP position, the therapist has the option of entering the escape key at step 865 to exit the subroutine. As will be noted at step 870, if the rotational element has not reached the STOP position and no escape key is hit, the torque, velocity, and repetition count are continuously displayed during the continuous passive motion mode.

A sample data output report for the system is shown in FIG. 28. As shown therein, the outputs of isometric subroutine 300 (average peak torque), isotonic subroutine 400 (work per repetition), isokinetic subroutine 500 (average peak torque), tap response (tap frequency and average tap time), and reaction time (average reaction time) are output to either monitor 210 or printer 207. In addition, a graph of the torque applied at each particular position throughout the rotation of element 10 (or the appropriate accessory) is also displayed, along with the subject's range of motion and the exercise stop positions.

The numerous aspects of the testing and evaluation system of the present invention will be apparent to those skilled in the art. Other aspects of the system are contemplated as being within the scope of the present invention and within the scope of the specification, and the attached claims.

APPENDIX A

© 1991 CEDARON MEDICAL, INC.

-76-

E.D.C. File Print-o  of AUTOCYCL.C,  on 11-3-91,  t 3:50 PM

```c
/* * * * * * * * * * * * * * * * * * * * * * * * * * * * * *
 *
 *   File: AUTOCYCL.C
 *   Date: 05/05/91
 *   Time: 11:27:48.15
 *   Author: Joe Forma
 *
 * * * * * * * * * * * * * * * * * * * * * * * * * * * * */ include <vcstdio.h>
include <alloc.h>
#include <string.h>
#include <conio.h>
include <dos.h> include "loadmsgs.h"
include "utility.h"
#include "status.h"
#include "setutil.h"
#include "siconver.h"
#include "cntrlrio.h"
include "setupdma.h"
#include "rtint.h"
#include "lowlevel.h"
#include "initstop.h"
#include "setstops.h"
#include "isomet.h"
#include "isotonic.h"
#include "isokinet.h"
#include "cpm.h"
#include "tap.h"
#include "reaction.h"
#include "summary.h"
#include "autocycl.h"

/****************************************************/
/*                       CODE                       */
/****************************************************/ void initAutoCycle(void)
{
}

COUNT runAutoCycleFunc(void)
{
    showAvail();
    autoCycle=wxxopen(5,0,23,79,(TEXT *)"",
                ACTIVE|BORDER|BD2|SCROLL|WDWRAP|COOKED|STANDARD|CURSOR,
                17,78,8,32);
    if( autoCycle == -1 )
        terror(msgListPtrs->Msg[Unable_To_Open_Init_Stops_Window]);
    wat(autoCycle,0,0);                    // need to position the cursor if (!runInitStopsFunc())
```

-77-

```
        if (!runSetStop   nc())
          if (!runIsome.  cFunc())
            if (!runIsotonicFunc())
              if (!runIsokineticFunc())
                if (!runTapFunc())
                  if (!runReactionFunc())
                    doSummary();

wclose(autoCycle);
    autoCycle = 0;
    showAvail();
    brakeOff();
    clutchOff();
    return(GOOD);
}

/*
 * End Of File
 */
```

E.D.C. File Print-out of BGISTUFF.C, on 11-3-91, 3:50 PM

```c
include <graphics.h> include "bgistuff.h"

int huge detectVGA256(void)
{
int DetectedDriver;
int SuggestedMode;

detectgraph(&DetectedDriver, &SuggestedMode);

if ((DetectedDriver == VGA) || (DetectedDriver == MCGA))
    return(0);
  else
    return(grError);
} void installVGA256(void)
{
  VGA256_driver = installuserdriver("VGA256", detectVGA256);
} int installFont(void)
{
  userFont = installuserfont("TRIP.CHR");
  return(graphresult());
}
```

-79-

E.D.C. File Print-   of BIOSTUFF.C,   on 11-3-91,   at 3:50 PM

```c
#include   <vcstdio.h>
#include   <graphics.h>
include   <string.h> include   "biostuff.h"

void displayBioInfo(int parm,

{
        int column,row;
        char outStr[2];

sprintf(tempStr,"%4d",parm);
        if (tempStr[*digit] != lastTempStr[*digit])
        {
                setcolor(BLACK);
                column = x + ((*digit)*FONT_WIDTH);
                for (row=y;row<(y+FONT_HEIGHT);row++)
                        line(column,row,column+FONT_HEIGHT-1,row);
                strncpy(outStr,&tempStr[*digit],1);
                outStr[1] = 0;
                setcolor(color);
                outtextxy(column,y,outStr);
        }
        lastTempStr[*digit] = tempStr[*digit];
        *digit -=1;
        if (*digit < 0)
                *digit = 3;
} void displayBioInfo1Place(int parm, int x,
                          int y,
                          int *digit,
                          char *tempStr,
                          char *lastTempStr)
{
  int column,row;
  char outStr[2];

sprintf(tempStr,"%3f",(float)(parm)/10);
  if (tempStr[*digit] != lastTempStr[*digit])
  {
    setcolor(BLACK);
    column = x + ((*digit)*FONT_WIDTH);
    for (row=y;row<(y+FONT_HEIGHT);row++)
      line(column,row,column+FONT_HEIGHT-1,row);
    strncpy(outStr,&tempStr[*digit],1);
    outStr[1] = 0;
    setcolor(color);
    outtextxy(column,y,outStr);
```

-80-

```
    }
    lastTempStr[*digit] = tempStr[*digit];
    *digit -=1;
    if (*digit < 0)
      *digit = 3;
} void displayBioInfoDigit(int parm,
                        int color,
                        int x,
                        int y,
                        char *tempStr,
                        char *lastTempStr)
{
  int column,row;
  char outStr[2];

if (parm > 9)
    parm = 9;
  sprintf(tempStr,"%1d",parm);
  if (tempStr[0] != lastTempStr[0])
  {
    setcolor(BLACK);
    column = x + FONT_WIDTH;
    for (row=y;row<(y+FONT_HEIGHT);row++)
      line(column,row,column+FONT_HEIGHT-1,row);
    strncpy(outStr,&tempStr[0],1);
    outStr[1] = 0;
    setcolor(color);
    outtextxy(column,y,outStr);
  }
  lastTempStr[0] = tempStr[0];
}
```

−81−

E.D.C. File Print-out  CPM.C,  on 11-3-91,  at 3  PM

```c
#define LINEARIZED
#define MOTORCURRENT
/* * * * * * * * * * * * * * * * * * * * * * * * * * *
 *
 *    File: CPM.C
 *    Date: 05/05/91
 *    Time: 11:27:48.15
 *    Author: Joe Forma
 *
 * * * * * * * * * * * * * * * * * * * * * * * * * * */ include <vcstdio.h>
include <graphics.h>
#include <alloc.h>
#include <string.h>
#include <conio.h>
include <dos.h>
include <math.h> include "loadmsgs.h"
include "utility.h"
#include "status.h"
#include "setutil.h"
#include "siconver.h"
#include "cntrlrio.h"
include "setupdma.h"
#include "rtint.h"
#include "lowlevel.h"
#include "biostuff.h"
#include "lineariz.h"
#include "autocycl.h"
#include "cpm.h"

/******************************************************/
/*                     CODE                           */
/******************************************************/ define MODE_Y          20
define MODE_X          220 define TORQUE_Y        120
define TORQUE_X        200 define VELOCITY_Y      240
define VELOCITY_X      200 static char torqueStr[8],
                                lastTorqueStr[8];
static int torqueDigit;
static char velocityStr[8],
                                lastVelocityStr[8];
static int velocityDigit;
static int displayTorque;
static int velocity;
static long endStop,startStop;
```

-82-

```
#ifndef MOTORCURRENT
static int repcount;
endif void initCPMBioFeedBack(void)
{
  velocity = 0;
  setcolor(WHITE);
  strcpy(torqueStr,"aaaa");
  strcpy(lastTorqueStr,torqueStr);
  strcpy(velocityStr,"aaaa");
  strcpy(lastVelocityStr,velocityStr);
  settextstyle(TRIPLEX_FONT,HORIZ_DIR,FONT_MULTIPLIER);
  outtextxy(MODE_X,MODE_Y,"   CPM");
  outtextxy(0,TORQUE_Y,"TORQUE");
  outtextxy(0,VELOCITY_Y,"VELOCITY");
  torqueDigit = 3;
  velocityDigit = 3;
} int CPMBioFeedBack(void)
{
  int i;

if (bioCount > 30)
  {
    captureBioData = true;
    while(captureBioData) ;
  }
  else
    return(0);

displayTorque = abs(bioTorque/10);
  velocity = bioVelocity;
  velocity = (int)((float)velocity*250.0*float_DPP);
  for (i=0;i<4;i++)
  {
    displayBioInfo(displayTorque,
                   YELLOW,
                   TORQUE_X,
                   TORQUE_Y,
                   &torqueDigit,
                   torqueStr,
                   lastTorqueStr);
    displayBioInfo(velocity,
                   YELLOW,
                   VELOCITY_X,
                   VELOCITY_Y,
                   &velocityDigit,
                   velocityStr,
                   lastVelocityStr);
  }
  return(0);
} void initCPM(void)
{
}
```

-83-

```c
COUNT runCPMFunc(void)
{
  enum {left,right};
  int quickExit = 0;
  int done2 = 0,done = 0;
  long inputStop1,inputStop2;
  int cpmVelocity;
  TEXT cpmVelocityStr[6];
  int  result = GOOD;
#ifndef MOTORCURRENT
  int hand;
  int velInCounts;
endif showAvail();
  cpm=wxxopen(5,0,23,79,(TEXT *)"",
              ACTIVE|BORDER|BD2|SCROLL|WDWRAP|COOKED|STANDARD|CURSOR,
              17,78,8,32);
  if( cpm == -1 )
    terror(msgListPtrs->Msg[Unable_To_Open_Cpm_Window]);
  wat(cpm,0,0);                          // need to position the cursor
  if (goodStops())
  {
    brakeOff();
    clutchOff();
    while ((!done) && (!quickExit))
    {
      atsay(0,34,(TEXT*)"CPM SET STOPS");
      sayLineFeed();
      sayLineFeed();
      sayString("Move stop #1");
      sayLineFeed();
      say(msgListPtrs->Msg[Press_Any_Key_Escape_To_Exit]);
      sayLineFeed();
      sayLineFeed();
      quickExit = waitHitThenFlushOrEscape();
      if (quickExit)
        break;
      inputStop1 = doInterrupt ? realTimePosition : readActualPosition();
      sayString("Move stop #2");
      sayLineFeed();
      say(msgListPtrs->Msg[Press_Any_Key_Escape_To_Exit]);
      sayLineFeed();
      sayLineFeed();
      quickExit = waitHitThenFlushOrEscape();
      if (quickExit)
        break;
      inputStop2 = doInterrupt ? realTimePosition : readActualPosition();
      if (labs(inputStop1 - inputStop2) > NINE_DEGREES)
        done = 1;
      else
      {
        sayString("Insufficient Range of Motion");
        sayLineFeed();
        say(msgListPtrs->Msg[Press_Any_Key_Escape_To_Exit]);
        sayLineFeed();
        quickExit = waitHitThenFlushOrEscape();
        if (quickExit)
```

-84-

```
          break;
        erase();
        wat(cpm,0,0);                             // need to position the cursor
      }
    }
    if (!quickExit)
    {
      while (!done2)
      {
        done = 0;
        while (!done)
        {
          erase();
          at(1,0);                                // need to position the curs
          sayString("Press Escape to Exit");
          at(0,0);                                // need to position the cursor
          sayString("Enter CPM Velocity in Degrees/Second = ");
          empty(cpmVelocityStr,sizeof(cpmVelocityStr));
          get(cpmVelocityStr,(TEXT *)"999");
          readgets();
          cpmVelocity = 0;
          sscanf((char *)cpmVelocityStr,"%d",&cpmVelocity);
#ifdef MOTORCURRENT
          if ((cpmVelocity >= 10) && (cpmVelocity <= 100))
             done = 1
#ifdef LINEARIZED
             ,cpmVelocity = calcCPMVelocity(cpmVelocity);
#else
             ;
#endif
#else
          if ((cpmVelocity >= 1) && (cpmVelocity <= 180))
             done = 1;
#endif
          if (cpmVelocity == 0)
             done2 = 1,done = 1,result = BAD;
        }
        if ((inputStop1 + inputStop2)/2 < (midpoint))  // assume right hand
        {
#ifndef MOTORCURRENT
          hand = right;
#endif
          if (inputStop1 < inputStop2)
          {
            startStop = inputStop2;
            endStop = inputStop1;
          }
          else
          {
            startStop = inputStop1;
            endStop = inputStop2;
          }
        }
        else // assume left hand
        {
#ifndef MOTORCURRENT
          hand = left;
#endif
          if (inputStop1 < inputStop2)
          {
```

-85-

```
              startSto   inputStop1;
              endStop     nputStop2;
            }
            else
            {
              startStop = inputStop2;
              endStop = inputStop1;
            }
          }
          if (!done2)
          {
            erase();
            done = idleMoveToPosition(startStop);
            say(msgListPtrs->Msg[Press_Any_Key_Escape_To_Exit]);
            sayLineFeed();
            sayString("cwStop = ");
            sayLong(cwStop);
            sayString("  ccwStop = ");
            sayLong(ccwStop);
            sayLineFeed();
            sayString("startStop = ");
            sayLong(startStop);
            sayString("  endStop = ");
            sayLong(endStop);
            sayLineFeed();
            quickExit = waitHitThenFlushOrEscape();
            if (!quickExit)
            {
              setgraphmode(getgraphmode());
              initCPMBioFeedBack();
#ifdef MOTORCURRENT
              startInt();                    //
              doInterrupt = true;                    //
              waitForInterrupt = true;
              while(waitForInterrupt) ;
              brakeOff();
              clutchOn(MAXCLUTCH);
              done = 0;  // reset done
              while (!done)
              {
                done = idleVelMoveToPosition(endStop,cpmVelocity,CPMBioFeedBack);
                if (!done)
                {
                  done = idleVelMoveToPosition(startStop,cpmVelocity,CPMBioFeedBac
                }
              }
              if (autoCycle)
                done2 = 1;
              enterIdleMode();
              doInterrupt = false;                    //
              stopInt();
#else
              startInt();                    //
              doInterrupt = true;                    //
              waitForInterrupt = true;
              while(waitForInterrupt) ;
              brakeOff();
              clutchOn(MAXCLUTCH);
              if (hand == left)
                enterIntegralVelocityMode();   // start velocity based mode
```

```
                       else
                         enterProportionalVelocityMode();
                       done = 0;  // reset done
                       velInCounts = calcVelocity(cpmVelocity);
                       repcount = 0;
                       while (!done)
                       {
                         done = velMoveToPosition(endStop,velInCounts,CPMBioFeedBack,0);
                         if (!done)
                         {
                           done = velMoveToPosition(startStop,velInCounts,CPMBioFeedBack,0)
                           repcount++;
                         }
                       }
                       if (autoCycle)
                         done2 = 1;
                       enterIdleMode();
                       doInterrupt = false;                       //
                       stopInt();
#endif
                       kbFlush();
                       restorecrtmode();
                       textbackground(WHITE);
                       clrscr();
                     }
                     else
                       result = BAD;
                   }
                 }
               }
               else
                 result = BAD;
             }
             else
             {
               result = BAD;
               sayString("Need to initialize controller first");
               sayLineFeed();
               sayString("Press any key to continue");
               waitHitThenFlush();
             }
             textbackground(WHITE);
             clrscr();
             wclose(cpm);
             showAvail();
             brakeOn(1);
             clutchOff();
             return(result);
           }
           /*
            * End Of File
            */
```

-87-

E.D.C. File Print-out ` DEXTER.C, on 11-3-91, a :51 PM

```c
/* * * * * * * * * * * * * * * * * * * * * * * * * *
 *
 *      File: dexter.c
 *      Date: 05/05/91
 *      Time: 11:27:48.15
 *    Author: Joe Forma
 *
 * * * * * * * * * * * * * * * * * * * * * * * * * */ include <vcstdio.h>
include <graphics.h>
#include <dos.h>
include <conio.h>
#include <string.h>
#include <stdlib.h>
include <alloc.h> define GLOBALS include "dexter.h"

void installPrintScreen(void);
void removePrintScreen(void);

static int gdriver = VGA,
                           gmode = VGAMED,
                           errorcode;
int dbg = 0; //runtime debug print flag
int isomcollect = 0; // isometric data collect flag static char programPath[80];  // path where this program resides
static char file1Path[80];    // used to combine path with filename where neede
static char file2Path[80];    // used to combine path with filename where neede COUNT set_colors(void);

/****************************************************/
/*                       CODE                       */
/****************************************************/
void main(int argc,char *argv[])
{
  int i;

strcpy(programPath,argv[0]);
          i = strlen(programPath);
  while (i > 0)
  {
    if (programPath[i] != '\\')
      i--;
    else
      programPath[++i] = 0,i=0;
  }
  if (argc > 1)
  {
    if (stricmp(argv[1],"HELP") == 0)
            {
```

-88-

```
                        clrscr();
                        puts("Usage: DEXTER [A1]");
                        puts("");
                        puts("Where A1 = HELP");
                        puts("           This message.");
                        puts("");
                        puts("Where A1 = CAL");
                        puts("           In isometric test display torque in un
                        puts("");
                        puts("Where A1 = DATA");
                        puts("           Collect data into isomdata.txt file in
                        puts("");
                        puts("Where A1 = DEBUG");
                        puts("           Display debug info and allow parametry
                        puts("");
                        puts("Where A1 = Some number between 10 and 100");
                        puts("           During autocycle when in isotonic test
                        puts("           in units of in/lbs.");
                        exit(1);
                }
                else
                        if (stricmp(argv[1],"CAL") == 0)
                                calibrate = true;
                else
                        if(stricmp(argv[1],"DEBUG") == 0)
                                dbg = true;
                else
                        if(stricmp(argv[1],"DATA") == 0)
                                isomcollect = true;
        else
                        {
                                sscanf(argv[1],"%4d",&autoIsotonicTorque);
                                if (autoIsotonicTorque != 0)
                                        if (autoIsotonicTorque > 100)
                                                autoIsotonicTorque = 100;
                                        else
                                                if (autoIsotonicTorque < 10)
                                                        autoIsotonicTorque = 10
                        }
        }
        installPrintScreen();
        vcstart(CLRSCRN);
        loadErrorMsgs(programPath);
        if (registerbgidriver(EGAVGA_driver) < 0)
                terror((TEXT *) "BGI EGAVGA file not registered" );
        if (registerbgifont(triplex_font) < 0)
                terror((TEXT *) "triplex font not registered" );
        initgraph(&gdriver,&gmode, "");
        errorcode = graphresult();
if (errorcode)
   terror((TEXT *) "unable to initialize graphics driver" );
restorecrtmode();
vcdgt = tblalloc(NULL); /* allocate the gettable starter for now */
set_colors();
xerase(vc.bg*vc.white);
strcpy(file1Path,programPath);
strcat(file1Path,"dexter.msg");
strcpy(file2Path,programPath);
strcat(file2Path,"dexter.ndx");
if (hopen((TEXT *)file1Path,(TEXT *)file2Path))
```

```
      terror(msgListPt  ->Msg[Help_File_Not_Found]);
    dflthlp((TEXT *)"h  LP");
    setkeyfunc(vcprokey);
    sethelp(vchelp);
    exitkey(ESC);
    wdokey(0);
    initStatusWindow();
    initInitStops();
    prepHeaderBox();
    prepMainMenu();
//    showHeaderBox();
    vxmenuopen(mainMenu,SINGLE);
    showAvail();
    dataPointer = malloc(sizeof(dataPoint[DATAMAX]));
    showAvail();
    if (!dataPointer)
      terror((TEXT*)"Unable to allocated data collection buffer");
    else
      if (makeLinearizationTableIsotonic() != 0)
        terror((TEXT *) "Unable to linearize torque table" );
      else
        if (makeLinearizationTableCPM() != 0)
          terror((TEXT *) "Unable to linearize velocity table" );
        else
//          doSummary();
          vxmenu(mainMenu,SINGLE);
    free(dataPointer);
    showAvail();
    undoMainMenu();
    hclose();
    closegraph();
    vcend(CLOSE);
    removePrintScreen();
    xerase(vc.white+(vc.bg*vc.black));
    } saveHooks(PFI *saveList)
{
  saveList[0] = vcmhook1;
  saveList[1] = vcmhook2;
  saveList[2] = vcmhook3;
  saveList[3] = vcmhook4;
  saveList[4] = vcmhook5;
  vcmhook1 = NULL;
  vcmhook2 = NULL;
  vcmhook3 = NULL;
  vcmhook4 = NULL;
  vcmhook5 = NULL;
  return(GOOD);
} restoreHooks(PFI *saveList)
{
  vcmhook1 = saveList[0];
  vcmhook2 = saveList[1];
  vcmhook3 = saveList[2];
  vcmhook4 = saveList[3];
```

```
    vcmhook5 = saveList   ;
    return(GOOD);
}

COUNT set_colors(void)
{

/* Color Set 0 */
    wtable[0].bd_t    =   vc.white+vc.bold+(vc.bg*vc.blue);
    wtable[0].bg_t    =   vc.white+vc.bold+(vc.bg*vc.blue);
    wtable[0].say_t   =   vc.brown+vc.bold+(vc.bg*vc.blue);
    wtable[0].nget_t  =   vc.brown;
    wtable[0].get_t   =   vc.red+vc.bold;
    wtable[0].tit_t   =   vc.white+vc.bold;

/* Color Set 1 */
    wtable[1].bd_t    =   vc.white+vc.bold+(vc.bg*vc.blue);
    wtable[1].bg_t    =   vc.white+vc.bold+(vc.bg*vc.blue);
    wtable[1].say_t   =   vc.brown+vc.bold+(vc.bg*vc.blue);
    wtable[1].nget_t  =   vc.brown;
    wtable[1].get_t   =   vc.red+vc.bold;
    wtable[1].tit_t   =   vc.white+vc.bold;

/* Color Set 2 */
    wtable[2].bd_t    =   vc.white+vc.bold+(vc.bg*vc.blue);
    wtable[2].bg_t    =   vc.white+vc.bold+(vc.bg*vc.blue);
    wtable[2].say_t   =   vc.brown+vc.bold+(vc.bg*vc.blue);
    wtable[2].nget_t  =   vc.brown;
    wtable[2].get_t   =   vc.red+vc.bold;
    wtable[2].tit_t   =   vc.white+vc.bold;

/* Color Set 3 */
    wtable[3].bd_t    =   vc.white+vc.bold+(vc.bg*vc.blue);
    wtable[3].bg_t    =   vc.white+vc.bold+(vc.bg*vc.blue);
    wtable[3].say_t   =   vc.brown+vc.bold+(vc.bg*vc.blue);
    wtable[3].nget_t  =   vc.white;
    wtable[3].get_t   =   vc.white;
    wtable[3].tit_t   =   vc.white;

/* Color Set 4 */
    wtable[4].bd_t    =   vc.white+vc.bold+(vc.bg*vc.blue);
    wtable[4].bg_t    =   vc.white+vc.bold+(vc.bg*vc.blue);
    wtable[4].say_t   =   vc.brown+vc.bold+(vc.bg*vc.blue);
    wtable[4].nget_t  =   vc.brown;
    wtable[4].get_t   =   vc.white+vc.bold;
    wtable[4].tit_t   =   vc.white+vc.bold;

/* Color Set 5 */
    wtable[5].bd_t    =   vc.white+vc.bold+(vc.bg*vc.blue);
    wtable[5].bg_t    =   vc.white+vc.bold+(vc.bg*vc.blue);
    wtable[5].say_t   =   vc.white+vc.bold+(vc.bg*vc.blue);
    wtable[5].nget_t  =   vc.brown+vc.bold+(vc.bg*vc.blue);
    wtable[5].get_t   =   vc.brown+vc.bold+(vc.bg*vc.red);
    wtable[5].tit_t   =   vc.white+vc.bold+(vc.bg*vc.blue);

/* Color Set 6 */
    wtable[6].bd_t    =   vc.white+vc.bold+(vc.bg*vc.black);
    wtable[6].bg_t    =   vc.white+vc.bold+(vc.bg*vc.black);
    wtable[6].say_t   =   vc.white+vc.bold+(vc.bg*vc.black);
```

```
wtable[6].nget_t =      .white+vc.bold;
wtable[6].get_t  =     ..brown+vc.bold+vc.blink+(vc.b_  vc.red);
wtable[6].tit_t  =    vc.white+vc.bold;

/* Color Set 7 */    /* */
wtable[7].bd_t   =    vc.brown+vc.bold+(vc.bg*vc.black);
wtable[7].bg_t   =    vc.brown+vc.bold+(vc.bg*vc.black);
wtable[7].say_t  =    vc.brown+vc.bold+(vc.bg*vc.black);
wtable[7].nget_t =    vc.brown+vc.bold+(vc.bg*vc.black);
wtable[7].get_t  =    vc.brown+vc.bold+(vc.bg*vc.black);
wtable[7].tit_t  =    vc.brown+vc.bold;

/* Color Set 8 */    /* */
wtable[8].bd_t   =    vc.blue+(vc.bg*vc.white);
wtable[8].bg_t   =    vc.blue+(vc.bg*vc.white);
wtable[8].say_t  =    vc.blue+(vc.bg*vc.white);
wtable[8].nget_t =    vc.black+(vc.bg*vc.white);
wtable[8].get_t  =    vc.black+(vc.bg*vc.cyan);
wtable[8].tit_t  =    vc.white+vc.bold;

/* Color Set 9 */
wtable[9].bd_t   =    vc.blue+(vc.bg*vc.white);
wtable[9].bg_t   =    vc.blue+(vc.bg*vc.white);
wtable[9].say_t  =    vc.blue+(vc.bg*vc.white);
wtable[9].nget_t =    vc.blue+(vc.bg*vc.white);
wtable[9].get_t  =    vc.blue;
wtable[9].tit_t  =    vc.blue+(vc.bg*vc.white);
return(GOOD);
}

/*
 * End Of File
 */
```

E.D.C. File Print-ou* ᶠ HEADER.C,    on 11-3-91,    a˙   :52 PM

```c
/* * * * * * * * * * * * * * * * * * * * * * * * * * * * *
 *
 *    File: HEADER.c
 *    Date: 05/05/91
 *    Time: 11:27:48.15
 *  Author: Joe Forma
 *
 * * * * * * * * * * * * * * * * * * * * * * * * * * * * */ include <vcstdio.h>
include <string.h> include "header.h"
include "loadmsgs.h"

/************************************************************/
/*                        CODE                            */
/************************************************************/ void prepHeaderBox()
{
 headerBox=wxxopen(0,0,4,79,(TEXT *)"",
                   BORDER|BD1,
                   3,78,0,32);
 if( headerBox == -1 )
    terror(msgListPtrs->Msg[Unable_To_Open_Header_Window]);
 xatsay(1,31,msgListPtrs->Msg[Name_And_Version],vc.dflt);
} void showHeaderBox()
{
  wshow(headerBox);
}

/*
 * End Of File
 */
```

—93—

E.D.C. File Print-out  INITSTOP.C,   on 11-3-91,    3:52 PM

```c
/* * * * * * * * * * * * * * * * * * * * * * * * * * *
 *
 *    File: INITSTOP.C
 *    Date: 05/05/91
 *    Time: 11:27:48.15
 *  Author: Joe Forma
 *
 * * * * * * * * * * * * * * * * * * * * * * * * * * */ include <vcstdio.h>
include <alloc.h>
#include <string.h>
#include <conio.h>
include <dos.h> include "loadmsgs.h"
include "utility.h"
#include "status.h"
#include "setutil.h"
#include "siconver.h"
#include "cntrlrio.h"
include "setupdma.h"
#include "rtint.h"
#include "lowlevel.h"
#include "initstop.h"

extern int zeroFlag;
extern int calibrate;
extern int dbg;
/***********************************************************/
/*                         CODE                            */
/***********************************************************/ void initInitStops(void)
{
}

COUNT runInitStopsFunc(void)
{
        int   resultBad = 0;

showAvail();
        initStops=wxxopen(5,0,23,79,(TEXT *)"",
                                                                ACTIVE|
        if( initStops == -1 )                                   17,78,8
                    terror(msgListPtrs->Msg[Unable_To_Open_Init_Stops_Window
        wat(initStops,0,0);                     // need to position the curs
        sayString("Hands Off Please - Initializing Controller");
        sayLineFeed();
        sayLineFeed();
        initController();
        resultBad = doInitialPosition();        // setup the controller
        if (resultBad)                          // do initial stops seek
```

-94-

```
        {
                if ( .sultBad == 1)
                        say(msgListPtrs->Msg[Initialize_Stops_Aborted]);
                else
                {
                        sayString("Insufficent range of motion");
                        sayLineFeed();
                        sayString("Please try again");
                        sayLineFeed();
                        sayString("cwStop = ");
                        sayLong(cwStop);
                        sayString("  ccwStop = ");
                        sayLong(ccwStop);
                        sayLineFeed();
                        brakeOff();
                        clutchOff();
                        beep(1);
                        delay(250);
                }
                beep(5);
                delay(250);
        }
        else
        {
                say(msgListPtrs->Msg[Initialize_Stops_Ok]);
                sayLineFeed();
                sayString("cwStop = ");
                sayLong(cwStop);
                sayString("  ccwStop = ");
                sayLong(ccwStop);
                sayLineFeed();
                brakeOff();
                clutchOff();
                beep(1);
                delay(250);
// zero torque transducer
                if(!calibrate)
                {
                        startInt();
                        sayString("zeroing torque transducer - HANDS OFF
                        sayLineFeed();
                        doInterrupt = true;
                        waitForInterrupt = true;
                        while(waitForInterrupt) ;
                        zeroFlag = true;
                        while(zeroFlag) ;
                        stopInt();
                        doInterrupt = false;
                        sayString("ADC offset = ");
                        sayInt(torqueOffset);
                        sayLineFeed();
                }
        }
if(dbg)
{
        say(msgListPtrs->Msg[Press_Any_Key_Escape_To_Exit]);
        sayLineFeed();

while(!kbhit())
        {
```

-95-

```
                wat(    :Stops,8,0);
                saySt _ng("position = ");
                sayLong(readActualPosition());
        }
        myGetch();
}
        wclose(initStops);
        showAvail();
        brakeOff();
        clutchOff();
        return(GOOD);
}
/*
 * End Of File
 */
```

-96-

E.D.C. File Print-out  ISOKINET.C,    on 11-3-91,        3:52 PM

```c
#define   DEBUG0
#define   WAVEFORM0
/* * * * * * * * * * * * * * * * * * * * * * * * * *
 *
 *     File: ISOKINETIC.C
 *     Date: 05/05/91
 *     Time: 11:27:48.15
 *  Author: Joe Forma
 *
 * * * * * * * * * * * * * * * * * * * * * * * * * */ include <vcstdio.h>
include <graphics.h>
#include <alloc.h>
#include <string.h>
#include <conio.h>
include <math.h> include "realtype.h"
include "worlddr.h"
#include "segraph.h"
#include "loadmsgs.h"
include "keycodes.h"
#include "utility.h"
#include "status.h"
#include "setutil.h"
#include "siconver.h"
#include "cntrlrio.h"
include "setupdma.h"
#include "rtint.h"
#include "lowlevel.h"
#include "biostuff.h"
#include "setisok.h"
#include "summary.h"
#include "autocycl.h"
#include "isokinet.h"

/***********************************************************/
/*                        CODE                             */
/***********************************************************/ define MODE_Y          20
define MODE_X          200 define TORQUE_Y        120
define TORQUE_X        200 define VELOCITY_Y      240
define VELOCITY_X      200 define REPCOUNT_Y      120
define REPCOUNT_X      500 static char torqueStr[8],
            lastTorqueStr[8];
```

-97-

```c
static int torqueDig
static int displayTo_ _e;
static char velocityStr[8],                              lastVelocityStr[8];
static int velocityDigit;
static int displayTorque;
static int velocity;
static long endStop,startStop;
static char repStr[8],                                   lastRepStr[8];
static int repCount;
static long peakTorqueAcc;

int displayIsokineticData(void)
{
#define THEWINDOW1 8
#define THEWINDOW2 10
  int result = 0;
  int direction;
  long offset;
  int i;
  int samples;
  unsigned size;
  void far *screenSavePtr1 = NULL;
  void far *screenSavePtr2 = NULL;

struct textsettingstype textinfo;
  struct viewporttype viewinfo;
  struct viewporttype savedviewinfo1;
  struct viewporttype savedviewinfo2;
  dataPoint *localPointer = dataPointer;
  int xasp,yasp;
  realtype *pdata, *ydata, *tdata;   /* Pointers used for data */ showAvail();
// printf("MemAvail = %8u  MemHigh = %8u  MemLow  = %8u\n",memAvail,memHigh,mem
  direction = (startStop > endStop);
  offset = (midpoint);  // in units of opto counts samples = DATAMAX-sampleCount;
// printf("Samples = %4u\n",samples);

pdata = GetMem(samples);
  if (BadMem(pdata)) return(1);
  ydata = GetMem(samples);
  if (BadMem(ydata)) {free(pdata); return(1);}
  tdata = GetMem(samples);
  if (BadMem(tdata)) {free(ydata);free(pdata); return(1);} for (i=0;i<samples;i++)
  {
    ydata[i] = ((float)abs(localPointer->torqueIndex))/10.0;
    if (direction)
      pdata[i] = ((float)(offset-localPointer->positionIndex)*float_DPP);
    else
    pdata[i] = ((float)(localPointer->positionIndex-offset)*float_DPP);
    tdata[i] = ((float)(i)/250.0);
    localPointer++;
  }
```

```
getaspectratio(&xa    yasp);  // save the old setti
gettextsettings(&t   info);
getviewsettings(&viewinfo);

InitSEGraphics("",0);

SetCurrentWindow(THEWINDOW1);                  /* Make the desired window active */
getviewsettings(&savedviewinfo1);
size = imagesize(savedviewinfo1.left,
                 savedviewinfo1.top,
                 savedviewinfo1.right,
                 savedviewinfo1.bottom);
screenSavePtr1 = malloc(size);
setviewport(viewinfo.left,viewinfo.top,viewinfo.right,viewinfo.bottom,viewinfo
setaspectratio(xasp,yasp);
if (screenSavePtr1 != NULL)
   getimage(savedviewinfo1.left,
            savedviewinfo1.top,
            savedviewinfo1.right,
            savedviewinfo1.bottom,
            screenSavePtr1);
SetCurrentWindow(THEWINDOW2);                  /* Make the desired window active */
getviewsettings(&savedviewinfo2);
size = imagesize(savedviewinfo2.left,
                 savedviewinfo2.top,
                 savedviewinfo2.right,
                 savedviewinfo2.bottom);
screenSavePtr2 = malloc(size);
setviewport(viewinfo.left,viewinfo.top,viewinfo.right,viewinfo.bottom,viewinfo
setaspectratio(xasp,yasp);
if (screenSavePtr2 != NULL)
   getimage(savedviewinfo2.left,
            savedviewinfo2.top,
            savedviewinfo2.right,
            savedviewinfo2.bottom,
            screenSavePtr2);
showAvail();
SetCurrentWindow(THEWINDOW1);      /* Make the desired window active */
SetViewBackground(15);             /* White View Background */
SetAxesType(0,0);                  /* Linear-Linear scale */
SelectColor(4);                    /* Color = 4 */
AutoAxes(ydata,pdata,samples,1);   /* Auto draw&label, all the points,
                                      intercepts at xmin, ymin */
LinePlotData(ydata, pdata,samples,1,0);   /* linePlot */
TitleYAxis("Position - degrees",0);
TitleXAxis("Torque - in/lbs",0);
TitleWindow("Isokinetic Data"); /* Throw up a title on top */

SetCurrentWindow(THEWINDOW2);                  /* Make current window 8 active */
SetViewBackground(15);             /* White View Background */
SetAxesType(0,0);                  /* Linear-Linear scale */
SelectColor(4);                    /* Color = 4 */
AutoAxes(tdata,pdata,samples,1);   /* Auto draw&label, all the points,
                                      intercepts at xmin, ymin */
LinePlotData(tdata,pdata,samples,1,0);   /* linePlot */
TitleYAxis("Position - degrees",0);
TitleXAxis("Time - seconds",0);
TitleWindow("Isokinetic Data"); /* Throw up a title on top */
```

```
  waitHitThenFlush();
  ClearWindow();

settextstyle(textinfo.font,textinfo.direction,textinfo.charsize);
  setviewport(viewinfo.left,viewinfo.top,viewinfo.right,viewinfo.bottom,viewinfo
  setaspectratio(xasp,yasp);
  settextjustify(textinfo.horiz,textinfo.vert);

if (screenSavePtr1 != NULL)
    putimage(savedviewinfo1.left,
             savedviewinfo1.top,
             screenSavePtr1,
             COPY_PUT);
  if (screenSavePtr1 != NULL)
    free(screenSavePtr1);
  screenSavePtr1 = NULL;

if (screenSavePtr2 != NULL)
    putimage(savedviewinfo2.left,
             savedviewinfo2.top,
             screenSavePtr2,
             COPY_PUT);
  if (screenSavePtr2 != NULL)
    free(screenSavePtr2);
  screenSavePtr2 = NULL;

free(tdata);
  free(ydata);
  free(pdata);   /* Dont forget to free heap */ showAvail();
// printf("MemAvail = %8u  MemHigh = %8u  MemLow  = %8u\n",memAvail,memHigh,mem return(result);
} void initIsokineticBioFeedBack(void)
{
  velocity = 0;
  setcolor(WHITE);
  strcpy(torqueStr,"aaaa");
  strcpy(lastTorqueStr,torqueStr);
  strcpy(velocityStr,"aaaa");
  strcpy(lastVelocityStr,velocityStr);
  strcpy(repStr,"a");
  strcpy(lastRepStr,repStr);
  settextstyle(TRIPLEX_FONT,HORIZ_DIR,FONT_MULTIPLIER);
  outtextxy(MODE_X,MODE_Y,"ISOKINETICS");
  outtextxy(0,TORQUE_Y,"TORQUE");
  outtextxy(0,VELOCITY_Y,"VELOCITY");
  outtextxy(REPCOUNT_X-60,REPCOUNT_Y,"REP");
  torqueDigit = 3;
  velocityDigit = 3;
  repCount = 0;
}
void isokineticBioFeedBack(void)
{
  int i;

if (bioCount > 30)
```

```
    {
      captureBioData =     e;
      while(captureBioData) ;
    }
    else
      return;

displayTorque = abs(realTimeTorque/10);
    velocity = realTimeVelocity;
    velocity = (int)((float)velocity*250.0/40000.0*360.0);
    for (i=0;i<4;i++)
    {
      displayBioInfo(displayTorque,
                    YELLOW,
                    TORQUE_X,
                    TORQUE_Y,
                    &torqueDigit,
                    torqueStr,
                    lastTorqueStr);
      displayBioInfo(velocity,
                    YELLOW,
                    VELOCITY_X,
                    VELOCITY_Y,
                    &velocityDigit,
                    velocityStr,
                    lastVelocityStr);

displayBioInfoDigit(repCount,
                         YELLOW,
                         REPCOUNT_X,
                         REPCOUNT_Y,
                         repStr,
                         lastRepStr);
    }
} void isokineticInterruptFunc(void)
{
  if (abs(realTimeTorque) > peakTorqueAcc)
    peakTorqueAcc = abs(realTimeTorque);
} void initIsokinetic(void)
{
}

COUNT runIsokineticFunc(void)
{
  int quickExit = 0;
  int done = 0;
  long inputStop1,inputStop2;
//    int isoVelocity;
//    TEXT isoVelocityStr[6];
  int servoFlag = 0;
  int result = GOOD;

showAvail();
```

—101—

```
isokinetic=wxxopen   ),23,79,(TEXT *)"",
                     fIVE|BORDER|BD2|SCROLL|WDWRAP|    .KED|STANDARD|CURSOR,
                  17,78,8,32);
if( isokinetic == -1 )
  terror(msgListPtrs->Msg[Unable_To_Open_Isokinetics_Window]);
wat(isokinetic,0,0);                              // need to position the cursor
if (goodStops())
{
  brakeOff();
  clutchOff();
  while ((!done) && (!quickExit))
  {
    if (!autoCycle)
    {
      atsay(0,26,(TEXT*)"ISOKINETIC SET STOPS");
      sayLineFeed();
      sayLineFeed();
      sayString("Move stop #1");
      sayLineFeed();
      say(msgListPtrs->Msg[Press_Any_Key_Escape_To_Exit]);
      sayLineFeed();
      sayLineFeed();
      quickExit = waitHitThenFlushOrEscape();
      if (quickExit)
        break;
      inputStop1 = doInterrupt ? realTimePosition : readActualPosition();
      sayString("Move stop #2");
      sayLineFeed();
      say(msgListPtrs->Msg[Press_Any_Key_Escape_To_Exit]);
      sayLineFeed();
      sayLineFeed();
      quickExit = waitHitThenFlushOrEscape();
      if (quickExit)
        break;
      inputStop2 = doInterrupt ? realTimePosition : readActualPosition();
      if (labs(inputStop1 - inputStop2) > NINE_DEGREES)
        done = 1;
      else
      {
        sayString("Insufficient Range of Motion");
        sayLineFeed();
        say(msgListPtrs->Msg[Press_Any_Key_Escape_To_Exit]);
        sayLineFeed();
        quickExit = waitHitThenFlushOrEscape();
        if (quickExit)
          break;
        erase();
        wat(isokinetic,0,0);                      // need to position the cu
      }
    }
    else
    {
      inputStop1 = theReport.startStop;
      inputStop2 = theReport.endStop;
      done = 1;
      quickExit = 0;
    }
  }
  if (!quickExit)
  {
```

-102-

```
  done = 0;
  while (!done)
  {
    erase();
    done = 1;
  }
  if ((inputStop1 + inputStop2)/2 < (midpoint)) // assume right hand
  {
    if (inputStop1 < inputStop2)
    {
      startStop = inputStop2;
      endStop = inputStop1;
    }
    else
    {
      startStop = inputStop1;
      endStop = inputStop2;
    }
    cwLimit = startStop;
    ccwLimit = endStop;
    servoFlag = 2; // going ccw
  }
  else // assume left hand
  {
    if (inputStop1 < inputStop2)
    {
      startStop = inputStop1;
      endStop = inputStop2;
    }
    else
    {
      startStop = inputStop2;
      endStop = inputStop1;
    }
    ccwLimit = startStop;
    cwLimit = endStop;
    servoFlag = 1; // going cw
  }
  setIsok();
  setgraphmode(getgraphmode());
  startInt();                              //
  initIsokineticBioFeedBack();
  doInterrupt = true;                      //
  waitForInterrupt = true;
  while(waitForInterrupt) ;
  idleMoveToPosition(startStop);
  servo = servoFlag;
  big_target_velocity = 0;
  done = 0;  // reset done
  while (!done)
  {
    peakTorqueAcc = 0;
    doIsokineticFlag = true;
    openDataCollection(dataPointer,DATAMAX,40);
    while ((servo) && !kbhit())
      isokineticBioFeedBack();
    doIsokineticFlag = false;
//    printf("SampleCount = %4u CollectData = %4u\n",sampleCount,collectData
    closeDataCollection();
    if ((autoCycle) && (repCount < 4))
```

-103-

```
         theReport.'  :ineticAvgPeakTorque[repCount`    (int)peakTorqueAcc;
         repCount++;
         if (repCount > 9)
           repCount = 0;
         isokineticBioFeedBack();
#ifdef WAVEFORM
         stopInt();                              //
         if ((!done) && (sampleCount != DATAMAX))
           displayIsokineticData();
         startInt();                             //
#endif
         if ((autoCycle) &&
#ifdef DEBUG
             (repCount >= 1))
#else
             (repCount >= 4))
#endif
           done = 1;
         else
           if (!kbhit())
           {
             brakeOn(MAXBRAKE);
             beep(2);
             idleMoveToPosition(startStop);
             doInterrupt = true;
             waitForInterrupt = true;
             while (waitForInterrupt) ;

servo = servoFlag;
             velocity = 0;
           }
           else
             if (myGetch() == escape)
               done = 1;
       }
       doInterrupt = false;                      //
       servo = false;
       isokineticBioFeedBack();
       isokineticBioFeedBack();
       isokineticBioFeedBack();
       isokineticBioFeedBack();
       stopInt();
       kbFlush();
       restorecrtmode();
     }
     else
       result = BAD;
  }
  else
  {
    result = BAD;
    sayString("Need to initialize controller first");
    sayLineFeed();
    sayString("Press any key to continue");
    waitHitThenFlush();
  }
  textbackground(WHITE);
  clrscr();
  wclose(isokinetic);
  showAvail();
```

—104—

```
  brakeOn(1);
  clutchOff();
  return(result);
}

/*
 * End Of File
 */
```

—105—

E.D.C. File Print-out  ISOMET.C, on 11-3-91, at 54 PM

```c
/* * * * * * * * * * * * * * * * * * * * * * * * * * *
 *
 *    File: ISOMET.C
 *    Date: 05/05/91
 *    Time: 11:27:48.15
 *    Author: Joe Forma
 *
 * * * * * * * * * * * * * * * * * * * * * * * * * * */ include <vcstdio.h>
include <graphics.h>
#include <alloc.h>
#include <string.h>
#include <conio.h>
include <math.h>
include <stdio.h> include "loadmsgs.h"
include "utility.h"
#include "status.h"
#include "keycodes.h"
#include "setutil.h"
#include "siconver.h"
#include "cntrlrio.h"
include "setupdma.h"
#include "rtint.h"
#include "lowlevel.h"
#include "biostuff.h"
#include "autocycl.h"
#include "summary.h"
#include "isomet.h"

/****************************************************/
/*                      CODE                        */
/****************************************************/ define MODE_Y          20
define MODE_X          200 define TORQUE_Y        120
define TORQUE_X        200 define MAXTORQUE_Y     240
define MAXTORQUE_X     200 define REPCOUNT_Y      120
define REPCOUNT_X      500 define ISOTOP      50      // 5 INCH LBS
define ISOBOTTOM   20      // 2 INCH LBS static char torqueStr[8],                           lastTorqueStr[8];

static int torqueDigit;
static char maxTorqueStr[8],                        lastMaxTorqueStr[8];
```

```
static int maxTorqueD   t;
static int displayToi _ _;
static int displayMaxTorque;
static int maxTorque;
static char repStr[8],
                                                          lastRepStr[8];
static int repCount;
static int lastRepCount;

static direction going;

#define maxcollect 10000
#define subdivide 25
extern int isomcollect;
static int isomdata[maxcollect];
static int dataindex;
static long subsum;
static int subindex;

void initIsometricBioFeedBack(void)
{
        setcolor(WHITE);
        strcpy(torqueStr,"aaaa");
        strcpy(lastTorqueStr,torqueStr);
        strcpy(maxTorqueStr,"aaaa");
        strcpy(lastMaxTorqueStr,maxTorqueStr);
        strcpy(repStr,"a");
        strcpy(lastRepStr,repStr);
        settextstyle(TRIPLEX_FONT,HORIZ_DIR,FONT_MULTIPLIER);
        outtextxy(MODE_X,MODE_Y,"ISOMETRICS");
        outtextxy(0,TORQUE_Y,"TORQUE");
        outtextxy(0,MAXTORQUE_Y,"MAXTORQUE");
        outtextxy(REPCOUNT_X-60,REPCOUNT_Y,"REP");
        torqueDigit = 3;
        maxTorqueDigit = 3;
        lastRepCount = 0;
        repCount = 0;
        maxTorque = 0;
        going = none;
        dataindex = 0;
        subsum = 0;
        subindex = 0;
} void isometricBioFeedBack(void)
{
        if (calibrate)
                displayTorque = abs(realTimeTorque);
        else
                displayTorque = abs(realTimeTorque/10);
        displayBioInfo(displayTorque,
                                                          YELLOW,
                                                          TORQUE_X,
                                                          TORQUE_Y,
                                                          &torqueDigit,
                                                          torqueStr,
                                                          lastTorqueStr);
        if (calibrate)
                displayMaxTorque = maxTorque;
        else
```

-107-

```
                disp:  !axTorque = maxTorque/10;
        displayBioInf. .displayMaxTorque,
                                                                YELLOW,
                                                                MAXTORQUE_X,
                                                                MAXTORQUE_Y,
                                                                &maxTorqueDigit
                                                                maxTorqueStr,
                                                                lastMaxTorqueSt
        displayBioInfoDigit(repCount, if (lastRepCount != repCount)
                beep(1);
        lastRepCount = repCount;
} void isometricInterruptFunc(void)
{
        switch (going)
        {
                case none :
                case down : if (abs(realTimeTorque) > ISOTOP)
                                                                        going =
                                                                break;
                case up   : if (abs(realTimeTorque) < ISOBOTTOM)
                                                                {
                                                                        going =
                                                                        if ((aut repCount
                                                                        if (repC maxTorqu
                                                                }
                                                                else
                                                                        if (abs( break;
        }
        if(isomcollect)
        {
                subindex++;
                subsum += abs(realTimeTorque);
                if((subindex % subdivide) == 0)
                {
                        isomdata[dataindex++] = (int)(subsum/subindex);
                        if(dataindex > maxcollect) dataindex = 0;
                        subindex = 0;
                        subsum = 0;
                }
        }
} void initIsometric(void)
{
}
```

-108-

```
COUNT runIsometricFu   oid)
{
        int quickExit = 0;
        int ani;
        int done = 0;
        int result = GOOD;
        int i;
        FILE *fp;

showAvail();
        isometric=wxxopen(5,0,23,79,(TEXT *)"",
                                                                        ACTIVE|
                                                                        17,78,8
        if( isometric == -1 )
                        terror(msgListPtrs->Msg[Unable_To_Open_Isometrics_Window
        wat(isometric,0,0);             // need to position the cursor
        if (goodStops())
        {
                brakeOff();
                clutchOff();
                if (!autoCycle)
                {
                        atsay(0,28,(TEXT*)"ISOMETRIC SET STOP");
                        sayLineFeed();
                        sayLineFeed();
                        sayString("Move to desired position");
                        sayLineFeed();
                        say(msgListPtrs->Msg[Press_Any_Key_Escape_To_Exit]);
                        sayLineFeed();
                        quickExit = waitHitThenFlushOrEscape();
                }
                else
                {
                        atsay(0,28,(TEXT*)"ISOMETRIC SET STOP");
                        sayLineFeed();
                        sayLineFeed();
                        sayString("Moving to desired position");
                        sayLineFeed();
                        quickExit = 0;
                        idleMoveToPosition(theReport.startStop);
                }
                if (!quickExit)
                {
                        setgraphmode(getgraphmode());
                        brakeOn(MAXBRAKE);
                        startInt();
                        initIsometricBioFeedBack();
                        doInterrupt = true;
                        waitForInterrupt = true;
                        while(waitForInterrupt) ;
                        doIsometricFlag = true;
                        while (!done)
                        {
                                isometricBioFeedBack();
                                if ((repCount == 4) && (autoCycle))
                                        break;
                                if (kbhit())
                                {
                                        ani = myGetch();
```

−109−

```
                                        if (ani == e    pe)
                                                done    1;
                                }
                        }
                        if(dataindex)
                        {
                                fp = fopen("isomdata.txt","w");
                                if(fp != NULL)
                                {
                                        for(i=0;i<dataindex;i++)
                                                fprintf(fp,"%d\n",isomdata[i]);
                                        fclose(fp);
                                }
                        }
                        doInterrupt = false;
                        doIsometricFlag = false;
                        stopInt();
                        kbFlush();
                        restorecrtmode();
                }
                else
                        result = BAD;
        }
        else
        {
                sayString("Need to initialize controller first");
                sayLineFeed();
                sayString("Press any key to continue");
                waitHitThenFlush();
                result = BAD;
        }
        textbackground(WHITE);
        clrscr();
        wclose(isometric);
        showAvail();
        brakeOff();
        clutchOff();
        return(result);
}
/*
 * End Of File
 */
```

-110-

E.D.C. File Print-out f ISOTONIC.C,   on 11-3-91,      3:55 PM

```c
#define LINEARIZED
#define WAVEFORM0
/* * * * * * * * * * * * * * * * * * * * * * * * *
 *
 *      File: ISOTONIC.C
 *      Date: 05/05/91
 *      Time: 11:27:48.15
 *      Author: Joe Forma
 *
 * * * * * * * * * * * * * * * * * * * * * * * * */ include <vcstdio.h>
include <graphics.h>
#include <alloc.h>
#include <string.h>
#include <conio.h>
include <math.h> include "realtype.h"
include "worlddr.h"
#include "segraph.h"
#include "loadmsgs.h"
include "utility.h"
#include "status.h"
#include "setutil.h"
#include "siconver.h"
#include "cntrlrio.h"
include "setupdma.h"
#include "rtint.h"
#include "lowlevel.h"
#include "biostuff.h"
#include "linearize.h"
#include "autocycl.h"
#include "summary.h"
#include "isotonic.h"

/*******************************************************/
/*                                                     */
/*                       CODE                        */
/*******************************************************/ define MODE_Y          20
define MODE_X          220 define TORQUE_Y        120
define TORQUE_X        200 define MAXTORQUE_Y     240
define MAXTORQUE_X     200 define REPCOUNT_Y      120
define REPCOUNT_X      500 ifndef LINEARIZED
 #define MAXFORCE  200
#else
 #define MAXFORCE  100
#endif
```

-111-

```
static char torqueStr[ ],
                                      lastTorqueStr[8];
static int torqueDigit;
static char maxTorqueStr[8],
                                      lastMaxTorqueStr[8];
static int maxTorqueDigit;
static int displayTorque;
static int maxTorque;
static long endStop,startStop;
static char repStr[8],
                                                        lastRepStr[8];
static int repCount;
static long workAcc;

int displayIsotonicData(void)
{
#define THEWINDOW1 8
#define THEWINDOW2 10
  int result = 0;
  int direction;
  long offset;
  int i;
  int samples;
  unsigned size;
  void far *screenSavePtr1 = NULL;
  void far *screenSavePtr2 = NULL;

struct textsettingstype textinfo;
  struct viewporttype viewinfo;
  struct viewporttype savedviewinfo1;
  struct viewporttype savedviewinfo2;
  dataPoint *localPointer = dataPointer;
  int xasp,yasp;
  realtype  *pdata, *ydata, *tdata;   /* Pointers used for data */ direction = (startStop > endStop);
  offset = (midpoint);   // in units of opto counts samples = DATAMAX-sampleCount;

pdata = GetMem(samples);
  if (BadMem(pdata)) return(1);
  ydata = GetMem(samples);
  if (BadMem(ydata)) {free(pdata); return(1);}
  tdata = GetMem(samples);
  if (BadMem(tdata)) {free(ydata);free(pdata); return(1);} for (i=0;i<samples;i++)
  {
    ydata[i] = ((float)abs(localPointer->torqueIndex))/10.0;
    if (direction)
      pdata[i] = ((float)(offset-localPointer->positionIndex)*float_DPP);
    else
    pdata[i] = ((float)(localPointer->positionIndex-offset)*float_DPP);
    tdata[i] = ((float)(i)/250.0);
    localPointer++;
  }
```

```
                                    -112-
getaspectratio(&xa    &yasp); // save the old sett:
gettextsettings(&t    info);
getviewsettings(&viewinfo);

InitSEGraphics("",0);

SetCurrentWindow(THEWINDOW1);                /* Make the desired window active *
getviewsettings(&savedviewinfo1);
size = imagesize(savedviewinfo1.left,
                 savedviewinfo1.top,
                 savedviewinfo1.right,
                 savedviewinfo1.bottom);
screenSavePtr1 = malloc(size);
setviewport(viewinfo.left,viewinfo.top,viewinfo.right,viewinfo.bottom,viewinfo
setaspectratio(xasp,yasp);
if (screenSavePtr1)
   getimage(savedviewinfo1.left,
            savedviewinfo1.top,
            savedviewinfo1.right,
            savedviewinfo1.bottom,
            screenSavePtr1);
SetCurrentWindow(THEWINDOW2);                /* Make the desired window active *
getviewsettings(&savedviewinfo2);
size = imagesize(savedviewinfo2.left,
                 savedviewinfo2.top,
                 savedviewinfo2.right,
                 savedviewinfo2.bottom);
screenSavePtr2 = malloc(size);
setviewport(viewinfo.left,viewinfo.top,viewinfo.right,viewinfo.bottom,viewinfo
setaspectratio(xasp,yasp);
if (screenSavePtr2)
   getimage(savedviewinfo2.left,
            savedviewinfo2.top,
            savedviewinfo2.right,
            savedviewinfo2.bottom,
            screenSavePtr2);
showAvail();
SetCurrentWindow(THEWINDOW1);    /* Make the desired window active */
SetViewBackground(15);           /* White View Background */
SetAxesType(0,0);                /* Linear-Linear scale */
SelectColor(4);                  /* Color = 4 */
AutoAxes(pdata,ydata,samples,1); /* Auto draw&label, all the points,
                                    intercepts at xmin, ymin */
LinePlotData(pdata, ydata,samples,1,0);   /* linePlot */
TitleYAxis("Torque - in/lbs",0);
TitleXAxis("Position - degrees",0);
TitleWindow("Isotonic Data"); /* Throw up a title on top */

SetCurrentWindow(THEWINDOW2);             /* Make current window 8 active */
SetViewBackground(15);           /* White View Background */
SetAxesType(0,0);                /* Linear-Linear scale */
SelectColor(4);                  /* Color = 4 */
AutoAxes(tdata,ydata,samples,1); /* Auto draw&label, all the points,
                                    intercepts at xmin, ymin */
LinePlotData(tdata, ydata,samples,1,0);   /* linePlot */
TitleYAxis("Torque - in/lbs",0);
TitleXAxis("Time - seconds",0);
TitleWindow("Isotonic Data"); /* Throw up a title on top */
```

-113-

```c
  waitHitThenFlush()
  ClearWindow();

settextstyle(textinfo.font,textinfo.direction,textinfo.charsize);
  setviewport(viewinfo.left,viewinfo.top,viewinfo.right,viewinfo.bottom,viewinfo
  setaspectratio(xasp,yasp);
  settextjustify(textinfo.horiz,textinfo.vert);

if (screenSavePtr1)
     putimage(savedviewinfo1.left,
              savedviewinfo1.top,
              screenSavePtr1,
              COPY_PUT);
  if (screenSavePtr1)
     free(screenSavePtr1);

if (screenSavePtr2)
     putimage(savedviewinfo2.left,
              savedviewinfo2.top,
              screenSavePtr2,
              COPY_PUT);
  if (screenSavePtr2)
     free(screenSavePtr2);

free(tdata);
  free(ydata);
  free(pdata);   /* Dont forget to free heap */ return(result);
} void initIsotonicBioFeedBack(void)
{
  maxTorque = 0;
  setcolor(WHITE);
  strcpy(torqueStr,"aaaa");
  strcpy(lastTorqueStr,torqueStr);
  strcpy(maxTorqueStr,"aaaa");
  strcpy(lastMaxTorqueStr,maxTorqueStr);
  strcpy(repStr,"a");
  strcpy(lastRepStr,repStr);
  settextstyle(TRIPLEX_FONT,HORIZ_DIR,FONT_MULTIPLIER);
  outtextxy(MODE_X,MODE_Y,"ISOTONICS");
  outtextxy(0,TORQUE_Y,"TORQUE");
  outtextxy(0,MAXTORQUE_Y,"MAXTORQUE");
  outtextxy(REPCOUNT_X-60,REPCOUNT_Y,"REP");
  torqueDigit = 3;
  maxTorqueDigit = 3;
  repCount = 0;
} int isotonicBioFeedBack(void)
{
  displayTorque = abs(realTimeTorque/10);
  displayBioInfo(displayTorque,
                 YELLOW,
                 TORQUE_X,
                 TORQUE_Y,
                 &torqueDigit,
```

```
                    t'  ieStr,
                    le  forqueStr);
  if (displayTorque > maxTorque)
    maxTorque = displayTorque;
  displayBioInfo(maxTorque,
                 YELLOW,
                 MAXTORQUE_X,
                 MAXTORQUE_Y,
                 &maxTorqueDigit,
                 maxTorqueStr,
                 lastMaxTorqueStr);
  displayBioInfoDigit(repCount,
                      YELLOW,
                      REPCOUNT_X,
                      REPCOUNT_Y,
                      repStr,
                      lastRepStr);
  return(0);
} void isotonicInterruptFunc(void)
{
  workAcc = workAcc+(realTimeDeltaPosition*realTimeTorque);
} void initIsotonic(void)
{
}

COUNT runIsotonicFunc(void)
{
  int quickExit = 0;
  int done2 = 0,done = 0;
  long inputStop1,inputStop2;
  int isoTorque;
  TEXT isoTorqueStr[6];
  int result = GOOD;

isotonic=wxxopen(5,0,23,79,(TEXT *)"",
                   ACTIVE|BORDER|BD2|SCROLL|WDWRAP|COOKED|STANDARD|CURSOR,
                   17,78,8,32);
  if ( isotonic == -1 )
    terror(msgListPtrs->Msg[Unable_To_Open_Isotonics_Window]);
  wat(isotonic,0,0);                           // need to position the cursor
  if (goodStops())
  {
    brakeOff();
    clutchOff();
    while ((!done) && (!quickExit))
    {
      if (!autoCycle)
      {
        atsay(0,28,(TEXT*)"ISOTONIC SET STOPS");
        sayLineFeed();
        sayLineFeed();
        sayString("Move stop #1");
        sayLineFeed();
```

-115-

```
        say(msgList'   s->Msg[Press_Any_Key_Escape_T  'xit]);
        sayLineFeed
        sayLineFeed();
        quickExit = waitHitThenFlushOrEscape();
        if (quickExit)
          break;
        inputStop1 = doInterrupt ? realTimePosition : readActualPosition();
        sayString("Move stop #2");
        sayLineFeed();
        say(msgListPtrs->Msg[Press_Any_Key_Escape_To_Exit]);
        sayLineFeed();
        sayLineFeed();
        quickExit = waitHitThenFlushOrEscape();
        if (quickExit)
          break;
        inputStop2 = doInterrupt ? realTimePosition : readActualPosition();
        if (labs(inputStop1 - inputStop2) > NINE_DEGREES)
          done = 1;
        else
        {
          sayString("Insufficient Range of Motion");
          sayLineFeed();
          say(msgListPtrs->Msg[Press_Any_Key_Escape_To_Exit]);
          sayLineFeed();
          quickExit = waitHitThenFlushOrEscape();
          if (quickExit)
            break;
          erase();
          wat(isotonic,0,0);                          // need to position the cur
        }
      }
      else
      {
        inputStop1 = theReport.startStop;
        inputStop2 = theReport.endStop;
        done = 1;
        quickExit = 0;
      }
    }
    if (!quickExit)
    {
      while (!done2)
      {
        done = 0;
        while (!done)
        {
          erase();
          if ((!autoCycle) || (!autoIsotonicTorque))
          {
            at(1,0);                                  // need to position the c
            sayString("Press Escape to Exit");
            at(0,0);                          // need to position the cursor
            sayString("Enter Isotonic Torque in IN/LBS = ");
            empty(isoTorqueStr,sizeof(isoTorqueStr));
            get(isoTorqueStr,(TEXT *)"999");
            readgets();
            isoTorque = 0;
            sscanf((char *)isoTorqueStr,"%d",&isoTorque);
            if ((isoTorque >= 10) && (isoTorque <= MAXFORCE))
              done = 1;
```

-116-

```
            if (isoTorque == 0)
              done2 = 1,done = 1,result = BAD;
          }
          else
          {
            isoTorque = autoIsotonicTorque;
            done = 1;
          }
        }
        if ((inputStop1 + inputStop2)/2 < (midpoint)) // assume right hand
        {
          if (inputStop1 < inputStop2)
          {
            startStop = inputStop2;
            endStop = inputStop1;
          }
          else
          {
            startStop = inputStop1;
            endStop = inputStop2;
          }
        }
        else // assume left hand
        {
          if (inputStop1 < inputStop2)
          {
            startStop = inputStop1;
            endStop = inputStop2;
          }
          else
          {
            startStop = inputStop2;
            endStop = inputStop1;
          }
        }
        if (!done2)
        {
          setgraphmode(getgraphmode());
          startInt();                                    //
          initIsotonicBioFeedBack();
          workAcc = 0;
          doInterrupt = true;                            //
          waitForInterrupt = true;
          while(waitForInterrupt) ;
          doIsotonicFlag = true;
          done = 0;  // reset done                       //
          while (!done)
          {
            done = idleMoveToPosition(startStop);
            maxTorque = 0;  // zero out the max torque
            openDataCollection(dataPointer,DATAMAX,40);
            if (!done)
              done = waitForPosition(0,
#ifdef LINEARIZED
#else                                     calcIsotonicTorque((float)isoTorque),
#endif                                    isoTorque,
                                          endStop,
                                          isotonicBioFeedBack);
```

-117-

```
            closeDa'  ollection();
            doInter.  c = false;                      //
            if ((autoCycle) && (repCount < 4))
              theReport.isotonicWorkAcc[repCount] = workAcc;
            repCount++;
            if (repCount > 9)
              repCount = 0;
            isotonicBioFeedBack();                    // make sure display is
            isotonicBioFeedBack();
            isotonicBioFeedBack();
            isotonicBioFeedBack();
            workAcc = 0;
            doInterrupt = true;
            waitForInterrupt = true;
            while(waitForInterrupt) ;
            if (!done)
              beep(2);
            if ((autoCycle) && (repCount >= 4))
              done = 1, done2 = 1;
#ifdef WAVEFORM
            stopInt();                                //
            if (!done)
              displayIsotonicData();
            startInt();                               //
#endif
          }
          doInterrupt = false;                        //
          doIsotonicFlag = false;                     //
          stopInt();
          kbFlush();
          restorecrtmode();
          textbackground(WHITE);
          clrscr();
        }
      }
    }
    else
      result = BAD;
  }
  else
  {
    result = BAD;
    sayString("Need to initialize controller first");
    sayLineFeed();
    sayString("Press any key to continue");
    waitHitThenFlush();
  }
  textbackground(WHITE);
  clrscr();
  wclose(isotonic);
  showAvail();
  brakeOn(1);
  clutchOff();
  return(result);
}

/*
 * End Of File
 */
```

E.D.C. File Print-ou  LINEARIZ.C,   on 11-3-91,      3:56 PM

```c
include <vcstdio.h>
include <math.h>
# include <stdlib.h>
# include <graphics.h>
# include <conio.h>
# include <ctype.h>
include <string.h> include "realtype.h"
include "curvefit.h"
# include "lineariz.h"

#define ORDER 5
define NUMBER_OF_OBJECTS 15 static realtype tdepvar[NUMBER_OF_OBJECTS] = {10.0,20.0,30.0,40.0,50.0,60.0,70.0
static realtype tindvar[NUMBER_OF_OBJECTS] = {1.0,2.0,2.5,3.0,9.0,17.0,27.0,40.0
//static realtype tindvar[NUMBER_OF_OBJECTS] = {0.0,1.0,6.0,13.0,25.0,40.0,56.5,
static int tnumobs = NUMBER_OF_OBJECTS;
static int torder = ORDER;
static realtype tpolycoef[ORDER+1];
static realtype tyest[NUMBER_OF_OBJECTS];
static realtype tresid[NUMBER_OF_OBJECTS];
static realtype tsee;
static realtype tcoefsig[ORDER+1];
static realtype trsqrval;
static realtype trvar;
static char tcferror;

int makeLinearizationTableIsotonic(void)
{

PolyCurveFit((realtype *)&tindvar,
               (realtype *)&tdepvar,
               tnumobs,
               torder,
               (realtype *)&tpolycoef,
               (realtype *)&tyest,
               (realtype *)&tresid,
               &tsee,
               (realtype *)&tcoefsig,
               &trsqrval,
               &trvar,
               &tcferror);

return(tcferror);
} int calcIsotonicTorque(float desiredTorque)
{
  realtype answer;

answer = tpolycoef[0]
         + tpolycoef[1]*(desiredTorque)
         + tpolycoef[2]*(desiredTorque*desiredTorque)
         + tpolycoef[3]*(desiredTorque*desiredTorque*desiredTorque)
         + tpolycoef[4]*(desiredTorque*desiredTorque*desiredTorque*desiredTorq
```

-119-

```
               + tpolycoe  ]*(desiredTorque*desiredTorq   iesiredTorque*desiredTorq return((int) answer);
} static realtype vdepvar[10] = {15,20.0,25.0,30.0,40.0,50.0,60.0,70.0,80.0,90.0};
static realtype vindvar[10] = {17.0,31.0,42.0,54.0,78.0,103.0,126.0,150.0,174.0,
static int vnumobs = 10;
static int vorder = ORDER;
static realtype vpolycoef[ORDER+1];
static realtype vyest[10];
static realtype vresid[10];
static realtype vsee;
static realtype vcoefsig[ORDER+1];
static realtype vrsqrval;
static realtype vrvar;
static char vcferror;

int makeLinearizationTableCPM(void)
{

PolyCurveFit((realtype *)&vindvar,
                (realtype *)&vdepvar,
                vnumobs,
                vorder,
                (realtype *)&vpolycoef,
                (realtype *)&vyest,
                (realtype *)&vresid,
                &vsee,
                (realtype *)&vcoefsig,
                &vrsqrval,
                &vrvar,
                &vcferror);

return(vcferror);
} int calcCPMVelocity(float desiredVelocity)
{
  realtype answer;
//   desiredVelocity = desiredVelocity*4096.0/360.0/250.0*16.0;

answer = vpolycoef[0]
          + vpolycoef[1]*(desiredVelocity)
          + vpolycoef[2]*(desiredVelocity*desiredVelocity)
          + vpolycoef[3]*(desiredVelocity*desiredVelocity*desiredVelocity)
          + vpolycoef[4]*(desiredVelocity*desiredVelocity*desiredVelocity*desir
          + vpolycoef[5]*(desiredVelocity*desiredVelocity*desiredVelocity*desir return((int) answer);
} int calcVelocity(int velocity)

{
        float n = 40000.0;
        float t = .009;
        float rpm_sec = 0.01667;
        float Vq;
```

-120-

```
    float localVelocity;

localVelocity = ((float)velocity)/360.0*60.0;  // convert to rpm
    Vq = (localVelocity*n*t*rpm_sec);
    return((int)(Vq*16));
} int calcAcceleration(int acceleration)

{
    float n = 40000.0;
    float t = 0.009;
    float rpm_sec = 0.01667;
    float Aq;
    float localAcceleration;

localAcceleration = ((float)acceleration)/360.0*60.0;   // convert to rpm
    Aq = (localAcceleration*n*t*t*rpm_sec);
    return((int)(Aq*256.0));
}
```

E.D.C. File Print-out: LOADMSGS.C,   on 11-3-91,      3:57 PM

```c
/* * * * * * * * * * * * * * * * * * * * * * * * * * *
 *
 *    File: LOADMSGS.C
 *    Date: 05/05/91
 *    Time: 11:27:48.15
 *  Author: Joe Forma
 *
 * * * * * * * * * * * * * * * * * * * * * * * * * * */ include <vcstdio.h>
include <string.h>
#include <fcntl.h>
#include <io.h>
include <alloc.h> include "loadmsgs.h"
include "loadmsgs.txt"

/****************************************************/
/*                    CODE                         */
/****************************************************/ void loadErrorMsgs(char * filePath)
{
  int theInputFile;
  unsigned long nbrOfMsgs = 0;
  unsigned long sizeOfText = 0;
  char fileName[80];
  int i;

strcpy(fileName,filePath);
  strcat(fileName,TEXT_FILE_NAME);
  if ((theInputFile = _open(fileName,O_RDONLY)) == -1)
    terror(loadMsgsMsgs[0]);
  if (_read(theInputFile,&nbrOfMsgs,sizeof(nbrOfMsgs)) != sizeof(nbrOfMsgs))  /*
    terror(loadMsgsMsgs[1]);
  if ((msgListPtrs = (struct XLATEMSGS *) farmalloc(nbrOfMsgs*4)) == NULL)  /* al
    terror(loadMsgsMsgs[2]);
  if (_read(theInputFile,&sizeOfText,sizeof(sizeOfText)) != sizeof(sizeOfText))
    terror(loadMsgsMsgs[3]);
  if ((msgListText = (TEXT *) farmalloc(sizeOfText)) == NULL)  /* allocate the nu
    terror(loadMsgsMsgs[4]);
  if (_read(theInputFile,msgListText,(int)sizeOfText) != sizeOfText)    /* get the
    terror(loadMsgsMsgs[5]);
  for (i=0;i<nbrOfMsgs;i++)
  {
    msgListPtrs->Msg[i] = msgListText;
    if (!msgListText[0])
      msgListPtrs->Msg[i] = NULL; /* assign a null pointer for this special case
    msgListText += (strlen((char*)msgListText)+1); /* increment the pointer */
  }
  _close(theInputFile);

}
```

```
/*
 * End Of File
 */
```

−123−

E.D.C. File Print-out : LOWLEVEL.C,    on 11-3-91,       3:57 PM

```c
include <vcstdio.h>
#include <conio.h>
include <dos.h> include "keycodes.h"

/*
|||||||||||||||||||||||||||||||||||||||||||||||||||||||||||||||||||||||||
|                                                                         |
| myGetch - This int function is used to get a key stroke even if it is a |
| function key and return a unique code associated with it                |
|                                                                         |
|||||||||||||||||||||||||||||||||||||||||||||||||||||||||||||||||||||||||
*/ int myGetch(void)

{
  int i;

i = getch();
  if (i == 0)            // get special keys
    i = getch() + 256;
  return(i);
} void sayLineFeed(void)

{
  say((TEXT *)"\n");
} void sayInt(int arg1)

{
  TEXT tStr[10];
  sprintf((char *)tStr,"%4d",arg1);
  say(tStr);
} void sayLong(long arg1)

{
        TEXT tStr[10];
        sprintf((char *)tStr,"%6ld",arg1);
        say(tStr);
} void sayStringLn(char *arg1)

{
  say((TEXT *) arg1);
  sayLineFeed();
} void sayString(char *arg1)
```

-124-

```c
{
  say((TEXT *) arg1);
} void kbFlush(void)

{
  while (kbhit())
    myGetch();
} void waitHitThenFlush(void)

{
  while (!kbhit()); /* wait for a key stroke */
  kbFlush();
} int waitHitThenFlushOrEscape(void)

{
  int ani;

while (!kbhit()); /* wait for a key stroke */
  ani = myGetch();
  return(ani == escape);
} void waitHit(void)

{
  while (!kbhit()); /* wait for a key stroke */
} void beep(int times)
{
  int i;
  for (i=0;i<times;i++)
  {
    sound(440);
    delay(100);
    nosound();
    if (i < (times-1))
      delay(100);
  }
}
```

-125-

E.D.C. File Print-out  MAINMENU.C,   on 11-3-91,    3:57 PM

```c
/* * * * * * * * * * * * * * * * * * * * * * * * * * *
 *
 *    File: MAINMENU.C
 *    Date: 05/05/91
 *    Time: 11:27:48.15
 *  Author: Joe Forma
 *
 * * * * * * * * * * * * * * * * * * * * * * * * * * */ include <vcstdio.h>
include <string.h> include "loadmsgs.h"
include "setutil.h"
#include "mainmenu.h"
#include "initstop.h"
#include "isomet.h"
#include "isotonic.h"
#include "isokinet.h"
#include "cpm.h"
#include "tap.h"
#include "reaction.h"
#include "autocycl.h"
#include "summary.h"
#include "status.h"

#define  MAINFIRSTITEMNUMBER 5

/*
   the following is the item number in the MAIN MENU
   used as an indicator to force the escape function
   in place of the RETURN
*/ define ESCAPEITEMNBR MAINFIRSTITEMNUMBER + 8

/***********************************************************/
/*                         CODE                            */
/***********************************************************/ static COUNT statusMainMenu(void)
{
//   displayStatusLine(None,None,None,None,None,None,None,None);
  return(0);
} static COUNT defeatEscape(VCMENU *currentWindow)
{
  if( currentWindow->keyhit == vckey.abort )
  {
    currentWindow->keyhit = 0;
    return(1);
  }
  if( currentWindow->keyhit == 0x39) /* exit on key 9 */
  {
    currentWindow->keyhit = vckey.abort;
```

```
    return(0);
  }
  if ((currentWindow->keyhit == RET)
       && (currentWindow->curitmnbr == ESCAPEITEMNBR)) /* exit on last key */
  {
    currentWindow->keyhit = vckey.abort;
    return(0);
  }
  return(0);
} static void blankItem(void)
{
  menuxitem(mainMenu,(TEXT *)"",NULL,0,NULLFUNC,NULL,(TEXT *)"",(TEXT *)"",BLANK
} static void mainMenuItem(COUNT number,PFI theFunc,TEXT *theHelp)
{
  menuxitem(mainMenu,
            msgListPtrs->Msg[Main_Menu_Line1+number],
            NULL,
            0x31+number,
            theFunc,
            (TEXT *) &mainMenuLine[number],
            statusLine,
            theHelp,
            HIDE|STAR);
} void prepMainMenu(void)
{
  mainMenu=menuxnew(4,20,40,(TEXT *)"",
                    VERTICAL|TITLECENTER,
                    vc.blue+(vc.bg*vc.white),
                    vc.black+(vc.bg*vc.white),
                    vc.blue+(vc.bg*vc.white),
                    vc.blue+(vc.bg*vc.white),
                    0,(TEXT *)"MAINMENU");
  blankItem();
  menuxitem(mainMenu,msgListPtrs->Msg[Main_Menu_Heading],NULL,0,NULLFUNC,NULL,(T
  blankItem();
  blankItem();
  mainMenuItem(0,runInitStopsFunc,(TEXT *)"initstops");
  mainMenuItem(1,runIsometricFunc,(TEXT *)"isometric");
  mainMenuItem(2,runIsotonicFunc,(TEXT *)"isotonics");
  mainMenuItem(3,runIsokineticFunc,(TEXT *)"isokinetics");
  mainMenuItem(4,runCPMFunc,(TEXT *)"cpm");
  mainMenuItem(5,runTapFunc,(TEXT *)"tap");
  mainMenuItem(6,runReactionFunc,(TEXT *)"reaction");
  mainMenuItem(7,runAutoCycleFunc,(TEXT *)"autocycle");
  mainMenuItem(8,NULLFUNC,(TEXT *)"toexit");
  blankItem();
  blankItem();
  vcmhook2 = statusMainMenu;
  vcmhook3 = defeatEscape;
} void undoMainMenu(void)
{
  freeMenuItems(mainMenu);
```

-127-

```
}

/*
 * End Of File
 */
```

-128-

E.D.C. File Print-ou  f OLDCPM.C,   on 11-3-91,   a  :57 PM

```c
#define LINEARIZED
#define MOTORCURRENT
/* * * * * * * * * * * * * * * * * * * * * * * * * * * *
 *
 *     File: CPM.C
 *     Date: 05/05/91
 *     Time: 11:27:48.15
 *  Author: Joe Forma
 *
 * * * * * * * * * * * * * * * * * * * * * * * * * * * */ include <vcstdio.h>
include <graphics.h>
#include <alloc.h>
#include <string.h>
#include <conio.h>
include <dos.h>
include <math.h> include "loadmsgs.h"
include "utility.h"
#include "status.h"
#include "setutil.h"
#include "siconver.h"
#include "cntrlrio.h"
include "setupdma.h"
#include "rtint.h"
#include "lowlevel.h"
#include "biostuff.h"
#include "lineariz.h"
#include "autocycl.h"
#include "cpm.h"

/**************************************************/
/*                      CODE                      */
/**************************************************/ define MODE_Y          20
define MODE_X          220 define TORQUE_Y        120
define TORQUE_X        200 define VELOCITY_Y      240
define VELOCITY_X      200 static char torqueStr[8],
            lastTorqueStr[8];
static int torqueDigit;
static char velocityStr[8],
            lastVelocityStr[8];
static int velocityDigit;
static int displayTorque;
static int velocity;
static int velArray[8];
static int velIndex;
```

-129-

```c
static int endStop,s tStop;

void initCPMBioFeedBack(void)
{
  velocity = 0;
  velIndex = -100;
  setcolor(WHITE);
  strcpy(torqueStr,"aaaa");
  strcpy(lastTorqueStr,torqueStr);
  strcpy(velocityStr,"aaaa");
  strcpy(lastVelocityStr,velocityStr);
  settextstyle(TRIPLEX_FONT,HORIZ_DIR,FONT_MULTIPLIER);
  outtextxy(MODE_X,MODE_Y,"   CPM");
  outtextxy(0,TORQUE_Y,"TORQUE");
  outtextxy(0,VELOCITY_Y,"VELOCITY");
  torqueDigit = 3;
  velocityDigit = 3;
} int CPMBioFeedBack(void)
{
  int i;

displayTorque = abs(realTimeTorque/10);
  displayBioInfo(displayTorque,
                 YELLOW,
                 TORQUE_X,
                 TORQUE_Y,
                 &torqueDigit,
                 torqueStr,
                 lastTorqueStr);
  velocity = realTimeVelocity;
  if (velIndex < -1)
    velocity = 0,velIndex++;
  else
  {
    if (velIndex == -1)
    {
      for (velIndex=0;velIndex<8;velIndex++)
        velArray[velIndex] = velocity;
      velIndex = 0;
    }
    velArray[velIndex] = velocity;
    velIndex = ++velIndex & 7;
    velocity = 0;
    for (i=0;i<8;i++)
      velocity = velocity + velArray[i];
    velocity = (velocity+4) >> 3;   // round divide by 8
  }
  velocity = (int)((float)velocity*250.0/16.0/4096.0*360.0);
  displayBioInfo(velocity,
                 YELLOW,
                 VELOCITY_X,
                 VELOCITY_Y,
                 &velocityDigit,
                 velocityStr,
                 lastVelocityStr);
  return(0);
}
```

-130-

```c
void initCPM(void)
{
}

COUNT runCPMFunc(void)
{
   int quickExit = 0;
   int done2 = 0,done = 0;
   int inputStop1,inputStop2;
   int cpmVelocity;
   TEXT cpmVelocityStr[6];
   int  result = GOOD;

showAvail();
   cpm=wxxopen(5,0,23,79,(TEXT *)"",
               ACTIVE|BORDER|BD2|SCROLL|WDWRAP|COOKED|STANDARD|CURSOR,
               17,78,8,32);
   if( cpm == -1 )
      terror(msgListPtrs->Msg[Unable_To_Open_Cpm_Window]);
   wat(cpm,0,0);                        // need to position the cursor
   if (goodStops())
   {
     brakeOff();
     clutchOff();
     while ((!done) && (!quickExit))
     {
       atsay(0,34,(TEXT*)"CPM SET STOPS");
       sayLineFeed();
       sayLineFeed();
       sayString("Move stop #1");
       sayLineFeed();
       say(msgListPtrs->Msg[Press_Any_Key_Escape_To_Exit]);
       sayLineFeed();
       sayLineFeed();
       quickExit = waitHitThenFlushOrEscape();
       if (quickExit)
         break;
       inputStop1 = (int)readActualPosition();
       sayString("Move stop #2");
       sayLineFeed();
       say(msgListPtrs->Msg[Press_Any_Key_Escape_To_Exit]);
       sayLineFeed();
       sayLineFeed();
       quickExit = waitHitThenFlushOrEscape();
       if (quickExit)
         break;
       inputStop2 = (int)readActualPosition();
       if (abs(inputStop1 - inputStop2) > 20)
         done = 1;
       else
       {
         sayString("Insufficient Range of Motion");
         sayLineFeed();
         say(msgListPtrs->Msg[Press_Any_Key_Escape_To_Exit]);
         sayLineFeed();
         quickExit = waitHitThenFlushOrEscape();
         if (quickExit)
```

```
              break;
            erase();
            wat(cpm,0,0);                          // need to position the cursor
          }
        }
        if (!quickExit)
        {
          while (!done2)
          {
            done = 0;
            while (!done)
            {
              erase();
              at(1,0);                             // need to position the cur
              sayString("Press Escape to Exit");
              at(0,0);                             // need to position the cursor
              sayString("Enter CPM Velocity in Degrees/Second = ");
              empty(cpmVelocityStr,sizeof(cpmVelocityStr));
              get(cpmVelocityStr,(TEXT *)"999");
              readgets();
              cpmVelocity = 0;
              sscanf((char *)cpmVelocityStr,"%d",&cpmVelocity);
#ifdef MOTORCURRENT
              if ((cpmVelocity >= 10) && (cpmVelocity <= 100))
                done = 1
#ifdef LINEARIZED
              ,cpmVelocity = calcCPMVelocity(cpmVelocity);
#else
              ;
#endif
#else
              if ((cpmVelocity >= 45) && (cpmVelocity <= 360))
                done = 1;
#endif
              if (cpmVelocity == 0)
                done2 = 1,done = 1,result = BAD;
            }
            if ((inputStop1 + inputStop2)/2 > ((cwStop+ccwStop)/2)) // assume right
            {
              if (inputStop1 > inputStop2)
              {
                startStop = inputStop2;
                endStop = inputStop1;
              }
              else
              {
                startStop = inputStop1;
                endStop = inputStop2;
              }
            }
            else // assume left hand
            {
              if (inputStop1 > inputStop2)
              {
                startStop = inputStop1;
                endStop = inputStop2;
              }
              else
              {
                startStop = inputStop2;
```

-131-

```
                                            -132-
            endStop    inputStop1;
         }
      }
      if (!done2)
      {
         erase();
         done = moveToPositionFromCw(startStop);
         say(msgListPtrs->Msg[Press_Any_Key_Escape_To_Exit]);
         sayLineFeed();
         quickExit = waitHitThenFlushOrEscape();
         if (!quickExit)
         {
            setgraphmode(getgraphmode());
            initCPMBioFeedBack();
#ifdef MOTORCURRENT
            startDmaInts();                         //
            doInterrupt = true;                     //
            brakeOff();
            clutchOn(MAXCLUTCH);
            done = 0;  // reset done
            while (!done)
            {
               done = velMoveToPositionFromCw(endStop,cpmVelocity,CPMBioFeedBack
               if (!done)
               {
                  done = velMoveToPositionFromCw(startStop,cpmVelocity,CPMBioFeed
               }
            }
            if (autoCycle)
               done2 = 1;
            enterIdleMode();
            doInterrupt = false;                    //
            stopDmaInts();
#else
            startDmaInts();                         //
            doInterrupt = true;                     //
            brakeOff();
            clutchOn(MAXCLUTCH);
            enterVelocityMode();                    // start velocity based
            done = 0;  // reset done
            while (!done)
            {
               done = velMoveCommandPositionFromCw(endStop,calcVelocity(-cpmVelo
               if (!done)
               {
                  done = velMoveCommandPositionFromCw(startStop,calcVelocity(cpmV
               }
            }
            if (autoCycle)
               done2 = 1;
            enterIdleMode();
            doInterrupt = false;                    //
            stopDmaInts();
#endif
            kbFlush();
            restorecrtmode();
            textbackground(WHITE);
            clrscr();
         }
         else
```

```
                result =    ;
          }
       }
     }
     else
        result = BAD;
  }
  else
  {
    result = BAD;
    sayString("Need to initialize controller first");
    sayLineFeed();
    sayString("Press any key to continue");
    waitHitThenFlush();
  }
  textbackground(WHITE);
  clrscr();
  wclose(cpm);
  showAvail();
  brakeOn(1);
  clutchOff();
  return(result);
}

/*
 * End Of File
 */
```

-134-

E.D.C. File Print-ou  f PATIENT.C,   on 11-3-91,     3:59 PM

```
/* * * * * * * * * * * * * * * * * * * * * * * * * * * * *
 *
 *    File: PATIENT.C
 *    Date: 05/05/91
 *    Time: 11:27:48.15
 *  Author: Joe Forma
 *
 * * * * * * * * * * * * * * * * * * * * * * * * * * * * */ include <vcstdio.h>
include <string.h>
include <alloc.h>
include <stdlib.h> include "constant.h"

include "patient.h"
#include "loadmsgs.h"
include "utility.h"
#include "status.h"
#include "setutil.h"
#include "siconver.h"

/***********************************************************/
/*                       CODE                              */
/***********************************************************/ void initPatientEntry()
{
 empty(patientData.last,sizeof(patientData.last));
 empty(patientData.first,sizeof(patientData.first));
 empty(patientData.id1,sizeof(patientData.id1));
 empty(patientData.id2,sizeof(patientData.id2));
 empty(patientData.physician,sizeof(patientData.physician));
 empty(patientData.clinician,sizeof(patientData.clinician));
 empty(patientData.pathology,sizeof(patientData.pathology));
 empty(patientData.diagsurg,sizeof(patientData.diagsurg));
 empty(patientData.weight,sizeof(patientData.weight));
 patientData.lweight = 0;
 empty(patientData.height,sizeof(patientData.height));
 patientData.lheight = 0;
 empty(patientData.age,sizeof(patientData.age));
 empty(patientData.domside,sizeof(patientData.domside));
 empty(patientData.invside,sizeof(patientData.invside));
 empty(patientData.gender,sizeof(patientData.gender));
 empty(patientData.comment1,sizeof(patientData.comment1));
 empty(patientData.comment2,sizeof(patientData.comment2));
 empty(weightbase,sizeof(weightbase));
 empty(heightbase,sizeof(heightbase));
}

COUNT redefinePatientEntrySetExit(GETTABLE *thistable)
{
```

-135-

```c
    if (thistable->res    == vckey.abort)   /* redefine  cape key if set table */
      if (thistable->cu .ode->selset)
        thistable->result = RET;
    if (thistable->result == vckey.fldright)   /* redefine down arrow key if last i
      if (!(thistable->curnode->next))
      {
        thistable->curnode = thistable->head;
        return(1); /* eat the key stroke */
      }
    if (thistable->result == vckey.fldleft)   /* redefine up arrow key if first ite
      if (thistable->curnode == thistable->head)
      {
        thistable->curnode = thistable->tail;
        return(1); /* eat the key stroke */
      }
    return(GOOD);
}

COUNT redefinePatientEntryExit(GETTABLE *thistable)
{
    if (thistable->result == vckey.abort)
      vcsaveds(thistable); /* save temp fields */
    return(GOOD);
}

COUNT entryFuncMaleFemale(GETTABLE *thistable)

{
    searchSet(thistable,Male_Female_Set_Parms);
    return(GOOD);
}

COUNT entryFuncSide(GETTABLE *thistable)

{
    searchSet(thistable,Side_Set_Parms);
    return(GOOD);
} static void contractParm(unsigned long theParm,TEXT *theString,COUNT theBase,COU {
    COUNT i;
    TEXT tStr[6];

i = contractNumber(theParm,theBase);
    itoa(i,(char *)tStr,10);
    strncpy((char *)theString,(char *)tStr,3);
    if (theString[0] == '0')
      theString[0] = ' '; /* do not display a 0 */
    padString((char *)theString,theWidth);
    stringRightJustify((char *)theString);
} static unsigned long expandParm(TEXT *theString,COUNT theBase)
{
    COUNT i;

i = atoi((char *)theString);
    return(expandNumber(i,theBase));
```

-136-

```
}
COUNT patientEntryFunc()
  {
    TEXT *statusSet;
    COUNT done = 0;
    COUNT result;
    VCSELSET *selsetGender;
    VCSELSET *selsetSide;

showAvail();
    statusSet = farmalloc(81);
//  displayStatusLine(To_Choose,To_Move,Cret,To_Select,None,None,None,None);
    strcpy((char *) statusSet,(char *) statusLine);
//  displayStatusLine(Up_Dn,To_Move,At_Cursor,None,None,None,None,None);
    patientEntry=wxxopen(5,0,23,79,(TEXT *)"",
                    ACTIVE|BORDER|BD1|CURSOR|CENTER,
                    17,78,8,32);
    if( patientEntry == -1 )
        terror(msgListPtrs->Msg[Unable_To_Open_Patient_Window]);
    selsetGender = bldset(&msgListPtrs->Msg[Male_Female_Set_Parms]);
    selsetSide = bldset(&msgListPtrs->Msg[Side_Set_Parms]);
    xatsay(0,29,msgListPtrs->Msg[Patient_Data_Heading],vc.dflt);
    xatsay(2,7,msgListPtrs->Msg[Name],vc.dflt);
    xatsay(2,12,msgListPtrs->Msg[Last],vc.dflt);
    xatsay(2,38,msgListPtrs->Msg[First],vc.dflt);
    xatsay(4,7,msgListPtrs->Msg[Id1],vc.dflt);
    xatsay(4,29,msgListPtrs->Msg[Id2],vc.dflt);
    xatsay(6,2,msgListPtrs->Msg[Physician],vc.dflt);
    xatsay(8,2,msgListPtrs->Msg[Clinician],vc.dflt);
    xatsay(10,2,msgListPtrs->Msg[Pathology],vc.dflt);
    xatsay(12,2,msgListPtrs->Msg[Diag_Surg],vc.dflt);
    xatsay(2,60,msgListPtrs->Msg[Weight],vc.dflt);
    xatsay(4,60,msgListPtrs->Msg[Height],vc.dflt);
    xatsay(6,68,msgListPtrs->Msg[Age],vc.dflt);
    xatsay(8,63,msgListPtrs->Msg[Dom_Side],vc.dflt);
    xatsay(10,63,msgListPtrs->Msg[Inv_Side],vc.dflt);
    xatsay(12,65,msgListPtrs->Msg[Gender],vc.dflt);
    xatsay(14,3,msgListPtrs->Msg[Comments1],vc.dflt);
    xatsay(16,3,msgListPtrs->Msg[Comments2],vc.dflt);
    strcpy((char *)weightbase,(char *)msgListPtrs->Msg[Weight_Base_Eng]);
    strcpy((char *)heightbase,(char *)msgListPtrs->Msg[Height_Base_Eng]);
    atsay(2,67,weightbase);
    atsay(4,67,heightbase);
    contractParm(patientData.lweight,
                patientData.weight,
                WEIGHT,
                sizeof(patientData.weight)-1);
    contractParm(patientData.lheight,
                patientData.height,
                HEIGHT,
                sizeof(patientData.height)-1);
    vcghook2 = redefinePatientEntrySetExit;
    vcghook3 = redefinePatientEntryExit;
    while (!done)
    {
    xxatgetc(vcdgt, patientEntry, 2, 17, patientData.last,(TEXT *)"xxxxxxxxxxxxxx
                NULLFUNC, statusLine,(TEXT *)"", vc.dflt, vc.dflt,
                DEFAULT, STRING, NULL, NULLFUNC, NULLFUNC);
```

-137-

```
xxatgetc(vcdgt, pa'  ntEntry, 2, 44, patientData.f   t,(TEXT *)"xxxxxxxxxxxx
         NU   UNC, statusLine,(TEXT *)"", \   flt, vc.dflt,
         DEFAULT, STRING, NULL, NULLFUNC, NULLFUNC);
xxatgetc(vcdgt, patientEntry, 4, 12, patientData.id1,(TEXT *)"999999999999",
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 4, 34, patientData.id2,(TEXT *)"999999999999",
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 6, 12, patientData.physician,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 8, 12, patientData.clinician,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 10, 12, patientData.pathology,(TEXT *)"xxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 12, 12, patientData.diagsurg,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 14, 12, patientData.comment1,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 16, 12, patientData.comment2,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 16, 12, patientData.comment2,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 16, 12, patientData.comment2,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 16, 12, patientData.comment2,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 16, 12, patientData.comment2,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 16, 12, patientData.comment2,(TEXT *)"xxxxxxxxx
         NULLFUNC, statusLine,(TEXT *)"", vc.dflt, vc.dflt,
         DEFAULT, STRING, NULL, NULLFUNC, NULLFUNC);
xxatgetc(vcdgt, patientEntry, 2, 72, patientData.weight,(TEXT *)"999",
         NULLFUNC, statusLine,(TEXT *)"", vc.dflt, vc.dflt,
         DEFAULT, STRING|FLDBLANK, NULL, NULLFUNC, rightJustify);
xxatgetc(vcdgt, patientEntry, 4, 72, patientData.height,(TEXT *)"999",
         NULLFUNC, statusLine,(TEXT *)"", vc.dflt, vc.dflt,
         DEFAULT, STRING|FLDBLANK, NULL, NULLFUNC, rightJustify);
xxatgetc(vcdgt, patientEntry, 6, 72, patientData.age,(TEXT *)"99",
         NULLFUNC, statusLine,(TEXT *)"", vc.dflt, vc.dflt,
         DEFAULT, STRING|FLDBLANK, NULL, NULLFUNC, rightJustify);
xxatgetc(vcdgt, patientEntry, 8, 72, patientData.domside,(TEXT *)"XXXXX",
         NULLFUNC, statusSet,(TEXT *)"", vc.dflt, vc.dflt,
         DEFAULT, SETONLY|STRING, selsetSide, entryFuncSide, NULLFUNC)
xxatgetc(vcdgt, patientEntry, 10, 72, patientData.invside,(TEXT *)"XXXXX",
         NULLFUNC, statusSet,(TEXT *)"", vc.dflt, vc.dflt,
         DEFAULT, SETONLY|STRING, selsetSide, entryFuncSide, NULLFUNC)
xxatgetc(vcdgt, patientEntry, 12, 72, patientData.gender,(TEXT *)"XXXXXX",
         NULLFUNC, statusSet,(TEXT *)"", vc.dflt, vc.dflt,
         DEFAULT, SETONLY|STRING, selsetGender, entryFuncMaleFemale, N
```

-138-

```
      result = readgets(
      if (result == vcke    ort)
        done = 1;
    }
    vcghook2 = NULL;
    vcghook3 = NULL;
    freeSet(selsetGender);
    freeSet(selsetSide);
    wclose(patientEntry);
    farfree(statusSet);
    patientData.lweight = expandParm(patientData.weight,WEIGHT);
    patientData.lheight = expandParm(patientData.height,HEIGHT);
    showAvail();
    return(GOOD);
}

/*
 * End Of File
 */
```

-139-

E.D.C. File Print-out - PRTSCRN.C, on 11-3-91, a' 1:00 PM define DEBUG0

```
/* * * * * * * * * * * * * * * * * * * * * * * * * * * * * * * * *
 *
 *      File: prtscrn.c
 *      Date: 07/19/91
 *      Time: 12:00:00
 *      Author: Joe Forma
 *
 *                      C O N T E N T S
 *
 *  function screenDump(
 *                  int printerType,        // 0 = epson 9 : 1 = epson 24 : 2
 *                  int linePrinterPort,    // 0 = lpt1 : 1 = lpt2
 *                  int orientation,        // 0 = portrait : 1 = landscape
 *                  int dotDensity,         // 75,100,150,300 dot per inch
 *                  int startAtXPos         // starting x coordinate pixel
 *                  int numberOfXPixels     // number of pixels in the x direc
 *                  int startAtYPos         // starting y coordinate pixel
 *                  int numberOfYPixels     // number of pixels in the y direc
 *                  int xOffsetAtPrinter    // offset in the x plane in units
 *                  int yOffsetAtPrinter    // offset in the y plane in units
 *                  );
 *
 *  This function will take any portion of a VGA 640 x 480 screen image and
 *  install it onto a page at appropriate Printer Type . The image can be offset
 *  within the boundaries of the page.  Colors 0 and 8 will be white and all
 *  other colors will be black.
 *
 *
 *  function printReport(
 *                  int linePrinterPort,    // 0 = lpt1 : 1 = lpt2
 *                  );
 *
 *  This function will send a form feed to the Printer to start the print.
 *
 * * * * * * * * * * * * * * * * * * * * * * * * * * * * * * * * */ include <stdio.h>
include <dos.h>
#include <io.h>
#include <fcntl.h>
#include <stat.h>
#include <graphics.h>
#include <stdlib.h>
include <string.h> include "..\home\rdvga.h"

static unsigned char *prtError = MK_FP(0x50,0);

#ifdef DEBUG
  static int debugHandle;
#endif
```

-140-

```c
#define MAXBYTES        // extra 1 for safety
#define MAXCOLUMN  480
#define MAXROW     640
define BITS 7 static void printChar(int lpt,char theChar)
{ ifdef DEBUG
 write(debugHandle,&theChar,1);
#else
   asm {
        mov al,theChar;
        mov ah,0;
        mov dx,lpt;
        int 23
      }
endif
} static void printString(int lpt,char *theString)
{
  int i,len;
  len = theString[0];
  for(i=1;i<=len;i++)
    printChar(lpt,theString[i]);
} static void zeroFill(char *tStr)
{
  int i;

for (i=0;i<strlen(tStr);i++)
    if (tStr[i] == ' ')
      tStr[i] = '0';
} static int reset9PinPrinter(int lpt)

{
  // Set line spacing
  char msgString[3] = {2,0x1b,'@'};

printString(lpt,msgString);
  return(*prtError == 0xff); // return true if error
} static int set9PinLineSpace(int lpt)

{
  // Set line spacing
  char msgString[4] = {3,0x1b,'A',8};

printString(lpt,msgString);
  return(*prtError == 0xff); // return true if error
}
```

-141-

```c
static int set9PinDens (int lpt)

{
  // Set quadruple density mode
  char msgString[5] = {4,0x1b,'Z',128,7};

printString(lpt,msgString);
  return(*prtError == 0xff); // return true if error
} static int setRasterGraphics(int lpt,int dotDensity)

{
  char tStr[4];
  // set raster graphics resolution
  char msgString[8] = {7,0x1b,'*','t','0','0','0','R'};
  sprintf(tStr,"%3d",dotDensity);
  zeroFill(tStr);
  strncpy(&msgString[4],tStr,3);

printString(lpt,msgString);
  return(*prtError == 0xff); // return true if error
} static int setXYCoordinates(int lpt,int x_offset,int y_offset)

{
  char tStr[5];

// set x y location
  char msgString[17] = {16,0x1b,'*','p','0','0','0','0','X',0x1b,'*','p','0','0' if (x_offset < 0)
    x_offset = 0;
  if (x_offset > 2399)
    x_offset = 2399;
  sprintf(tStr,"%4d",x_offset);
  zeroFill(tStr);
  strncpy(&msgString[4],tStr,4);

if (y_offset < 0)
    y_offset = 0;
  if (y_offset > 3299)
    y_offset = 3299;
  sprintf(tStr,"%4d",y_offset);
  zeroFill(tStr);
  strncpy(&msgString[12],tStr,4);

printString(lpt,msgString);
  return(*prtError == 0xff); // return true if error
} static int setLeftMargin(int lpt)

{
  // set graphics left margin
```

-142-

```c
  char msgString[6] =    ,0x1b,'*','r','1','A'};

printString(lpt,msgString);
  return(*prtError == 0xff); // return true if error
} static int sendGraphicsLine(int lpt,int numBytes)

{
  char tStr[4];

//  send graphics data
  char msgString[8] = {7,0x1b,'*','b','0','0','0','W'};

sprintf(tStr,"%3d",numBytes);
  zeroFill(tStr);
  strncpy(&msgString[4],tStr,3);

printString(lpt,msgString);
  return(*prtError == 0xff); // return true if error
} static int setEndGraphicsMode(int lpt)

{
  // send end graphics command
  char msgString[5] = {4,0x1b,'*','r','B'};

printString(lpt,msgString);
  return(*prtError == 0xff); // return true if error
} static int doTheLaserDump(int lpt,
                          int direction,
                          int dotDensity,
                          int x_start,
                          int x_length,
                          int y_start,
                          int y_length,
                          int x_offset,
                          int y_offset,
                          int maxrow,
                          int maxcolumn)

{
    struct lBufArray {
                         unsigned char lBuf[MAXBYTES];
                     };

struct lBufArray *lineBuffer;
    int i;
    unsigned int row,column;
    int rowIndex;
    unsigned char pixel;
    int bitIndex = BITS;

#ifdef DEBUG
    if ((debugHandle =  open("printer.dat",O_CREAT|O_WRONLY|O_BINARY|O_TRUNC,S_IR
      return(1);
    }
```

```
#endif                           -143-
    if (direction == 1)
    {
      i = 300 / dotDensity;   // get the multiplier
      x_offset = 2399-x_offset-(i*x_length);
    } lineBuffer = malloc(sizeof(struct lBufArray));

if (setRasterGraphics(lpt,dotDensity)) // set raster graphics resolution
    {
      free(lineBuffer);
      return(1);
    } if (setXYCoordinates(lpt,x_offset,y_offset)) // position the cursor
    {
      free(lineBuffer);
      return(1);
    } if (setLeftMargin(lpt)) // set left margin
    {
      free(lineBuffer);
      return(1);
    } column = y_start;
    while ((column < (y_start+y_length))&&(column < maxcolumn))
    {
      rowIndex = 0;
      for (row = x_start;(row < (x_start+x_length)&&(row < maxrow));row++)   // cr
      {
        if (direction == 0)
//          pixel = ((getpixel(row,column) & 7) > 0);
            pixel = ((readVGApix(row,column) & 7) > 0);
        else
//          pixel = ((getpixel(column,maxrow-row-1) & 7) > 0);
            pixel = ((readVGApix(column,maxrow-row-1) & 7) > 0);
        switch (bitIndex)
        {
          case 7 : lineBuffer->lBuf[rowIndex] = (pixel << bitIndex); // insert
                   break;
          case 0 :
          case 1 :
          case 2 :
          case 3 :
          case 4 :
          case 5 :
          case 6 : lineBuffer->lBuf[rowIndex] = lineBuffer->lBuf[rowIndex] | (pix
                   break;
        }
        if ((--bitIndex) < 0)
        {
          bitIndex = BITS;
          if (rowIndex++ > MAXBYTES)
            return(1);
        }
      }
```

-144-

```c
    if (bitIndex == B  )  // stopped on even boundar
      rowIndex--;         // back off last increment
    if (sendGraphicsLine(lpt,rowIndex+1))
    {
      free(lineBuffer);
      return(1);
    }
    for (i=0;i<=rowIndex;i++)
    {
      printChar(lpt,lineBuffer->lBuf[i]);
    }
    column++;
  }
  if (setEndGraphicsMode(lpt))
  {
    free(lineBuffer);
    return(1);
  } free(lineBuffer);
ifdef DEBUG
  close(debugHandle);
#endif
  return(0);
} static int doThe9PinDump(int lpt)

{
    struct lBufArray {
                    unsigned char lBuf[641];
                    };

struct lBufArray *lineBuffer;
    int i;
    unsigned int row,column;
    unsigned char pixel;
    int bitIndex;

#ifdef DEBUG
    if ((debugHandle =  open("printer.dat",O_CREAT|O_WRONLY|O_BINARY|O_TRUNC,S_IR
      return(1);
    }
endif lineBuffer = malloc(sizeof(struct lBufArray));

if (reset9PinPrinter(lpt)) // set line spacing
    {
      free(lineBuffer);
      return(1);
    } if (set9PinLineSpace(lpt)) // set line spacing
    {
      free(lineBuffer);
      return(1);
    }
```

-145-

```c
    column = 0;
    while (column < MAXCOLUMN)
    {
      for (row = 0; row < MAXROW; row++)
      {
        pixel = 0;
        bitIndex = 0;
        for (bitIndex = 0;bitIndex <= 7;bitIndex++)   // create the line buffer
        {
          pixel = pixel + (((readVGApix(row,column+7-bitIndex) & 7) > 0) << bitIn
        }
        lineBuffer->lBuf[row] = pixel; // insert
      }
      if (set9PinDensity(lpt)) // set graphics resolution and data width
      {
        free(lineBuffer);
        return(1);
      }
      for (i=0;i<MAXROW;i++)
      {
       printChar(lpt,lineBuffer->lBuf[i]);
       printChar(lpt,lineBuffer->lBuf[i]);
       printChar(lpt,lineBuffer->lBuf[i]);
      }
      column+=8;
    } free(lineBuffer);
ifdef DEBUG
  close(debugHandle);
#endif
  return(0);
} int printReport(int lpt)
{
  // send form feed
  char msgString[2] = {1,0xc};

printString(lpt,msgString);
  return(*prtError == 0xff); // return true if error
} int screenDump(int printerType,
               int lpt,
               int direction,
               int dotDensity,
               int x_start,
               int x_length,
               int y_start,
               int y_length,
               int x_offset,
               int y_offset)

{
  int result;

switch (printerType)
  {
```

-146-

```
case 0 : {
          result   doThe9PinDump(lpt);
        }
        break;
case 1 : {
        }
        break;
case 2 : {
          if (x_start < 0)
            x_start = 0;
          if (x_start > (MAXROW-1))
            x_start = MAXROW-1;
          if (x_length < 1)
            x_length = 1;
          if (x_length > MAXROW)
            x_length = MAXROW;

if (y_start < 0)
            y_start = 0;
          if (y_start > (MAXCOLUMN-1))
            y_start = MAXCOLUMN-1;
          if (y_length < 1)
            y_length = 1;
          if (y_length > MAXCOLUMN)
            y_length = MAXCOLUMN;

if (dotDensity < 100)
            dotDensity = 75;
          else
            if (dotDensity < 150)
              dotDensity = 100;
            else
              if (dotDensity < 300)
                dotDensity = 150;
              else
                dotDensity = 300;

switch (direction)
          {
            case 1   : result = doTheLaserDump(lpt,
                                                1,
                                                dotDensity,
                                                y_start,
                                                y_length,
                                                x_start,
                                                x_length,
                                                y_offset,
                                                x_offset,
                                                MAXCOLUMN,
                                                MAXROW);
                       break;
            default : result = doTheLaserDump(lpt,
                                                0,
                                                dotDensity,
                                                x_start,
                                                x_length,
                                                y_start,
                                                y_length,
                                                x_offset,
```

-147-

```
                    break;
            }
        }
        break;
    }
    return(result);
}
```

```
            y_    set,
            MA.   w,
            MAXCOLUMN);
```

-148-

E.D.C. File Print-out    REACTION.C,   on 11-3-91,    4:01 PM

```c
#define DODMA
#define CURRENTMODE
#define CREEPRATE 15.0
/* * * * * * * * * * * * * * * * * * * * * * * * * *
 *
 *    File: REACTION.C
 *    Date: 05/05/91
 *    Time: 11:27:48.15
 *  Author: Joe Forma
 *
 * * * * * * * * * * * * * * * * * * * * * * * * * */ include <vcstdio.h>
include <graphics.h>
#include <alloc.h>
#include <string.h>
#include <stdlib.h>
#include <conio.h>
#include <time.h>
#include <dos.h>
include <math.h> include "loadmsgs.h"
include "utility.h"
#include "keycodes.h"
#include "status.h"
#include "setutil.h"
#include "siconver.h"
#include "cntrlrio.h"
include "setupdma.h"
#include "rtint.h"
#include "lowlevel.h"
#include "lineariz.h"
#include "biostuff.h"
#include "summary.h"
#include "setstops.h"
#include "autocycl.h"
#include "reaction.h"

/****************************************************/
/*                      CODE                        */
/****************************************************/ define MODE_Y          20
define MODE_X         200 define AVGTORQUE_Y    120
define AVGTORQUE_X    300 define AVGTIME_Y      240
define AVGTIME_X      300 define REPCOUNT_Y     120
define REPCOUNT_X     550 define MINMOVE    MINROM-500
```

-149-

```c
static char avgTorque_[8],
                                                        lastAvgTorqueStr[8];
static int avgTorqueDigit;
static char avgTimeStr[8],
                                                        lastAvgTimeStr[8];
static int avgTimeDigit;
static long peakTorque;
static long displayTorque;
static long displayTime;
static whichWay testDirection;
static long reactionTime;
static char repStr[8],
                                                        lastRepStr[8];
static int repCount;
static long startStop,endStop;
static int randomOffset;

static int state;

#define REACTION_POSITION_DRIVETHRU    MINMOVE
#define REACTION_TORQUE_STOP_LIMIT       200    // 20.0 IN/LBS
define REACTION_POSITION_STOP_LIMIT     200    // almost 2 degrees define REACTION_TIME_MAX    1000 void reactionInterruptFunc(void)
{
  if (abs(realTimeTorque) > REACTION_TORQUE_STOP_LIMIT)
    doReactionFlag = false;  // stop counting time
  if (testDirection == decreasing)
  {
    if (((startStop-randomOffset)-REACTION_POSITION_STOP_LIMIT) > realTimePositi
      doReactionFlag = false;   // stop counting time
  }
  else
  {
    if (((startStop+randomOffset)+REACTION_POSITION_STOP_LIMIT) < realTimePositi
      doReactionFlag = false;   // stop counting time
  }
  if (reactionTime < 1000)
    reactionTime++;
} int reactionTimeBioFeedBack(void)
{
/*
debug
   if ((doInterrupt == true) && (doReactionFlag == false))
               return(1);   // break
        return(0);
}
*/ displayTorque = abs(realTimeTorque);
  if (displayTorque > peakTorque)
    peakTorque = displayTorque;
  displayBioInfo((int)peakTorque/10,
              YELLOW,
              AVGTORQUE_X,
```

```
                            AVG_QUE_Y,
                            &avgTorqueDigit,
                            avgTorqueStr,
                            lastAvgTorqueStr);
    displayTime = reactionTime*1000/250;
    displayBioInfo((int)displayTime,
                   YELLOW,
                   AVGTIME_X,
                   AVGTIME_Y,
                   &avgTimeDigit,
                   avgTimeStr,
                   lastAvgTimeStr);
    displayBioInfoDigit(repCount, //state,
                        YELLOW,
                        REPCOUNT_X,
                        REPCOUNT_Y,
                        repStr, if ((doInterrupt == true) && (doReactionFlag == false))
        return(1);   // break
    return(0);
} void initReactionBioFeedBack(void)
{
    setcolor(WHITE);
    strcpy(avgTorqueStr,"aaaa");
    strcpy(lastAvgTorqueStr,avgTorqueStr);
    strcpy(avgTimeStr,"aaaa");
    strcpy(lastAvgTimeStr,avgTimeStr);
    strcpy(repStr,"a");
    strcpy(lastRepStr,repStr);
    settextstyle(TRIPLEX_FONT,HORIZ_DIR,FONT_MULTIPLIER);
    outtextxy(MODE_X,MODE_Y,"REACTION TIME");
    outtextxy(0,AVGTORQUE_Y,"PEAK TORQUE");
    outtextxy(0,AVGTIME_Y,"TIME");
    outtextxy(REPCOUNT_X-60,REPCOUNT_Y,"REP");

avgTorqueDigit = 3;
    avgTimeDigit = 3;
    peakTorque = 0;
    repCount = 0;
    reactionTime = 0;
} void initReaction(void)
{
}

COUNT runReactionFunc(void)
{
    int quickExit = 0;
    int done = 0;
    int result = GOOD;
    long tempPosition;
    long moveRange;
```

-151-

```
    showAvail();
    reaction=wxxopen(5, -3,79,(TEXT *)"",
                    ACTIVE|BORDER|BD2|SCROLL|WDWRAP|COOKED|STANDARD|CURSOR,
                    17,78,8,32);
    if ( reaction == -1 )
       terror(msgListPtrs->Msg[Unable_To_Open_Reaction_Time_Window]);
    wat(reaction,0,0);                          // need to position the cursor
    if (goodStops())
    {
       brakeOff();
       clutchOff();
       if (!autoCycle)
          quickExit = runSetStopsFunc();
       atsay(0,28,(TEXT*)"REACTION TIME TEST");
       sayLineFeed();
       sayLineFeed();
       sayString("Moving to desired position");
       sayLineFeed();
       quickExit = idleMoveToPosition(theReport.startStop);
       if (!quickExit)
       {
          startStop = theReport.startStop;
          endStop = theReport.endStop;
/*
          sayLineFeed();
          sayString("startStop = ");
          sayLong(startStop);
          sayString("   endStop = ");
          sayLong(endStop);
          sayLineFeed();
          sayString("MINMOVE = ");
          sayLong(MINMOVE);
          sayLineFeed();
          sayString("   REACTION_POSITION_DRIVETHRU = ");
          sayLong(REACTION_POSITION_DRIVETHRU);
          sayLineFeed();
          quickExit = waitHitThenFlushOrEscape();
*/
          brakeOn(MAXBRAKE);
          setgraphmode(getgraphmode());
          state = 0;
#ifdef DODMA
          startInt();                           //
#endif
          if (startStop > endStop)
             testDirection = decreasing;   // right hand
          else
             testDirection = increasing;   // left hand
//printf("testDirection = %s\n",(testDirection==increasing)?"increasing":"decrea
          brakeOff();
          initReactionBioFeedBack();
          while (!done)
          {
             doInterrupt = false;
             doReactionFlag = false;
//printf("moving to startStop: %5ld      \n",startStop);
             state = 1;
             done = idleVelMoveToPosition(startStop,calcCPMVelocity(25.0),reactionTim
             state = 2;
             reactionTime = 0;
```

-152-

```
           realTimeTorqu     0;
           peakTorque = 
           reactionTimeBioFeedBack();
           reactionTimeBioFeedBack();
           reactionTimeBioFeedBack();
           reactionTimeBioFeedBack();
           if (!done)
           {
              doInterrupt = true;                              //
              waitForInterrupt = true;
              while(waitForInterrupt) ;
              randomize();
              moveRange = labs(startStop-endStop);
              if (moveRange > 30000) moveRange = 30000;
                 randomOffset = random(moveRange-MINMOVE)+MINMOVE;
//printf("randomOffset = %d\n",randomOffset);
              if (testDirection == decreasing)
              {
                 if (!done)
                    done = idleVelMoveToPosition(startStop-randomOffset,calcCPMVelocit
                 state = 3;
//printf("just moved to %5ld, setting doReaction flag        \n",startStop-randomOf
                 doReactionFlag = true;
                 if (!done)    // not escaped
#ifdef CURRENTMODE
                    done = idleVelMoveToPosition(startStop-randomOffset+REACTION_POSIT
//                  done = idleVelMoveToPosition(startStop+REACTION_POSITION_DRIVETHRU,c
                 state = 4;
//printf("just moved to %5ld, doReactionFlag = %d        \n",startStop-randomOffset
#else
                 {
                    clutchOn(MAXCLUTCH);
                    enterIntegralVelocityMode();
                    if (!done)
                       done = velMoveToPosition(startStop-randomOffset+REACTION_POSITIO
                    state = 4;
                    enterIdleMode();
                 }
endif
              }
              else
              {
                 if (!done)
                    done = idleVelMoveToPosition(startStop+randomOffset,calcCPMVelocit
                 state = 3;
                 doReactionFlag = true;
                 if (!done)   // not escaped
#ifdef CURRENTMODE
//                                                    done = idleVelMoveToPos
                    done = idleVelMoveToPosition(startStop-REACTION_POSITION_DRIVETHRU
                 state = 4;
#else
                 {
                    clutchOn(MAXCLUTCH);
                    enterIntegralVelocityMode();
                    if (!done)
                       done = velMoveToPosition(startStop+randomOffset-REACTION_POSITIO
                    state = 4;
                    enterIdleMode();
                 }
```

-153-

```
#endif
          }
          doReactionFlag = false;                          //
          brakeOn(MAXBRAKE);
          clutchOff();
          repCount++;
          if (repCount > 9)
             repCount = 0;
          reactionTimeBioFeedBack();
          reactionTimeBioFeedBack();
          reactionTimeBioFeedBack();
          reactionTimeBioFeedBack();
          if ((autoCycle) && (repCount > 0) && (repCount < 5))
          {
             theReport.reactionTorque[repCount-1] = (int) peakTorque;
             theReport.reactionTime[repCount-1] = (int) reactionTime * 4;
          }
          beep(1);
          if ((autoCycle) && (repCount >= 4))
          {
             done = true;
             delay(500);
          }
          while (!done)
          {
             if (kbhit())
             {
                if (myGetch() == escape)
                   done = true;
             }
             else
             {
                if (abs(realTimeTorque) < REACTION_TORQUE_STOP_LIMIT)
                   brakeOff();
                tempPosition = doInterrupt ? realTimePosition : readActualPosition
//wat(reaction,0,0);
//printf("tempPosition - endStop = %5ld - %5ld = %6ld      \n",tempPosition,endSt
                if (testDirection == decreasing)
                {
                   if (tempPosition < endStop)
                      break;
                }
                else
                {
                   if (tempPosition > endStop)
                      break;
                }
             }
          }
//printf("end of cycle\n");
       }
    }
       doInterrupt = false;                              //
#ifdef DODMA
       stopInt();
#endif
       doReactionFlag = false;
       kbFlush();
       restorecrtmode();
   }
```

```
      else
         result = BAD;
    }
    else
    {
      result = BAD;
      sayString("Need to initialize controller first");
      sayLineFeed();
      sayString("Press any key to continue");
      waitHitThenFlush();
    }
    textbackground(WHITE);
    clrscr();
    wclose(reaction);
    showAvail();
    brakeOff();
    clutchOff();
    return(result);
}

/*
 * End Of File
 */
```

-155-

E.D.C. File Print-out  SETSTOPS.C,  on 11-3-91,  4:02 PM

```c
/* * * * * * * * * * * * * * * * * * * * * * * * * * * *
 *
 *    File: SETSTOPS.C
 *    Date: 05/05/91
 *    Time: 11:27:48.15
 *  Author: Joe Forma
 *
 * * * * * * * * * * * * * * * * * * * * * * * * * * * */ include <vcstdio.h>
include <graphics.h>
#include <alloc.h>
#include <string.h>
#include <conio.h>
include <math.h> include "loadmsgs.h"
include "keycodes.h"
#include "utility.h"
#include "status.h"
#include "setutil.h"
#include "cntrlrio.h"
#include "lowlevel.h"
#include "summary.h"
#include "setstops.h"
#include "rtint.h"

/***********************************************************/
/*                       CODE                              */
/***********************************************************/

COUNT runSetStopsFunc(void)
{
        int quickExit = 0;
        int done = 0;
        long inputStop1, inputStop2;
        int result = GOOD;

kbFlush();
        showAvail();
        setStops=wxxopen(5,0,23,79,(TEXT *)"",
                                                                                ACTIVE|
                                                                                17,78,8
        if( setStops == -1 )
                        terror(msgListPtrs->Msg[Unable_To_Open_Set_Stops_Window]
        wat(setStops,0,0);                              // need to position the curso
        brakeOff();
        clutchOff();
        while ((!done) && (!quickExit))
        {
                atsay(0,30,(TEXT*)"SET STOPS");
                sayLineFeed();
                sayLineFeed();
                sayString("Move stop #1");
```

```
                        -156-
        say:  Feed();
        say(msgListPtrs->Msg[Press_Any_Key_Escape_To_Exit]);
        sayLineFeed();
        sayLineFeed();
        quickExit = waitHitThenFlushOrEscape();
        if (quickExit)
                break;
        inputStop1 = doInterrupt ? realTimePosition : readActualPositio
        sayString("Move stop #2");
        sayLineFeed();
        say(msgListPtrs->Msg[Press_Any_Key_Escape_To_Exit]);
        sayLineFeed();
        sayLineFeed();
        quickExit = waitHitThenFlushOrEscape();
        if (quickExit)
                break;
        inputStop2 = doInterrupt ? realTimePosition : readActualPositio
        if (labs(inputStop1 - inputStop2) > MINROM)
                done = 1;
        else
{
  sayString("Insufficient Range of Motion");
  sayLineFeed();
                say(msgListPtrs->Msg[Press_Any_Key_Escape_To_Exit]);
                sayLineFeed();
                quickExit = waitHitThenFlushOrEscape();
                if (quickExit)
                        break;
                erase();
                wat(setStops,0,0);                          // need to po
        }
    }
    if (!quickExit)
    {
        erase();
        if ((inputStop1 + inputStop2)/2 < (midpoint)) // assume right h
        {
                if (inputStop1 < inputStop2)
                {
                        theReport.startStop = inputStop2;
                        theReport.endStop = inputStop1;
                }
                else
                {
                        theReport.startStop = inputStop1;
                        theReport.endStop = inputStop2;
                }
        }
        else // assume left hand
        {
                if (inputStop1 < inputStop2)
                {
                        theReport.startStop = inputStop1;
                        theReport.endStop = inputStop2;
                }
                else
                {
                        theReport.startStop = inputStop2;
                        theReport.endStop = inputStop1;
                }
```

-157-

```
                }
        else
                result = BAD;

textbackground(WHITE);
        clrscr();
        wclose(setStops);
        showAvail();
        brakeOn(1);
        clutchOff();
        return(result);
}

/*
 * End Of File
 */
```

-158-

E.D.C. File Print-out: SETUTIL.C, on 11-3-91, : :02 PM

```c
/* * * * * * * * * * * * * * * * * * * * * * * * * * * *
 *
 *    File: SETUTIL.C
 *    Date: 05/05/91
 *    Time: 11:27:48.15
 *  Author: Joe Forma
 *
 * * * * * * * * * * * * * * * * * * * * * * * * * * * */ include <vcstdio.h>
include <string.h> include "loadmsgs.h"
include "utility.h"

/*********************************************
 *
 *  searches a selection set for the appropriate
 *  index into the set in order to start the set
 *  off at that index
 *
 *********************************************/ void searchSet(GETTABLE *thistable,MSGINDEX theIndex)
{
  COUNT done = 0;
  COUNT i = 1;
  TEXT tStr[10];

if (thistable->curnode->selset)
  {
    while (!done)
    {
      if (msgListPtrs->Msg[theIndex+i] == NULL)
        done = 1;
      else
        if (strcmp((char *)thistable->curnode->tmpfld,(char *)msgListPtrs->Msg[the
           break;
    };
    if (done)
      i = 1;
    else
      i -=1;
    sprintf((char *)tStr,"%2d",i); /* convert to a string */
    strncpy((char *)&thistable->curnode->selset->display[9],(char *)tStr,2);   /*
  }
}

/*********************************************
 *
 *  free up all memory allocate to a selection set
 *
 *********************************************/ void freeSet(VCSELSET *thisset)
{
  VCSELSET *localCopy,*freeCopy;
```

-159-

```c
  localCopy = thisset,
  while (localCopy->next != NULL)
    localCopy = localCopy->next;
  while (localCopy != thisset)
  {
    freeCopy = localCopy;
    localCopy = localCopy->prev;
    vcfree((TEXT *) freeCopy);
  }
  vcfree((TEXT *) thisset);
}

COUNT rightJustify(GETTABLE *thisgetTable)
{
  stringRightJustify((char *)thisgetTable->curnode->tmpfld);
  return(GOOD);
} void freeMenuItems(VCMENU *thisitem)
{
  MENUITEM *localCopy,*freeCopy;

localCopy = thisitem->itemtail;
  while (localCopy != NULL)      /* first free all the menu items */
  {
    freeCopy = localCopy;
    localCopy = localCopy->prev;
    vcfree((TEXT *) freeCopy);
  }
  wclose(thisitem->wno); /* close the window */
  if (thisitem->next != NULL) /* this is not the first in the list */
  {
    thisitem->next->prev = thisitem->prev; /* unlink the item */
    if (thisitem->prev != NULL) /* not the last in the list */
      thisitem->prev->next = thisitem->next; /* unlink the item */
    else
    {
      vcmchain = thisitem->next; /* now the last in the chain */
    }
  }
  vcfree((TEXT *) thisitem);
}

/*
 * End Of File
 */
```

-160-

E.D.C. File Print-out    SICONVER.C,    on 11-3-91,       4:03 PM

```c
/* * * * * * * * * * * * * * * * * * * * * * * * * * *
 *
 *    File: SICONVER.C
 *    Date: 05/05/91
 *    Time: 11:27:48.15
 * Author: Joe Forma
 *
 * * * * * * * * * * * * * * * * * * * * * * * * * * */ include <vcstdio.h> include "siconver.h"

/**********************************************************/
/*                       CODE                             */
/**********************************************************/ int convertNumber(int theNumber,int theBase)  /* convert number to si or british {
//  if (1 != 1)
     return(theNumber*baseMultiplier[1][theBase]);
//  else
//     return(theNumber*baseMultiplier[0][theBase]);
} float convertFnumber(float theNumber,int theBase)  /* convert number to si or bri {
//  if (1 != 1)
     return(theNumber*baseMultiplier[1][theBase]);
//  else
//     return(theNumber*baseMultiplier[0][theBase]);
}

/* convert number for internal storage */ unsigned long expandNumber(int theNumber, int theBase)   /* convert number to si {
  float temp;

//  if (1 != 1)
     temp = theNumber*storageConversionScale/baseMultiplier[1][theBase];
//  else
//     temp = theNumber*storageConversionScale/baseMultiplier[0][theBase];
  if (temp > storageConversionMax) temp = storageConversionMax;
  return(temp+0.5);
};

/* convert number for display */ int contractNumber(unsigned long theNumber,int theBase)  /* convert number to si

{
```

-161-

```
   float temp;

// if (1 != 1)
      temp = theNumber/storageConversionScale*baseMultiplier[1][theBase];
// else
//    temp = theNumber/storageConversionScale*baseMultiplier[0][theBase];
   if (temp > maxInt)
     temp = maxInt;
   return(temp);
};

/*
 * End Of File
 */
```

-162-

E.D.C. File Print-out : STATUS.C, on 11-3-91, at 03 PM

```c
/* * * * * * * * * * * * * * * * * * * * * * * * * * * *
 *
 *    File: STATUS.C
 *    Date: 05/05/91
 *    Time: 11:27:48.15
 *  Author: Joe Forma
 *
 * * * * * * * * * * * * * * * * * * * * * * * * * * * */ include <vcstdio.h>
include <string.h> include "loadmsgs.h"
include "status.h"

/***********************************************************/
/*                        CODE                             */
/***********************************************************/ void initStatusWindow(void)
{
  empty(statusLine,sizeof(statusLine));
  statusWindow=wxxopen(24,0,24,79,(TEXT *)"",
                    ACTIVE,
                    2,80,9,32);
  if( statusWindow == -1 )
     terror(msgListPtrs->Msg[Unable_To_Open_Status_Window]);
  setswdo(statusWindow);
} void displayStatusLine(MSGINDEX msg1,
                       MSGINDEX msg2,
                       MSGINDEX msg3,
                       MSGINDEX msg4,
                       MSGINDEX msg5,
                       MSGINDEX msg6,
                       MSGINDEX msg7,
                       MSGINDEX msg8)
{
  COUNT i;

strcpy((char *)statusLine," ");
  strcat((char *)statusLine,(char *)msgListPtrs->Msg[msg1]);
  strcat((char *)statusLine,(char *)msgListPtrs->Msg[msg2]);
  strcat((char *)statusLine,(char *)msgListPtrs->Msg[msg3]);
  strcat((char *)statusLine,(char *)msgListPtrs->Msg[msg4]);
  strcat((char *)statusLine,(char *)msgListPtrs->Msg[msg5]);
  strcat((char *)statusLine,(char *)msgListPtrs->Msg[msg6]);
  strcat((char *)statusLine,(char *)msgListPtrs->Msg[msg7]);
  strcat((char *)statusLine,(char *)msgListPtrs->Msg[msg8]);
  i = strlen((char *)statusLine);
  while (i < 79)
  {
    statusLine[i++] = ' ';
  }
```

```
  statusLine[79] = 0
}
/*
 * End Of File
 */
```

-163-

—164—

E.D.C. File Print-out   SUMMARY.C,   on 11-3-91,   1:03 PM

```c
define DEBUG0 include <vcstdio.h>
include <graphics.h>
#include <alloc.h>
#include <string.h>
#include <dos.h>
include <conio.h>
include <math.h> include "realtype.h"
include "worlddr.h"
#include "segraph.h"
#include "lowlevel.h"
#include "utility.h"
#include "cntrlrio.h"
include "rtint.h"
#include "prtscrn.h"
#include "summary.h"

static int displayData(void)
{
#define THEWINDOW1  8
#define THEWINDOW2  5
define THEWINDOW3 10 define WSCALE 651.90 define LINE1OFFSET_X 10
define LINE1OFFSET_Y 20
#define LINE2OFFSET_X 10
#define LINE2OFFSET_Y 35
#define ISOMETRICBASE_X    5
#define ISOMETRICBASE_Y    15
#define ISOTONICBASE_X     5
#define ISOTONICBASE_Y     ISOMETRICBASE_Y+60
#define ISOKINETICBASE_X   5
#define ISOKINETICBASE_Y   ISOTONICBASE_Y+60
#define TAPBASE_X          5
#define TAPBASE_Y          ISOKINETICBASE_Y+60
#define REACTIONBASE_X     5
#define REACTIONBASE_Y     TAPBASE_Y+75
#define ROMBASE_X          5
#define ROMBASE_Y          15
#define CEDARONBASE_X      75
#define CEDARONBASE_Y      65
#define BIOMEDBASE_X       CEDARONBASE_X+5
define BIOMEDBASE_Y       CEDARONBASE_Y+35 int result = 0;
    int done = 0;
    int direction;
    long offset;
    int i;
    float tempFAcc;
    char tempStr[80];
    char tempData[10];
    int samples;
```

-165-

```c
   struct viewporttype  ewinfo;
   char *prtScrnHit = ._FP(0x50,0);

dataPoint *localPointer = dataPointer;
   realtype  *pdata, *ydata, *tdata;    /* Pointers used for data */ direction = (theReport.startStop < theReport.endStop);
   offset = ((cwStop-ccwStop) >> 1);   // in units of opto counts /* Allocate some heap memory, check for null pointers */
ifdef DEBUG
#else
   samples = DATAMAX-sampleCount;

pdata = GetMem(samples);
   if (BadMem(pdata)) return(1);
   ydata = GetMem(samples);
   if (BadMem(ydata)) {free(pdata); return(1);}
   tdata = GetMem(samples);
   if (BadMem(tdata)) {free(ydata);free(pdata); return(1);} for (i=0;i<samples;i++)
   {
      ydata[i] = (float)(abs(localPointer->torqueIndex))/10.0;
      if (!direction)
         pdata[i] = ((float)(offset-localPointer->positionIndex)*float_DPP);
      else
         pdata[i] = ((float)(localPointer->positionIndex-offset)*float_DPP);
      tdata[i] = ((float)(i)/250.0);
      localPointer++;
//    printf("%5d   %5.2f   %5.2f\n",i,ydata,pdata);
   }
endif
   setgraphmode(getgraphmode());
   InitSEGraphics("",0);

SetCurrentWindow(THEWINDOW1);       /* Make the desired window active */
   SetViewBackground(8);               /* Gray View Background */
   SetAxesType(0,0);                   /* Linear-Linear scale */
#ifdef DEBUG
#else
   SelectColor(15);                    /* Color = 14 */
   AutoAxes(pdata,ydata,samples,1);    /* Auto draw&label, all the points,
                                          intercepts at xmin, ymin */
   LinePlotData(pdata, ydata,samples,14,0);   /* linePlot */
   TitleYAxis("Torque - in/lbs",0);
   TitleXAxis("Position - degrees",0);
   TitleWindow("Isokinetic Data"); /* Throw up a title on top */
endif SetCurrentWindow(THEWINDOW2);       /* Make the desired window active */
   SetViewBackground(0);               /* View Background */
   getviewsettings(&ewinfo);
   SelectColor(15);                    /* Color = 14 */
   settextstyle(DEFAULT_FONT,HORIZ_DIR,1);
   settextjustify(LEFT_TEXT,TOP_TEXT);
   outtextxy(ISOMETRICBASE_X,ISOMETRICBASE_Y,"ISOMETRIC RESULTS");
   tempFAcc = 0;
   for (i=0;i<=3;i++)
```

-166-

```
   tempFAcc = tempFA    + theReport.isometricPeakTorc   i];
tempFAcc = tempFAcc,  ,10;
strcpy(tempStr,"Average Peak Torque       ");
sprintf(tempData,"%4.1f",tempFAcc);
strcat(tempStr,tempData);
strcat(tempStr," in/lbs");
outtextxy(ISOMETRICBASE_X+LINE1OFFSET_X,ISOMETRICBASE_Y+LINE1OFFSET_Y,tempStr)
outtextxy(ISOTONICBASE_X,ISOTONICBASE_Y,"ISOTONIC RESULTS");
tempFAcc = 0;
for (i=0;i<=3;i++)
   tempFAcc = tempFAcc + theReport.isotonicWorkAcc[i];
tempFAcc = tempFAcc / 4;
tempFAcc = tempFAcc/WSCALE;
tempFAcc = tempFAcc/10;
tempFAcc = abs(tempFAcc);
strcpy(tempStr,"Work Per Repetition       ");
sprintf(tempData,"%4.1f",tempFAcc);
strcat(tempStr,tempData);
strcat(tempStr," in/lbs");
   outtextxy(ISOTONICBASE_X+LINE1OFFSET_X,ISOTONICBASE_Y+LINE1OFFSET_Y,tempStr)
outtextxy(ISOKINETICBASE_X,ISOKINETICBASE_Y,"ISOKINETIC RESULTS");
tempFAcc = 0;
for (i=0;i<=3;i++)
   tempFAcc = tempFAcc + theReport.isokineticAvgPeakTorque[i];
tempFAcc = tempFAcc/4/10;
strcpy(tempStr,"Average Peak Torque       ");
sprintf(tempData,"%4.1f",tempFAcc);
strcat(tempStr,tempData);
strcat(tempStr," in/lbs");
outtextxy(ISOKINETICBASE_X+LINE1OFFSET_X,ISOKINETICBASE_Y+LINE1OFFSET_Y,tempSt
outtextxy(TAPBASE_X,TAPBASE_Y,"TAP RESPONSE RESULTS");
tempFAcc = 0;
for (i=0;i<=3;i++)
   tempFAcc = tempFAcc + theReport.tapTime[i];
tempFAcc = (tempFAcc / 4)/250;
strcpy(tempStr,"Tap Frequency          ");
     sprintf(tempData,"%4.2f",1.0/tempFAcc);
strcat(tempStr,tempData);
strcat(tempStr," Hz");
       outtextxy(TAPBASE_X+LINE1OFFSET_X,TAPBASE_Y+LINE1OFFSET_Y,tempStr);
tempFAcc = tempFAcc*1000;
strcpy(tempStr,"Average Tap Time       ");
sprintf(tempData,"%5.0f",tempFAcc);
strcat(tempStr,tempData);
strcat(tempStr," ms");
outtextxy(TAPBASE_X+LINE2OFFSET_X,TAPBASE_Y+LINE2OFFSET_Y,tempStr);
outtextxy(REACTIONBASE_X,REACTIONBASE_Y,"REACTION TIME RESULTS");
tempFAcc = 0;
for (i=0;i<=3;i++)
   tempFAcc = tempFAcc + theReport.reactionTime[i];
tempFAcc = tempFAcc / 4;
strcpy(tempStr,"Average Reaction Time   ");
sprintf(tempData,"%5.0f",tempFAcc);
strcat(tempStr,tempData);
strcat(tempStr," ms");
outtextxy(REACTIONBASE_X+LINE1OFFSET_X,REACTIONBASE_Y+LINE1OFFSET_Y,tempStr);

SetCurrentWindow(THEWINDOW3);    /* Make the desired window active */
SetViewBackground(0);            /* View Background */
SelectColor(15);                 /* Color = 14 */
```

```
                                      -167-
settextstyle(DEFAI    FONT,HORIZ_DIR,1);
settextjustify(LEF   TEXT,TOP_TEXT);
if (theReport.startStop > theReport.endStop) // left hand
{
  tempFAcc = theReport.startStop-theReport.endStop;  // get rom
  tempFAcc = tempFAcc * float_DPP;  // convert to degrees
  strcpy(tempStr,"RANGE OF MOTION = ");
  sprintf(tempData,"%4.0f",tempFAcc);
  strcat(tempStr,tempData);
  strcat(tempStr," Degrees");   // copy
  outtextxy(ROMBASE_X,ROMBASE_Y,tempStr);
  strcpy(tempStr,"stop 1 = ");
  tempFAcc = (midpoint)-theReport.startStop;  // get start relative to 0 degre
  tempFAcc = tempFAcc * float_DPP;
  sprintf(tempData,"%3.0f",tempFAcc);   // start stop in degrees
  strcat(tempStr,tempData);   // copy
  strcat(tempStr," Degrees");   // copy
  outtextxy(ROMBASE_X+LINE1OFFSET_X,ROMBASE_Y+LINE1OFFSET_Y,tempStr);
  strcpy(tempStr,"stop 2 = ");
  tempFAcc = (midpoint)-theReport.endStop;   // get start relative to 0 degrees
  tempFAcc = tempFAcc * float_DPP;
  sprintf(tempData,"%3.0f",tempFAcc);       // end stop in degrees
  strcat(tempStr,tempData);                 // append
  strcat(tempStr," Degrees");   // copy
  outtextxy(ROMBASE_X+LINE2OFFSET_X,ROMBASE_Y+LINE2OFFSET_Y,tempStr);
}
else
{
  tempFAcc = theReport.endStop-theReport.startStop;  // get rom
  tempFAcc = tempFAcc * float_DPP;  // convert to degrees
  strcpy(tempStr,"RANGE OF MOTION = ");
  sprintf(tempData,"%4.0f",tempFAcc);
  strcat(tempStr,tempData);
  strcat(tempStr," Degrees");   // copy
  outtextxy(ROMBASE_X,ROMBASE_Y,tempStr);
  strcpy(tempStr,"stop 1 = ");
  tempFAcc = theReport.startStop-(midpoint);  // get start relative to 0 degre
  tempFAcc = tempFAcc * float_DPP;
  sprintf(tempData,"%3.0f",tempFAcc);   // start stop in degrees
  strcat(tempStr,tempData);   // copy
  strcat(tempStr," Degrees");   // copy
  outtextxy(ROMBASE_X+LINE1OFFSET_X,ROMBASE_Y+LINE1OFFSET_Y,tempStr);
  strcpy(tempStr,"stop 2 = ");
  tempFAcc = theReport.endStop-(midpoint);   // get start relative to 0 degrees
  tempFAcc = tempFAcc * float_DPP;
  sprintf(tempData,"%3.0f",tempFAcc);       // end stop in degrees
  strcat(tempStr,tempData);                 // append
  strcat(tempStr," Degrees");   // copy
  outtextxy(ROMBASE_X+LINE2OFFSET_X,ROMBASE_Y+LINE2OFFSET_Y,tempStr);
}
SelectColor(14);                  /* Color = 14 */
settextstyle(TRIPLEX_FONT,HORIZ_DIR,4);
outtextxy(CEDARONBASE_X,CEDARONBASE_Y,"Cedaron");
outtextxy(BIOMEDBASE_X,BIOMEDBASE_Y,"Medical");
setviewport(0,0,getmaxx(),getmaxy(),1);
while (!done)
{
  while (!kbhit() && (*prtScrnHit == 0));
  if (*prtScrnHit == 1)
  {
```

-168-

```
      *prtScrnHit =
      screenDump(2,0, 75,0,640,0,480,250,600);
      printReport(0);
//      screenDump();
      kbFlush();
    }
    else
      done = true;
  }
#ifdef DEBUG
#else
  free(tdata);
  free(ydata);
  free(pdata);  /* Dont forget to free heap */
#endif
  restorecrtmode();
  textbackground(WHITE);
  clrscr();
  return(result);
}

COUNT doSummary(void)
{
  displayData();
  return(GOOD);
}
```

-169-

E.D.C. File Print-out   TAP.C,   on 11-3-91,   at 4:   ?M

```c
/* * * * * * * * * * * * * * * * * * * * * * * * * * * *
 *
 *    File: TAP.C
 *    Date: 05/05/91
 *    Time: 11:27:48.15
 *  Author: Joe Forma
 *
 * * * * * * * * * * * * * * * * * * * * * * * * * * * */ include <vcstdio.h>
include <graphics.h>
#include <alloc.h>
#include <string.h>
#include <conio.h>
include <dos.h>
include <math.h> include "loadmsgs.h"
include "utility.h"
#include "status.h"
#include "setutil.h"
#include "siconver.h"
#include "cntrlrio.h"
include "setupdma.h"
#include "rtint.h"
#include "lowlevel.h"
#include "biostuff.h"
#include "summary.h"
#include "autocycl.h"
#include "tap.h"

/***********************************************************/
/*                        CODE                             */
/***********************************************************/ define MODE_Y              20
define MODE_X              200 define AVGTORQUE_Y         120
define AVGTORQUE_X         300 define AVGTIME_Y           240
define AVGTIME_X           300 define REPCOUNT_Y          120
define REPCOUNT_X          550 define TOP_TAP_WINDOW      15
define BOTTOM_TAP_WINDOW   5
define TAP_TIME_MAX        32000 define TAP_DATA_SAMPLES 4
static int lastPeakTorque;
static direction tapDirection;
static int tapCounter;
```

-170-

```c
static int tapDataAr    [2][TAP_DATA_SAMPLES];
static int tapIndex;
static long averagePeakTapTorque;
static long averageTapFreq;
static int  arraySize;
static int  beepFlag;
static char avgTorqueStr[8],
            lastAvgTorqueStr[8];
static int avgTorqueDigit;
static char avgTimeStr[8],
            lastAvgTimeStr[8];
static int avgTimeDigit;
static char repStr[8],
            lastRepStr[8];
static long displayTorque;
static long displayTime;
static int repCount;

void initTapInterruptFunc(void)

{ for (tapIndex=0;tapIndex < TAP_DATA_SAMPLES;tapIndex++)
    tapDataArray[0][tapIndex] = 0, // peak torque
    tapDataArray[1][tapIndex] = -1; // time tapIndex = 0;
  arraySize = 0;
  lastPeakTorque = abs(realTimeTorque);
  tapDirection = down;
  tapCounter = 0;
  averagePeakTapTorque = 0;
  averageTapFreq = 0;
  beepFlag = false;
} void tapInterruptFunc(void)

{
  int i;
  int localRealTimeTorque = abs(realTimeTorque);

if (++tapCounter > TAP_TIME_MAX)
    tapCounter = TAP_TIME_MAX;

if (localRealTimeTorque >= lastPeakTorque)
    lastPeakTorque = localRealTimeTorque;

if ((localRealTimeTorque < BOTTOM_TAP_WINDOW) && (tapDirection == up))
  {
    tapDirection = down;
  }
  else
    if ((localRealTimeTorque > TOP_TAP_WINDOW) && (tapDirection == down))
    {
      tapDirection = up;
      beepFlag = true;
      repCount++;
      if (repCount > 9)
```

-171-
```
      repCount = 0;
      tapDataArray[0][tapIndex] = lastPeakTorque;
      lastPeakTorque = localRealTimeTorque;
      tapDataArray[1][tapIndex] = tapCounter;
      tapCounter = 0;
      if (++tapIndex >= TAP_DATA_SAMPLES)
        tapIndex = 0;
      averagePeakTapTorque = averageTapFreq = arraySize = 0;
      for (i=0;i<TAP_DATA_SAMPLES;i++)
      {
        if (tapDataArray[1][i] >= 0)
        {
          averagePeakTapTorque+= tapDataArray[0][i];
          averageTapFreq+= tapDataArray[1][i];
          arraySize++;
        }
      }
    }
} void tapBioFeedBackFunc(void)
{
  if (beepFlag)
  {
    sound(880);
    delay(30);
    nosound();
    beepFlag = false;
  }
  displayBioInfo((int)displayTorque,
                 YELLOW,
                 AVGTORQUE_X,
                 AVGTORQUE_Y,
                 &avgTorqueDigit,
                 avgTorqueStr,
                 lastAvgTorqueStr);
  if (beepFlag)
  {
    sound(880);
    delay(30);
    nosound();
    beepFlag = false;
  }
  displayBioInfo((int)displayTime,
                 YELLOW,
                 AVGTIME_X,
                 AVGTIME_Y,
                 &avgTimeDigit,
                 avgTimeStr,
                 lastAvgTimeStr);
  displayBioInfoDigit(repCount,
                      YELLOW,
                      REPCOUNT_X,
                      REPCOUNT_Y,
                      repStr,
                      lastRepStr);
} void initTapBioFeedBackFunc(void)
{
```

-172-

```c
    setcolor(WHITE);
    strcpy(avgTorqueStr, aaaa");
    strcpy(lastAvgTorqueStr,avgTorqueStr);
    strcpy(avgTimeStr,"aaaa");
    strcpy(lastAvgTimeStr,avgTimeStr);
    strcpy(repStr,"a");
    strcpy(lastRepStr,repStr);
    settextstyle(TRIPLEX_FONT,HORIZ_DIR,FONT_MULTIPLIER);
    outtextxy(MODE_X,MODE_Y,"TAP RESPONSE");
    outtextxy(0,AVGTORQUE_Y,"AVERAGE TORQUE");
    outtextxy(0,AVGTIME_Y,"AVERAGE TIME");
    outtextxy(REPCOUNT_X-60,REPCOUNT_Y,"REP");
    avgTorqueDigit = 3;
    avgTimeDigit = 3;
    repCount = 0;
} void initTap(void)
{
}

COUNT runTapFunc(void)
{
    int quickExit = 0;
    int result = GOOD;
    long localDivisor;
    int done = false;
    int tapWait = 5;
    int i;

showAvail();
    tap=wxxopen(5,0,23,79,(TEXT *)"",
                    ACTIVE|BORDER|BD2|SCROLL|WDWRAP|COOKED|STANDARD|CURSOR,
                    17,78,8,32);
    if( tap == -1 )
        terror(msgListPtrs->Msg[Unable_To_Open_Tap_Response_Window]);
    wat(tap,0,0);                           // need to position the cursor
    if (goodStops())
    {
        brakeOff();
        clutchOff();
        if (!autoCycle)
        {
            atsay(0,28,(TEXT*)"TAP RESPONSE SET STOP");
            sayLineFeed();
            sayLineFeed();
            sayString("Move to desired position");
            sayLineFeed();
            say(msgListPtrs->Msg[Press_Any_Key_Escape_To_Exit]);
            sayLineFeed();
            quickExit = waitHitThenFlushOrEscape();
        }
        else
        {
            atsay(0,28,(TEXT*)"TAP RESPONSE SET STOP");
            sayLineFeed();
            sayLineFeed();
            sayString("Moving to desired position");
            sayLineFeed();
```

```
                                  -/73-
    quickExit = 0;
    idleMoveToPosition(theReport.endStop);
  }
  if (!quickExit)
  {
    brakeOn(MAXBRAKE);
    setgraphmode(getgraphmode());
                   startInt();                              //
    doInterrupt = true;                       //
                   waitForInterrupt = true;
                   while(waitForInterrupt) ;
                   initTapInterruptFunc();
    doTapFlag = true;
    initTapBioFeedBackFunc();
    while (!kbhit() && (!done))                             //
    {                                         //
      disable();
      localDivisor = arraySize;               // capture realtime info
      displayTorque = averagePeakTapTorque;
      displayTime  = averageTapFreq;
      enable();
      if (localDivisor)
      {
        displayTorque = abs((int)(displayTorque/10L/localDivisor));
        displayTime = abs((int)(displayTime/localDivisor));
        displayTime = displayTime*1000/250;
      }
      else
      {
        displayTorque = 0;
        displayTime = 0;
      }
      tapBioFeedBackFunc();
      if ((autoCycle) && (repCount >= 5))
        doTapFlag = false;
      if (!doTapFlag)
        if (tapWait--)
          delay(100);
        else
          done = true;
    }
    doTapFlag = false;
    doInterrupt = false;                      //
    stopInt();
    kbFlush();
    restorecrtmode();
    if ((autoCycle) && (done))
    {
      for (i=0;i<=3;i++)
      {
        theReport.tapTorque[i] = tapDataArray[0][i];
        theReport.tapTime[i]   = tapDataArray[1][i];
      }
    }
  }
  else
     result = BAD;
}
else
{
```

```
    result = BAD;
    sayString("Need to initialize controller first");
    sayLineFeed();
    sayString("Press any key to continue");
    waitHitThenFlush();
  }
  textbackground(WHITE);
  clrscr();
  wclose(tap);
  showAvail();
  brakeOff();
  clutchOff();
  return(result);
}

/*
 * End Of File
 */
```

E.D.C. File Print-out    UTILITY.C,   on 11-3-91,     :05 PM

```c
/* * * * * * * * * * * * * * * * * * * * * * * * * *
 *
 *    File: UTILITY.C
 *    Date: 05/05/91
 *    Time: 11:27:48.15
 *  Author: Joe Forma
 *
 * * * * * * * * * * * * * * * * * * * * * * * * * */ include <vcstdio.h>
include <string.h>
include <alloc.h> include "utility.h"

/**********************************************************/
/*                         CODE                           */
/**********************************************************/

/****************************************************************************
 *
 *  centers a string withing another string with spaces leading and trailing
 *
 ****************************************************************************/ void centerString(const char *theInputString,char *theOutputString, int theWidth
{
  int theLength;
  int theLoop;

theWidth--;  /* get the max num of characters */
  strcpy(theOutputString,theInputString);
  trim((TEXT *)theOutputString);
  theLength = strlen(theOutputString);
  if (theLength >= theWidth)
    theOutputString[theLength] = 0;
  else
  {
    theLoop = (theWidth-theLength) >> 1;
    while (theLoop--)
    {
      memmove(&theOutputString[1],theOutputString,++theLength);
      theOutputString[0] = ' ';
    }
    while ((theLength = strlen(theOutputString)) < theWidth)
    {
      theOutputString[theLength] = 0x20;
      theOutputString[theLength+1] = 0;
    }
  }
}

/*********************************************
 *
 *  Overlays arg2 onto arg1 no null is copied
 *
 *********************************************/
```

-176-

```c
void stopcpy(char *arg1,const char *arg2)
{
  strncpy(arg1,arg2,strlen(arg2));
}

/**********************************************
 *
 *  Adds blanks to a string up to width
 *
 **********************************************/ void padString(char *theString,int maxWidth)
{
  while (strlen(theString) < maxWidth)
    strcat(theString," ");
}

/**********************************************
 *
 *  right justifies string within a field
 *
 **********************************************/ char *stringRightJustify(char *theString)
{
  int theLength;
  int theMax;

theLength = strlen(theString);
  theMax = theLength;
  while ((theString[theLength-1] == ' ') && (theMax--))
  {
    memmove(&theString[1],
            &theString[0],
            theLength-1);
    theString[0] = 0x20;
  }
  return(theString);
}

COUNT showAvail(void)
{
  memAvail = coreleft();
  if (memHigh == 0)
  {
    memHigh = memAvail;
    memLow = memAvail;
  }
  else
  {
    if (memAvail < memLow)
      memLow = memAvail;
  }
  return(GOOD);
}

/*
```

```
* End Of File
*/
```

-177-

E.D.C. File Print-out    CNTRLRIO.C,   on 11-3-91,    1:29 PM

```c
#define FASTINIT0
#define MINROM 300001
#include <vcstdio.h>
include <dos.h>
include <conio.h>
include <math.h> include "keycodes.h"
include "lineariz.h"
#include "lowlevel.h"
#include "cntrlrio.h"
include "rtint.h"

#define WINDOW 50
#define CLUTCHCURRENT 70

/*
||||||||||||||||||||||||||||||||||||||||||||||||||||||||||||||||||||||||||
|                                                                        |
| OutHctlByte - This function was written in order to guarantee proper   |
| timing of outputs to the HCTL1100                                      |
|                                                                        |
||||||||||||||||||||||||||||||||||||||||||||||||||||||||||||||||||||||||||
*/ int OutHctlByte(unsigned int theRegister,long theByte)
{
        while(!(inportb(BOARD_STATUS_REG) & HCTL_WAIT_MASK))  /*timeout counter*/
   outportb(theRegister,theByte);                   // write
   return(0); // return with success
}

/*
||||||||||||||||||||||||||||||||||||||||||||||||||||||||||||||||||||||||||
|                                                                        |
| InHctlByte - This function was written in order to guarantee proper    |
| timing of inputs from the HCTL1100                                     |
|                                                                        |
||||||||||||||||||||||||||||||||||||||||||||||||||||||||||||||||||||||||||
*/ int InHctlByte(unsigned int theRegister)
{
  int status;

while(!((status = inportb(BOARD_STATUS_REG)) & HCTL_WAIT_MASK))  /*timeou
        if((status & HCTL_ACCESS_CODE_MASK) != HCTLWR1)
                return(-1); // error
        else
     inportb(theRegister); // first data is a throw away
        while(!((status = inportb(BOARD_STATUS_REG)) & HCTL_WAIT_MASK))  /*timeou
        if((status & HCTL_ACCESS_CODE_MASK) != HCTLWR2)
                return(-2); // error
        else
                return(inportb(theRegister));
}
```

```
/*
|||||||||||||||||||||||||||||||||||||||||||||||||||||||||||||||||||||||||
|                                                                         |
| setBrakeCurrent - This function will sent to DAC-A of the AD7528 which  |
| drives the brake current, a value 0..255 = 0..2.5 Amps                  |
|                                                                         |
|||||||||||||||||||||||||||||||||||||||||||||||||||||||||||||||||||||||||
*/ void setBrakeCurrent(int current)
{
  if (current > MAXBRAKE)   // limit the current
              current = MAXBRAKE;
   outportb(BRAKE_CONTROL_REG,current);    // write
}

/*
|||||||||||||||||||||||||||||||||||||||||||||||||||||||||||||||||||||||||
|                                                                         |
| setClutchCurrent - This function will sent to DAC-B of the AD7528 which |
| drives the clutch current, a value 0..255 = 0..2.5 Amps                 |
|                                                                         |
|||||||||||||||||||||||||||||||||||||||||||||||||||||||||||||||||||||||||
*/ void setClutchCurrent(int current)
{
  if (current > MAXCLUTCH)   // limit the current
     current = MAXCLUTCH;
   outportb(CLUTCH_CONTROL_REG,current);    // write
}

/*
|||||||||||||||||||||||||||||||||||||||||||||||||||||||||||||||||||||||||
|                                                                         |
| brakeOff - This function will set the current to the brake = 0 as well  |
| as turn off brake enable.                                               |
|                                                                         |
|||||||||||||||||||||||||||||||||||||||||||||||||||||||||||||||||||||||||
*/ void brakeOff(void)
{
        setBrakeCurrent(0);
        outportb(_8255_PORTA_REG,inportb(_8255_PORTA_REG) | BRAKE_BIT);
}

/*
|||||||||||||||||||||||||||||||||||||||||||||||||||||||||||||||||||||||||
|                                                                         |
| brakeOn - This function will set the specified current to the brake     |
| as well as turn on the brake enable.                                    |
|                                                                         |
|||||||||||||||||||||||||||||||||||||||||||||||||||||||||||||||||||||||||
*/ void brakeOn(int current)
{
        setBrakeCurrent(current);
```

```c
        outportb(_8255_PORTA_REG,inportb(_8255_PORTA_REG) & ~BRAKE_BIT);
}
/*
|||||||||||||||||||||||||||||||||||||||||||||||||||||||||||||||||||||||||||||
|                                                                             |
| clutchOff - This function will set the current to the clutch = 0 as well    |
| as turn off clutch enable.                                                  |
|                                                                             |
|||||||||||||||||||||||||||||||||||||||||||||||||||||||||||||||||||||||||||||
*/
void clutchOff(void)
{
        setClutchCurrent(0);
        outportb(_8255_PORTA_REG,inportb(_8255_PORTA_REG) | CLUTCH_BIT);
}
/*
|||||||||||||||||||||||||||||||||||||||||||||||||||||||||||||||||||||||||||||
|                                                                             |
| clutchOn - This function will set the specified current to the clutch       |
| as well as turn on the clutch enable.                                       |
|                                                                             |
|||||||||||||||||||||||||||||||||||||||||||||||||||||||||||||||||||||||||||||
*/
void clutchOn(int current)
{
        setClutchCurrent(current);
        outportb(_8255_PORTA_REG,inportb(_8255_PORTA_REG) & ~CLUTCH_BIT);
}
/*
|||||||||||||||||||||||||||||||||||||||||||||||||||||||||||||||||||||||||||||
|                                                                             |
| setActualPosition - This function is used to set the actual position        |
| register.  Generally only used during initializeation.                      |
|                                                                             |
|||||||||||||||||||||||||||||||||||||||||||||||||||||||||||||||||||||||||||||
*/
void setActualPosition(long position)
{
        OutHctlByte(HCTL_SET_ACTUAL_POS_HIGH8_REG,position >> 16);  // write
        OutHctlByte(HCTL_SET_ACTUAL_POS_MID8_REG,position >> 8);    // write
        OutHctlByte(HCTL_SET_ACTUAL_POS_LOW8_REG,position);         // write
}
/*
|||||||||||||||||||||||||||||||||||||||||||||||||||||||||||||||||||||||||||||
|                                                                             |
| readActualPosition - This function is used to read the actual position      |
| register.                                                                   |
|                                                                             |
|||||||||||||||||||||||||||||||||||||||||||||||||||||||||||||||||||||||||||||
*/
long readActualPosition(void)
{
```

```
       unsigned char mid,1              -181-
       char high;

low  = InHctlByte(HCTL_READ_ACTUAL_POS_LOW8_REG);
       mid  = InHctlByte(HCTL_READ_ACTUAL_POS_MID8_REG);
       high = InHctlByte(HCTL_READ_ACTUAL_POS_HIGH8_REG);
       return(((long)high << 16)+((long)mid << 8) + low);
}

/*
|||||||||||||||||||||||||||||||||||||||||||||||||||||||||||||||||||||||||||
|                                                                         |
| setCommandPosition - This function is used to set the command position  |
| register.  Can be used in position mode to seek a position.             |
|                                                                         |
|||||||||||||||||||||||||||||||||||||||||||||||||||||||||||||||||||||||||||
*/ void setCommandPosition(long position)
{
        OutHctlByte(HCTL_COMMAND_POS_HIGH8_REG,position >> 16);  // write
        OutHctlByte(HCTL_COMMAND_POS_MID8_REG,position >> 8);    // write
        OutHctlByte(HCTL_COMMAND_POS_LOW8_REG,position);         // write
}

/*
|||||||||||||||||||||||||||||||||||||||||||||||||||||||||||||||||||||||||||
|                                                                         |
| enterResetMode - This function is used to put the HCTL chip into reset  |
|                                                                         |
|||||||||||||||||||||||||||||||||||||||||||||||||||||||||||||||||||||||||||
*/ void enterResetMode(void)
{
        OutHctlByte(HCTL_EXEC_PROG_FUNC_REG,0);   // software reset
}

/*
|||||||||||||||||||||||||||||||||||||||||||||||||||||||||||||||||||||||||||
|                                                                         |
| enterIdleMode - This function is used to put the HCTL chip into idle.   |
| This mode is generally used when using direct control of motor current. |
|                                                                         |
|||||||||||||||||||||||||||||||||||||||||||||||||||||||||||||||||||||||||||
*/ void enterIdleMode(void)
{
        OutHctlByte(HCTL_EXEC_PROG_FUNC_REG,1);     // enter idle mode
        OutHctlByte(HCTL_SAMPLE_TIMER_REG,0x7c);    // 7c = 1 kHz
        OutHctlByte(HCTL_SELECT_PROG_FUNC_REG,0);   // clear F0
        OutHctlByte(HCTL_SELECT_PROG_FUNC_REG,3);   // clear F3
        OutHctlByte(HCTL_SELECT_PROG_FUNC_REG,5);   // clear F5
        outportb(_8255_PORTA_REG,inportb(_8255_PORTA_REG) & ~LIMIT_BIT & ~MOTOR_
        outportb(_8255_PORTC_REG,inportb(_8255_PORTC_REG) | CW_ENABLE_BIT | CCW_
        OutHctlByte(HCTL_PWM_SIGN_REV_REG,0x01);    // inhibit PWM pulse at sign
}

/*
```

-182-

```
/*
|||||||||||||||||||||   ||||||||||||||||||||||||||||   :|||||||||||||||||||
|                                                                          |
| enterPositionMode - This function is used to put the HCTL chip into the  |
| position mode and can be used to seek a position define by the command   |
| position register.                                                       |
|                                                                          |
|||||||||||||||||||||||||||||||||||||||||||||||||||||||||||||||||||||||||||
*/ void enterPositionMode(void)
{
        OutHctlByte(HCTL_DIG_FILTER_ZERO_REG,0xD0); //
        OutHctlByte(HCTL_DIG_FILTER_GAIN_REG,0x2); //
        OutHctlByte(HCTL_DIG_FILTER_POLE_REG,0x40); //
        OutHctlByte(HCTL_EXEC_PROG_FUNC_REG,3);    // enter control mode
        OutHctlByte(HCTL_SAMPLE_TIMER_REG,0x7c);   // 7c = 1 kHz
        OutHctlByte(HCTL_SELECT_PROG_FUNC_REG,0);  // clear F0
        OutHctlByte(HCTL_SELECT_PROG_FUNC_REG,3);  // clear F3
        OutHctlByte(HCTL_SELECT_PROG_FUNC_REG,5);  // clear F5
        outportb(_8255_PORTA_REG,inportb(_8255_PORTA_REG) & ~LIMIT_BIT & ~MOTOR_
        outportb(_8255_PORTC_REG,inportb(_8255_PORTC_REG) | CW_ENABLE_BIT | CCW_
        OutHctlByte(HCTL_PWM_SIGN_REV_REG,0x01);    // inhibit PWM pulse at sign
}

/*
|||||||||||||||||||||||||||||||||||||||||||||||||||||||||||||||||||||||||||
|                                                                          |
| enterIntegralVelocityMode - This function is used to put the HCTL chip into th
| integral velocity mode and can be used to seek a position define by the comman
| position register.                                                       |
|                                                                          |
|||||||||||||||||||||||||||||||||||||||||||||||||||||||||||||||||||||||||||
*/ void enterIntegralVelocityMode(void)
{
        OutHctlByte(HCTL_DIG_FILTER_ZERO_REG,0x40); //
        OutHctlByte(HCTL_DIG_FILTER_GAIN_REG,0x2); //
        OutHctlByte(HCTL_DIG_FILTER_POLE_REG,0x40); //
        OutHctlByte(HCTL_SAMPLE_TIMER_REG,111);    // 111 = 111 Hz just lucky
        OutHctlByte(HCTL_SELECT_PROG_FUNC_REG,0);  // clear F0
        OutHctlByte(HCTL_SELECT_PROG_FUNC_REG,3);  // clear F3
        OutHctlByte(HCTL_SELECT_PROG_FUNC_REG,0xD); // set F5
        outportb(_8255_PORTA_REG,inportb(_8255_PORTA_REG) & ~LIMIT_BIT & ~MOTOR_
        outportb(_8255_PORTC_REG,inportb(_8255_PORTC_REG) & ~CW_ENABLE_BIT & ~CC
        OutHctlByte(HCTL_PWM_SIGN_REV_REG,0x01);    // inhibit PWM pulse at sign
        setVelocityAndAcceleration(0,0,0); // zero velocity and acceleration
        OutHctlByte(HCTL_EXEC_PROG_FUNC_REG,3);    // enter control mode
}
/*
|||||||||||||||||||||||||||||||||||||||||||||||||||||||||||||||||||||||||||
|                                                                          |
| enterProportionalVelocityMode - This function is used to put the HCTL chip int
| proportional velocity mode and can be used to seek a position define by the co
| position register.                                                       |
|                                                                          |
|||||||||||||||||||||||||||||||||||||||||||||||||||||||||||||||||||||||||||
*/
```

-183-

```c
void enterProportiona    locityMode(void)
{
        OutHctlByte(HCTL_DIG_FILTER_GAIN_REG,0x2); //
        OutHctlByte(HCTL_SAMPLE_TIMER_REG,111);   // 111 = 111 Hz just lucky
        OutHctlByte(HCTL_SELECT_PROG_FUNC_REG,0); // clear F0
        OutHctlByte(HCTL_SELECT_PROG_FUNC_REG,0xb); // set F3
        OutHctlByte(HCTL_SELECT_PROG_FUNC_REG,0x5); // clear F5
        outportb(_8255_PORTA_REG,inportb(_8255_PORTA_REG) & ~LIMIT_BIT & ~MOTOR_
        outportb(_8255_PORTC_REG,inportb(_8255_PORTC_REG) & ~CW_ENABLE_BIT & ~CC
        OutHctlByte(HCTL_PWM_SIGN_REV_REG,0x01);    // inhibit PWM pulse at sign
        setVelocityAndAcceleration(0,0,0); // zero velocity and acceleration
        OutHctlByte(HCTL_EXEC_PROG_FUNC_REG,3);    // enter control mode
}

/*
|||||||||||||||||||||||||||||||||||||||||||||||||||||||||||||||||||||||||||
|                                                                          |
| initController - This function will reset and then initialize the HCTL   |
| controller.  On exit you are left in the idle mode with both the brake   |
| and clutch off.                                                          |
|                                                                          |
|||||||||||||||||||||||||||||||||||||||||||||||||||||||||||||||||||||||||||
*/ void initController(void)
{
        outportb(_8254_MODE_REG,COUNTER0_MODE);
        outportb(_8254_MODE_REG,COUNTER1_MODE);
        outportb(_8254_MODE_REG,COUNTER2_MODE);

outportb(_8254_COUNTER0,COUNTER0_INIT_DATA);

outportb(_8254_COUNTER1,COUNTER1_INIT_DATA & 0XFF);
        outportb(_8254_COUNTER1,COUNTER1_INIT_DATA >> 8);

outportb(_8254_COUNTER2,COUNTER2_INIT_DATA & 0XFF);
        outportb(_8254_COUNTER2,COUNTER2_INIT_DATA >> 8);

outportb(_8255_MODE_REG, _8255_MODE_DATA);          // set the mode
        outportb(_8255_PORTA_REG,DISABLE_ALL);
        brakeOff();                                         // no brake
        clutchOff();                                        // no clutch
        outportb(_8255_PORTA_REG,inportb(_8255_PORTA_REG) | RESET_BIT); // hardw
        OutHctlByte(HCTL_SELECT_PROG_FUNC_REG,0);    // dummy write to clear r/w
        delay(1);
        outportb(_8255_PORTA_REG,inportb(_8255_PORTA_REG) & ~RESET_BIT); // rele
        delay(1);
        InHctlByte(HCTL_SELECT_PROG_FUNC_REG);    // dummy read
        enterResetMode();                                   // first do a reset
        delay(20);                                          //
        OutHctlByte(HCTL_SAMPLE_TIMER_REG,0x7c);    // 7c = 1 kHz
        OutHctlByte(HCTL_PWM_SIGN_REV_REG,0x01);    // inhibit PWM pulse at sign
        OutHctlByte(HCTL_DIG_FILTER_ZERO_REG,0xD0); //
        OutHctlByte(HCTL_DIG_FILTER_GAIN_REG,0x2);  //
        OutHctlByte(HCTL_DIG_FILTER_POLE_REG,0x40); //
        enterIdleMode();                                    // go to idle
}
```

-184-

```c
/*
|||||||||||||||||||||||,,||||||||||||||||||||||||||||,,|||||||||||||||||||
|                                                                          |
| doInitialPosition - This function will tell the motor to seek home       |
| position (home is currently defined as full clockwise) and set that      |
| position as 0 and set cwstop to that position also.  Then move full ccw  |
| and read that position as the ccwStop (position is incremented in a      |
| counter clockwise direction)                                             |
|                                                                          |
|||||||||||||||||||||||||||||||||||||||||||||||||||||||||||||||||||||||||||
*/ int doInitialPosition(void)
{
        int done = false;
        int result = 0;
        long lastPosition;
        long tempPosition;

clutchOn(50);                                           // small clutch
        brakeOff();                                             // no brake
        delay(100);                                             // wait for brake to go off
        enterIdleMode();                                        // enter init/idle mode
        OutHctlByte(HCTL_MOTOR_CMD_REG,CCW_SEEK);               // move ccw
        lastPosition = doInterrupt ? realTimePosition : readActualPosition();
        delay(500);
        while (!done)                                           // look for movement to stop
        {
                delay(100);                                     // wait .1 seconds
                tempPosition = doInterrupt ? realTimePosition : readActualPositi
                if (labs(tempPosition - lastPosition) < HALF_DEGREE)
                        done = true;
                lastPosition = tempPosition;
                if (kbhit())
                {
                        if (myGetch() == escape)
                        {
                         result = 1;
                         enterIdleMode();                       // enter i
                         return(result);
                        }
                }
        }
        enterIdleMode();                                        // back to idle
        setActualPosition(0l);                                  // initialize this as 0
        setCommandPosition(0l);                                 // just in case
        lastPosition = doInterrupt ? realTimePosition : readActualPosition();
        ccwStop = lastPosition;                                 // capture ccwStop
#ifdef FASTINIT
        cwStop = ccwStop + MINROM;
        midpoint = (cwStop+ccwStop)/2;
//      brakeOn(MAXBRAKE);                                      // full brake
        clutchOff();                                            // no clutch
#else
        OutHctlByte(HCTL_MOTOR_CMD_REG,CW_SEEK);                // move cw
        done = false;
        delay(500);
        while (!done)                                           // look for movement to stop
        {
                delay(100);                                     // wait .1 seconds
```

-185-

```
              tempPosition = doInterrupt ? realTimePosition : readActualPositi
              if (labs(tempPosition - lastPosition) < HALF_DEGREE)
                      done = true;
              lastPosition = tempPosition;
              if (kbhit())
              {
                      if (myGetch() == escape)
                      {
                       result = 1;
                       enterIdleMode();                                // enter i
                       return(result);
                      }
              }
        }
        enterIdleMode();                               // back to idle
//      brakeOn(MAXBRAKE);                             // full brake
        clutchOff();                                   // no clutch
        cwStop = doInterrupt ? realTimePosition : readActualPosition();
        midpoint = (cwStop+ccwStop)/2;
        if ((cwStop-ccwStop) < MINROM)
                result = 2;    // flag bad range of motion
#endif
        return(result);
}

/*
|||||||||||||||||||||||||||||||||||||||||||||||||||||||||||||||||||||||||||||
|                                                                             |
| idleMoveToPosition - This function will move the arm to the position        |
| that it was told to move to.  Moving is done in                             |
| the idle mode and direct control of motor current.                          |
|                                                                             |
|||||||||||||||||||||||||||||||||||||||||||||||||||||||||||||||||||||||||||||
*/ int idleMoveToPosition(long newPosition)
{
        int done = false;
        int result = 0;
        whichWay direction;
        long lastPosition;

clutchOn(CLUTCHCURRENT);                       // small clutch
        brakeOff();                                    // no brake
        delay(100);                                    // wait for brake to come of
        enterIdleMode();                               // enter init/idle mode
        lastPosition = doInterrupt ? realTimePosition : readActualPosition();
        if (lastPosition < newPosition)
        {
                OutHctlByte(HCTL_MOTOR_CMD_REG,CW_SEEK);       // move
                direction = increasing;
        }
        else
        {
                OutHctlByte(HCTL_MOTOR_CMD_REG,CCW_SEEK);      // move
                direction = decreasing;
        }
        while (!done)
        {
```

-186-

```
                lastI   tion = doInterrupt ? realTime   ition : readActualPositi
                if (d..ection == increasing)
                {
                        if (lastPosition > (newPosition - WINDOW))
                          done = true;
                }
                else
                {
                        if (lastPosition < (newPosition + WINDOW))
                          done = true;
                }
                if (kbhit())
                {
                        if (myGetch() == escape)
                        result = 1,done = true;
                }
        }
        enterIdleMode();                                // this will set motor curre
        brakeOn(MAXBRAKE);                              // full brake
        clutchOff();                                    // no clutch
        return(result);
}

/*
|||||||||||||||||||||||||||||||||||||||||||||||||||||||||||||||||||||||||||||
|                                                                           |
| positionMoveToPosition - This function will move the arm to the           |
| position that it was told to move to.  Moving is                          |
| done in the position mode and with the HCTL having control of the motor   |
| current.                                                                  |
|                                                                           |
|||||||||||||||||||||||||||||||||||||||||||||||||||||||||||||||||||||||||||||
*/ int positionMoveToPosition(long newPosition)
{ int  done = false;
        int  result = 0;
        long lastPosition;

clutchOn(MAXCLUTCH);                            // max clutch current
        brakeOff();                                     // no brake current
        enterPositionMode();                            // start position based mode
        setCommandPosition(newPosition);                // set the position to seek
        while (!done)
        {
                lastPosition = doInterrupt ? realTimePosition : readActualPositi
                if (
                                (lastPosition < (newPosition + WINDOW)) &&
                                (lastPosition > (newPosition - WINDOW))
                        )
                        done = true;
                if (kbhit())
                {
                        if (myGetch() == escape)
                                result = 1,done = true;
                }
        }
        brakeOn(MAXBRAKE);                              // full brake current
```

–187–

```
        clutchOff();                                    ,   o clutch
        enterIdleMode ;                                /,  stop
        return(result);
}
/*
|||||||||||||||||||||||||||||||||||||||||||||||||||||||||||||||||||||||||
|                                                                         |
| waitForPosition - This function wait until the arm is at the position   |
| asked for brake and clutch currents are programed as asked.             |
|                                                                         |
|||||||||||||||||||||||||||||||||||||||||||||||||||||||||||||||||||||||||
*/ int waitForPosition(int clutchCurrent,

{
        int done = false;
        int result = 0;
        whichWay direction;
        long lastPosition;

if (clutchCurrent == 0)
                clutchOff();
        else
                clutchOn(clutchCurrent);
        if (brakeCurrent == 0)
                brakeOff();
        else
                brakeOn(brakeCurrent);
        if(doInterrupt) lastPosition = realTimePosition;
        else lastPosition = readActualPosition();        // read the current pos
        if (lastPosition < thePosition)
                direction = increasing;
        else
                direction = decreasing;
        while (!done)
        {
                (*bioFeedBack)();
                if(doInterrupt) lastPosition = realTimePosition;
                else lastPosition = readActualPosition();      // read the cur
                if (direction == increasing)
                {
                        if (lastPosition > (thePosition - WINDOW))
                          done = true;
                }
                else
                {
                        if (lastPosition < (thePosition + WINDOW))
                          done = true;
                }
                if (kbhit())
                {
                        if (myGetch() == escape)
                                result = 1,done = true;
                }
        }
```

-188-

```c
        return(result)
}
/*
|||||||||||||||||||||||||||||||||||||||||||||||||||||||||||||||||||||||||
|                                                                         |
| goodStops - This function will return a 0 (false) if the variables      |
| cwStop and ccwStop are both = -1.                                       |
|                                                                         |
|||||||||||||||||||||||||||||||||||||||||||||||||||||||||||||||||||||||||
*/ int goodStops(void)

{
        if ((cwStop == -1) && (ccwStop == -1))
                return(0);
        else
                return(1);
}
/*
|||||||||||||||||||||||||||||||||||||||||||||||||||||||||||||||||||||||||
|                                                                         |
| setVelocityAndAcceleration - This function will set the velocity and    |
| acceleration controls for integral and proportional vel modes           |
| it will also set the direction enables based on the velocity and the    |
| fullServo Parameter. if fullServo is true the both directions are enabled |
|                                                                         |
|||||||||||||||||||||||||||||||||||||||||||||||||||||||||||||||||||||||||
*/ void setVelocityAndAcceleration(int velocity, long acceleration,int fullServo)
{
        int integral_vel;

integral_vel = velocity >> 4;
        if(integral_vel > 127) integral_vel = 127;
        else if (integral_vel < -128) integral_vel = -128;
        if(fullServo) outportb(_8255_PORTC_REG,inportb(_8255_PORTC_REG) | CW_ENA
        else
        {
                outportb(_8255_PORTC_REG,inportb(_8255_PORTC_REG) & ~CW_ENABLE_B
                if(velocity > 0) outportb(_8255_PORTC_REG,inportb(_8255_PORTC_RE
                if(velocity < 0) outportb(_8255_PORTC_REG,inportb(_8255_PORTC_RE
        }
        OutHctlByte(HCTL_ACCELERATION_LOW8_REG,acceleration);         // write
        OutHctlByte(HCTL_ACCELERATION_HIGH8_REG,acceleration >> 8);   // write
        OutHctlByte(HCTL_INTG_VELOCITY_REG,integral_vel & 0xff);
        OutHctlByte(HCTL_PROP_VEL_HIGH8_REG,velocity>>8);
        OutHctlByte(HCTL_PROP_VEL_LOW8_REG,velocity & 0xff);
}
/*
|||||||||||||||||||||||||||||||||||||||||||||||||||||||||||||||||||||||||
|                                                                         |
| velMoveToPosition - This function will move the arm to the absolute     |
| position that it was told.  Moving is |
| done in the velocity mode and with the HCTL having control of the motor |
| current.                                                                |
```

-189-

```
int velMoveToPosition(long newPosition,int velocity,PBF bioFeedBack,int fullServ
{
        int  done = false;
        int result = 0;
        whichWay direction;
        long lastPosition;

if(doInterrupt) lastPosition = realTimePosition;
        else lastPosition = readActualPosition();
        if (newPosition > lastPosition)
        {
                direction = increasing;
                setVelocityAndAcceleration(velocity,2561,fullServo);
        }
        else
        {
                direction = decreasing;
                setVelocityAndAcceleration(-velocity,2561,fullServo);
        }
        while (!done)
        {
                if (*bioFeedBack != NULL)
                        done = (*bioFeedBack)();
                if (done)
                        break;
                if(doInterrupt) lastPosition = realTimePosition;
                else lastPosition = readActualPosition();
                if (direction == increasing)
                {
                        if (lastPosition > (newPosition - WINDOW))
                          done = true;
                }
                else
                {
                        if (lastPosition < (newPosition + WINDOW))
                          done = true;
                }
                if (kbhit())
                {
                        if (myGetch() == escape)
                                result = 1,done = true;
                }
        }
        return(result);
}
```

/*
| idleVelMoveToPosition - This function will move the arm to the position |
| that it was told to move to relative to the cwStop.  Moving is done in  |
| the idle mode and direct control of motor current.                      |
*/

-190-

```c
int idleVelMoveToPosition(long newPosition,int current,PBF bioFeedBack)
{
        int done = false;
        int result = 0;
        whichWay direction;
        long lastPosition;

enterIdleMode();
        brakeOff();
        clutchOn(CLUTCHCURRENT);                        // small clutch
        if(doInterrupt) lastPosition = realTimePosition;
        else lastPosition = readActualPosition();        // read the current pos
        if (lastPosition < newPosition)
        {
                OutHctlByte(HCTL_MOTOR_CMD_REG,current);     // move
                direction = increasing;
        }
        else
        {
                OutHctlByte(HCTL_MOTOR_CMD_REG,-current);    // move
                direction = decreasing;
        }
        while (!done)
        {
                if (*bioFeedBack != NULL)
                        done = (*bioFeedBack)();
                if (done)
                        break;
                lastPosition = doInterrupt ? realTimePosition : readActualPositi
                if (direction == increasing)
                {
                        if (lastPosition > (newPosition - WINDOW))
                          done = true;
                }
                else
                {
                        if (lastPosition < (newPosition + WINDOW))
                          done = true;
                }
                lastPosition = doInterrupt ? realTimePosition : readActualPositi
                if (kbhit())
                {
                        if (myGetch() == escape)
                          result = 1,done = true;
                }
        }
        OutHctlByte(HCTL_MOTOR_CMD_REG,0);      // remove the current
        return(result);
}
```

-191-

E.D.C. File Print-out    LOWTEMP.C,    on 11-3-91,   a   :31 PM

```c
#include <conio.h>

/*
|||||||||||||||||||||||||||||||||||||||||||||||||||||||||||||||||||||
|                                                                    |
| myGetch - This int function is used to get a key stroke even if it is a |
| function key and return a unique code associated with it           |
|                                                                    |
|||||||||||||||||||||||||||||||||||||||||||||||||||||||||||||||||||||
*/ int myGetch(void)

{
   int i;

i = getch();
   if (i == 0)           // get special keys
     i = getch() + 256;
   return(i);
} void kbFlush(void)

{
   while (kbhit())
     myGetch();
} void waitHitThenFlush(void)

{
   while (!kbhit()); /* wait for a key stroke */
   kbFlush();
} void waitHit(void)

{
   while (!kbhit()); /* wait for a key stroke */
}
```

—192—

E.D.C. File Print-out    RTINT.C,    on 11-3-91,    at   ?1 PM

```c
include <vcstdio.h>
include <math.h>
include <dos.h> include "cntrlrio.h"
include "setupdma.h"
#include "tap.h"
#include "reaction.h"
#include "isomet.h"
#include "isotonic.h"
#include "isokinet.h"
#include "setisok.h"
#include "rtint.h"

/*
|||||||||||||||||||||||||||||||||||||||||||||||||||||||||||||||||||||||||
|                                                                         |
| realTimeInt - This int function is called after each A/D conversion     |
| has been DMA'ed into memory.                                            |
|                                                                         |
|||||||||||||||||||||||||||||||||||||||||||||||||||||||||||||||||||||||||
*/
/* copyright (C) 1991 Cedaron Medical Inc. Davis Ca all rights reserved the following section of code implements the isokinetic servo loop
this loop computes the proper drive to apply to the brake to maintain
the isokinetic velocity
*/ void interrupt realTimeInt()
{
  static int zerocount = 0;
  static long torqueSum = 0;
  static int counttimes = 100;
  static long bioTorqueAcc = 0;
  static long bioVelocityAcc = 0;

extern long target_velocity;
  extern long target_position;
  static long last_velocity_error;
  static long last_position_error;
  static long last_drive;
  static long velocity_error;
  static long position_error;
  static int  brake_dac_out;
  static int  acceleration;

static int adc_error = 0;

if (doInterrupt)
  {
    waitForInterrupt = false; // always reset
    lastRealTimePosition = realTimePosition;
    if (inportb(BOARD_STATUS_REG) & ADC1_BIT)
```

-193-

```
      adc_error = true
   else
   {
      realTimeTorque =   (inportb(ADC1_MS8)*16 + inportb(ADC1_LS4)/16)-2048;
      adc_error = false;
      inportb(ADC1_12BIT_START); // start adc for next conversion
   } realTimePosition = readActualPosition();
realTimeDeltaPosition = abs((int)(realTimePosition-lastRealTimePosition));
realTimeVelocity = realTimeDeltaPosition;
realTimeTorque -= torqueOffset;

if (collectData)
{
   if (sampleCount)
      if (dataPtr)
      {
         if (abs(realTimeTorque) > torqueTrigger)
         {
            dataPtr->torqueIndex = realTimeTorque;
            if (realTimePosition < 0)
               dataPtr->positionIndex = 0;  // don't allow a negative in
            else
               dataPtr->positionIndex = (unsigned int) realTimePosition;
            dataPtr++;
            sampleCount--;
            torqueTrigger = -1; // keep it going
         }
      }
} if (doTapFlag)
   {
      tapInterruptFunc();
   } if (doReactionFlag)
   {
      reactionInterruptFunc();
   } if (doIsometricFlag)
   {
      isometricInterruptFunc();
   } if (doIsotonicFlag)
   {
      isotonicInterruptFunc();
   } if (doIsokineticFlag)
   {
      isokineticInterruptFunc();
   } if (zeroFlag)
   {
      torqueSum += realTimeTorque;
```

```
                                    -194-
    zerocount++;
    if(zerocount .  counttimes)
    {
      torqueOffset = (int)(((torqueSum*2)/zerocount)+1)/2;
      zeroFlag = false;
      torqueSum = 0;
      zerocount = 0;
    }
}
if (servo)   // if zero then servo operation is disabled
{
  acceleration = abs(realTimeTorque) * InvInertia;    // compute the accele
  acceleration -= deceleration;   // subtract the deceleration
  big_target_velocity += acceleration; // compute the target velocity
  if (big_target_velocity < 0)
    big_target_velocity = 0; // limit to zero
  if ((big_target_velocity>>8) > isokinetic_velocity)   // limit to set poi
    big_target_velocity = isokinetic_velocity << 8;
  target_velocity = big_target_velocity >> 8;  // put into proper units
  if (servo == 1)  // going cw if == 1
  {
    target_position += target_velocity;   // compute target position for po
  }
  else // going ccw
  {
    target_position -= target_velocity;
  }
  velocity_error = abs(realTimeDeltaPosition) - target_velocity; // comput
  position_error = realTimePosition - target_position;

drive = last_drive + ((velocity_error
               -((last_velocity_error*zero_gain)/256))*error_gain
               -((last_drive*pole_gain)/256))/16; // this is the servo last_velocity_error = velocity_error; // save errors for next interrupt
  last_position_error = position_error;

if (drive > maxdrive)
    drive = maxdrive; // limit drive
  last_drive = drive; // save drive for next interrupt if ((servo == 1) && (realTimePosition >= cwLimit) ||
      (servo == 2) && (realTimePosition <= ccwLimit))  // see if at limit
  {                                      // shut down if at limit
    target_velocity = 0;
    big_target_velocity = 0;
    target_position = realTimePosition;
    servo = 0;
    drive = 0;
    last_drive = 0;
  } drive += drive_offset;
  if (drive < 0 )
    drive = 0;
  brake_dac_out = (int)(drive >> 8) & 0xff;
  setBrakeCurrent(brake_dac_out);
  if (collectFlag)
    brake_dac[data_index++] = brake_dac_out;
}
```

-195-

```
      else
      {
        last_velocity_error = 0;
        last_drive = 0;
        last_position_error = 0;
        target_position = realTimePosition;
        target_velocity = 0;
      }
      bioVelocityAcc += realTimeVelocity;
      bioTorqueAcc += realTimeTorque;
      bioCount++;
      if(captureBioData)
      {
        bioVelocity = (int)(bioCount ? bioVelocityAcc/bioCount: realTimeVelocity
        bioVelocityAcc = 0;
        bioTorque = (int)(bioCount ? bioTorqueAcc/bioCount : realTimeVelocity);
        bioTorqueAcc = 0;
        bioCount = 0;
        captureBioData = false;
      }

} // if dointerrupt
    outportb(EOI,EOICODE);
} void openDataCollection(dataPoint *thePointer,int maxSamples, int torque)
{
  disable();
  dataPtr = thePointer;
  collectData = true;
  sampleCount = maxSamples;
  torqueTrigger = torque;
  enable();
} void closeDataCollection(void)
{
  disable();
  dataPtr = NULL;
  collectData = false;
  enable();
}
```

—196—

E.D.C. File Print-out  SETISOK.C,  on 11-3-91,  1:32 PM

```c
include <vcstdio.h>
include <dos.h>
include <conio.h> include "cntrlrio.h"
include "rtint.h"
#include "setisok.h"

extern int dbg;
void setIsok(void)
{
#define DEBUG
ifdef DEBUG char inputline[256];
if(dbg)
{
 printf("enter the desired isokinetic velocity (%3ld)>>",isokinetic_velocity);
 fflush(stdin);
 if(gets(inputline)[0] != '\n')
 sscanf(inputline,"%ld",&isokinetic_velocity);

printf("enter the threshold torque (%4d)>>",thresholdTorque);
 fflush(stdin);
 if(gets(inputline)[0] != '\n')
 sscanf(inputline,"%d",&thresholdTorque);

printf("enter the deceleration (%4d)>>",deceleration);
 fflush(stdin);
 if(gets(inputline)[0] != '\n')
 sscanf(inputline,"%d",&deceleration);

printf("enter the drive offset (%4ld)>>",drive_offset);
 fflush(stdin);
 if(gets(inputline)[0] != '\n')
 sscanf(inputline,"%ld",&drive_offset);

printf("enter the Inverse Inertia (%4d)>>",InvInertia);
 fflush(stdin);
 if(gets(inputline)[0] != '\n')
 sscanf(inputline,"%d",&InvInertia);

printf("enter the error, zero, and pole gains (%3d, %3d, %3d)>>",error_gain,zer
 fflush(stdin);
 if(gets(inputline)[0] != '\n')
 sscanf(inputline,"%d%d%d",&error_gain,&zero_gain,&pole_gain);
}
endif
 nominaldrive = (thresholdTorque * 2561)/5 + drive_offset;
 maxdrive = 0xff001;
}
```

—197—

E.D.C. File Print-out    SETUPDMA.C,    on 11-3-91,    4:32 PM

```c
include <vcstdio.h>
include <dos.h> include "cntrlrio.h"
include "rtint.h"
#include "setupdma.h"

/*
|||||||||||||||||||||||||||||||||||||||||||||||||||||||||||||||||||||||
|                                                                     |
| startInt - This function will setup and start the DIB interrupt     |
|                                                                     |
|||||||||||||||||||||||||||||||||||||||||||||||||||||||||||||||||||||||
*/ void startInt(void)

{

/*  ;Load interrupt handler vectors for terminal interrupt at end of DMA */
             disable();
    oldfunc = getvect(INTNUM);
    setvect(INTNUM,realTimeInt);
    outportb(IMR,!(1 << INTLEV) & inportb(IMR));
    enable();

/* set control register of board */ outportb(BOARD_CONTROL_REG,inportb(BOARD_CONTROL_REG) & ~IRQ_BIT);

}

/*
|||||||||||||||||||||||||||||||||||||||||||||||||||||||||||||||||||||||
|                                                                     |
| stopInt - This function will stop the DIB INTERRUPT                 |
|                                                                     |
|||||||||||||||||||||||||||||||||||||||||||||||||||||||||||||||||||||||
*/ void stopInt(void)
{
  disable();
  outportb(BOARD_CONTROL_REG,inportb(BOARD_CONTROL_REG) | IRQ_BIT);

setvect(INTNUM,oldfunc);
  outportb(IMR,(1 << INTLEV) | inportb(IMR));
  enable();
}
```

−198−

E.D.C. File Print-out    TESTBED.C,   on 11-3-91,   a'  :32 PM

```c
#include <dos.h>
include <conio.h>
#include <stdio.h>
include <math.h> define  GLOBALS
include "cntrlrio.h"
include "setupdma.h"
#include "rtint.h"
#include "setisok.h"

void main()
{
  long lastPosition = 0;
  int lastForce = 0;
  int done;
  int i;

servo = false;
  initController();                              // setup the controller
  doInitialPosition();                           // seek max limits
  printf("cwStop = %d   ccwStop = %d\n",cwStop,ccwStop);
  moveToPositionFromCw(1024);                    // move cw one quarter
  brakeOff();                       //
  clutchOff();                      //
  setisok(true);
  startDmaInts();
  doInterrupt = true;               //
  servo = true;
  done = false;
  while (!done)                     //
  {
  if(kbhit())
  {
    switch(getch())
    {
      case 'i': //set isokinetic limits
      case 'I':
          doInterrupt = false;
          servo = false;
          brakeOff();
          setisok(false);
          brakeOn(10); // turn brake back on
          doInterrupt = true;
          servo = true;
          break;
      case 'q': //quit
      case 'Q':
          done = true;
          brakeOff();
          clutchOff();
          enterIdleMode();
          break;
      case 'c':
          data_index = 0;
          collectFlag = true;
```

```
                    -199-
            break;
        case 's':
            collectFlag = false;
            break;
        case 'p':
            collectFlag = false;
            stopDmaInts();
            for (i=0;i<data_index; i++)
            {
              printf("%3d\t",brake_dac[i++]);
              printf("%3d\t",brake_dac[i++]);
              printf("%3d\t",brake_dac[i++]);
              printf("%3d\t",brake_dac[i++]);
              printf("%3d\t",brake_dac[i++]);
              printf("%3d\t",brake_dac[i++]);
              printf("%3d\t",brake_dac[i++]);
              printf("%3d\n",brake_dac[i++]);
            }
            startDmaInts();
            data_index = 0;                                    //
            break;
        case 'z':
            collectFlag = false;
            zeroFlag = true;
            printf("zeroing torque transducer - DON'T TOUCH !!\n");
            while(zeroFlag) ;
            printf("forceOffset = %d\n",forceOffset);
            break;

}
  } if (!servo)
    {
/*      doInterrupt = false; */
      moveToPositionFromCw(cwLimit);
      doInterrupt = true;
      servo = true;
    } if((realTimePosition != lastPosition)
       || (abs(realTimeForce-lastForce)>10))
    {                                              //
      printf("force = %4d",lastForce = realTimeForce);         //
      printf("  position = %4d ",lastPosition = realTimePosition);
      printf("(%4ld)",target_position);            //
      printf("  velocity = %4d (%4ld)",realTimeDeltaPosition,target_velocity);
      printf("  drive = %5ld\n",drive/256);
    }
  }
  stopDmaInts();
}
```

-200-

E.D.C. File Print-out    AUTOCYCL.H,   on 11-3-91,    4:46 PM

```
/*      ProtoTypes      */
void   initAutoCycle(void);
COUNT  runAutoCycleFunc(void);

#ifdef GLOBALS
  #define EXTERN
#else
  #define EXTERN extern
endif ifdef GLOBALS
  COUNT autoCycle = 0;
#else
  extern COUNT autoCycle;
#endif
```

-201-

E.D.C. File Print-out    BGISTUFF.H,   on 11-3-91,    4:46 PM

```c
/*      ProtoTypes       */
int  huge detectVGA256(void);
int  installFont(void);
void installVGA256(void);

#ifdef GLOBALS
  #define EXTERN
#else
  #define EXTERN extern
endif

/* * * * * * * * * Other Variables * * * * * * * * */

EXTERN int VGA256_driver;
EXTERN int userFont;
```

—202—

E.D.C. File Print-out    BIOSTUFF.H,    on 11-3-91,    4:46 PM

```c
/*      ProtoTypes      */
void displayBioInfo(int parm,
                    int color,
                    int x,
                    int y,
                    int *digit,
                    char *tempStr,
                    char *lastTempStr);
void displayBioInfo1Place(int parm,
                          int color,
                          int x,
                          int y,
                          int *digit,
                          char *tempStr,
                          char *lastTempStr);

void displayBioInfoDigit(int parm,
                         int color,
                         int x,
                         int y,
                         char *tempStr,
                         char *lastTempStr);

#define FONT_MULTIPLIER    4
#define FONT_WIDTH        (FONT_MULTIPLIER * 8)
#define FONT_HEIGHT       (FONT_MULTIPLIER * 8)

#ifdef GLOBALS
  #define EXTERN
#else
  #define EXTERN extern
endif

/* * * * * * * * * Other Variables * * * * * * * */
```

−203−

E.D.C. File Print-out    CONSTANT.H,    on 11-3-91,    4:46 PM

```
#define WEIGHT   0
#define HEIGHT   1
```

-204-

E.D.C. File Print-out - CPM.H, on 11-3-91, at 4: PM

```
/*      ProtoTypes      */
void  initCPM(void);
COUNT runCPMFunc(void);

#ifdef GLOBALS
  #define EXTERN
#else
  #define EXTERN extern
endif

/* * * * * * * * * Window Variables   * * * * * * * */
EXTERN COUNT cpm;

/* * * * * * * * Other Variables * * * * * * * */
```

E.D.C. File Print-out  DEXTER.H,   on 11-3-91,   at   46 PM

```
#include "loadmsgs.h"
include "loadmsgs.txt"
#include "cntrlrio.h"
#include "lineariz.h"
#include "mainmenu.h"
#include "status.h"
#include "patient.h"
#include "initstop.h"
#include "isomet.h"
#include "isotonic.h"
#include "isokinet.h"
#include "cpm.h"
#include "tap.h"
#include "reaction.h"
#include "autocycl.h"
#include "setutil.h"
#include "utility.h"
#include "siconver.h"
#include "header.h"
#include "setupdma.h"
#include "rtint.h"
#include "setisok.h"
#include "lowlevel.h"
#include "bgistuff.h"
#include "summary.h"
#include "setstops.h"
#include "prtscrn.h"
```

–206–

E.D.C. File Print-out   HEADER.H,   on 11-3-91,   at   46 PM

```
/*      ProtoTypes      */
void prepHeaderBox(void);
void showHeaderBox(void);

#ifdef GLOBALS
  #define EXTERN
#else
  #define EXTERN extern
endif

/* * * * * * * * * * Window Variables  * * * * * * * */
EXTERN COUNT headerBox;
```

E.D.C. File Print-out    INITSTOP.H,    on 11-3-91,    4:46 PM

```
/*      ProtoTypes       */
void  initInitStops(void);
COUNT runInitStopsFunc(void);

#ifdef GLOBALS
  #define EXTERN
#else
  #define EXTERN extern
endif

/* * * * * * * * * * Window Variables    * * * * * * * * */
EXTERN COUNT initStops;

/* * * * * * * * * Other Variables * * * * * * * */
```

```
E.D.C. File Print-out    ISOKINET.H,   on 11-3-91,    4:46 PM
/*       ProtoTypes        */
void  initIsokinetic(void);
COUNT runIsokineticFunc(void);
void  isokineticInterruptFunc(void);

#ifdef GLOBALS
  #define EXTERN
#else
  #define EXTERN extern
endif ifdef GLOBALS
  int doIsokineticFlag = false;
#else
  extern int doIsokineticFlag;
endif /* * * * * * * * * Window Variables    * * * * * * * */
EXTERN COUNT isokinetic;
```

-209-

E.D.C. File Print-out    ISOMET.H,    on 11-3-91,    at    46 PM

```
/*      ProtoTypes       */
void  initIsometric(void);
COUNT runIsometricFunc(void);
void  isometricInterruptFunc(void);

#ifdef GLOBALS
  #define EXTERN
#else
  #define EXTERN extern
endif ifdef GLOBALS
  int doIsometricFlag = false;
  int calibrate = false;
#else
  extern int doIsometricFlag;
  extern int calibrate;
endif /* * * * * * * * * * Window Variables   * * * * * * * * */
EXTERN COUNT isometric;

/* * * * * * * * * Other Variables * * * * * * * * */
```

E.D.C. File Print-out : ISOTONIC.H,    on 11-3-91,    4:46 PM

```
/*      ProtoTypes      */
void   initIsotonic(void);
COUNT  runIsotonicFunc(void);
void   isotonicInterruptFunc(void);

#ifdef GLOBALS
  #define EXTERN
#else
  #define EXTERN extern
endif ifdef GLOBALS
  int doIsotonicFlag = false;
  int autoIsotonicTorque = 0;
#else
  extern int doIsotonicFlag;
  extern int autoIsotonicTorque;
endif /* * * * * * * * * *  Window Variables   * * * * * * * * */
EXTERN COUNT isotonic;

/* * * * * * * * * Other Variables * * * * * * * */
```

E.D.C. File Print-out  KEYCODES.H,  on 11-3-91,   4:46 PM define escape  27

-212-

E.D.C. File Print-out    LINEARIZ.H,    on 11-3-91,    4:46 PM

```c
/*      ProtoTypes        */
int makeLinearizationTableIsotonic(void);
int calcIsotonicTorque(float desiredTorque);
int makeLinearizationTableCPM(void);
int calcCPMVelocity(float desiredVelocity);
int calcVelocity(int velocity);
int calcAcceleration(int acceleration);

#ifdef GLOBALS
  #define EXTERN
#else
  #define EXTERN extern
endif

/* * * * * * * * * *  Window Variables    * * * * * * * */

/* * * * * * * * *  Other Variables * * * * * * * * */
```

-213-

E.D.C. File Print-out    LOADMSGS.H,    on 11-3-91,    1:46 PM

```c
/*      ProtoTypes      */
void loadErrorMsgs(char * fileName);

#ifdef GLOBALS
  #define EXTERN
#else
  #define EXTERN extern
endif include "..\language\textmsgs.h"

struct XLATEMSGS
{
  TEXT *Msg[2];
};

EXTERN struct XLATEMSGS *msgListPtrs;

EXTERN TEXT *msgListText;
```

-214-

E.D.C. File Print-out     LOWLEVEL.H,    on 11-3-91,      4:46 PM

```c
/*      ProtoTypes       */
int  myGetch(void);
void sayLineFeed(void);
void sayInt(int arg1);
void sayLong(long arg1);
void sayStringLn(char *arg1);
void sayString(char *arg1);
void kbFlush(void);
void waitHitThenFlush(void);
int  waitHitThenFlushOrEscape(void);
void waitHit(void);
void beep(int times);

#ifdef GLOBALS
  #define EXTERN
#else
  #define EXTERN extern
endif
```

E.D.C. File Print-out    MAINMENU.H,    on 11-3-91,    4:46 PM

```c
/*      ProtoTypes      */
void prepMainMenu(void);
void undoMainMenu(void);
COUNT statusMainMenu(void);

#ifdef GLOBALS
   #define EXTERN
#else
   #define EXTERN extern
endif

EXTERN VCMENU *mainMenu;

#ifndef GLOBALS
   extern COUNT mainMenuLine[9];
   extern COUNT currentMainSelect;
#else
   COUNT mainMenuLine[9] = {1,0,0,0,0,0,0,0,0};
   COUNT currentMainSelect = 0;
#endif
```

−216−

```
E.D.C. File Print-out     PATIENT.H,   on 11-3-91,       1:46 PM

/*      ProtoTypes      */
void   initPatientEntry(void);
COUNT patientEntryFunc(void);

#ifdef GLOBALS
   #define EXTERN
#else
   #define EXTERN extern
endif struct PATIENT_DATA
{
 TEXT last[19+1];
 TEXT first[15+1];
 TEXT id1[12+1];
 TEXT id2[12+1];
 TEXT physician[50+1];
 TEXT clinician[50+1];
 TEXT pathology[12+1];
 TEXT diagsurg[50+1];
 TEXT weight[3+1];
 long lweight;
 TEXT height[3+1];
 long lheight;
 TEXT age[2+1];
 TEXT domside[5+1];
 TEXT invside[5+1];
 TEXT gender[6+1];
 TEXT comment1[50+1];
 TEXT comment2[50+1];
};

/* * * * * * * * * *  Window Variables    * * * * * * * */
EXTERN COUNT patientEntry;

/* * * * * * * * * Other Variables * * * * * * * */

EXTERN struct PATIENT_DATA patientData;
EXTERN TEXT weightbase[4+1];
EXTERN TEXT heightbase[4+1];
```

-217-

E.D.C. File Print-out    PRTSCRN.H,    on 11-3-91,   ε   :47 PM

```
/*      ProtoTypes      */
int screenDump(int printerType,
               int lpt,
               int direction,
               int dotDensity,
               int x_start,
               int x_length,
               int y_start,
               int y_length,
               int x_offset,
               int y_offset);
int printReport(int lpt);

#ifdef GLOBALS
  #define EXTERN
#else
  #define EXTERN extern
endif
```

-218-
E.D.C. File Print-out    RDVGA.H,    on 11-3-91,    at    7 PM

```
unsigned char readVGApix(int x,int y);
void writeVGApix (int x,int y,int color);
void xorVGApix (int x,int y,int color);
```

E.D.C. File Print-out    REACTION.H,    on 11-3-91,    4:47 PM

```
/*      ProtoTypes       */
void   initReaction(void);
COUNT  runReactionFunc(void);
void   reactionInterruptFunc(void);

#ifdef GLOBALS
  #define EXTERN
#else
  #define EXTERN extern
endif ifdef GLOBALS
   int doReactionFlag = false;
#else
   extern int doReactionFlag;
endif /* * * * * * * * * * Window Variables    * * * * * * * * */
EXTERN COUNT reaction;
```

-220-

E.D.C. File Print-out   SETSTOPS.H,   on 11-3-91,    1:47 PM

```
/*      ProtoTypes      */
COUNT runSetStopsFunc(void);

define  MINROM  2500  // about 25 degrees ifdef GLOBALS
   #define EXTERN
#else
   #define EXTERN extern
endif

EXTERN COUNT setStops;
```

-221-

E.D.C. File Print-out    SETUTIL.H,   on 11-3-91,        1:47 PM

```
/*      ProtoTypes      */
void searchSet(GETTABLE *thistable,MSGINDEX theIndex);
void freeSet(VCSELSET *thisset);
COUNT rightJustify(GETTABLE *thisgetTable);
void freeMenuItems(VCMENU *thisitem);
```

E.D.C. File Print-out    SICONVER.H,    on 11-3-91,    4:47 PM

```
/*      ProtoTypes      */
int convertNumber(int theNumber,int theBase);
float convertFnumber(float theNumber,int theBase);
unsigned long expandNumber(int theNumber, int theBase);
int contractNumber(unsigned long theNumber,int theBase);

#ifdef GLOBALS
  #define EXTERN
#else
  #define EXTERN extern
endif ifndef GLOBALS
  extern float storageConversionMax;
  extern float storageConversionScale;
  extern float maxInt;
  extern float baseMultiplier[2][4];
else float storageConversionMax = 65535.0;
  float storageConversionScale = 64.0;
  float maxInt = 32767.0;
  float baseMultiplier[2][4] = {
                                1.0000000,
                                1.0000000,
                                1.0000000,
                                1.0000000,
                                0.4535924,
                                2.5400000,
                                1.3558180,
                                1.3558180
                                };
#endif
```

—223—

E.D.C. File Print-out  STATUS.H,  on 11-3-91,  a  47 PM

```
/*      ProtoTypes       */
void initStatusWindow(void);
void displayStatusLine(MSGINDEX msg1,
                       MSGINDEX msg2,
                       MSGINDEX msg3,
                       MSGINDEX msg4,
                       MSGINDEX msg5,
                       MSGINDEX msg6,
                       MSGINDEX msg7,
                       MSGINDEX msg8);

#ifdef GLOBALS
   #define EXTERN
#else
   #define EXTERN extern
endif

EXTERN COUNT statusWindow;

EXTERN TEXT statusLine[101];   /* extra just in case */
```

-224-

E.D.C. File Print-out    SUMMARY.H,    on 11-3-91,    a    :47 PM

```
/*      ProtoTypes        */
COUNT doSummary(void);

struct summaryRecord {
                    long  startStop;
                    long  endStop;
                 int  isometricPeakTorque[4];
                    long isotonicWorkAcc[4];
                    int  isokineticAvgPeakTorque[4];
                    int  tapTorque[4];
                    int  tapTime[4];
                    int  reactionTorque[4];
                    int  reactionTime[4];
                };

#ifdef GLOBALS
  #define EXTERN
#else
  #define EXTERN extern
endif define DATAMAX 1000    // 4 SECONDS

EXTERN struct summaryRecord theReport;

#ifdef GLOBALS
#else
#endif
```

-225-

E.D.C. File Print-out    TAP.H,    on 11-3-91,    at 4    PM

```
/*      ProtoTypes       */
void  initTap(void);
COUNT runTapFunc(void);
void  tapInterruptFunc(void);

#ifdef GLOBALS
  #define EXTERN
#else
  #define EXTERN extern
endif ifdef GLOBALS
  int doTapFlag = false;
#else
  extern int doTapFlag;
#endif

/* * * * * * * * * *  Window Variables   * * * * * * * * */
EXTERN COUNT tap;

/* * * * * * * * * * Other Variables * * * * * * * * */
```

E.D.C. File Print-out    UTILITY.H,    on 11-3-91,    ε  :48 PM

```
/*      ProtoTypes     */
void centerString(const char *theInputString,char *theOutputString, int theWidth
void stopcpy(char *arg1,const char *arg2);
void padString(char *theString,int maxWidth);
char *stringRightJustify(char *theString);
COUNT showAvail(void);

#ifdef GLOBALS
  #define EXTERN
#else
  #define EXTERN extern
endif

EXTERN  unsigned long memAvail;
#ifndef GLOBALS
  extern unsigned long memHigh;
  extern unsigned long memLow;
#else
  unsigned long memHigh = 0;
  unsigned long memLow = 0;
#endif
```

-227-
E.D.C. File Print-out    CNTRLRIO.H,   on 11-3-91,        1:48 PM

```c
#define HAND_WIRED_BOARD0

/*      ProtoTypes      */
void setBrakeCurrent(int current);
void setClutchCurrent(int current);
void brakeOff(void);
void brakeOn(int current);
void clutchOff(void);
void clutchOn(int current);
void setActualPosition(long position);
long readActualPosition(void);
void setCommandPosition(long position);
void enterResetMode(void);
void enterIdleMode(void);
void enterPositionMode(void);
void enterIntegralVelocityMode(void);
void enterProportionalVelocityMode(void);
void initController(void);
int  doInitialPosition(void);
int  idleMoveToPosition(long newPosition);
int  positionMoveToPosition(long thePosition);
int  waitForPosition(int clutchCurrent, int  goodStops(void);
void setVelocityAndAcceleration(int velocity, long acceleration,int fullServo);
int  idleVelMoveToPosition(long newPosition,int current,PBF bioFeedBack);
int  velMoveToPosition(long newPosition,int velocity,PBF bioFeedBack,int fullSer ifdef GLOBALS
        #define EXTERN
#else
        #define EXTERN extern
endif ifdef HAND_WIRED_BOARD
 #define HCTL_ACCESS_CODE_MASK 0X44
 #define HCTL_WAIT_MASK 0X40
 #define HCTLWR1 0X44
 #define HCTLWAITWR1 0X04
 #define HCTLWAITR2 0
 #define HCTLWR2 0X40
#else
 #define HCTL_ACCESS_CODE_MASK 0X0C
 #define HCTL_WAIT_MASK 0X04
 #define HCTLWR1 0X0C
 #define HCTLWAITWR1 0X08
 #define HCTLWAITR2 0
 #define HCTLWR2 0X04
endif define BRAKE_BIT 0X01
define CLUTCH_BIT 0X02
#define STOP_BIT 0X04
#define MOTOR_BIT 0X08
#define IRQ_BIT 0X10
```

-228-

```c
#define RESET_BT 0X20
#define LIMIT_BIT 0X40
define CAL_BIT 0X80 define ADC1_BIT 0X01
define ADC2_BIT 0X02
#define INIT_BIT 0X40
define PROF_BIT 0X80 define CW_ENABLE_BIT 1
define CCW_ENABLE_BIT 2 define _8255_MODE_DATA 0X8A
define DISABLE_ALL 0XFF define COUNTER0_MODE 0X16
define COUNTER1_MODE 0X76
define COUNTER2_MODE 0XB6 define COUNTER0_INIT_DATA 20
define COUNTER1_INIT_DATA 250
define COUNTER2_INIT_DATA 2000 define false 0
define true 1
#define MAXBRAKE   250
define MAXCLUTCH 150 define CW_SEEK 40
define CCW_SEEK -40 enum whichWay { increasing, decreasing };

typedef whichWay;

#define HALF_DEGREE 56
#define ONE_DEGREE 111
#define TWO_DEGREES 222
#define THREE_DEGREES 333
#define FOUR_DEGREES 444
#define FIVE_DEGREES 556
#define SIX_DEGREES 667
#define SEVEN_DEGREES 778
#define EIGHT_DEGREES 889
#define NINE_DEGREES 1000
define TEN_DEGREES 1111 define float_DPP 0.009
define int_PPD 111
#define float_PPD 111.11111
define CPR 40000 define BRAKE_CONTROL_REG    0x4280
define CLUTCH_CONTROL_REG   0x4281
#define _8255_PORTA_REG      0x4284
#define BOARD_CONTROL_REG    0x4284
#define _8255_PORTB_REG      0x4285
#define BOARD_STATUS_REG     0x4285
#define _8255_PORTC_REG      0x4286
#define _8255_MODE_REG       0x4287
```

–229–

```
#define _8254_COUNTER0        0X4288
#define _8254_COUNTER1        0X4289
#define _8254_COUNTER2        0X428A
define _8254_MODE_REG        0X428B define ADC1_12BIT_START      0X428C
define ADC1_8BIT_START       0X428D
#define ADC1_MS8              0X428E
define ADC1_LS4              0X428F define ADC2_12BIT_START      0X428C
define ADC2_8BIT_START       0X428D
#define ADC2_MS8              0X428E
define ADC2_LS4              0X428F define HCTL_SELECT_PROG_FUNC_REG        0x280
define HCTL_EXEC_PROG_FUNC_REG          0x285
#define HCTL_PWM_SIGN_REV_REG            0x287
#define HCTL_MOTOR_CMD_REG               0x289
#define HCTL_SAMPLE_TIMER_REG            0x28f
#define HCTL_DIG_FILTER_ZERO_REG         0x2a0
#define HCTL_DIG_FILTER_POLE_REG         0x2a1
#define HCTL_DIG_FILTER_GAIN_REG         0x2a2
#define HCTL_SET_ACTUAL_POS_HIGH8_REG    0x295
#define HCTL_SET_ACTUAL_POS_MID8_REG     0x296
#define HCTL_SET_ACTUAL_POS_LOW8_REG     0x297
#define HCTL_READ_ACTUAL_POS_HIGH8_REG   0x292
#define HCTL_READ_ACTUAL_POS_MID8_REG    0x293
#define HCTL_READ_ACTUAL_POS_LOW8_REG    0x294
#define HCTL_COMMAND_POS_HIGH8_REG       0x28c
#define HCTL_COMMAND_POS_MID8_REG        0x28d
#define HCTL_COMMAND_POS_LOW8_REG        0x28e
#define HCTL_ACCELERATION_LOW8_REG       0x2a6
#define HCTL_ACCELERATION_HIGH8_REG      0x2a7
#define HCTL_PROP_VEL_HIGH8_REG          0x2a4
#define HCTL_PROP_VEL_LOW8_REG           0x2a3
define HCTL_INTG_VELOCITY_REG           0x2bc ifdef GLOBALS
        long cwStop = -1;
        long ccwStop = -1;
        long midpoint = -1;
#else
        extern long cwStop;
        extern long ccwStop;
        extern long midpoint;
#endif
```

-230-

E.D.C. File Print-out    LOWTEMP.H,    on 11-3-91,    a    :50 PM

```
/*      ProtoTypes      */
int myGetch(void);
void kbFlush(void);
void waitHitThenFlush(void);
void waitHit(void);

#ifdef GLOBALS
  #define EXTERN
#else
  #define EXTERN extern
endif
```

-231-

E.D.C. File Print-out    RDVGA.H,    on 11-3-91,    at    0 PM

```
unsigned char readVGApix(int x,int y);
void writeVGApix (int x,int y,int color);
void xorVGApix (int x,int y,int color);
```

-232-

E.D.C. File Print-out   RTINT.H,   on 11-3-91,   at   0 PM

```
#ifdef GLOBALS
        #define EXTERN
        #define EQUALS =
#else
        #define EXTERN extern
        #define EQUALS ; /##/
endif define COUNTSPERREV   40000
define DEGREESPERREV  360 enum direction {none,up,down};

typedef direction;

typedef struct {int torqueIndex;
                unsigned int positionIndex;} dataPoint;

EXTERN long nominaldrive;
EXTERN long maxdrive;
EXTERN int realTimeVelocity;
EXTERN int torqueTrigger;
EXTERN int torqueOffset;
EXTERN int bioVelocity;
EXTERN int bioTorque;
EXTERN int captureBioData;

EXTERN  int bioCount EQUALS 0;
EXTERN  int realTimeTorque EQUALS 0;
EXTERN  long realTimePosition EQUALS 0;
EXTERN  long lastRealTimePosition EQUALS 0;
EXTERN  int realTimeDeltaPosition EQUALS 0;
EXTERN  int doInterrupt EQUALS false;
EXTERN  int servo EQUALS false;
EXTERN  int collectData EQUALS false;
EXTERN  dataPoint *dataPtr EQUALS NULL;
EXTERN  int sampleCount EQUALS 0;
EXTERN  dataPoint *dataPointer EQUALS NULL;
EXTERN  int waitForInterrupt EQUALS 1;

void interrupt realTimeInt();
void openDataCollection(dataPoint *thePointer,int maxSamples, int torque);
void closeDataCollection(void);
```

E.D.C. File Print-out    SETISOK.H,    on 11-3-91,    1:50 PM

```c
/*      ProtoTypes        */
void setIsok(void);

#ifdef GLOBALS
        #define EXTERN
        #define EQUALS =
#else
        #define EXTERN extern
        #define EQUALS ; /##/
endif EXTERN long target_velocity;
EXTERN long big_target_velocity;
EXTERN long target_position;
EXTERN unsigned char brake_dac[10000];
EXTERN long ccwLimit;
EXTERN long cwLimit;
EXTERN long drive;

EXTERN  int  data_index EQUALS 0;
EXTERN  int  collectFlag EQUALS false;
EXTERN  int  zeroFlag EQUALS false;
EXTERN  long isokinetic_velocity EQUALS 50;
EXTERN  int  thresholdTorque EQUALS 30;
EXTERN  int  error_gain EQUALS 81;
EXTERN  int  zero_gain EQUALS 2;
EXTERN  int  pole_gain EQUALS 0;
EXTERN  int  deceleration EQUALS 625;
EXTERN  long drive_offset EQUALS 0x2000;
EXTERN  int  InvInertia EQUALS 5;
```

-234-

E.D.C. File Print-out   SETUPDMA.H,   on 11-3-91,    4:50 PM

```c
#ifdef GLOBALS
  #define EXTERN
#else
  #define EXTERN extern
endif define INTNUM          15
define INTLEV          7

/* interupt controller */
#define IMR             0x21
#define EOI             0x20
define EOICODE         0x20 void startInt(void);
void stopInt(void);

EXTERN void interrupt (*oldfunc)();
```

-235-

APPENDIX B

© 1991 CEDARON MEDICAL, INC.

```
                                                                    Page 1
ABEL(tm) 3.00a  -  Document Generator           11-Sep-91 05:23 PM
DEXTER Host Interface
        by Gary Engle  08/20/91
        Cedaron Medical Inc.
Equations for Module DEXTER_host_interface Device DIBHOST

- Reduced Equations:

PSEL~ = !(!AEN & !SA12_15 & SA14 & !SA6 & SA7 & !SA8 & SA9);

HCTLWAIT~ = !(!CKG & !HCTLWAIT~ # !CS~ & !IORW~);

HCTLSTATE = !(ALE~ & !HCTLSTATE & OE~ # !CS~ & !IORW~ & !IOR~);

CS~ := (ALE~);

ALE~ = !(!ALE~ & CKB
           # !ALE~ & !CKA
           # !ALE~ & CS~
           # !AEN & CKA & CKB & CS~ & HCTLSTATE & HCTLWAIT~ & !IORW~ &
        !IOR~ & OE~ & !SA12_15 & !SA14 & !SA6 & SA7 & !SA8 & SA9
           # !AEN & CKA & CKB & DBS~ & !IORW~ & IOR~ & !SA12_15 & !SA14 &
        !SA6 & SA7 & !SA8 & SA9);

OE~ = !(!AEN & !IOR~ & !OE~ & !SA12_15 & !SA14 & !SA6 & SA7 & !SA8 &
        SA9
           # !AEN & !HCTLSTATE & HCTLWAIT~ & !IORW~ & !IOR~ & !SA12_15 &
        !SA14 & !SA6 & SA7 & !SA8 & SA9);

RDY = !(!AEN & !CS~ & !IORW~ & !RDY & !SA12_15 & !SA14 & !SA6 & SA7 &
        !SA8 & SA9
           # !AEN & DBS~ & !IORW~ & OE~ & !SA12_15 & !SA14 & !SA6 & SA7 &
        !SA8 & SA9
           # !AEN & DBS~ & !IOR~ & OE~ & !SA12_15 & !SA14 & !SA6 & SA7 &
        !SA8 & SA9);

enable RDY = (!AEN & !IORW~ & !SA12_15 & !SA6 & SA7 & !SA8 & SA9);

ADS~ = !(!AEN & !ALE~ & !IORW~ & !SA12_15 & !SA14 & !SA6 & SA7 & !SA8 &
        SA9
           # !AEN & !ALE~ & !IOR~ & !SA12_15 & !SA14 & !SA6 & SA7 & !SA8 &
        SA9);

DBS~ = !(ADS~ & !AEN & !IORW~ & !SA12_15 & SA14 & !SA6 & SA7 & !SA8 &
        SA9
           # ADS~ & !AEN & !IOR~ & !SA12_15 & SA14 & !SA6 & SA7 & !SA8 &
        SA9
           # !AEN & !HCTLSTATE & HCTLWAIT~ & !IORW~ & !IOR~ & !SA12_15 &
        !SA14 & !SA6 & SA7 & !SA8 & SA9
           # ADS~ & !DBS~ & !IORW~
           # ADS~ & !AEN & !CS~ & !IORW~ & !SA12_15 & !SA6 & SA7 & !SA8 &
        SA9
           # ADS~ & !AEN & !CS~ & !IOR~ & !SA12_15 & !SA6 & SA7 & !SA8 &
        SA9);
```

We claim:

1. A system for isolating, evaluating and exercising muscle groups of a hand of a test subject, comprising:

means for detecting the movements of the hand during abduction, opposition, flexion or extension of several or individual digits of the hand, said means for detecting translating the movements into rotational data for the system and effectively isolating the movements of said several or individual digits so that movements of other muscle groups of the test subject are not detected by the system; and means for providing a variable resistance to the means for detecting and for ascertaining the force applied to the means for detecting by the movements of said several or individual digits, said variable resistance including isotonic, isokinetic, and isometric modes of resistance against said several or individual digits.

2. The system of claim 1 wherein the means for detecting comprises a stationary element for securing a first portion of the hand; and a rotational element mounted for rotation about an axis positioned adjacent the stationary element and coupled to the means for providing resistance, the rotational element interacting with a second, moving portion of the hand, such that any movement of the second portion of the hand rotates the rotational element about the axis subject to the means for providing resistance.

3. The system of claim 2 wherein the means for providing and ascertaining comprises resistance means for providing a controlled resistance to the rotational element;

means for sensing torque applied to the rotational element by the movements of said moving portion of the hand;

means for measuring the rotational velocity and position of the rotatable element;

means for selectively positioning the rotational element; and control means, coupled to the resistance means, means for sensing, means for measuring, and means for selectively positioning, for controlling the resistance applied by the resistance means, for receiving data input from the means for sensing and means for measuring, and for directing the means for selectively positioning, wherein the control means may direct the resistance means and means for selectively positioning to perform said isokinetic, isotonic, and isometric modes, and continuous passive motion, and proprioceptive test sequences.

4. The system of claim 2 wherein the means for providing a selective variable resistance further includes:

means for controlling the resistance to rotation of the rotational element about said axis, such that the isokinetic, isotonic, and isometric modes of resistance are provided to the rotational element.

5. The system of claim 1 wherein the means for detecting the movements of said at least one muscle group includes means for detecting the supination and pronation of the forearm.

6. The system of claim 5 wherein the means for detecting the movements of said at least one muscle group further includes means for detecting internal and external rotation of the shoulder.

7. The system of claim 1 further including a housing enclosing the means for providing and means for detecting, wherein the means for detecting includes a stationary member coupled to the housing, and a rotational member rotatable about an axis positioned adjacent to the stationary element such that, upon rotation of the rotational member, a linear distance between the stationary element and the rotational element is varied.

8. The system of claim 7 wherein the rotational member may be rotated in a counterclockwise direction and a clockwise direction thereby providing measurement of both a left and a right hand, respectively.

9. A compact apparatus for evaluation and correction of various actions of the human hand, comprising:

means for isolating and testing the abduction, opposition, flexion or extension functions of the hand and individual digits of the hand, the means including a rotational element and means for providing a variable resistance to the rotational element;

control means for controlling the magnitude of the variable resistance applied to the rotational means such that the resistance is varied to provide at least isotonic, isokinetic, and isometric modes of resistance; and means for providing data signals from the rotational means to the control means, including means for providing data as to the rotational position of the rotational means and means for providing the magnitude of the torque exerted on the rotational means.

10. A device for evaluating and exercising a hand of a test subject, comprising:

means for isolating and testing the abduction, opposition, flexion and extension of the hand and individual digits of the hand, said means including a first fixture and a second fixture, the first fixture being movably positioned adjacent to the second fixture to translate movements of the hand and individual digits into rotational data, the second fixture being fixed, the first and second fixtures effectively isolating said movements from movements of other parts of a human body; and means, coupled to the first fixture, for providing isotonic, isometric, and isokinetic resistance modes to the movements of the hand and digits.

11. The system of claim 10 wherein the means for providing includes means for providing a variable resistance to the first fixture responsive to a force applied thereto by the movements of the test subject, and means for measuring the force applied by the movements of the test subject, wherein during the isokinetic mode a force applied by the means for providing, relative to the force applied by the test subject, is such that a constant rotational velocity is maintained for the first fixture.

12. The system of claim 10 wherein the means for providing includes means for providing a variable resistance to the first fixture responsive to a force applied thereto by the movements of the test subject, and means for measuring the force applied to the first fixture by the movements of the test subject, wherein during the isotonic mode a force applied by the means for providing, relative to the force applied by the test subject, is constant, such that the first fixture has a variable rotational velocity.

13. The system of claim 10 wherein the means for providing includes means for providing a constant, high resistance to the first fixture responsive to a force applied thereto by the movements of the test subject, and means for measuring the force applied by the movements of the test subject, wherein during the isometric mode a force applied by the means for providing which is greater than the force applied by the test subject such that the test subject cannot move the rotational element.

14. The system of claim 10 wherein the means for providing includes means for providing a constant, high resistance to the first fixture responsive to a force applied thereto by the movements of the test subject, means for measuring the force applied by the movements of the test subject, and means for positioning the first fixture along a rotational path, wherein the means for positioning initiates movement of the first fixture which elicits a reactive response from the test subject, and the means for controlling further includes means for measuring the reaction time of the test subject.

15. The device of claim 10 wherein the movements of the hand include palmar flexion, digit flexion, dorsiflexion, abduction, opposition, radial deviation and ulnar deviation.

16. The device of claim 10 further including means attachable to the first and second fixtures for adapting said fixtures to one or more of the digits of the hand.

17. A hand exercise and evaluation apparatus, comprising:

a grip fixture, the grip fixture including a stationary component and a moving component, the moving component measuring and isolating movements of at least one muscle group of the human hand and the individual digits of the hand; and a resistance control system, coupled to the moving component, the resistance control system including means for providing resistance to the moving element in a variety of modes of operation such that the resistance provided to the moving component provides an isometric, isokinetic, isotonic and passive resistance on the moving element.

* * * * *